United States Patent
Nagy et al.

(10) Patent No.: US 7,521,047 B2
(45) Date of Patent: *Apr. 21, 2009

(54) HUMAN POLYPEPTIDES CAUSING OR LEADING TO THE KILLING OF CELLS INCLUDING LYMPHOID TUMOR CELLS

(75) Inventors: Zoltan Nagy, Wolfratshausen (DE); Christoph Brunner, Bad Heilbrunn (DE); Michael Tesar, Weilheim (DE); Elisabeth Thomassen-Wolf, München (DE); Robert Rauchenberger, Farchant (DE)

(73) Assignees: GPC Biotech AG, Munich (DE); Morphosys AG, Munich (DE)

( * ) Notice: Subject to any disclaimer, the term of this patent is extended or adjusted under 35 U.S.C. 154(b) by 887 days.

This patent is subject to a terminal disclaimer.

(21) Appl. No.: 10/001,934

(22) Filed: Nov. 15, 2001

(65) Prior Publication Data
US 2003/0032782 A1 Feb. 13, 2003

Related U.S. Application Data

(63) Continuation-in-part of application No. PCT/US01/15625, filed on May 14, 2001.

(51) Int. Cl.
*A31K 39/395* (2006.01)
*C07K 16/00* (2006.01)
*C07K 16/28* (2006.01)
*C07K 16/30* (2006.01)
*C07K 16/46* (2006.01)

(52) U.S. Cl. .............. 424/133.1; 424/141.1; 424/143.1; 424/155.1; 424/156.1; 424/173.1; 424/174.1; 530/387.9; 530/388.1; 530/388.15; 530/388.7; 530/388.73; 530/388.8; 530/388.85

(58) Field of Classification Search .............. 424/130.1, 424/133.1, 135.1, 141.1, 142.1, 152.1, 153.1, 424/143.1, 178.1; 530/378.1, 387.3, 388.1, 530/388.15, 388.22
See application file for complete search history.

(56) References Cited

U.S. PATENT DOCUMENTS

| | | | |
|---|---|---|---|
| 6,180,377 B1 | 1/2001 | Morgan et al. | |
| 6,300,064 B1 | 10/2001 | Knappik et al. | |

FOREIGN PATENT DOCUMENTS

| | | | |
|---|---|---|---|
| WO | WO-94/29451 | 12/1994 | |
| WO | WO-96/17874 | 6/1996 | |
| WO | WO 96/17874 | * 6/1996 | |
| WO | WO-97/08320 | 3/1997 | |
| WO | WO 98/37200 | 8/1998 | |
| WO | WO-99/45031 | 9/1999 | |
| WO | WO 99/45031 | 9/1999 | |
| WO | WO-99/53953 | 10/1999 | |
| WO | WO-00/12560 | 3/2000 | |

OTHER PUBLICATIONS

Rudikoff et al (Proc Natl Acad Sci USA 1982 vol. 79 p. 1979).*
Schlom (Monoclonal Antibodies: They're More and Less Than You Think, In: Molecular foundations of Oncology, 1991, pp. 95-134).*
The abstract of George et al (Journal of Immunology, 1988, vol. 141, pp. 2168-2174).*
Drenou et al (Journal of Immunology, Oct. 1999, vol. 163, pp. 4115-4124).*
Ackerman, R.C. et al. Induction of apoptotic or lytic death in an ovarian adenocarcinoma cell line by antibodies generated against a synthetic N-terminal extracellular domain gonadotropin-releasing hormone receptor peptide. *Cancer Letters* 81, 177-184 (1994).
Billing, R. & Chatterjee, S. Prolongation of Skin Allograft Survival in Monkeys Treated with Anti-Ia and Anti-Blast / Monocyte Monoclonal Antibodies. *Transplant. Proc.* 15, 649 (1983).
Bonagura, V.R. et al. Anti-clonotypic Autoantibodies in Pregnancy. *Cell. Immunol.* 108, 356 (1987).
Bunce, M. et al. The production of a human monoclonal antibody defining a split of HLA-DRw13 (DRw13b). *Tissue Antigens* 36, 100-102 (Sep. 1990).
DeNardo, S.J. et al. Treatment of B Cell Malignancies with 131I Lym-1 Monoclonal Antibodies. *Int. J. Cancer* Suppl. 3, 96-101 (1988).
Dueymes, M. et al. Anti-Endothelial Cell Antibody Binding Causes Apoptosis of Endothelial Cells. *Arthritis & Rheumatism* 40, S103 (Sep. 1997).
Dyer, M.J.S. et al. Effects of CAMPATH-1 Antibodies in Vivo in Patients with Lymphoid Malignancies: Influence of Antibody Isotype. *Blood* 73, 1431-1439 (1989).
Dyer, M.J.S. The Role of CAMPATH-I Antibodies in the Treatment of Lymphoid Malignancies. *Seminars in Oncology* 26, Suppl. 14, 52-57 (Oct. 1999).

(Continued)

*Primary Examiner*—Karen A Canella
(74) *Attorney, Agent, or Firm*—Leon R. Yankwich; David G. O'Brien; Yankwich & Associates, P.C.

(57) ABSTRACT

The present invention relates to polypeptide compositions which bind to cell surface epitopes and, in multivalent forms, cause or lead to the killing of cells including lymphoid tumor cells, and in the case of monovalent forms, cause immunosuppression or otherwise inhibit activation of lymphocytes. The invention further relates to nucleic acids encoding the polypeptides, methods for the production of the polypeptides, methods for killing cells, methods for immunosuppressing a patient, pharmaceutical, diagnostic and multivalent compositions and kits comprising the polypeptides and uses of the polypeptides.

65 Claims, 68 Drawing Sheets

OTHER PUBLICATIONS

Epstein, A.L. et al. Two New Monoclonal Antibodies, Lym-1 and Lym-2, Reactive with Human B-Lymphocytes and Derived Tumors, with Immunodiagnostic and Immunotherapeutic Potential. *Cancer Res.* 47, 830-840 (1987).

Eray, M. et al. Cross-linking of surface lgG induces apoptosis in a bcl-2 expressing human follicular lymphoma line of mature B cell phenotype. *Int. Immunol.* 6, 1817-1827 (1994).

Ghahremani, M. et al. Activation of Fas Ligand/Receptor System Kills Ovarian Cancer Cell Lines by an Apoptotic Mechanism. *Gynecologic Onocol.* 70, 275-281 (1998).

Golding et al., "Common Epitope in Human Immunodeficiency Virus (HIV) I-GP41 and HLA Class II Elicits Immunosuppressive Autoantibodies Capable of Contributing to Immune Dysfunction in HIV I-infected Individuals," The Journal of Clinical Investigation 83:1430-1435 (1989).

Golding et al., "Identification of Homologous Regions in Human Immunodeficiency Virus I gp41 and Human MHC Class II $\beta$ 1 Domain," Journal of Experimental Medicine 167:914-923 (1988).

Okudaira et al., "Anti-la Reactivity in Sera from Patients with Systemic Lupus Erythematosus," J. Clin. Invest. 69:17-24 (1982).

Jia Dong Shi et al., "In Vivo Pharmacodynamic Effects of Hu1D10 (Remitogen), a Humanized Antibody Reactive Against a Polymorphic Determinant of HLA-DR Expressed on B Cells," Leukemia and Lymphoma 43:1303-1312 (2002).

Newell et al., "Does the Oxidative/Glycolytic Ratio Determine Proliferation or Death in Immune Recognition?" Annals New York Academy of Sciences pp. 77-82.

Bridges et al., "Selective In Vivo Antitumor Effects of Monoclonal Anti-I-A Antibody on B Cell Lymphoma," The Journal of Immunology 139(12):4242-4249 (1987).

Truman et al., "Lymphocyte programmed cell death is mediated via HLA class II DR", International Immunol. 6(6): 887-96, (1994).

Blakey et al., "Antibody Toxin Conjugates: A Perspective", Prog. Allergy, vol. 45, pp. 50-90 (1988).

Schlom, "Monoclonal Antibodies: They're More and Less Than You Think." Molecular Foundation of Oncology pp. 95-134 (1994).

Ge, et al., "A Human Hybridoma Monoclonal Antibody (TrJ11) Recognizing a New HLA-DR Epitope Shared by DR4, DR8, DR11, and DRB1*1303," *Human Immunology*, 42:27-34 (1995).

Hancock, et al., "Production of Monoclonal Human Antibody to HLA-DR5(DRw11) by Mouse/Human Heterohybridomas," *Human Immunology*, 22:135-142 (1998).

Pistillo, et al., "A Novel Approach to Human Anti-HLA mABs Production: Use of Phage Display Libraries," *Human Immunology*, 57:19-26 (1997).

Queen, et al., "A humanized antibody that binds to the interleukin 2 receptor," *Proc. Natl. Acad. Sci. USA*, 86:10029-10033 (1989).

Vaughan, et al., "Human antibodies by design," *Nature Biotechnology*, 16:535-539 (1998).

* cited by examiner

| | MS-GPC-8-27-7 | MS-GPC-8-27-10 | MS-GPC-8-6-13 | MS-GPC-8-27-41 | MS-GPC-8-6-47 | MS-GPC-8-10-57 | MS-GPC-8-6-27 | MS-GPC-8 | MS-GPC-8-6 |
|---|---|---|---|---|---|---|---|---|---|
| Plastic | -0.004 | -0.020 | -0.022 | -0.025 | -0.001 | 0.005 | 0.007 | -0.022 | -0.018 |
| BSA | -0.003 | -0.019 | -0.021 | -0.022 | 0.008 | 0.003 | 0.003 | -0.016 | -0.019 |
| Testosterone-BSA | -0.005 | -0.010 | -0.012 | -0.007 | 0.011 | 0.003 | 0.002 | -0.009 | -0.012 |
| Lysozyme | -0.005 | -0.079 | -0.079 | -0.073 | 0.013 | 0.014 | 0.006 | -0.081 | -0.072 |
| human Apotransferrin | -0.009 | -0.016 | -0.018 | -0.018 | -0.005 | -0.008 | -0.004 | -0.014 | -0.016 |
| MHCII (DRA*0101/ DRB1*0401) | 1.549 | 1.493 | 1.467 | 1.525 | 1.400 | 1.256 | 1.297 | 1.058 | 1.306 |

Fig. 1A

| Target Proteins | scFv | | | | | | | | | | | | IgG | | |
|---|---|---|---|---|---|---|---|---|---|---|---|---|---|---|---|
| | 17 | 2E | 45 | 5C | 73 | 8A | A1 | B8 | E6 | FD | 159 | 170 | 1D09C3 | 1C7277 | 305D3 |
| DR4Dw4 Purified | +[a] | + | + | + | + | + | + | + | + | + | + | + | + | + | + |
| Chimeric DR-IE purified | +[b] | + | + | + | + | + | + | + | + | + | + | + | + | + | + |
| Lysozyme | - | - | - | - | - | - | - | - | - | - | - | - | - | - | - |
| Transferrin | - | - | - | - | - | - | - | - | - | - | - | - | - | - | - |
| BSA | - | - | - | - | - | - | - | - | - | - | - | - | - | - | - |
| Human gamma globulin | - | - | - | - | - | - | - | - | - | - | - | - | - | - | - | a. In Elisa, OD (at 370 nm - background): > 1.5
b. In Elisa, OD (at 370 nm - background): < 0.5

Fig. 1C

| Cell Line | HLA- | DRB1* | scFv | | | | | | | | | | | | | IgG | | |
|---|---|---|---|---|---|---|---|---|---|---|---|---|---|---|---|---|---|---|
| | | | 17 | 2E | 45 | 5C | 73 | 8A | A1 | B8 | E6 | FD | 159 | 170 | 1D09C3 | 1C7277 | 305D3 |
| LG2 | DR1 | 0101 | +a | + | -b | - | + | + | + | + | + | + | + | + | + | + | + |
| E4181324 | DR2 | 15021 | + | + | - | - | + | + | + | + | + | + | + | + | + | + | + |
| VAVY | DR3 | 0301 | + | + | - | - | + | + | + | + | + | + | + | + | + | + | + |
| PRIESS | DR4Dw4 | 0401 | + | + | + | +/- | + | + | + | + | + | + | + | + | + | + | +/-c |
| TS10 | DR4Dw10 | 0402 | + | + | - | +/- | + | + | + | + | + | + | + | + | + | + | + |
| BIN40 | DR4Dw14 | 0404 | + | + | - | +/- | + | + | + | + | + | + | + | + | + | + | + |
| TAB089 | DR8 | 8031 | + | + | + | - | + | + | + | + | + | + | + | + | + | + | + |
| DKB | DR9 | 9012 | + | + | +/- | +/- | + | + | - | + | + | + | + | + | + | + | +/- |
| WT47 | DR13 | 1302 | + | + | + | +/- | + | + | + | + | + | + | + | + | + | + | + |
| TEM | DR14 | 1401 | +/- | + | + | +/- | +/- | + | +/- | + | - | + | + | + | + | + | + |
| L105.1 | DRw52 | B3*0101 | - | - | - | - | ntd | + | - | - | + | + | nt | nt | +/- | +/- | +/- |
| L257.6 | DRw53 | B4*0101 | +/- | - | + | - | nt | + | - | +/- | +/- | + | nt | nt | + | + | + |
| L25.4 | DPw4/w4.2 | DP0103/0402 | - | - | - | - | nt | + | - | - | - | +/- | nt | nt | +/- | - | - |
| L256.12 | DPw2/w2.1 | DP0202/0201 | - | - | - | - | nt | +/- | - | - | - | - | nt | nt | - | - | - |
| L21.3 | DQ7/w2 | DQ0201/0602 | - | - | - | - | nt | + | - | + | - | - | nt | nt | - | - | - |
| Target Cell | | | | | | | | | | % Cells Killede | | | | | | | | |
| PRIESS | | | 75 | 20 | 28 | 32 | 22 | 89 | 33 | 59 | 75 | 34 | 1 | 5 | 88 | 93 | 74 | a. FACS analysis, mAb + FITC-anti human IgG4, mean fluorescence intensity < 10.
b. Mean fluorescence intensity 10-30.
c. Mean fluorescence intensity > 30.
d. Not tested.
e. Based on viable cell recovery after treatment with 200nM scFv plus 100 nM anti-FLAG or 50 nM mab at 37°C for 4h. Determined by light.

Fig. 2

```
            XbaISphI
            ~~~~~~~~~~
  1   AGAGCATGCG TAGGAGAAAA TAAAATGAAA CAAAGCACTA TTGCACTGGC
      TCTCGTACGC ATCCTCTTTT ATTTTACTTT GTTTCGTGAT AACGTGACCG

51   ACTCTTACCG TTGCTCTTCA CCCCTGTTAC CAAAGCCGAC TACAAAGATG
      TGAGAATGGC AACGAGAAGT GGGGACAATG GTTTCGGCTG ATGTTTCTAC

MfeI
           ~~~~~~~
101   AAGTGCAATT GGTTCAGTCT GGCGCGGAAG TGAAAAAACC GGGCAGCAGC
      TTCACGTTAA CCAAGTCAGA CCGCGCCTTC ACTTTTTTGG CCCGTCGTCG

BspEI
                              ~~~~~~
151   GTGAAAGTGA GCTGCAAAGC CTCCGGAGGC ACTTTTAGCA GCTATGCGAT
      CACTTTCACT CGACGTTTCG GAGGCCTCCG TGAAAATCGT CGATACGCTA

XhoI
                                         ~~~~~~
                                         AvaI
                                         ~~~~~~
201   TAGCTGGGTG CGCCAAGCCC CTGGGCAGGG TCTCGAGTGG ATGGGCGGCA
      ATCGACCCAC GCGGTTCGGG GACCCGTCCC AGAGCTCACC TACCCGCCGT

BstEII
                                                   ~
251   TTATTCCGAT TTTTGGCACG GCGAACTACG CGCAGAAGTT TCAGGGCCGG
      AATAAGGCTA AAAACCGTGC CGCTTGATGC GCGTCTTCAA AGTCCCGGCC

BstEII
      ~~~~~~
301   GTGACCATTA CCGCGGATGA AGCACCAGC ACCGCGTATA TGGAACTGAG
      CACTGGTAAT GGCGCCTACT TTCGTGGTCG TGGCGCATAT ACCTTGACTC

EagI         BssHII
                              ~~~~~~       ~~~~~~~
351   CAGCCTGCGT AGCGAAGATA CGGCCGTGTA TTATTGCGCG CGTTATTATG
      GTCGGACGCA TCGCTTCTAT GCCGGCACAT AATAACGCGC GCAATAATAC

StyI
                                         ~~~~~~~
401   ATCGTATGTA TAATATGGAT TATTGGGGCC AAGGCACCCT GGTGACGGTT
      TAGCATACAT ATTATACCTA ATAACCCCGG TTCCGTGGGA CCACTGCCAA

BlpI
          ~~~~~~~
          CeIII
          ~~~~~~~
451   AGCTCAGCGG GTGGCGGTTC TGGCGGCGGT GGGAGCGGTG GCGGTGGTTC
```

Fig. 11 (cont.)

```
            TCGAGTCGCC CACCGCCAAG ACCGCCGCCA CCCTCGCCAC CGCCACCAAG

EcoRV
                           ~~~~~~~
      501   TGGCGGTGGT GGTTCCGATA TCGAACTGAC CCAGCCGCCT TCAGTGAGCG
            ACCGCCACCA CCAAGGCTAT AGCTTGACTG GGTCGGCGGA AGTCACTCGC

SexAI
                ~~~~~~~~
      551   TTGCACCAGG TCAGACCGCG CGTATCTCGT GTAGCGGCGA TGCGCTGGGC
            AACGTGGTCC AGTCTGGCGC GCATAGAGCA CATCGCCGCT ACGCGACCCG

XmaI
                                                ~~~~~~
                             KpnI              SmaI
                             ~~~~~~~           ~~~~~~
                           Acc65I              AvaI
                           ~~~~~~~             ~~~~~~
      601   GATAAATACG CGAGCTGGTA CCAGCAGAAA CCCGGGCAGG CGCCAGTTCT
            CTATTTATGC GCTCGACCAT GGTCGTCTTT GGGCCCGTCC GCGGTCAAGA

Bsu36I
                                    ~~~~~~~~
      651   GGTGATTTAT GATGATTCTG ACCGTCCCTC AGGCATCCCG GAACGCTTTA
            CCACTAAATA CTACTAAGAC TGGCAGGGAG TCCGTAGGGC CTTGCGAAAT

BamHI
                ~~~~~~
      701   GCGGATCCAA CAGCGGCAAC ACCGCGACCC TGACCATTAG CGGCACTCAG
            CGCCTAGGTT GTCGCCGTTG TGGCGCTGGG ACTGGTAATC GCCGTGAGTC

BpuAI
                ~~~~~~
                BbsI
                ~~~~~~
      751   GCGGAAGACG AAGCGGATTA TTATTGCCAG AGCTATGACG CTCATATGCG
            CGCCTTCTGC TTCGCCTAAT AATAACGGTC TCGATACTGC GAGTATACGC

HpaI       MscI    EcoRI
                                          ~~~~~~    ~~~~~~~  ~~~~~~
      801   TCCTGTGTTT GGCGGCGGCA CGAAGTTAAC CGTTCTTGGC CAGGAATTCG
            AGGACACAAA CCGCCGCCGT GCTTCAATTG GCAAGAACCG GTCCTTAAGC

851   AGCAGAAGCT GATCTCTGAG GAGGATCTGA ACTAGGGTGG TGGCTCTGGT
            TCGTCTTCGA CTAGAGACTC CTCCTAGACT TGATCCCACC ACCGAGACCA

901   TCCGGTGATT TTGATTATGA AAAGATGGCA AACGCTAATA AGGGGGCTAT
            AGGCCACTAA AACTAATACT TTTCTACCGT TTGCGATTAT TCCCCCGATA
                                               gIIIseq9  100.0%
                                            ========================

951   GACCGAAAAT GCCGATGAAA ACGCGCTACA GTCTGACGCT AAAGGCAAAC
```

Fig. 11 (cont.)

```
              CTGGCTTTTA CGGCTACTTT TGCGCGATGT CAGACTGCGA TTTCCGTTTG

ClaI
                                              ~~~~~~
1001  TTGATTCTGT CGCTACTGAT TACGGTGCTG CTATCGATGG TTTCATTGGT
      AACTAAGACA GCGATGACTA ATGCCACGAC GATAGCTACC AAAGTAACCA

1051  GACGTTTCCG GCCTTGCTAA TGGTAATGGT GCTACTGGTG ATTTTGCTGG
      CTGCAAAGGC CGGAACGATT ACCATTACCA CGATGACCAC TAAAACGACC

1101  CTCTAATTCC CAAATGGCTC AAGTCGGTGA CGGTGATAAT TCACCTTTAA
      GAGATTAAGG GTTTACCGAG TTCAGCCACT GCCACTATTA AGTGGAAATT

1151  TGAATAATTT CCGTCAATAT TTACCTTCCC TCCCTCAATC GGTTGAATGT
      ACTTATTAAA GGCAGTTATA AATGGAAGGG AGGGAGTTAG CCAACTTACA

1201  CGCCCTTTTG TCTTTGGCGC TGGTAAACCA TATGAATTTT CTATTGATTG
      GCGGGAAAAC AGAAACCGCG ACCATTTGGT ATACTTAAAA GATAACTAAC

1251  TGACAAAATA AACTTATTCC GTGGTGTCTT TGCGTTTCTT TTATATGTTG
      ACTGTTTTAT TTGAATAAGG CACCACAGAA ACGCAAAGAA AATATACAAC

1301  CCACCTTTAT GTATGTATTT TCTACGTTTG CTAACATACT GCGTAATAAG
      GGTGGAAATA CATACATAAA AGATGCAAAC GATTGTATGA CGCATTATTC

HindIII
              ~~~~~~
1351  GAGTCTTGAT AAGCTTGACC TGTGAAGTGA AAAATGGCGC AGATTGTGCG
      CTCAGAACTA TTCGAACTGG ACACTTCACT TTTTACCGCG TCTAACACGC
                         OGIII3  100.0%
                    ====================

1401  ACATTTTTTT TGTCTGCCGT TTAATGAAAT TGTAAACGTT AATATTTTGT
      TGTAAAAAAA ACAGACGGCA AATTACTTTA ACATTTGCAA TTATAAAACA

1451  TAAAATTCGC GTTAAATTTT TGTTAAATCA GCTCATTTTT TAACCAATAG
      ATTTTAAGCG CAATTTAAAA ACAATTTAGT CGAGTAAAAA ATTGGTTATC

1501  GCCGAAATCG GCAAAATCCC TTATAAATCA AAAGAATAGA CCGAGATAGG
      CGGCTTTAGC CGTTTTAGGG AATATTTAGT TTTCTTATCT GGCTCTATCC

1551  GTTGAGTGTT GTTCCAGTTT GGAACAAGAG TCCACTATTA AGAACGTGG
      CAACTCACAA CAAGGTCAAA CCTTGTTCTC AGGTGATAAT TTCTTGCACC

1601  ACTCCAACGT CAAAGGGCGA AAAACCGTCT ATCAGGGCGA TGGCCCACTA
      TGAGGTTGCA GTTTCCCGCT TTTTGGCAGA TAGTCCCGCT ACCGGGTGAT

1651  CGAGAACCAT CACCCTAATC AAGTTTTTTG GGGTCGAGGT GCCGTAAAGC
      GCTCTTGGTA GTGGGATTAG TTCAAAAAAC CCCAGCTCCA CGGCATTTCG

1701  ACTAAATCGG AACCCTAAAG GGAGCCCCCG ATTTAGAGCT TGACGGGGAA
      TGATTTAGCC TTGGGATTTC CCTCGGGGGC TAAATCTCGA ACTGCCCCTT
```

Fig. 11 (cont.)

```
1751  AGCCGGCGAA CGTGGCGAGA AAGGAAGGGA AGAAAGCGAA AGGAGCGGGC
      TCGGCCGCTT GCACCGCTCT TTCCTTCCCT TCTTTCGCTT TCCTCGCCCG

1801  GCTAGGGCGC TGGCAAGTGT AGCGGTCACG CTGCGCGTAA CCACCACACC
      CGATCCCGCG ACCGTTCACA TCGCCAGTGC GACGCGCATT GGTGGTGTGG

1851  CGCCGCGCTT AATGCGCCGC TACAGGGCGC GTGCTAGCCA TGTGAGCAAA
      GCGGCGCGAA TTACGCGGCG ATGTCCCGCG CACGATCGGT ACACTCGTTT

1901  AGGCCAGCAA AAGGCCAGGA ACCGTAAAAA GGCCGCGTTG CTGGCGTTTT
      TCCGGTCGTT TTCCGGTCCT TGGCATTTTT CCGGCGCAAC GACCGCAAAA

1951  TCCATAGGCT CCGCCCCCT GACGAGCATC ACAAAAATCG ACGCTCAAGT
      AGGTATCCGA GGCGGGGGGA CTGCTCGTAG TGTTTTTAGC TGCGAGTTCA

2001  CAGAGGTGGC GAAACCCGAC AGGACTATAA AGATACCAGG CGTTTCCCCC
      GTCTCCACCG CTTTGGGCTG TCCTGATATT TCTATGGTCC GCAAAGGGGG

2051  TGGAAGCTCC CTCGTGCGCT CTCCTGTTCC GACCCTGCCG CTTACCGGAT
      ACCTTCGAGG GAGCACGCGA GAGGACAAGG CTGGGACGGC GAATGGCCTA

2101  ACCTGTCCGC CTTTCTCCCT TCGGGAAGCG TGGCGCTTTC TCATAGCTCA
      TGGACAGGCG GAAAGAGGGA AGCCCTTCGC ACCGCGAAAG AGTATCGAGT

2151  CGCTGTAGGT ATCTCAGTTC GGTGTAGGTC GTTCGCTCCA AGCTGGGCTG
      GCGACATCCA TAGAGTCAAG CCACATCCAG CAAGCGAGGT TCGACCCGAC

ApaLI
          ~~~~~~
2201  TGTGCACGAA CCCCCCGTTC AGTCCGACCG CTGCGCCTTA TCCGGTAACT
      ACACGTGCTT GGGGGGCAAG TCAGGCTGGC GACGCGGAAT AGGCCATTGA

2251  ATCGTCTTGA GTCCAACCCG GTAAGACACG ACTTATCGCC ACTGGCAGCA
      TAGCAGAACT CAGGTTGGGC CATTCTGTGC TGAATAGCGG TGACCGTCGT

2301  GCCACTGGTA ACAGGATTAG CAGAGCGAGG TATGTAGGCG GTGCTACAGA
      CGGTGACCAT TGTCCTAATC GTCTCGCTCC ATACATCCGC CACGATGTCT

2351  GTTCTTGAAG TGGTGGCCTA ACTACGGCTA CACTAGAAGA ACAGTATTTG
      CAAGAACTTC ACCACCGGAT TGATGCCGAT GTGATCTTCT TGTCATAAAC

2401  GTATCTGCGC TCTGCTGTAG CCAGTTACCT TCGGAAAAAG AGTTGGTAGC
      CATAGACGCG AGACGACATC GGTCAATGGA AGCCTTTTTC TCAACCATCG

2451  TCTTGATCCG GCAAACAAAC CACCGCTGGT AGCGGTGGTT TTTTTGTTTG
      AGAACTAGGC CGTTTGTTTG GTGGCGACCA TCGCCACCAA AAAAACAAAC

2501  CAAGCAGCAG ATTACGCGCA GAAAAAAAGG ATCTCAAGAA GATCCTTTGA
      GTTCGTCGTC TAATGCGCGT CTTTTTTTCC TAGAGTTCTT CTAGGAAACT

2551  TCTTTTCTAC GGGGTCTGAC GCTCAGTGGA ACGAAAACTC ACGTTAAGGG
```

Fig. 11 (cont.)

```
           AGAAAAGATG  CCCCAGACTG  CGAGTCACCT  TGCTTTTGAG  TGCAATTCCC

2601    ATTTTGGTCA  GATCTAGCAC  CAGGCGTTTA  AGGGCACCAA  TAACTGCCTT
           TAAAACCAGT  CTAGATCGTG  GTCCGCAAAT  TCCCGTGGTT  ATTGACGGAA

2651    AAAAAAATTA  CGCCCCGCCC  TGCCACTCAT  CGCAGTACTG  TTGTAATTCA
           TTTTTTTAAT  GCGGGGCGGG  ACGGTGAGTA  GCGTCATGAC  AACATTAAGT

2701    TTAAGCATTC  TGCCGACATG  GAAGCCATCA  CAAACGGCAT  GATGAACCTG
           AATTCGTAAG  ACGGCTGTAC  CTTCGGTAGT  GTTTGCCGTA  CTACTTGGAC

2751    AATCGCCAGC  GGCATCAGCA  CCTTGTCGCC  TTGCGTATAA  TATTTGCCCA
           TTAGCGGTCG  CCGTAGTCGT  GGAACAGCGG  AACGCATATT  ATAAACGGGT

2801    TAGTGAAAAC  GGGGGCGAAG  AAGTTGTCCA  TATTGGCTAC  GTTTAAATCA
           ATCACTTTTG  CCCCCGCTTC  TTCAACAGGT  ATAACCGATG  CAAATTTAGT

2851    AAACTGGTGA  AACTCACCCA  GGGATTGGCT  GAGACGAAAA  ACATATTCTC
           TTTGACCACT  TTGAGTGGGT  CCCTAACCGA  CTCTGCTTTT  TGTATAAGAG

2901    AATAAACCCT  TTAGGGAAAT  AGGCCAGGTT  TTCACCGTAA  CACGCCACAT
           TTATTTGGGA  AATCCCTTTA  TCCGGTCCAA  AAGTGGCATT  GTGCGGTGTA

2951    CTTGCGAATA  TATGTGTAGA  AACTGCCGGA  AATCGTCGTG  GTATTCACTC
           GAACGCTTAT  ATACACATCT  TTGACGGCCT  TTAGCAGCAC  CATAAGTGAG

3001    CAGAGCGATG  AAAACGTTTC  AGTTTGCTCA  TGGAAAACGG  TGTAACAAGG
           GTCTCGCTAC  TTTTGCAAAG  TCAAACGAGT  ACCTTTTGCC  ACATTGTTCC

3051    GTGAACACTA  TCCCATATCA  CCAGCTCACC  GTCTTTCATT  GCCATACGGA
           CACTTGTGAT  AGGGTATAGT  GGTCGAGTGG  CAGAAAGTAA  CGGTATGCCT

3101    ACTCCGGGTG  AGCATTCATC  AGGCGGGCAA  GAATGTGAAT  AAAGGCCGGA
           TGAGGCCCAC  TCGTAAGTAG  TCCGCCCGTT  CTTACACTTA  TTTCCGGCCT

3151    TAAAACTTGT  GCTTATTTTT  CTTTACGGTC  TTTAAAAAGG  CCGTAATATC
           ATTTTGAACA  CGAATAAAAA  GAAATGCCAG  AAATTTTTCC  GGCATTATAG

3201    CAGCTGAACG  GTCTGGTTAT  AGGTACATTG  AGCAACTGAC  TGAAATGCCT
           GTCGACTTGC  CAGACCAATA  TCCATGTAAC  TCGTTGACTG  ACTTTACGGA

3251    CAAAATGTTC  TTTACGATGC  CATTGGGATA  TATCAACGGT  GGTATATCCA
           GTTTTACAAG  AAATGCTACG  GTAACCCTAT  ATAGTTGCCA  CCATATAGGT

3301    GTGATTTTTT  TCTCCATTTT  AGCTTCCTTA  GCTCCTGAAA  ATCTCGATAA
           CACTAAAAAA  AGAGGTAAAA  TCGAAGGAAT  CGAGGACTTT  TAGAGCTATT

3351    CTCAAAAAAT  ACGCCCGGTA  GTGATCTTAT  TTCATTATGG  TGAAAGTTGG
           GAGTTTTTTA  TGCGGGCCAT  CACTAGAATA  AAGTAATACC  ACTTTCAACC

3401    AACCTCACCC  GACGTCTAAT  GTGAGTTAGC  TCACTCATTA  GGCACCCCAG
           TTGGAGTGGG  CTGCAGATTA  CACTCAATCG  AGTGAGTAAT  CCGTGGGGTC
```

Fig. 11 (cont.)

```
3451   GCTTTACACT TTATGCTTCC GGCTCGTATG TTGTGTGGAA TTGTGAGCGG
       CGAAATGTGA AATACGAAGG CCGAGCATAC AACACACCTT AACACTCGCC

M13 Reverse  primer 100.0%              XbaI
              ==================                      ~~
3501   ATAACAATTT CACACAGGAA ACAGCTATGA CCATGATTAC GAATTTCT
       TATTGTTAAA GTGTGTCCTT TGTCGATACT GGTACTAATG CTTAAAGA
```

Fig. 11 (cont.)

```
         XbaI   SphI
       ~~~~~~~~~~~~~
  1    TCTAGAGCAT GCGTAGGAGA AAATAAAATG AAACAAAGCA CTATTGCACT
       AGATCTCGTA CGCATCCTCT TTTATTTTAC TTTGTTTCGT GATAACGTGA

51    GGCACTCTTA CCGTTGCTCT TCACCCCTGT TACCAAAGCC GACTACAAAG
       CCGTGAGAAT GGCAACGAGA AGTGGGGACA ATGGTTTCGG CTGATGTTTC

MfeI
            ~~~~~~~
101    ATGAAGTGCA ATTGGTGGAA AGCGGCGGCG GCCTGGTGCA ACCGGGCGGC
       TACTTCACGT TAACCACCTT TCGCCGCCGC CGGACCACGT TGGCCCGCCG

BspEI
                            ~~~~~~
151    AGCCTGCGTC TGAGCTGCGC GGCCTCCGGA TTTACCTTTA GCAGCTATGC
       TCGGACGCAG ACTCGACGCG CCGGAGGCCT AAATGGAAAT CGTCGATACG

XhoI
                                      ~~~~~~
                                        AvaI
                                      ~~~~~~
201    GATGAGCTGG GTGCGCCAAG CCCCTGGGAA GGGTCTCGAG TGGGTGAGCG
       CTACTCGACC CACGCGGTTC GGGGACCCTT CCCAGAGCTC ACCCACTCGC

251    CGATTAGCGG TAGCGGCGGC AGCACCTATT ATGCGGATAG CGTGAAAGGC
       GCTAATCGCC ATCGCCGCCG TCGTGGATAA TACGCCTATC GCACTTTCCG

BstBI
                   ~~~~~~
                     SfuI
                   ~~~~~~
                     NspV
                   ~~~~~~
301    CGTTTTACCA TTTCACGTGA TAATTCGAAA AACACCCTGT ATCTGCAAAT
       GCAAAATGGT AAAGTGCACT ATTAAGCTTT TTGTGGGACA TAGACGTTTA

EagI              BssHII
                  ~~~~~~            ~~~~~~
351    GAACAGCCTG CGTGCGGAAG ATACGGCCGT GTATTATTGC GCGCGTGTTA
       CTTGTCGGAC GCACGCCTTC TATGCCGGCA CATAATAACG CGCGCACAAT

StyI
                                                ~~~~~~
401    AGAAGCATTT TTCTCGTAAG AATTGGTTTG ATTATTGGGG CCAAGGCACC
       TCTTCGTAAA AAGAGCATTC TTAACCAAAC TAATAACCCC GGTTCCGTGG
```

Fig. 12 (cont.)

```
                    BlpI
                   ~~~~~~
                    CelII
                   ~~~~~~~
451  CTGGTGACGG  TTAGCTCAGC  GGGTGGCGGT  TCTGGCGGCG  GTGGGAGCGG
     GACCACTGCC  AATCGAGTCG  CCCACCGCCA  AGACCGCCGC  CACCCTCGCC

EcoRV
                                         ~~~~~~~
501  TGGCGGTGGT  TCTGGCGGTG  GTGGTTCCGA  TATCGTGATG  ACCCAGAGCC
     ACCGCCACCA  AGACCGCCAC  CACCAAGGCT  ATAGCACTAC  TGGGTCTCGG

PstI
                                                      ~~~~~~
551  CACTGAGCCT  GCCAGTGACT  CCGGGCGAGC  CTGCGAGCAT  TAGCTGCAGA
     GTGACTCGGA  CGGTCACTGA  GGCCCGCTCG  GACGCTCGTA  ATCGACGTCT

KpnI
                                                      ~~~~
                                                      Acc65I
                                                      ~~~~
601  AGCAGCCAAA  GCCTGCTGCA  TAGCAACGGC  TATAACTATC  TGGATTGGTA
     TCGTCGGTTT  CGGACGACGT  ATCGTTGCCG  ATATTGATAG  ACCTAACCAT

KpnI
     ~~
     Acc65I        SexAI
     ~~         ~~~~~~~~
651  CCTTCAAAAA  CCAGGTCAAA  GCCCGCAGCT  ATTAATTTAT  CTGGGCAGCA
     GGAAGTTTTT  GGTCCAGTTT  CGGGCGTCGA  TAATTAAATA  GACCCGTCGT

BamHI
                                                      ~~~~~~~
701  ACCGTGCCAG  TGGGGTCCCG  GATCGTTTTA  GCGGCTCTGG  ATCCGGCACC
     TGGCACGGTC  ACCCCAGGGC  CTAGCAAAAT  CGCCGAGACC  TAGGCCGTGG

BpuAI
                                         ~~~~~~
                                          BbsI
                                         ~~~~~~
751  GATTTTACCC  TGAAAATTAG  CCGTGTGGAA  GCTGAAGACG  TGGGCGTGTA
     CTAAAATGGG  ACTTTTAATC  GGCACACCTT  CGACTTCTGC  ACCCGCACAT

MscI
                                                      ~~~~~~~
801  TTATTGCCAG  CAGCATTATA  CCACCCCGCC  GACCTTTGGC  CAGGGTACGA
     AATAACGGTC  GTCGTAATAT  GGTGGGGCGG  CTGGAAACCG  GTCCCATGCT
```

Fig. 12 (cont.)

```
                      BsiWI   EcoRI
                     ~~~~~~~~~~~~~~
 851  AAGTTGAAAT TAAACGTACG GAATTCGACT ATAAAGATGA CGATGACAAA
      TTCAACTTTA ATTTGCATGC CTTAAGCTGA TATTTCTACT GCTACTGTTT

BssHII                                    HindIII
      ~~~~~~                                    ~~~~~~~
 901  GGCGCGCCGT GGAGCCACCC GCAGTTTGAA AAATGATAAG CTTGACCTGT
      CCGCGCGGCA CCTCGGTGGG CGTCAAACTT TTTACTATTC GAACTGGACA
                                                 OGIII3     100.0%
                                                 =======

951  GAAGTGAAAA ATGGCGCAGA TTGTGCGACA TTTTTTTTGT CTGCCGTTTA
      CTTCACTTTT TACCGCGTCT AACACGCTGT AAAAAAAACA GACGGCAAAT
      OGIII3    100.0%
      ============

1001  ATTAAAGGGG GGGGGGGGCC GGCCTGGGGG GGGGTGTACA TGAAATTGTA
      TAATTTCCCC CCCCCCCCGG CCGGACCCCC CCCCACATGT ACTTTAACAT

1051  AACGTTAATA TTTTGTTAAA ATTCGCGTTA AATTTTTGTT AAATCAGCTC
      TTGCAATTAT AAAACAATTT TAAGCGCAAT TTAAAAACAA TTTAGTCGAG

1101  ATTTTTTAAC CAATAGGCCG AAATCGGCAA AATCCCTTAT AAATCAAAAG
      TAAAAAATTG GTTATCCGGC TTTAGCCGTT TTAGGGAATA TTTAGTTTTC

1151  AATAGACCGA GATAGGGTTG AGTGTTGTTC CAGTTTGGAA CAAGAGTCCA
      TTATCTGGCT CTATCCCAAC TCACAACAAG GTCAAACCTT GTTCTCAGGT

1201  CTATTAAAGA ACGTGGACTC CAACGTCAAA GGGCGAAAAA CCGTCTATCA
      GATAATTTCT TGCACCTGAG GTTGCAGTTT CCCGCTTTTT GGCAGATAGT

1251  GGGCGATGGC CCACTACGAG AACCATCACC CTAATCAAGT TTTTTGGGGT
      CCCGCTACCG GGTGATGCTC TTGGTAGTGG GATTAGTTCA AAAAACCCCA

1301  CGAGGTGCCG TAAAGCACTA AATCGGAACC CTAAAGGGAG CCCCCGATTT
      GCTCCACGGC ATTTCGTGAT TTAGCCTTGG GATTTCCCTC GGGGGCTAAA

1351  AGAGCTTGAC GGGGAAAGCC GGCGAACGTG GCGAGAAAGG AAGGGAAGAA
      TCTCGAACTG CCCCTTTCGG CCGCTTGCAC CGCTCTTTCC TTCCCTTCTT

1401  AGCGAAAGGA GCGGGCGCTA GGGCGCTGGC AAGTGTAGCG GTCACGCTGC
      TCGCTTTCCT CGCCCGCGAT CCCGCGACCG TTCACATCGC CAGTGCGACG

1451  GCGTAACCAC CACACCCGCC GCGCTTAATG CGCCGCTACA GGGCGCGTGC
      CGCATTGGTG GTGTGGGCGG CGCGAATTAC GCGGCGATGT CCCGCGCACG
```

Fig. 12 (cont.)

```
1501  TAGACTAGTG TTTAAACCGG ACCGGGGGGG GGCTTAAGTG GGCTGCAAAA
      ATCTGATCAC AAATTTGGCC TGGCCCCCCC CCGAATTCAC CCGACGTTTT

1551  CAAAACGGCC TCCTGTCAGG AAGCCGCTTT TATCGGGTAG CCTCACTGCC
      GTTTTGCCGG AGGACAGTCC TTCGGCGAAA ATAGCCCATC GGAGTGACGG

1601  CGCTTTCCAG TCGGGAAACC TGTCGTGCCA GCTGCATCAG TGAATCGGCC
      GCGAAAGGTC AGCCCTTTGG ACAGCACGGT CGACGTAGTC ACTTAGCCGG

1651  AACGCGCGGG GAGAGGCGGT TTGCGTATTG GGAGCCAGGG TGGTTTTTCT
      TTGCGCGCCC CTCTCCGCCA AACGCATAAC CCTCGGTCCC ACCAAAAAGA

1701  TTTCACCAGT GAGACGGGCA ACAGCTGATT GCCCTTCACC GCCTGGCCCT
      AAAGTGGTCA CTCTGCCCGT TGTCGACTAA CGGGAAGTGG CGGACCGGGA

1751  GAGAGAGTTG CAGCAAGCGG TCCACGCTGG TTTGCCCCAG CAGGCGAAAA
      CTCTCTCAAC GTCGTTCGCC AGGTGCGACC AAACGGGGTC GTCCGCTTTT

1801  TCCTGTTTGA TGGTGGTCAG CGGCGGGATA TAACATGAGC TGTCCTCGGT
      AGGACAAACT ACCACCAGTC GCCGCCCTAT ATTGTACTCG ACAGGAGCCA

1851  ATCGTCGTAT CCCACTACCG AGATGTCCGC ACCAACGCGC AGCCCGGACT
      TAGCAGCATA GGGTGATGGC TCTACAGGCG TGGTTGCGCG TCGGGCCTGA

1901  CGGTAATGGC ACGCATTGCG CCCAGCGCCA TCTGATCGTT GGCAACCAGC
      GCCATTACCG TGCGTAACGC GGGTCGCGGT AGACTAGCAA CCGTTGGTCG

1951  ATCGCAGTGG GAACGATGCC CTCATTCAGC ATTTGCATGG TTTGTTGAAA
      TAGCGTCACC CTTGCTACGG GAGTAAGTCG TAAACGTACC AAACAACTTT

2001  ACCGGACATG GCACTCCAGT CGCCTTCCCG TTCCGCTATC GGCTGAATTT
      TGGCCTGTAC CGTGAGGTCA GCGGAAGGGC AAGGCGATAG CCGACTTAAA

2051  GATTGCGAGT GAGATATTTA TGCCAGCCAG CCAGACGCAG ACGCGCCGAG
      CTAACGCTCA CTCTATAAAT ACGGTCGGTC GGTCTGCGTC TGCGCGGCTC

2101  ACAGAACTTA ATGGGCCAGC TAACAGCGCG ATTTGCTGGT GGCCCAATGC
      TGTCTTGAAT TACCCGGTCG ATTGTCGCGC TAAACGACCA CCGGGTTACG

2151  GACCAGATGC TCCACGCCCA GTCGCGTACC GTCCTCATGG GAGAAAATAA
      CTGGTCTACG AGGTGCGGGT CAGCGCATGG CAGGAGTACC CTCTTTTATT

2201  TACTGTTGAT GGGTGTCTGG TCAGAGACAT CAAGAAATAA CGCCGGAACA
      ATGACAACTA CCCACAGACC AGTCTCTGTA GTTCTTTATT GCGGCCTTGT

2251  TTAGTGCAGG CAGCTTCCAC AGCAATAGCA TCCTGGTCAT CCAGCGGATA
      AATCACGTCC GTCGAAGGTG TCGTTATCGT AGGACCAGTA GGTCGCCTAT
                                                    ApaLI
                                                    -------
```

Fig. 12 (cont.)

```
2301  GTTAATAATC AGCCCACTGA CACGTTGCGC GAGAAGATTG TGCACCGCCG
      CAATTATTAG TCGGGTGACT GTGCAACGCG CTCTTCTAAC ACGTGGCGGC

2351  CTTTACAGGC TTCGACGCCG CTTCGTTCTA CCATCGACAC GACCACGCTG
      GAAATGTCCG AAGCTGCGGC GAAGCAAGAT GGTAGCTGTG CTGGTGCGAC

2401  GCACCCAGTT GATCGGCGCG AGATTTAATC GCCGCGACAA TTTGCGACGG
      CGTGGGTCAA CTAGCCGCGC TCTAAATTAG CGGCGCTGTT AAACGCTGCC

2451  CGCGTGCAGG GCCAGACTGG AGGTGGCAAC GCCAATCAGC AACGACTGTT
      GCGCACGTCC CGGTCTGACC TCCACCGTTG CGGTTAGTCG TTGCTGACAA

2501  TGCCCGCCAG TTGTTGTGCC ACGCGGTTAG GAATGTAATT CAGCTCCGCC
      ACGGGCGGTC AACAACACGG TGCGCCAATC CTTACATTAA GTCGAGGCGG

2551  ATCGCCGCTT CCACTTTTTC CCGCGTTTTC GCAGAAACGT GGCTGGCCTG
      TAGCGGCGAA GGTGAAAAAG GGCGCAAAAG CGTCTTTGCA CCGACCGGAC

2601  GTTCACCACG CGGGAAACGG TCTGATAAGA GACACCGGCA TACTCTGCGA
      CAAGTGGTGC GCCCTTTGCC AGACTATTCT CTGTGGCCGT ATGAGACGCT

2651  CATCGTATAA CGTTACTGGT TTCACATTCA CCACCCTGAA TTGACTCTCT
      GTAGCATATT GCAATGACCA AAGTGTAAGT GGTGGGACTT AACTGAGAGA

2701  TCCGGGCGCT ATCATGCCAT ACCGCGAAAG GTTTTGCGCC ATTCGATGCT
      AGGCCCGCGA TAGTACGGTA TGGCGCTTTC CAAAACGCGG TAAGCTACGA

2751  AGCCATGTGA GCAAAAGGCC AGCAAAAGGC CAGGAACCGT AAAAAGGCCG
      TCGGTACACT CGTTTTCCGG TCGTTTTCCG GTCCTTGGCA TTTTTCCGGC

2801  CGTTGCTGGC GTTTTTCCAT AGGCTCCGCC CCCCTGACGA GCATCACAAA
      GCAACGACCG CAAAAAGGTA TCCGAGGCGG GGGGACTGCT CGTAGTGTTT

2851  AATCGACGCT CAAGTCAGAG GTGGCGAAAC CCGACAGGAC TATAAAGATA
      TTAGCTGCGA GTTCAGTCTC CACCGCTTTG GGCTGTCCTG ATATTTCTAT

2901  CCAGGCGTTT CCCCCTGGAA GCTCCCTCGT GCGCTCTCCT GTTCCGACCC
      GGTCCGCAAA GGGGGACCTT CGAGGGAGCA CGCGAGAGGA CAAGGCTGGG

2951  TGCCGCTTAC CGGATACCTG TCCGCCTTTC TCCCTTCGGG AAGCGTGGCG
      ACGGCGAATG GCCTATGGAC AGGCGGAAAG AGGGAAGCCC TTCGCACCGC

3001  CTTTCTCATA GCTCACGCTG TAGGTATCTC AGTTCGGTGT AGGTCGTTCG
      GAAAGAGTAT CGAGTGCGAC ATCCATAGAG TCAAGCCACA TCCAGCAAGC

ApaLI
                                 ‾‾‾‾‾‾‾
3051  CTCCAAGCTG GGCTGTGTGC ACGAACCCCC CGTTCAGCCC GACCGCTGCG
      GAGGTTCGAC CCGACACACG TGCTTGGGGG GCAAGTCGGG CTGGCGACGC

3101  CCTTATCCGG TAACTATCGT CTTGAGTCCA ACCCGGTAAG ACACGACTTA
      GGAATAGGCC ATTGATAGCA GAACTCAGGT TGGGCCATTC TGTGCTGAAT
```

Fig. 12 (cont.)

```
3151  TCGCCACTGG CAGCAGCCAC TGGTAACAGG ATTAGCAGAG CGAGGTATGT
      AGCGGTGACC GTCGTCGGTG ACCATTGTCC TAATCGTCTC GCTCCATACA

3201  AGGCGGTGCT ACAGAGTTCT TGAAGTGGTG GCCTAACTAC GGCTACACTA
      TCCGCCACGA TGTCTCAAGA ACTTCACCAC CGGATTGATG CCGATGTGAT

3251  GAAGAACAGT ATTTGGTATC TGCGCTCTGC TGTAGCCAGT TACCTTCGGA
      CTTCTTGTCA TAAACCATAG ACGCGAGACG ACATCGGTCA ATGGAAGCCT

3301  AAAAGAGTTG GTAGCTCTTG ATCCGGCAAA CAAACCACCG CTGGTAGCGG
      TTTTCTCAAC CATCGAGAAC TAGGCCGTTT GTTTGGTGGC GACCATCGCC

3351  TGGTTTTTTT GTTTGCAAGC AGCAGATTAC GCGCAGAAAA AAAGGATCTC
      ACCAAAAAAA CAAACGTTCG TCGTCTAATG CGCGTCTTTT TTTCCTAGAG

3401  AAGAAGATCC TTTGATCTTT TCTACGGGGT CTGACGCTCA GTGGAACGAA
      TTCTTCTAGG AAACTAGAAA AGATGCCCCA GACTGCGAGT CACCTTGCTT

3451  AACTCACGTT AAGGGATTTT GGTCAGATCT AGCACCAGGC GTTTAAGGGC
      TTGAGTGCAA TTCCCTAAAA CCAGTCTAGA TCGTGGTCCG CAAATTCCCG

3501  ACCAATAACT GCCTTAAAAA AATTACGCCC CGCCCTGCCA CTCATCGCAG
      TGGTTATTGA CGGAATTTTT TTAATGCGGG GCGGGACGGT GAGTAGCGTC

3551  TACTGTTGTA ATTCATTAAG CATTCTGCCG ACATGGAAGC CATCACAAAC
      ATGACAACAT TAAGTAATTC GTAAGACGGC TGTACCTTCG GTAGTGTTTG

3601  GGCATGATGA ACCTGAATCG CCAGCGGCAT CAGCACCTTG TCGCCTTGCG
      CCGTACTACT TGGACTTAGC GGTCGCCGTA GTCGTGGAAC AGCGGAACGC

3651  TATAATATTT GCCCATAGTG AAAACGGGGG CGAAGAAGTT GTCCATATTG
      ATATTATAAA CGGGTATCAC TTTTGCCCCC GCTTCTTCAA CAGGTATAAC

3701  GCTACGTTTA AATCAAAACT GGTGAAACTC ACCCAGGGAT TGGCTGAGAC
      CGATGCAAAT TTAGTTTTGA CCACTTTGAG TGGGTCCCTA ACCGACTCTG

3751  GAAAAACATA TTCTCAATAA ACCCTTTAGG GAAATAGGCC AGGTTTTCAC
      CTTTTTGTAT AAGAGTTATT TGGGAAATCC CTTTATCCGG TCCAAAAGTG

3801  CGTAACACGC CACATCTTGC GAATATATGT GTAGAAACTG CCGGAAATCG
      GCATTGTGCG GTGTAGAACG CTTATATACA CATCTTTGAC GGCCTTTAGC

3851  TCGTGGTATT CACTCCAGAG CGATGAAAAC GTTTCAGTTT GCTCATGGAA
      AGCACCATAA GTGAGGTCTC GCTACTTTTG CAAAGTCAAA CGAGTACCTT

3901  AACGGTGTAA CAAGGGTGAA CACTATCCCA TATCACCAGC TCACCGTCTT
      TTGCCACATT GTTCCCACTT GTGATAGGGT ATAGTGGTCG AGTGGCAGAA

3951  TCATTGCCAT ACGGAACTCC GGGTGAGCAT TCATCAGGCG GGCAAGAATG
      AGTAACGGTA TGCCTTGAGG CCCACTCGTA AGTAGTCCGC CCGTTCTTAC
```

Fig. 12 (cont.)

```
4001  TGAATAAAGG CCGGATAAAA CTTGTGCTTA TTTTTCTTTA CGGTCTTTAA
      ACTTATTTCC GGCCTATTTT GAACACGAAT AAAAAGAAAT GCCAGAAATT

4051  AAAGGCCGTA ATATCCAGCT GAACGGTCTG GTTATAGGTA CATTGAGCAA
      TTTCCGGCAT TATAGGTCGA CTTGCCAGAC CAATATCCAT GTAACTCGTT

4101  CTGACTGAAA TGCCTCAAAA TGTTCTTTAC GATGCCATTG GGATATATCA
      GACTGACTTT ACGGAGTTTT ACAAGAAATG CTACGGTAAC CCTATATAGT

4151  ACGGTGGTAT ATCCAGTGAT TTTTTTCTCC ATTTTAGCTT CCTTAGCTCC
      TGCCACCATA TAGGTCACTA AAAAAAGAGG TAAAATCGAA GGAATCGAGG

4201  TGAAAATCTC GATAACTCAA AAAATACGCC CGGTAGTGAT CTTATTTCAT
      ACTTTTAGAG CTATTGAGTT TTTTATGCGG GCCATCACTA GAATAAAGTA

4251  TATGGTGAAA GTTGGAACCT CACCCGACGT CTAATGTGAG TTAGCTCACT
      ATACCACTTT CAACCTTGGA GTGGGCTGCA GATTACACTC AATCGAGTGA

4301  CATTAGGCAC CCCAGGCTTT ACACTTTATG CTTCCGGCTC GTATGTTGTG
      GTAATCCGTG GGGTCCGAAA TGTGAAATAC GAAGGCCGAG CATACAACAC

M13  Reverse   primer   100.0%
                            ==================
4351  TGGAATTGTG AGCGGATAAC AATTTCACAC AGGAAACAGC TATGACCATG
      ACCTTAACAC TCGCCTATTG TTAAAGTGTG TCCTTTGTCG ATACTGGTAC

4401  ATTACGAATT
      TAATGCTTAA
```

Fig. 12 (cont.)

```
            EcoRV                              SexAI
            ~~~                                ~~~~~~~~
  1  ATCGTGCTGA CCCAGCCGCC TTCAGTGAGT GGCGCACCAG GTCAGCGTGT
     TAGCACGACT GGGTCGGCGG AAGTCACTCA CCGCGTGGTC CAGTCGCACA

51  GACCATCTCG TGTAGCGGCA GCAGCAGCAA CATTGGCAGC AACTATGTGA
     CTGGTAGAGC ACATCGCCGT CGTCGTCGTT GTAACCGTCG TTGATACACT

XmaI
                         ~~~~~~~
          KpnI           SmaI
          ~~~~~~         ~~~~~~~
          Acc65I         AvaI
          ~~~~~          ~~~~~~
101  GCTGGTACCA GCAGTTGCCC GGGACGGCGC CGAAACTGCT GATTTATGAT
     CGACCATGGT CGTCAACGGG CCCTGCCGCG GCTTTGACGA CTAAATACTA

Bsu36I                         BamHI
                    ~~~~~~~                        ~~~~~~
151  AACAACCAGC GTCCCTCAGG CGTGCCGGAT CGTTTTAGCG GATCCAAAAG
     TTGTTGGTCG CAGGGAGTCC GCACGGCCTA GCAAAATCGC CTAGGTTTTC

BpuAI
                                                ~~~~~~
                                                BbsI
                                                ~~~~~~
201  CGGCACCAGC GCGAGCCTTG CGATTACGGG CCTGCAAAGC GAAGACGAAG
     GCCGTGGTCG CGCTCGGAAC GCTAATGCCC GGACGTTTCG CTTCTGCTTC

Bsu36I
                                 ~~~~~~~~
251  CGGATTATTA TTGCCAGAGC TATGACATGC CTCAGGCTGT GTTTGGCGGC
     GCCTAATAAT AACGGTCTCG ATACTGTACG GAGTCCGACA CAAACCGCCG

MscI                DraIII
                          ~~~~~~              ~~~~~~~~~~~
301  GGCACGAAGT TTAACCGTTC TTGGCCAGCC GAAAGCCGCA CCGAGTGTGA
     CCGTGCTTCA AATTGGCAAG AACCGGTCGG CTTTCGGCGT GGCTCACACT

351  CGCTGTTTCC GCCGAGCAGC GAAGAATTGC AGGCGAACAA AGCGACCCTG
     GCGACAAAGG CGGCTCGTCG CTTCTTAACG TCCGCTTGTT TCGCTGGGAC

401  GTGTGCCTGA TTAGCGACTT TTATCCGGGA GCCGTGACAG TGGCCTGGAA
     CACACGGACT AATCGCTGAA AATAGGCCCT CGGCACTGTC ACCGGACCTT

451  GGCAGATAGC AGCCCCGTCA AGGCGGGAGT GGAGACCACC ACACCCTCCA
     CCGTCTATCG TCGGGGCAGT TCCGCCCTCA CCTCTGGTGG TGTGGGAGGT

501  AACAAAGCAA CAACAAGTAC GCGGCCAGCA GCTATCTGAG CCTGACGCCT
     TTGTTTCGTT GTTGTTCATG CGCCGGTCGT CGATAGACTC GGACTGCGGA
```

Fig. 13 (cont.)

```
                                                                    StuI           SphI
                                                                  ~~~~~~~        ~~~~~~~
551  GAGCAGTGGA AGTCCCACAG AAGCTACAGC TGCCAGGTCA CGCATGAGGG
     CTCGTCACCT TCAGGGTGTC TTCGATGTCG ACGGTCCAGT GCGTACTCCC

601  GAGCACCGTG GAAAAAACCG TTGCGCCGAC TGAGGCCTGA TAAGCATGCG
     CTCGTGGCAC CTTTTTTGGC AACGCGGCTG ACTCCGGACT ATTCGTACGC

651  TAGGAGAAAA TAAAATGAAA CAAAGCACTA TTGCACTGGC ACTCTTACCG
     ATCCTCTTTT ATTTTACTTT GTTTCGTGAT AACGTGACCG TGAGAATGGC

MfeI
                                          ~~~~~~~
701  TTGCTCTTCA CCCCTGTTAC CAAAGCCCAG GTGCAATTGA AAGAAAGCGG
     AACGAGAAGT GGGGACAATG GTTTCGGGTC CACGTTAACT TTCTTTCGCC

BspEI
                                                          ~
751  CCCGGCCCTG GTGAAACCGA CCCAAACCCT GACCCTGACC TGTACCTTTT
     GGGCCGGGAC CACTTTGGCT GGGTTTGGGA CTGGGACTGG ACATGGAAAA

BspEI
     ~~~~~
801  CCGGATTTAG CCTGTCCACG TCTGGCGTTG GCGTGGGCTG GATTCGCCAG
     GGCCTAAATC GGACAGGTGC AGACCGCAAC CGCACCCGAC CTAAGCGGTC

XhoI
                ~~~~~~~
                 AvaI
                ~~~~~~~
851  CCGCCTGGGA AAGCCCTCGA GTGGCTGGCT CTGATTGATT GGGATGATGA
     GGCGGACCCT TTCGGGAGCT CACCGACCGA GACTAACTAA CCCTACTACT

901  TAAGTATTAT AGCACCAGCC TGAAAACGCG TCTGACCATT AGCAAAGATA
     ATTCATAATA TCGTGGTCGG ACTTTTGCGC AGACTGGTAA TCGTTTCTAT

BstBI
     ~~~~~~
     SfuI
     ~~~~~~
     NspV
     ~~~~~~
951  CTTCGAAAAA TCAGGTGGTG CTGACTATGA CCAACATGGA CCCGGTGGAT
     GAAGCTTTTT AGTCCACCAC GACTGATACT GGTTGTACCT GGGCCACCTA

BssHII
          ~~~~~~~
1001 ACGGCCACCT ATTATTGCGC GCGTTCTCCT CGTTATCGTG GTGCTTTTGA
     TGCCGGTGGA TAATAACGCG CGCAAGAGGA GCAATAGCAC CACGAAAACT
                                                     BlpI
```

Fig. 13 (cont.)

```
                StyI                      CelII
               ~~~~~~                    ~~~~~~
1051  TTATTGGGGC CAAGGCACCC TGGTGACGGT TAGCTCAGCG TCGACCAAAG
      AATAACCCCG GTTCCGTGGG ACCACTGCCA ATCGAGTCGC AGCTGGTTTC

1101  GTCCAAGCGT GTTTCCGCTG GCTCCGAGCA GCAAAAGCAC CAGCGGCGGC
      CAGGTTCGCA CAAAGGCGAC CGAGGCTCGT CGTTTTCGTG GTCGCCGCCG

1151  ACGGCTGCCC TGGGCTGCCT GGTTAAAGAT TATTTCCCGG AACCAGTCAC
      TGCCGACGGG ACCCGACGGA CCAATTTCTA ATAAAGGGCC TTGGTCAGTG

1201  CGTGAGCTGG AACAGCGGGG CGCTGACCAG CGGCGTGCAT ACCTTTCCGG
      GCACTCGACC TTGTCGCCCC GCGACTGGTC GCCGCACGTA TGGAAAGGCC

1251  CGGTGCTGCA AAGCAGCGGC CTGTATAGCC TGAGCAGCGT TGTGACCGTG
      GCCACGACGT TTCGTCGCCG GACATATCGG ACTCGTCGCA ACACTGGCAC

1301  CCGAGCAGCA GCTTAGGCAC TCAGACCTAT ATTTGCAACG TGAACCATAA
      GGCTCGTCGT CGAATCCGTG AGTCTGGATA TAAACGTTGC ACTTGGTATT

EcoRI
                                                    ~~~~~~
1351  ACCGAGCAAC ACCAAAGTGG ATAAAAAAGT GGAACCGAAA AGCGAATTCG
      TGGCTCGTTG TGGTTTCACC TATTTTTTCA CCTTGGCTTT TCGCTTAAGC

BssHII
                          ~~~~~~
1401  ACTATAAAGA TGACGATGAC AAAGGCGCGC CGTGGAGCCA CCCGCAGTTT
      TGATATTTCT ACTGCTACTG TTTCCGCGCG GCACCTCGGT GGGCGTCAAA

HindIII
              ~~~~~~
1451  GAAAAATGAT AAGCTTGACC TGTGAAGTGA AAAATGGCGC AGATTGTGCG
      CTTTTTACTA TTCGAACTGG ACACTTCACT TTTTACCGCG TCTAACACGC
                           OGIII3  100.0%
             ==================

1501  ACATTTTTTT TGTCTGCCGT TTAATTAAAG GGGGGGGGGG GCCGGCCTGG
      TGTAAAAAAA ACAGACGGCA AATTAATTTC CCCCCCCCCC CGGCCGGACC

1551  GGGGGGGTGT ACATGAAATT GTAAACGTTA ATATTTGTT AAAATTCGCG
      CCCCCCCACA TGTACTTTAA CATTTGCAAT TATAAAACAA TTTTAAGCGC

1601  TTAAATTTTT GTTAAATCAG CTCATTTTTT AACCAATAGG CCGAAATCGG
      AATTTAAAAA CAATTTAGTC GAGTAAAAAA TTGGTTATCC GGCTTTAGCC

1651  CAAAATCCCT TATAAATCAA AAGAATAGAC CGAGATAGGG TTGAGTGTTG
      GTTTTAGGGA ATATTTAGTT TTCTTATCTG GCTCTATCCC AACTCACAAC

1701  TTCCAGTTTG GAACAAGAGT CCACTATTAA AGAACGTGGA CTCCAACGTC
      AAGGTCAAAC CTTGTTCTCA GGTGATAATT TCTTGCACCT GAGGTTGCAG
```

Fig. 13 (cont.)

| | | | | | |
|---|---|---|---|---|---|
| 1751 | AAAGGGCGAA | AAACCGTCTA | TCAGGGCGAT | GGCCCACTAC | GAGAACCATC |
| | TTTCCCGCTT | TTTGGCAGAT | AGTCCCGCTA | CCGGGTGATG | CTCTTGGTAG |
| 1801 | ACCCTAATCA | AGTTTTTTGG | GGTCGAGGTG | CCGTAAAGCA | CTAAATCGGA |
| | TGGGATTAGT | TCAAAAAACC | CCAGCTCCAC | GGCATTTCGT | GATTTAGCCT |
| 1851 | ACCCTAAAGG | GAGCCCCCGA | TTTAGAGCTT | GACGGGGAAA | GCCGGCGAAC |
| | TGGGATTTCC | CTCGGGGGCT | AAATCTCGAA | CTGCCCCTTT | CGGCCGCTTG |
| 1901 | GTGGCGAGAA | AGGAAGGGAA | GAAAGCGAAA | GGAGCGGGCG | CTAGGGCGCT |
| | CACCGCTCTT | TCCTTCCCTT | CTTTCGCTTT | CCTCGCCCGC | GATCCCGCGA |
| 1951 | GGCAAGTGTA | GCGGTCACGC | TGCGCGTAAC | CACCACACCC | GCCGCGCTTA |
| | CCGTTCACAT | CGCCAGTGCG | ACGCGCATTG | GTGGTGTGGG | CGGCGCGAAT |
| 2001 | ATGCGCCGCT | ACAGGGCGCG | TGCTAGACTA | GTGTTTAAAC | CGGACCGGGG |
| | TACGCGGCGA | TGTCCCGCGC | ACGATCTGAT | CACAAATTTG | GCCTGGCCCC |
| 2051 | GGGGGCTTAA | GTGGGCTGCA | AAACAAAACG | GCCTCCTGTC | AGGAAGCCGC |
| | CCCCCGAATT | CACCCGACGT | TTTGTTTTGC | CGGAGGACAG | TCCTTCGGCG |
| 2101 | TTTTATCGGG | TAGCCTCACT | GCCCGCTTTC | CAGTCGGGAA | ACCTGTCGTG |
| | AAAATAGCCC | ATCGGAGTGA | CGGGCGAAAG | GTCAGCCCTT | TGGACAGCAC |
| 2151 | CCAGCTGCAT | CAGTGAATCG | GCCAACGCGC | GGGGAGAGGC | GGTTTGCGTA |
| | GGTCGACGTA | GTCACTTAGC | CGGTTGCGCG | CCCCTCTCCG | CCAAACGCAT |
| 2201 | TTGGGAGCCA | GGGTGGTTTT | TCTTTTCACC | AGTGAGACGG | GCAACAGCTG |
| | AACCCTCGGT | CCCACCAAAA | AGAAAAGTGG | TCACTCTGCC | CGTTGTCGAC |
| 2251 | ATTGCCCTTC | ACCGCCTGGC | CCTGAGAGAG | TTGCAGCAAG | CGGTCCACGC |
| | TAACGGGAAG | TGGCGGACCG | GGACTCTCTC | AACGTCGTTC | GCCAGGTGCG |
| 2301 | TGGTTTGCCC | CAGCAGGCGA | AAATCCTGTT | TGATGGTGGT | CAGCGGCGGG |
| | ACCAAACGGG | GTCGTCCGCT | TTTAGGACAA | ACTACCACCA | GTCGCCGCCC |
| 2351 | ATATAACATG | AGCTGTCCTC | GGTATCGTCG | TATCCCACTA | CCGAGATGTC |
| | TATATTGTAC | TCGACAGGAG | CCATAGCAGC | ATAGGGTGAT | GGCTCTACAG |
| 2401 | CGCACCAACG | CGCAGCCCGG | ACTCGGTAAT | GGCACGCATT | GCGCCCAGCG |
| | GCGTGGTTGC | GCGTCGGGCC | TGAGCCATTA | CCGTGCGTAA | CGCGGGTCGC |
| 2451 | CCATCTGATC | GTTGGCAACC | AGCATCGCAG | TGGGAACGAT | GCCCTCATTC |
| | GGTAGACTAG | CAACCGTTGG | TCGTAGCGTC | ACCCTTGCTA | CGGGAGTAAG |
| 2501 | AGCATTTGCA | TGGTTTGTTG | AAAACCGGAC | ATGGCACTCC | AGTCGCCTTC |
| | TCGTAAACGT | ACCAAACAAC | TTTTGGCCTG | TACCGTGAGG | TCAGCGGAAG |
| 2551 | CCGTTCCGCT | ATCGGCTGAA | TTTGATTGCG | AGTGAGATAT | TTATGCCAGC |
| | GGCAAGGCGA | TAGCCGACTT | AAACTAACGC | TCACTCTATA | AATACGGTCG |

Fig. 13 (cont.)

```
2601  CAGCCAGACG CAGACGCGCC GAGACAGAAC TTAATGGGCC AGCTAACAGC
      GTCGGTCTGC GTCTGCGCGG CTCTGTCTTG AATTACCCGG TCGATTGTCG

2651  GCGATTTGCT GGTGGCCCAA TGCGACCAGA TGCTCCACGC CCAGTCGCGT
      CGCTAAACGA CCACCGGGTT ACGCTGGTCT ACGAGGTGCG GGTCAGCGCA

2701  ACCGTCCTCA TGGGAGAAAA TAATACTGTT GATGGGTGTC TGGTCAGAGA
      TGGCAGGAGT ACCCTCTTTT ATTATGACAA CTACCCACAG ACCAGTCTCT

2751  CATCAAGAAA TAACGCCGGA ACATTAGTGC AGGCAGCTTC CACAGCAATA
      GTAGTTCTTT ATTGCGGCCT TGTAATCACG TCCGTCGAAG GTGTCGTTAT

2801  GCATCCTGGT CATCCAGCGG ATAGTTAATA ATCAGCCCAC TGACACGTTG
      CGTAGGACCA GTAGGTCGCC TATCAATTAT TAGTCGGGTG ACTGTGCAAC

ApaLI
                 ------
2851  CGCGAGAAGA TTGTGCACCG CCGCTTTACA GGCTTCGACG CCGCTTCGTT
      GCGCTCTTCT AACACGTGGC GGCGAAATGT CCGAAGCTGC GGCGAAGCAA

2901  CTACCATCGA CACGACCACG CTGGCACCCA GTTGATCGGC GCGAGATTTA
      GATGGTAGCT GTGCTGGTGC GACCGTGGGT CAACTAGCCG CGCTCTAAAT

2951  ATCGCCGCGA CAATTTGCGA CGGCGCGTGC AGGGCCAGAC TGGAGGTGGC
      TAGCGGCGCT GTTAAACGCT GCCGCGCACG TCCCGGTCTG ACCTCCACCG

3001  AACGCCAATC AGCAACGACT GTTTGCCCGC CAGTTGTTGT GCCACGCGGT
      TTGCGGTTAG TCGTTGCTGA CAAACGGGCG GTCAACAACA CGGTGCGCCA

3051  TAGGAATGTA ATTCAGCTCC GCCATCGCCG CTTCCACTTT TTCCCGCGTT
      ATCCTTACAT TAAGTCGAGG CGGTAGCGGC GAAGGTGAAA AAGGGCGCAA

3101  TTCGCAGAAA CGTGGCTGGC CTGGTTCACC ACGCGGGAAA CGGTCTGATA
      AAGCGTCTTT GCACCGACCG GACCAAGTGG TGCGCCCTTT GCCAGACTAT

3151  AGAGACACCG GCATACTCTG CGACATCGTA TAACGTTACT GGTTTCACAT
      TCTCTGTGGC CGTATGAGAC GCTGTAGCAT ATTGCAATGA CCAAAGTGTA

3201  TCACCACCCT GAATTGACTC TCTTCCGGGC GCTATCATGC CATACCGCGA
      AGTGGTGGGA CTTAACTGAG AGAAGGCCCG CGATAGTACG GTATGGCGCT

3251  AAGGTTTTGC GCCATTCGAT GCTAGCCATG TGAGCAAAAG GCCAGCAAAA
      TTCCAAAACG CGGTAAGCTA CGATCGGTAC ACTCGTTTTC CGGTCGTTTT

3301  GGCCAGGAAC CGTAAAAAGG CCGCGTTGCT GGCGTTTTTC CATAGGCTCC
      CCGGTCCTTG GCATTTTTCC GGCGCAACGA CCGCAAAAAG GTATCCGAGG

3351  GCCCCCCTGA CGAGCATCAC AAAAATCGAC GCTCAAGTCA GAGGTGGCGA
      CGGGGGGACT GCTCGTAGTG TTTTTAGCTG CGAGTTCAGT CTCCACCGCT

3401  AACCCGACAG GACTATAAAG ATACCAGGCG TTTCCCCCTG GAAGCTCCCT
```

Fig. 13 (cont.)

```
            TTGGGCTGTC CTGATATTTC TATGGTCCGC AAAGGGGGAC CTTCGAGGGA
3451    CGTGCGCTCT CCTGTTCCGA CCCTGCCGCT TACCGGATAC CTGTCCGCCT
        GCACGCGAGA GGACAAGGCT GGGACGGCGA ATGGCCTATG GACAGGCGGA
3501    TTCTCCCTTC GGGAAGCGTG GCGCTTTCTC ATAGCTCACG CTGTAGGTAT
        AAGAGGGAAG CCCTTCGCAC CGCGAAAGAG TATCGAGTGC GACATCCATA
                                                     ApaLI
                                                     ~~~~~~~
3551    CTCAGTTCGG TGTAGGTCGT TCGCTCCAAG CTGGGCTGTG TGCACGAACC
        GAGTCAAGCC ACATCCAGCA AGCGAGGTTC GACCCGACAC ACGTGCTTGG
3601    CCCCGTTCAG CCCGACCGCT GCGCCTTATC CGGTAACTAT CGTCTTGAGT
        GGGGCAAGTC GGGCTGGCGA CGCGGAATAG GCCATTGATA GCAGAACTCA
3651    CCAACCCGGT AAGACACGAC TTATCGCCAC TGGCAGCAGC CACTGGTAAC
        GGTTGGGCCA TTCTGTGCTG AATAGCGGTG ACCGTCGTCG GTGACCATTG
3701    AGGATTAGCA GAGCGAGGTA TGTAGGCGGT GCTACAGAGT TCTTGAAGTG
        TCCTAATCGT CTCGCTCCAT ACATCCGCCA CGATGTCTCA AGAACTTCAC
3751    GTGGCCTAAC TACGGCTACA CTAGAAGAAC AGTATTTGGT ATCTGCGCTC
        CACCGGATTG ATGCCGATGT GATCTTCTTG TCATAAACCA TAGACGCGAG
3801    TGCTGTAGCC AGTTACCTTC GGAAAAAGAG TTGGTAGCTC TTGATCCGGC
        ACGACATCGG TCAATGGAAG CCTTTTCTC AACCATCGAG AACTAGGCCG
3851    AAACAAACCA CCGCTGGTAG CGGTGGTTTT TTGTTTGCA AGCAGCAGAT
        TTTGTTTGGT GGCGACCATC GCCACCAAAA AACAAACGT TCGTCGTCTA
3901    TACGCGCAGA AAAAAAGGAT CTCAAGAAGA TCCTTTGATC TTTTCTACGG
        ATGCGCGTCT TTTTTTCCTA GAGTTCTTCT AGGAAACTAG AAAAGATGCC
3951    GGTCTGACGC TCAGTGGAAC GAAAACTCAC GTTAAGGGAT TTTGGTCAGA
        CCAGACTGCG AGTCACCTTG CTTTTGAGTG CAATTCCCTA AAACCAGTCT
4001    TCTAGCACCA GGCGTTTAAG GCACCAATA ACTGCCTTAA AAAAATTACG
        AGATCGTGGT CCGCAAATTC CCGTGGTTAT TGACGGAATT TTTTTAATGC
4051    CCCCGCCCTG CCACTCATCG CAGTACTGTT GTAATTCATT AAGCATTCTG
        GGGGCGGGAC GGTGAGTAGC GTCATGACAA CATTAAGTAA TTCGTAAGAC
4101    CCGACATGGA AGCCATCACA AACGGCATGA TGAACCTGAA TCGCCAGCGG
        GGCTGTACCT TCGGTAGTGT TTGCCGTACT ACTTGGACTT AGCGGTCGCC
4151    CATCAGCACC TTGTCGCCTT GCGTATAATA TTTGCCCATA GTGAAAACGG
        GTAGTCGTGG AACAGCGGAA CGCATATTAT AAACGGGTAT CACTTTTGCC
4201    GGGCGAAGAA GTTGTCCATA TTGGCTACGT TTAAATCAAA ACTGGTGAAA
        CCCGCTTCTT CAACAGGTAT AACCGATGCA AATTTAGTTT TGACCACTTT
```

Fig. 13 (cont.)

```
4251  CTCACCCAGG GATTGGCTGA GACGAAAAAC ATATTCTCAA TAAACCCTTT
      GAGTGGGTCC CTAACCGACT CTGCTTTTTG TATAAGAGTT ATTTGGGAAA

4301  AGGGAAATAG GCCAGGTTTT CACCGTAACA CGCCACATCT TGCGAATATA
      TCCCTTTATC CGGTCCAAAA GTGGCATTGT GCGGTGTAGA ACGCTTATAT

4351  TGTGTAGAAA CTGCCGGAAA TCGTCGTGGT ATTCACTCCA GAGCGATGAA
      ACACATCTTT GACGGCCTTT AGCAGCACCA TAAGTGAGGT CTCGCTACTT

4401  AACGTTTCAG TTTGCTCATG GAAAACGGTG TAACAAGGGT GAACACTATC
      TTGCAAAGTC AAACGAGTAC CTTTTGCCAC ATTGTTCCCA CTTGTGATAG

4451  CCATATCACC AGCTCACCGT CTTTCATTGC CATACGGAAC TCCGGGTGAG
      GGTATAGTGG TCGAGTGGCA GAAAGTAACG GTATGCCTTG AGGCCCACTC

4501  CATTCATCAG GCGGGCAAGA ATGTGAATAA AGGCCGGATA AAACTTGTGC
      GTAAGTAGTC CGCCCGTTCT TACACTTATT TCCGGCCTAT TTTGAACACG

4551  TTATTTTTCT TTACGGTCTT TAAAAGGCC GTAATATCCA GCTGAACGGT
      AATAAAAAGA AATGCCAGAA ATTTTTCCGG CATTATAGGT CGACTTGCCA

4601  CTGGTTATAG GTACATTGAG CAACTGACTG AAATGCCTCA AAATGTTCTT
      GACCAATATC CATGTAACTC GTTGACTGAC TTTACGGAGT TTTACAAGAA

4651  TACGATGCCA TTGGGATATA TCAACGGTGG TATATCCAGT GATTTTTTC
      ATGCTACGGT AACCCTATAT AGTTGCCACC ATATAGGTCA CTAAAAAAAG

4701  TCCATTTTAG CTTCCTTAGC TCCTGAAAAT CTCGATAACT CAAAAAATAC
      AGGTAAAATC GAAGGAATCG AGGACTTTTA GAGCTATTGA GTTTTTATG

4751  GCCCGGTAGT GATCTTATTT CATTATGGTG AAAGTTGGAA CCTCACCCGA
      CGGGCCATCA CTAGAATAAA GTAATACCAC TTTCAACCTT GGAGTGGGCT

4801  CGTCTAATGT GAGTTAGCTC ACTCATTAGG CACCCCAGGC TTTACACTTT
      GCAGATTACA CTCAATCGAG TGAGTAATCC GTGGGGTCCG AAATGTGAAA

4851  ATGCTTCCGG CTCGTATGTT GTGTGGAATT GTGAGCGGAT AACAATTTCA
      TACGAAGGCC GAGCATACAA CACACCTTAA CACTCGCCTA TTGTTAAAGT

M13 Reverse  primer 100.0%            XbaI
      =========================             ~~~~~~
4901  CACAGGAAAC AGCTATGACC ATGATTACGA ATTTCTAGAT AACGAGGGCA
      GTGTCCTTTG TCGATACTGG TACTAATGCT TAAAGATCTA TTGCTCCCGT 4951  AAAAATGAAA AAGACAGCTA TCGCGATTGC AGTGGCACTG GCTGGTTTCG
      TTTTTACTTT TTCTGTCGAT AGCGCTAACG TCACCGTGAC CGACCAAAGC EcoRV
                              ~~~
5001  CTACCGTAGC GCAGGCCGAT
      GATGGCATCG CGTCCGGCTA
```

Fig. 13 (cont.)

```
  1 TCAGATAACG AGGGCAAAAA ATGAAAAAGA CAGCTATCGC GATTGCAGTG
    AGTCTATTGC TCCCGTTTTT TACTTTTTCT GTCGATAGCG CTAACGTCAC

EcoRV
                                             ~~~~~~
 51 GCACTGGCTG GTTTCGCTAC CGTAGCGCAG GCCGATATCG TGCTGACCCA
    CGTGACCGAC CAAAGCGATG GCATCGCGTC CGGCTATAGC ACGACTGGGT

SexAI
                      ~~~~~~~
101 GCCGCCTTCA GTGAGTGGCG CACCAGGTCA GCGTGTGACC ATCTCGTGTA
    CGGCGGAAGT CACTCACCGC GTGGTCCAGT CGCACACTGG TAGAGCACAT

KpnI
                                                     ~~~~~~
                                                    Acc65I
                                                    ~~~~~~~
151 GCGGCAGCAG CAGCAACATT GGCAGCAACT ATGTGAGCTG GTACCAGCAG
    CGCCGTCGTC GTCGTTGTAA CCGTCGTTGA TACACTCGAC CATGGTCGTC

XmaI
    ~~~~~~
    SmaI
    ~~~~~~
    AvaI                                              Bsu36I
    ~~~~~~                                            ~
201 TTGCCCGGGA CGGCGCCGAA ACTGCTGATT TATGATAACA ACCAGCGTCC
    AACGGGCCCT GCCGCGGCTT TGACGACTAA ATACTATTGT TGGTCGCAGG

Bsu36I                BamHI
    ~~~~~~                ~~~~~~~
251 CTCAGGCGTG CCGGATCGTT TTAGCGGATC CAAAAGCGGC ACCAGCGCGA
    GAGTCCGCAC GGCCTAGCAA AATCGCCTAG GTTTTCGCCG TGGTCGCGCT

BpuAI
                                  ~~~~~~~
                                  BbsI
                                  ~~~~~~~
301 GCCTTGCGAT TACGGGCCTG CAAAGCGAAG ACGAAGCGGA TTATTATTGC
    CGGAACGCTA ATGCCCGGAC GTTTCGCTTC TGCTTCGCCT AATAATAACG

Bsu36I
                   ~~~~~~~~
351 CAGAGCTATG ACATGCCTCA GGCTGTGTTT GGCGGCGGCA CGAAGTTTAA
    GTCTCGATAC TGTACGGAGT CCGACACAAA CCGCCGCCGT GCTTCAAATT

MscI           DraIII
            ~~~~~~~        ~~~~~~~~~~~
401 CCGTTCTTGG CCAGCCGAAA GCCGCACCGA GTGTGACGCT GTTTCGCCG
    GGCAAGAACC GGTCGGCTTT CGGCGTGGCT CACACTGCGA CAAAGGCGGC

451 AGCAGCGAAG AATTGCAGGC GAACAAAGCG ACCCTGGTGT GCCTGATTAG
    TCGTCGCTTC TTAACGTCCG CTTGTTTCGC TGGGACCACA CGGACTAATC

501 CGACTTTTAT CCGGGAGCCG TGACAGTGGC CTGGAAGGCA GATAGCAGCC
```

Fig. 14 (cont.)

```
            GCTGAAAATA GGCCCTCGGC ACTGTCACCG GACCTTCCGT CTATCGTCGG

551    CCGTCAAGGC GGGAGTGGAG ACCACCACAC CCTCCAAACA AAGCAACAAC
            GGCAGTTCCG CCCTCACCTC TGGTGGTGTG GGAGGTTTGT TTCGTTGTTG

601    AAGTACGCGG CCAGCAGCTA TCTGAGCCTG ACGCCTGAGC AGTGGAAGTC
            TTCATGCGCC GGTCGTCGAT AGACTCGGAC TGCGGACTCG TCACCTTCAG

651    CCACAGAAGC TACAGCTGCC AGGTCACGCA TGAGGGGAGC ACCGTGGAAA
            GGTGTCTTCG ATGTCGACGG TCCAGTGCGT ACTCCCCTCG TGGCACCTTT

StuI         SphI
                          ~~~~~~       ~~~~~~
     701    AAACCGTTGC GCCGACTGAG GCCTGATAAG CATGCGTAGG AGAAAATAAA
            TTTGGCAACG CGGCTGACTC CGGACTATTC GTACGCATCC TCTTTTATTT

751    ATGAAACAAA GCACTATTGC ACTGGCACTC TTACCGTTGC TCTTCACCCC
            TACTTTGTTT CGTGATAACG TGACCGTGAG AATGGCAACG AGAAGTGGGG

MfeI
                                  ~~~~~~
     801    TGTTACCAAA GCCCAGGTGC AATTGAAAGA AAGCGGCCCG GCCCTGGTGA
            ACAATGGTTT CGGGTCCACG TTAACTTTCT TTCGCCGGGC CGGGACCACT

BspEI
                                            ~~~~~~
     851    AACCGACCCA AACCCTGACC CTGACCTGTA CCTTTTCCGG ATTTAGCCTG
            TTGGCTGGGT TTGGGACTGG GACTGGACAT GGAAAAGGCC TAAATCGGAC

901    TCCACGTCTG GCGTTGGCGT GGGCTGGATT CGCCAGCCGC CTGGGAAAGC
            AGGTGCAGAC CGCAACCGCA CCCGACCTAA GCGGTCGGCG GACCCTTTCG

XhoI
            ~~~~~~
            AvaI
            ~~~~~~
     951    CCTCGAGTGG CTGGCTCTGA TTGATTGGGA TGATGATAAG TATTATAGCA
            GGAGCTCACC GACCGAGACT AACTAACCCT ACTACTATTC ATAATATCGT

BstBI
                                            ~~~~~~
                                            SfuI
                                            ~~~~~~
                                            NspV
                                            ~~~~~~
    1001    CCAGCCTGAA AACGCGTCTG ACCATTAGCA AAGATACTTC GAAAAATCAG
            GGTCGGACTT TTGCGCAGAC TGGTAATCGT TTCTATGAAG CTTTTTAGTC

1051    GTGGTGCTGA CTATGACCAA CATGGACCCG GTGGATACGG CCACCTATTA
            CACCACGACT GATACTGGTT GTACCTGGGC CACCTATGCC GGTGGATAAT

BssHII                                                StyI
            ~~~~~~                                                ~~~~~
    1101    TTGCGCGCGT TCTCCTCGTT ATCGTGGTGC TTTTGATTAT TGGGGCCAAG
            AACGCGCGCA AGAGGAGCAA TAGCACCACG AAAACTAATA ACCCCGGTTC

BlpI                          Fig. 14 (cont.)
```

```
                StyI              CelII
1151   GCACCCTGGT GACGGTTAGC TCAGCGTCGA CCAAAGGTCC AAGCGTGTTT
       CGTGGGACCA CTGCCAATCG AGTCGCAGCT GGTTTCCAGG TTCGCACAAA

1201   CCGCTGGCTC CGAGCAGCAA AAGCACCAGC GGCGGCACGG CTGCCCTGGG
       GGCGACCGAG GCTCGTCGTT TTCGTGGTCG CCGCCGTGCC GACGGGACCC

1251   CTGCCTGGTT AAAGATTATT CCCGGAACC  AGTCACCGTG AGCTGGAACA
       GACGGACCAA TTTCTAATAA AGGGCCTTGG TCAGTGGCAC TCGACCTTGT

1301   GCGGGGCGCT GACCAGCGGC GTGCATACCT TTCCGGCGGT GCTGCAAAGC
       CGCCCCGCGA CTGGTCGCCG CACGTATGGA AAGGCCGCCA CGACGTTTCG

1351   AGCGGCCTGT ATAGCCTGAG CAGCGTTGTG ACCGTGCCGA GCAGCAGCTT
       TCGCCGGACA TATCGGACTC GTCGCAACAC TGGCACGGCT CGTCGTCGAA

1401   AGGCACTCAG ACCTATATTT GCAACGTGAA CCATAAACCG AGCAACACCA
       TCCGTGAGTC TGGATATAAA CGTTGCACTT GGTATTTGGC TCGTTGTGGT

EcoRI
1451   AAGTGGATAA AAAAGTGGAA CCGAAAAGCG AATTCGGGGG AGGGAGCGGG
       TTCACCTATT TTTTCACCTT GGCTTTTCGC TTAAGCCCCC TCCCTCGCCC

1501   AGCGGTGATT TTGATTATGA AAAGATGGCA AACGCTAATA AGGGGGCTAT
       TCGCCACTAA AACTAATACT TTTCTACCGT TTGCGATTAT TCCCCCGATA
                                        gIIIseq9  100.0%
                                        ====================

1551   GACCGAAAAT GCCGATGAAA ACGCGCTACA GTCTGACGCT AAAGGCAAAC
       CTGGCTTTTA CGGCTACTTT TGCGCGATGT CAGACTGCGA TTTCCGTTTG

ClaI
1601   TTGATTCTGT CGCTACTGAT TACGGTGCTG CTATCGATGG TTTCATTGGT
       AACTAAGACA GCGATGACTA ATGCCACGAC GATAGCTACC AAAGTAACCA

1651   GACGTTTCCG GCCTTGCTAA TGGTAATGGT GCTACTGGTG ATTTTGCTGG
       CTGCAAAGGC CGGAACGATT ACCATTACCA CGATGACCAC TAAAACGACC

1701   CTCTAATTCC CAAATGGCTC AAGTCGGTGA CGGTGATAAT TCACCTTTAA
       GAGATTAAGG GTTTACCGAG TTCAGCCACT GCCACTATTA AGTGGAAATT

1751   TGAATAATTT CCGTCAATAT TTACCTTCCC TCCCTCAATC GGTTGAATGT
       ACTTATTAAA GGCAGTTATA AATGGAAGGG AGGGAGTTAG CCAACTTACA

1801   CGCCCTTTTG TCTTTGGCGC TGGTAAACCA TATGAATTTT CTATTGATTG
       GCGGGAAAAC AGAAACCGCG ACCATTTGGT ATACTTAAAA GATAACTAAC

1851   TGACAAAATA AACTTATTCC GTGGTGTCTT TGCGTTTCTT TTATATGTTG
       ACTGTTTTAT TTGAATAAGG CACCACAGAA ACGCAAAGAA AATATACAAC

1901   CCACCTTTAT GTATGTATTT TCTACGTTTG CTAACATACT GCGTAATAAG
       GGTGGAAATA CATACATAAA AGATGCAAAC GATTGTATGA CGCATTATTC
```

Fig. 14 (cont.)

```
                HindIII
                ~~~~~~
1951  GAGTCTTGAT AAGCTTGACC TGTGAAGTGA AAAATGGCGC AGATTGTGCG
      CTCAGAACTA TTCGAACTGG ACACTTCACT TTTTACCGCG TCTAACACGC
                         OGIII3   100.0%
                ===================

2001  ACATTTTTTT TGTCTGCCGT TTAATGAAAT TGTAAACGTT AATATTTTGT
      TGTAAAAAAA ACAGACGGCA AATTACTTTA ACATTTGCAA TTATAAAACA

2051  TAAAATTCGC GTTAAATTTT TGTTAAATCA GCTCATTTTT TAACCAATAG
      ATTTTAAGCG CAATTTAAAA ACAATTTAGT CGAGTAAAAA ATTGGTTATC

2101  GCCGAAATCG GCAAAATCCC TTATAAATCA AAAGAATAGA CCGAGATAGG
      CGGCTTTAGC CGTTTTAGGG AATATTTAGT TTTCTTATCT GGCTCTATCC

2151  GTTGAGTGTT GTTCCAGTTT GGAACAAGAG TCCACTATTA AGAACGTGG
      CAACTCACAA CAAGGTCAAA CCTTGTTCTC AGGTGATAAT TCTTGCACC

2201  ACTCCAACGT CAAAGGGCGA AAAACCGTCT ATCAGGGCGA TGGCCCACTA
      TGAGGTTGCA GTTTCCCGCT TTTTGGCAGA TAGTCCCGCT ACCGGGTGAT

2251  CGAGAACCAT CACCCTAATC AAGTTTTTTG GGGTCGAGGT GCCGTAAAGC
      GCTCTTGGTA GTGGGATTAG TTCAAAAAAC CCCAGCTCCA CGGCATTTCG

2301  ACTAAATCGG AACCCTAAAG GGAGCCCCCG ATTTAGAGCT TGACGGGGAA
      TGATTTAGCC TTGGGATTTC CCTCGGGGGC TAAATCTCGA ACTGCCCCTT

2351  AGCCGGCGAA CGTGGCGAGA AAGGAAGGGA AGAAAGCGAA AGGAGCGGGC
      TCGGCCGCTT GCACCGCTCT TTCCTTCCCT TCTTTCGCTT TCCTCGCCCG

2401  GCTAGGGCGC TGGCAAGTGT AGCGGTCACG CTGCGCGTAA CCACCACACC
      CGATCCCGCG ACCGTTCACA TCGCCAGTGC GACGCGCATT GGTGGTGTGG

2451  CGCCGCGCTT AATGCGCCGC TACAGGGCGC GTGCTAGCCA TGTGAGCAAA
      GCGGCGCGAA TTACGCGGCG ATGTCCCGCG CACGATCGGT ACACTCGTTT

2501  AGGCCAGCAA AAGGCCAGGA ACCGTAAAAA GGCCGCGTTG CTGGCGTTTT
      TCCGGTCGTT TTCCGGTCCT TGGCATTTTT CCGGCGCAAC GACCGCAAAA

2551  TCCATAGGCT CCGCCCCCCT GACGAGCATC ACAAAAATCG ACGCTCAAGT
      AGGTATCCGA GGCGGGGGGA CTGCTCGTAG TGTTTTTAGC TGCGAGTTCA

2601  CAGAGGTGGC GAAACCCGAC AGGACTATAA AGATACCAGG CGTTTCCCCC
      GTCTCCACCG CTTTGGGCTG TCCTGATATT TCTATGGTCC GCAAAGGGGG

2651  TGGAAGCTCC CTCGTGCGCT CTCCTGTTCC GACCCTGCCG CTTACCGGAT
      ACCTTCGAGG GAGCACGCGA GAGGACAAGG CTGGGACGGC GAATGGCCTA

2701  ACCTGTCCGC CTTTCTCCCT TCGGGAAGCG TGGCGCTTTC TCATAGCTCA
      TGGACAGGCG GAAAGAGGGA AGCCCTTCGC ACCGCGAAAG AGTATCGAGT

2751  CGCTGTAGGT ATCTCAGTTC GGTGTAGGTC GTTCGCTCCA AGCTGGGCTG
      GCGACATCCA TAGAGTCAAG CCACATCCAG CAAGCGAGGT TCGACCCGAC
      ApaLI
      ~~~~~~
```

Fig. 14 (cont.)

```
2801  TGTGCACGAA CCCCCCGTTC AGTCCGACCG CTGCGCCTTA TCCGGTAACT
      ACACGTGCTT GGGGGGCAAG TCAGGCTGGC GACGCGGAAT AGGCCATTGA

2851  ATCGTCTTGA GTCCAACCCG GTAAGACACG ACTTATCGCC ACTGGCAGCA
      TAGCAGAACT CAGGTTGGGC CATTCTGTGC TGAATAGCGG TGACCGTCGT

2901  GCCACTGGTA ACAGGATTAG CAGAGCGAGG TATGTAGGCG GTGCTACAGA
      CGGTGACCAT TGTCCTAATC GTCTCGCTCC ATACATCCGC CACGATGTCT

2951  GTTCTTGAAG TGGTGGCCTA ACTACGGCTA CACTAGAAGA ACAGTATTTG
      CAAGAACTTC ACCACCGGAT TGATGCCGAT GTGATCTTCT TGTCATAAAC

3001  GTATCTGCGC TCTGCTGTAG CCAGTTACCT TCGGAAAAAG AGTTGGTAGC
      CATAGACGCG AGACGACATC GGTCAATGGA AGCCTTTTTC TCAACCATCG

3051  TCTTGATCCG GCAAACAAAC CACCGCTGGT AGCGGTGGTT TTTTTGTTTG
      AGAACTAGGC CGTTTGTTTG GTGGCGACCA TCGCCACCAA AAAAACAAAC

3101  CAAGCAGCAG ATTACGCGCA GAAAAAAAGG ATCTCAAGAA GATCCTTTGA
      GTTCGTCGTC TAATGCGCGT CTTTTTTTCC TAGAGTTCTT CTAGGAAACT

3151  TCTTTTCTAC GGGGTCTGAC GCTCAGTGGA ACGAAAACTC ACGTTAAGGG
      AGAAAAGATG CCCCAGACTG CGAGTCACCT TGCTTTTGAG TGCAATTCCC

3201  ATTTTGGTCA GATCTAGCAC CAGGCGTTTA AGGGCACCAA TAACTGCCTT
      TAAAACCAGT CTAGATCGTG GTCCGCAAAT TCCCGTGGTT ATTGACGGAA

3251  AAAAAAATTA CGCCCCGCCC TGCCACTCAT CGCAGTACTG TTGTAATTCA
      TTTTTTTAAT GCGGGGCGGG ACGGTGAGTA GCGTCATGAC AACATTAAGT

3301  TTAAGCATTC TGCCGACATG GAAGCCATCA CAAACGGCAT GATGAACCTG
      AATTCGTAAG ACGGCTGTAC CTTCGGTAGT GTTTGCCGTA CTACTTGGAC

3351  AATCGCCAGC GGCATCAGCA CCTTGTCGCC TTGCGTATAA TATTTGCCCA
      TTAGCGGTCG CCGTAGTCGT GGAACAGCGG AACGCATATT ATAAACGGGT

3401  TAGTGAAAAC GGGGGCGAAG AAGTTGTCCA TATTGGCTAC GTTTAAATCA
      ATCACTTTTG CCCCCGCTTC TTCAACAGGT ATAACCGATG CAAATTTAGT

3451  AAACTGGTGA AACTCACCCA GGGATTGGCT GAGACGAAAA ACATATTCTC
      TTTGACCACT TTGAGTGGGT CCCTAACCGA CTCTGCTTTT TGTATAAGAG

3501  AATAAACCCT TTAGGGAAAT AGGCCAGGTT TTCACCGTAA CACGCCACAT
      TTATTTGGGA AATCCCTTTA TCCGGTCCAA AAGTGGCATT GTGCGGTGTA

3551  CTTGCGAATA TATGTGTAGA AACTGCCGGA AATCGTCGTG GTATTCACTC
      GAACGCTTAT ATACACATCT TTGACGGCCT TTAGCAGCAC CATAAGTGAG

+1
3601  CAGAGCGATG AAAACGTTTC AGTTTGCTCA TGGAAAACGG TGTAACAAGG
      GTCTCGCTAC TTTTGCAAAG TCAAACGAGT ACCTTTTGCC ACATTGTTCC

3651  GTGAACACTA TCCCATATCA CCAGCTCACC GTCTTTCATT GCCATACGGA
      CACTTGTGAT AGGGTATAGT GGTCGAGTGG CAGAAAGTAA CGGTATGCCT
```

Fig. 14 (cont.)

```
3701  ACTCCGGGTG  AGCATTCATC  AGGCGGGCAA  GAATGTGAAT  AAAGGCCGGA
      TGAGGCCCAC  TCGTAAGTAG  TCCGCCCGTT  CTTACACTTA  TTTCCGGCCT

3751  TAAAACTTGT  GCTTATTTTT  CTTTACGGTC  TTTAAAAAGG  CCGTAATATC
      ATTTTGAACA  CGAATAAAAA  GAAATGCCAG  AAATTTTTCC  GGCATTATAG

3801  CAGCTGAACG  GTCTGGTTAT  AGGTACATTG  AGCAACTGAC  TGAAATGCCT
      GTCGACTTGC  CAGACCAATA  TCCATGTAAC  TCGTTGACTG  ACTTTACGGA

3851  CAAAATGTTC  TTTACGATGC  CATTGGGATA  TATCAACGGT  GGTATATCCA
      GTTTTACAAG  AAATGCTACG  GTAACCCTAT  ATAGTTGCCA  CCATATAGGT

3901  GTGATTTTTT  TCTCCATTTT  AGCTTCCTTA  GCTCCTGAAA  ATCTCGATAA
      CACTAAAAAA  AGAGGTAAAA  TCGAAGGAAT  CGAGGACTTT  TAGAGCTATT

3951  CTCAAAAAAT  ACGCCCGGTA  GTGATCTTAT  TTCATTATGG  TGAAAGTTGG
      GAGTTTTTTA  TGCGGGCCAT  CACTAGAATA  AAGTAATACC  ACTTTCAACC

4001  AACCTCACCC  GACGTCTAAT  GTGAGTTAGC  TCACTCATTA  GGCACCCCAG
      TTGGAGTGGG  CTGCAGATTA  CACTCAATCG  AGTGAGTAAT  CCGTGGGGTC

4051  GCTTTACACT  TTATGCTTCC  GGCTCGTATG  TTGTGTGGAA  TTGTGAGCGG
      CGAAATGTGA  AATACGAAGG  CCGAGCATAC  AACACACCTT  AACACTCGCC
                         M13 Reverse  primer 100.0%
                         ==================
4101  ATAACAATTT  CACACAGGAA  ACAGCTATGA  CCATGATTAC  GAATT
      TATTGTTAAA  GTGTGTCCTT  TGTCGATACT  GGTACTAATG  CTTAA
```

Fig. 14 (cont.)

MS-GPC-1:
VH
QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
QYGHRGGFDHWGQGTLVTVSS (SEQ ID NO: 37)
VL
DIVLTQPPSVSGAPGQRVTISCSGSSSNIGSNYVSWYQQLPGTAPKLLIY
DNNQRPSGVPDRFSGSKSGTSASLAITGLQSEDEADYYCQSYDFNESVF
GGGTKLTVLG (SEQ ID NO: 38)

MS-GPC-6
VH
EVQLVESGGGLVQPGGSLRLSCAASGFTFSSYAMSWVRQAPGKGLEWV
SAISGSGGSTYYADSVKGRFTISRDNSKNTLYLQMNSLRAEDTAVYYCAR
GYGRYSPDLWGQGTLVTVSS (SEQ ID NO: 39)
VL
DIVLTQSPATLSLSPGERATLSCRASQSVSSSYLAWYQQKPGQAPRLLIY
GASSRATGVPARFSGSGSGTDFTLTISSLEPEDFAVYYCQQYSNLPFTFG
QGTKVEIKRT (SEQ ID NO: 40)

MS-GPC-8
VH
QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

DIVLTQPPSVSGAPGQRVTISCSGSSSNIGSNYVSWYQQLPGTAPKLLIY
DNNQRPSGVPDRFSGSKSGTSASLAITGLQSEDEADYYCQSYDMPQAV
FGGGTKLTVLG   (SEQ ID NO: 42)

MS-GPC-10

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
QLHYRGGFDLWGQGTLVTVSS   (SEQ ID NO: 43)

VL

DIVLTQPPSVSGAPGQRVTISCSGSSSNIGSNYVSWYQQLPGTAPKLLIY
DNNQRPSGVPDRFSGSKSGTSASLAITGLQSEDEADYYCQSYDLTMGVF
GGGTKLTVLG   (SEQ ID NO: 44)

MS-GPC-8-6

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS   (SEQ ID NO: 41)

VL

DIVLTQPPSVSGAPGQRVTISCSGSSSNIGSNYVSWYQQLPGTAPKLLIY
DNNQRPSGVPDRFSGSKSGTSASLAITGLQSEDEADYYCQSYDYDHYVF
GGGTKLTVLG   (SEQ ID NO: 46)

MS-GPC-8-10

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

VL

DIVLTQPPSVSGAPGQRVTISCSGSSSNIGSNYVSWYQQLPGTAPKLLIY
DNNQRPSGVPDRFSGSKSGTSASLAITGLQSEDEADYYCQSYDLIRHVF
GGGTKLTVLG (SEQ ID NO: 48)

MS-GPC-8-17

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

VL

DIVLTQPPSVSGAPGQRVTISCSGSSSNIGSNYVSWYQQLPGTAPKLLIY
DNNQRPSGVPDRFSGSKSGTSASLAITGLQSEDEADYYCQSYDFSVYVF
GGGTKLTVLG (SEQ ID NO: 50)

MS-GPC-8-27

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

DIVLTQPPSVSGAPGQRVTISCSGSSSNIGSNYVSWYQQLPGTAPKLLIY
DNNQRPSGVPDRFSGSKSGTSASLAITGLQSEDEADYYCQSYDMNVHV
FGGGTKLTVLG (SEQ ID NO: 52)

MS-GPC-8-6-13

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

VL

DIVLTQPPSVSGAPGQRVTISCSGSESNIGANYVTWYQQLPGTAPKLLIYD
NNQRPSGVPDRFSGSKSGTSASLAITGLQSEDEADYYCQSYDYDHYVFG
GGTKLTVLG (SEQ ID NO: 54)

MS-GPC-8-10-57

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

VL

DIVLTQPPSVSGAPGQRVTISCSGSESNIGNNYVQWYQQLPGTAPKLLIY
DNNQRPSGVPDRFSGSKSGTSASLAITGLQSEDEADYYCQSYDLIRHVF
GGGTKLTVLG (SEQ ID NO: 56)

MS-GPC-8-27-41

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

VL

DIVLTQPPSVSGAPGQRVTISCSGSESNIGNNYVQWYQQLPGTAPKLLIY
DNNQRPSGVPDRFSGSKSGTSASLAITGLQSEDEADYYCQSYDMNVHV
FGGGTKLTVLG (SEQ ID NO: 58)

MS-GPC-8-1

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

VL

DIVLTQPPSVSGAPGQRVTISCSGSSSNIGSNYVSWYQQLPGTAPKLLIY
DNNQRPSGVPDRFSGSKSGTSASLAITGLQSEDEADYYCQSYDFSHYVF
GGGTKLTVLG (SEQ ID NO: 28)

MS-GPC-8-9

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

VL

DIVLTQPPSVSGAPGQRVTISCSGSSSNIGSNYVSWYQQLPGTAPKLLIY
DNNQRPSGVPDRFSGSKSGTSASLAITGLQSEDEADYYCQSYDIQLHVF
GGGTKLTVLG (SEQ ID NO: 31)

Fig. 15 (cont.)

MS-GPC-8-18

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

VL

DIVLTQPPSVSGAPGQRVTISCSGSSSNIGSNYVSWYQQLPGTAPKLLIY
DNNQRPSGVPDRFSGSKSGTSASLAITGLQSEDEADYYCQSYDFSIYVF
GGGTKLTVLG (SEQ ID NO: 32)

MS-GPC-8-6-2

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

VL

DIVLTQPPSVSGAPGQRVTISCSGSESNIGSNYVHWYQQLPGTAPKLLIY
DNNQRPSGVPDRFSGSKSGTSASLAITGLQSEDEADYYCQSYDYDHYVF
GGGTKLTVLG (SEQ ID NO: 45)

MS-GPC-8-6-19

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

DIVLTQPPSVSGAPGQRVTISCSGSESNIGSNYVAWYQQLPGTAPKLLIY
DNNQRPSGVPDRFSGSKSGTSASLAITGLQSEDEADYYCQSYDYDHYVF
GGGTKLTVLG (SEQ ID NO: 47)

MS-GPC-8-6-27

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

VL

DIVLTQPPSVSGAPGQRVTISCSGSDSNIGANYVTWYQQLPGTAPKLLIY
DNNQRPSGVPDRFSGSKSGTSASLAITGLQSEDEADYYCQSYDYDHYVF
GGGTKLTVLG (SEQ ID NO: 49)

MS-GPC-8-6-45

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

VL

DIVLTQPPSVSGAPGQRVTISCSGSEPNIGSNYVFWYQQLPGTAPKLLIYD
NNQRPSGVPDRFSGSKSGTSASLAITGLQSEDEADYYCQSYDYDHYVFG
GGTKLTVLG (SEQ ID NO: 51)

MS-GPC-8-6-47

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

VL

DIVLTQPPSVSGAPGQRVTISCSGSESNIGSNYVSWYQQLPGTSPKLLIY
DNNQRPSGVPDRFSGSKSGTSASLAITGLQSEDEADYYCQSYDYDHYVF
GGGTKLTVLG (SEQ ID NO: 53)

MS-GPC-8-27-7

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

VL

DIVLTQPPSVSGAPGQRVTISCSGSESNIGNNYVGWYQQLPGTAPKLLIY
DNNQRPSGVPDRFSGSKSGTSASLAITGLQSEDEADYYCQSYDMNVHV
FGGGTKLTVLG (SEQ ID NO: 55)

MS-GPC-8-27-10

VH

QVQLKESGPALVKPTQTLTLTCTFSGFSLSTSGVGVGWIRQPPGKALEW
LALIDWDDDKYYSTSLKTRLTISKDTSKNQVVLTMTNMDPVDTATYYCAR
SPRYRGAFDYWGQGTLVTVSS (SEQ ID NO: 41)

DIVLTQPPSVSGAPGQRVTISCSGSESNIGANYVNWYQQLPGTAPKLLIY
DNNQRPSGVPDRFSGSKSGTSASLAITGLQSEDEADYYCQSYDMNVHV
FGGGTKLTVLG (SEQ ID NO: 57)

Fig. 15 (cont.)

MOUSE #2, UNTREATED, DAY 32; TUMOR AREA 4.76 cm²

MOUSE #13, mAb i.v., DAY 32; TUMOR AREA 0.01 cm²

HUMAN POLYPEPTIDES CAUSING OR LEADING TO THE KILLING OF CELLS INCLUDING LYMPHOID TUMOR CELLS

APPLICATION INFORMATION

This application is a continuation-in-part of International Application No. PCT/US01/15625, filed on May 14, 2001, which designated the U.S. and will be published under PCT Article 21(2) in English, and which claims priority to EP 00110065.0, filed on May 12, 2000, the entire contents of which are incorporated by reference herein.

BACKGROUND OF THE INVENTION

Every mammalian species, which has been studied to date, carries a cluster of genes coding for the so-called major histocompatibility complex (MHC). This tightly linked cluster of genes code for surface antigens, which play a central role in the development of both humoral and cell-mediated immune responses. In humans the products coded for by the MHC are referred to as Human Leukocyte Antigens or HLA. The MHC-genes are organized into regions encoding three classes of molecules, class I to III.

Class I MHC molecules are 45 kD transmembrane glycoproteins, noncovalently associated with another glycoprotein, the 12 kD beta-2 microglobulin (Brown et al., 1993). The latter is not inserted into the cell membrane, and is encoded outside the MHC. Human class I molecules are of three different isotypes, termed HLA-A, -B, and -C, encoded in separate loci. The tissue expression of class I molecules is ubiquitous and codominant. MHC class I molecules present peptide antigens necessary for the activation of cytotoxic T-cells.

Class II MHC molecules are noncovalently associated heterodimers of two transmembrane glycoproteins, the 35 kD α chain and the 28 kD β chain (Brown et al., 1993). In humans, class II molecules occur as three different isotypes, termed human leukocyte antigen DR (HLA-DR), HLA-DP and HLA-DQ. Polymorphism in DR is restricted to the β chain, whereas both chains are polymorphic in the DP and DQ isotypes. Class II molecules are expressed codominantly, but in contrast to class I, exhibit a restricted tissue distribution: they are present only on the surface of cells of the immune system, for example dendritic cells, macrophages, B lymphocytes, and activated T lymphocytes. They are also expressed on human adrenocortical cells in the zona reticularis of normal adrenal glands and on granulosa-lutein cells in corpora lutea of normal ovaries (Kahoury et al., 1990). Their major biological role is to bind antigenic peptides and present them on the surface of antigen presenting cells (APC) for recognition by CD4 helper T (Th) lymphocytes (Babbitt et al., 1985). MHC class II molecules can also be expressed on the surface of non-immune system cells, for example, cells that express MHC class II molecules during a pathological inflammatory response. These cells may include synovial cells, endothelial cells, thyroid stromal cells and glial cells.

Class III MHC molecules are also associated with immune responses, but encode somewhat different products. These include a number of soluble serum proteins, enzymes and proteins like tumor necrosis factor or steroid 21-hydroxylase enzymes. In humans, class III molecules occur as three different isotypes, termed Ca, C2 and Bf (Kuby, 1994).

Since Th cell activation is a crucial event of the initiation of virtually all immune responses and is mediated through class II molecules, class II MHC offers itself as a target for immunomodulation (Baxevanis et al., 1980; Rosenbaum et al., 1981; Adorini et al., 1988). Besides peptide presentation, class II molecules can transduce various signals that influence the physiology of APC. Such signals arise by the interaction of multiple class II molecules with an antibody or with the antigen receptor of Th cells (Vidovic et al., 1995a; Vidovic et al., 1995b), and can induce B cell activation and immunoglobulin secretion (Cambier et al., 1991; Palacios et al., 1983), cytokine production by monocytes (Palacios, 1985) as well as the up-regulation of co-stimulatory (Nabavi et al., 1992) and cell adhesion molecules (Mourad et al., 1990).

There is also a set of observations suggesting that class II ligation, under certain conditions, can lead to cell growth arrest or be cytotoxic. Ligation under these conditions is the interaction of a polypeptide with a class II MHC molecule. There is substantial contradiction about the latter effects and their possible mechanisms. Certain authors claim that formation of a complex of class II molecules on B cells leads to growth inhibition (Vaickus et al., 1989; Kabelitz et al., 1989), whereas according to others class II complex formation results in cell death (Vidovic et al., 1995a; Newell et al., 1993; Truman et al., 1994; Truman et al., 1997; Drenou et al., 1999). In certain experimental systems, the phenomenon was observed with resting B cells only (Newell et al., 1993), or in other systems with activated B cells only (Vidovic et al., 1995a; Truman et al., 1994).

Based on these observations, anti-class II monoclonal antibodies (mAbs) have been envisaged for a number of years as therapeutic candidates. Indeed, this proposal has been supported by the beneficial effect of mouse-derived anti-class II mAbs in a series of animal disease models (Waldor et al., 1983; Jonker et al., 1988; Stevens et al., 1990; Smith et al., 1994; Vidovic & Torral, 1998; Vidovic & Laus, 2000).

Despite these early supporting data, to date no anti-MHC class II mAb of human composition has been described that displays the desired cytotoxic and other biological properties which may include affinity, efficiency of killing and selectivity. Indeed, despite the relative ease by which mouse-derived mAbs may be derived, work using mouse-derived mAbs has demonstrated the difficulty of obtaining an antibody with the desired biological properties. For example, significant and not fully understood differences were observed in the T cell inhibitory capacity of different murine anti-class II mAbs (Naquet et al., 1983). Furthermore, the application of certain mouse-derived mAbs in vivo was associated with unexpected side effects, sometimes resulting in death of laboratory primates (Billing et al., 1983; Jonker et al., 1991).

It is generally accepted that mouse-derived mAbs (including chimeric and so-called "humanized" mAbs) carry an increased risk of generating an adverse immune response (Human anti-murine antibody—HAMA) in patients compared to treatment with a human mAb (for example, Vose et al, 2000; Kashmiri et al., 2001). This risk is potentially increased when treating chronic diseases such as rheumatoid arthritis or multiple sclerosis with any mouse-derived mAb or where regular treatment may be required, for example in the treatment of certain cancers; prolonged exposure of the human immune system to a non-human molecule often leads to the development of an adverse immune reaction. Furthermore, it has proven very difficult to obtain mouse-derived antibodies with the desired specificity or affinity to the desired antigen (Pichla et al. 1997). Such observation may significantly reduce the overall therapeutic effect or advantage provided by mouse-derived mAbs. Examples of disadvantages for mouse-derived mAbs may include the following. First, mouse-derived mAbs may be limited in the medical conditions or length of treatment for a condition for which they are appropriate. Second, the dose rate for mouse-derived mAbs may need to be relatively high in order to compensate for a relatively low affinity or therapeutic effect, hence making the dose not only more severe but potentially more immunogenic and perhaps dangerous. Third, such restrictions in suitable treatment regimes and high-dose rates requiring high production amounts may significantly add to the cost of treatment and could mean that such a mouse-derived mAb be uneconomical to develop as a commercial therapeutic. Finally, even if a mouse mAb could be identified that displayed the desired specificity or affinity, often these desired features are detrimentally affected during the "humanization" or "chimerization" procedures necessary to reduce immunogenic potential (Slavin-Chiorini et al., 1997). Once a mouse-derived mAb has been "humanized" or chimerized, then it is very difficult to optimize its specificity or affinity.

The art has sought over a number of years for anti-MHC class II mAbs of human composition that show biological properties suitable for use in a pharmaceutical composition for the treatment of humans. Workers in the field have practiced the process steps of first identifying a mouse-derived mAb, and then modifying the structure of this mAb with the aim of improving immunotolerance of this non-human molecule for human patients (for further details, see Jones et al., 1986; Riechmann et al., 1988; Presta, 1992). This modification is typically made using so-called "humanization" procedures or by fabricating a human-mouse chimeric mAb. Other workers have attempted to identify human antibodies that bind to human antigens having desired properties within natural repertoires of human antibody diversity. For example, by exploring the fetal-tolerance mechanism in pregnant women (Bonagura et al., 1987) or by panning libraries of natural diversities of antibodies (Stausbøl-Grøn et al., 1996; Winter et al., 1994). However, to date no anti-MHC class II mAb of human composition has been described that displays the desired biological properties of cytotoxicity, selectivity, specificity, low immunogenicity and affinity.

For therapeutic purposes a polypeptide reacting with most or at least many of the common allelic forms of a human class II MHC molecule would be desirable—e.g., to enable its use in diverse patient populations. Moreover, the candidate polypeptide should be cytotoxic to a wide range of lymphoid tumors, and preferably is cytotoxic by way of a mechanism common to such a range of tumor cells. To allow for a wide range of possible applications, the polypeptide desired should mediate its cytotoxic effect without the dependence on further components of the immune system. For therapeutic purposes, most patients receive for the treatment of, e.g. cancer, standard chemo- or radiotherapy. Most of these treatments leave the patient immunocompromised. Any additional treatment that relies on an intact immune system is therefore likely to fail. The underlying problem is further demonstrated in humans who suffer from a disease that destroys the immune system, e.g. HIV. Opportunistic infections and malignant transformations are able to escape the immune-surveillance and cause further complications.

SUMMARY OF THE INVENTION

One aspect of the present invention relates to a composition including a polypeptide comprising at least one antibody-based antigen-binding domain of human composition with binding specificity for an antigen expressed on the surface of a human cell, wherein treating cells expressing the antigen with a multivalent polypeptide having two or more of said antigen binding domains causes or leads to killing of the cells in a manner where neither cytotoxic entities nor immunological mechanisms are needed for killing. In certain preferred embodiments the antigen is an MHC antigen, preferably an MHC class II antigen, such as DR/DP/DQ or DR. For instance, in certain preferred embodiments, the subject compositions include a polypeptide comprising at least one antibody-based antigen-binding domain which binds to human HLA-DR with a $K_d$ of 1 μM, 100 nM, 10 nM or even 1 nM or less.

Another aspect of the present invention provides a composition including a multivalent polypeptide comprising a plurality of antibody-based antigen-binding domains of human composition with binding specificity for human HLA-DR. Treating cells expressing HLA-DR with the multivalent polypeptide causes or leads to killing of the cell in a manner where neither cytotoxic entities nor immunological mechanisms are needed for killing. In certain preferred embodiments, the said antigen-binding domains individually bind to the human HLA-DR with a $K_d$ of 1 μM, 100 nM, 10 nM or even 1 nM or less. In certain preferred embodiments, the multivalent polypeptide has an $EC_{50}$ of 100 nM, 10 nM or even 1 nM or less for killing activated lymphoid cells, transformed cells and/or lymphoid tumor cells.

Still another aspect of the present invention provides a composition including a polypeptide comprising at least one antibody-based antigen-binding domain that binds to human HLA-DR with a $K_d$ of 1 μM, 100 nM, 10 nM or even 1 nM or less, the antigen-binding domain being isolated by a method which includes isolation of human VL and VH domains from a recombinant antibody library by ability to bind to at least one epitope of human HLA-DR. Treating a cell expressing HLA-DR with a multivalent polypeptide having two or more of the antigen binding domains causes or leads to killing of the cells in a manner where neither cytotoxic entities nor immunological mechanisms are needed for killing. In certain embodiments, the method for isolating the antigen-binding domain includes the further steps of: a) generating a library of variants of at least one of the CDR1, CDR2 and CDR3 sequences of one or both of the VL and VH domains, and, b) isolation of VL and VH domains from the library of variants by ability to bind to human HLA-DR with a $K_d$ of 1 μM or less.

In certain preferred embodiments, the composition of the present invention can be characterized as including multivalent polypeptides having an $EC_{50}$ for killing transformed cells at least 5-fold lower than the $EC_{50}$ for killing normal cells, and even more preferably at least 10-fold, 100-fold and even 1000-fold less than for killing normal cells.

In certain preferred embodiments, the composition of the present invention are characterized as including multivalent polypeptides having an $EC_{50}$ for killing activated cells at least 5-fold lower than the $EC_{50}$ for killing unactivated cells, and even more preferably at least 10-folded, 100-fold and even 1000-fold less than for killing unactivated cells.

In certain preferred embodiments, the composition of the present invention are characterized as including multivalent polypeptides having an $EC_{50}$ of 50 nM or less for killing transformed cells, and even more preferably an $EC_{50}$ of less than 10 nM, 1 nM and even 0.1 nM. In certain embodiments, the subject multivalent polypeptides have an $EC_{50}$ for killing activated lymphoid cells, transformed cells and/or lymphoid tumor cells of 100 nM, 10 nM or even 1 nM or less.

In certain embodiments, the subject compositions including multivalent polypeptides that selectively kill activated lymphoid cells. For example, such multivalent forms of the subject compositions can be used to kill activated lymphoid cells are lymphoid tumor cells representing a disease selected from B cell non-Hodgkin lymphoma, B cell lymphoma, B cell acute lymphoid leukemia, Burkitt lymphoma, Hodgkin lymphoma, hairy cell leukemia, acute myeloid leukemia, T cell lymphoma, T cell non-Hodgkin lymphoma, chronic myeloid leukemia, chronic lymphoid leukemia, and multiple myeloid leukemia. Exemplary activated lymphoid tumor cells which can be killed include PRIESS (ECACC Accession No: 86052111), GRANTA-519 (DSMZ Accession No: ACC 342), KARPAS-422 (DSMZ Accession No: ACC 32), KARPAS-299, DOHH-2, SR-786, MHH-CALL-4, MN-60, BJAB, RAJI, L-428, HDLM-2, HD-MY-Z, KM-H2, L1236, BONNA-12, HC-1, NALM-1, L-363, EOL-1, LP-1, RPMI-8226, and MHH-PREB-1 cell lines. In certain preferred embodiments, the subject compositions have an $EC_{50}$ of 100 nM or less, and preferably less than 10 uM or even 1 nM, for killing at least one of B cell lymphoma cells and T cell lymphoma cells selected from the list of KARPAS-422, DOHH-2, SR-786 MHH-CALL-4, MN-60, HD-MY-Z, NALM-1 and LP-1. In certain instances, to effect cell killing, the target cells may require further activation or pre-activation, such as by by incubation with Lipopolysaccharide (LPS, 10 µg/ml), Interferon-gamma (IFN-γ, Roche, 40 ng/ml) and/or phyto-hemagglutinin (PHA, 5 µg/ml) to name but a few.

In certain embodiments, the multivalent forms of the subject compositions can be used to kill non-lymphoid cells that express MHC class II molecules.

In certain embodiments, one or more of the antigen binding domains of the subject compositions bind to the β-chain of HLA-DR, e.g., the antigen-binding domain binds to the first domain of the β-chain of HLA-DR.

In certain other embodiments, one or more of the antigen binding domains of the subject compositions bind to the α-chain of HLA-DR, e.g., the antigen-binding domain binds to the first domain of the α-chain of HLA-DR.

In certain preferred embodiments, the antigen binding domain(s) of the subject compositions bind to one or more HLA-DR types selected from the group consisting of DR1-0101, DR2-15021, DR3-0301, DR4Dw4-0401, DR4Dw10-0402, DR4Dw14-0404, DR6-1302, DR6-1401, DR8-8031, DR9-9012, DRW53-B4*0101 and DRW52-B3*0101. In preferred embodiments, the antigen binding domains of the subject compositions provide broad-DR reactivity, that is, the antigen-binding domain(s) of a given composition binds to epitopes on at least 5 different of said HLA-DR types. In certain embodiments, the antigen binding domain(s) of a polypeptide(s) of the subject compositions binds to a plurality of HLA-DR types as to bind to HLA-DR expressing cells for at least 60 percent of the human population, more preferably at least 75 percent, and even more preferably 85 percent of the human population.

In certain embodiments, the antigen-binding domains of the subject compositions include a combination of a VH domain and a VL domain, wherein said combination is found in one of the clones taken from the list of MS-GPC-1, MS-GPC-6, MS-GPC-8, MS-GPC-10, MS-GPC-8-1, MS-GPC-8-6, MS-GPC-8-9, MS-GPC-8-10, MS-GPC-8-17, MS-GPC-8-18, MS-GPC-8-27, MS-GPC-8-6-2, MS-GPC-8-6-19, MS-GPC-8-6-27, MS-GPC-8-6-45, MS-GPC-8-6-13, MS-GPC-8-6-47, MS-GPC-8-10-57, MS-GPC-8-27-7, MS-GPC-8-27-10 and MS-GPC-8-27-41.

In certain embodiments, the antigen-binding domains of the subject compositions include a combination of HuCAL VH2 and HuCAL Vλ1, wherein the VH CDR3, VL CDR1 And VL CDR3 is found in one of the clones taken from the list of MS-GPC-1, MS-GPC-8, MS-GPC-10, MS-GPC-8-1, MS-GPC-8-6, MS-GPC-8-9, MS-GPC-8-10, MS-GPC-8-17, MS-GPC-8-18, MS-GPC-8-27, MS-GPC-8-6-2, MS-GPC -8-6-19, MS-GPC-8-6-27, MS-GPC-8-6-45, MS-GPC-8-6-13, MS-GPC-8-6-47, MS-GPC-8-10-57, MS-GPC-8-27-7, MS-GPC-8-27-10 and MS-GPC-8-27-41.

In a further preferred embodiment, the antigen-binding domain is modified compared to a parental antigen-binding domain of the present invention by addition, deletion and/or substitution of amino acid residues, while maintaining the properties according to the present invention, or improving one or more of said properties, of said parental antigen-binding domain. This may include, but is not limited to, the modification of a nucleic acid sequence encoding a parental antigen-binding domain for cloning purposes, the modification of CDR regions in order to improve or modify antigen-binding affinity and/or specificity, including the exchange of one or more CDR sequences of a parental antigen-binding domain by corresponding CDR sequences from one or more different antigen-binding domains, and the addition of peptide sequences for detection and/or purification purposes. It is well within the scope of one of ordinary skill in the art to identify positions in a given parental antigen-binding domain where an addition, deletion and/or substitution should occur, to design and pursue the approach to achieve said addition, deletion and/or substitution, and to test or assay whether the modified antigen-binding domain has maintained the properties of, or exhibits one or more improved properties compared to, the parental antigen-binding domain. Furthermore, one of ordinary skill would be able to design approaches where collections or libraries of modified antigen-binding domains are designed, constructed and screened to identify one or more modified antigen-binding domain which have maintained the properties, or exhibit one or more improved properties compared to the parental antigen-binding domain. In one example, the first amino acid residue of a HuCAL VH domain comprised in any antigen-binding domain or the present invention, which is either E or Q depending on the expression construct, may be exchanged by Q or E, respectively. Preferred regions to optimize an antigen-binding domain by designing, constructing and screening collections or libraries of modified antigen-binding domains according to the present invention comprise the CDR regions, and most preferably CDR3 of VH and VL, CDR1 of VL and CDR2 of VH domains.

In certain embodiments, the antigen-binding domains includes a combination of HuCAL VH2 and HuCAL Vλ1, wherein the VH CDR3 sequence is taken from the consensus CDR3 sequence:

XXXXRGXFDX (SEQ ID No. 1)

wherein each X independently represents any amino acid residue; and/or, wherein the VL CDR3 sequence is taken from the consensus CDR3 sequence:

QSYDXXXX (SEQ ID No. 2)

wherein each X independently represents any amino acid residue. For instance, the VH CDR3 sequence can be SPRYRGAFDY (SEQ ID No. 3) and/or the VL CDR3 sequence can be QSYDLIRH (SEQ ID No. 4) or QSYDMNVH (SEQ ID No. 5).

In certain embodiments, the antigen-binding domains of the subject antigen-binding domain competes for antigen binding with an antibody including a combination of HuCAL VH2 and HuCAL Vλ1, wherein the VH CDR3 sequence is taken from the consensus CDR3 sequence:

XXXXRGXFDX (SEQ ID No. 1)

each X independently represents any amino acid residue; and/or, the VL CDR3 sequence is taken from the consensus CDR3 sequence:

QSYDXXXX (SEQ ID No. 2)

each X independently represents any amino acid residue. For instance, the VH CDR3 sequence can be SPRYRGAFDY (SEQ ID No. 3) and/or the VL CDR3 sequence can be QSYDLIRH (SEQ ID No. 4) or QSYDMNVH (SEQ ID No. 5).

In certain preferred embodiments, the antigen-binding domain includes a VL CDR1 sequence represented in the general formula:

SGSXXNIGXNYVX (SEQ ID No. 6)

wherein each X independently represents any amino acid residue. For instance, the CDR1 sequence is SGSESNIGNNYVQ (SEQ ID No. 7).

In preferred embodiments, the mechanism of killing by multivalent forms of the subject compositions involves an innate pre-programmed process of said cell. For instance, the killing is non-apoptotic. Killing by the subject compositions can be dependent on the action of non-caspase proteases, and/or killing which cannot be inhibited by zVAD-fmk or zDEVD-fmk.

In certain preferred embodiments, the antibody-based antigen-binding domain is part of a multivalent polypeptide including at least a F(ab')$_2$ antibody fragment or a miniantibody fragment.

In certain preferred embodiments, the antibody-based antigen-binding domain is part of a multivalent polypeptide comprising at least two monovalent antibody fragments selected from Fv, scFv, dsFv and Fab fragments, and further comprises a cross-linking moiety or moieties.

In certain preferred embodiments, the antibody-based antigen-binding domain is part of a multivalent polypeptide comprising at least one full antibody selected from the antibodies of classes IgG$_1$, 2a, 2b, 3, 4, IgA, and IgM.

In certain preferred embodiments, the antibody-based antigen-binding domain is part of a multivalent polypeptide is formed prior to binding to said cell.

In certain preferred embodiments, the antibody-based antigen-binding domain is part of a multivalent polypeptide is formed after binding to said cell.

In certain preferred embodiments, the antigen binding sites are cross-linked to a polymer.

Another aspect of the present invention provides a nucleic acid comprising a coding sequence for an antigen-binding domain, such as those antigen binding domains described above, or a multivalent polypeptide thereof. For example, in certain embodiments, the nucleic acid includes a coding sequence for a polypeptide comprising at least one antibody-based antigen-binding domain of human composition with binding specificity for an antigen expressed on the surface of a human cell, wherein treating cells expressing the antigen with a multivalent form of the polypeptide causes or leads to killing of said cell in a manner where neither cytotoxic entities nor immunological mechanisms are needed for killing. In certain embodiments, the nucleic acid includes a coding sequence for a polypeptide comprising at least one antibody-based antigen-binding domain which binds to at least one epitope of human HLA-DR with a K$_d$ of 1 μM, 100 nM, 10 nM or even 1 nM or less.

In certain embodiments, the nucleic acid includes a coding sequence for a polypeptide comprising a plurality of antibody-based antigen-binding domains of human composition with binding specificity for human HLA-DR, wherein treating a cell expressing HLA-DR with the multivalent polypeptide causes or leads to killing of the cell in a manner where neither cytotoxic entities nor immunological mechanisms are needed for killing. In preferred embodiments, the antigen-binding domains individually bind to epitopes on the human HLA-DR with a K$_d$ of 1 μM, 100 nM, 10 nM or even 1 nM or less.

In certain embodiments, the nucleic acid includes a coding sequence for a multivalent polypeptide comprising a plurality of antibody-based antigen-binding domains of human composition with binding specificity for human HLA-DR, wherein treating a cell expressing HLA-DR with said multivalent polypeptide causes or leads to killing of said cell in a manner where neither cytotoxic entities nor immunological mechanisms are needed for said cell killing. Preferably, the multivalent polypeptide has an EC$_{50}$ for killing activated lymphoid cells, transformed cells and/or lymphoid tumor cells of 100 nM, 10 nM or even 1 nM or less.

Another aspect of the invention provides a vector comprising the coding sequence of any one of the subject nucleic acids, e.g., as described above, and a transcriptional regulatory sequence operably linked thereto.

Still another aspect of the present invention provides a host cell harboring at least one subject nucleic acids or the subject vector. Another aspect of the present invention provides a method for the production of a multivalent composition that causes or leads to killing of cells in a manner where neither cytotoxic entities nor immunological mechanisms are needed to cause or lead to said killing comprising culturing the host cells under conditions wherein the nucleic acid is expressed either as a polypeptide comprising a plurality of antigen binding domains or as a polypeptide comprising at least one antigen binding domains which is subsequently treated to form a multivalent composition.

Another aspect of the present invention provides forms of the subject polypeptide or nucleic acid compositions, formulated in a pharmaceutically acceptable carrier and/or diluent. The present invention specifically contemplates the use of such compositions for preparing a pharmaceutical preparation for the treatment of animals, especially humans.

Such pharmaceutical compositions can be used for the treatment of conditions involving unwanted cell proliferation, particularly the treatment of a disorder involving transformed cells expressing MHC class II antigens. For instance, the formulations can be used for the treatment of a disorder selected from B cell non-Hodgkin lymphoma, B cell lymphoma, B cell acute lymphoid leukemia, Burkitt lymphoma, Hodgkin lymphoma, hairy cell leukemia, acute myeloid leukemia, T cell lymphoma, T cell non-Hodgkin lymphoma, chronic myeloid leukemia, chronic lymphoid leukemia, multiple myeloid leukemia and B cell precursor leukemia.

Such pharmaceutical preparations can be used for the treatment of diseases involving unwanted activation of immune cells, such as in the treatment of a disorder selected from rheumatoid arthritis, juvenile arthritis, multiple sclerosis, Grave's disease, insulin-dependent diabetes, narcolepsy, psoriasis, systemic lupus erythematosus, ankylosing spondylitis, transplant rejection, graft vs. host disease, Hashimoto's disease, myasthenia gravis, pemphigus vulgaris, glomerulonephritis, thyroiditis, pancreatitis, insulitis, primary biliary cirrhosis, irritable bowel disease and Sjogren syndrome.

Another aspect of the present invention provides a diagnostic composition including the polypeptide or nucleic acid compositions of the present invention. In certain embodiments, the diagnostic composition includes a polypeptide composition and a cross-linking moiety or moieties.

Still another aspect of the present invention provides a method for killing a cell expressing an antigen on the surface of said cell comprising the step of contacting the cell with a multivalent polypeptide composition of the subject invention.

Another aspect of the invention provides a method to identify patients that can be treated with a multivalent polypeptide composition, formulated in a pharmaceutically acceptable carrier and/or diluent comprising the steps of:

a. isolating cells from a patient;
b. contacting said cells with the composition; and
c. measuring the degree of killing or immunosuppression of said cells.

The present invention also provides a kit to identify patients that can be treated with a multivalent polypeptide composition of the present invention, formulated in a pharmaceutically acceptable carrier and/or diluent comprising:
a. a multivalent polypeptide composition; and
b. means to measure the degree of killing or immunosuppression of said cells.

In certain embodiments, the kit includes a multivalent polypeptide composition, and a cross-linking moiety. In other embodiments, the kit includes
a. a multivalent polypeptide composition,
b. a detectable moiety or moieties, and
c. reagents and/or solutions to effect and/or detect binding of (a) to an antigen.

Another aspect of the present invention provides a cytotoxic composition comprising a multivalent polypeptide composition operably linked to a cytotoxic agent.

Stil another aspect of the invention provides an immunogenic composition comprising a multivalent polypeptide composition operablly linked to an immunogenic agent.

Another aspect of the present invention provides a method to kill a cell comprising contacting the cell with a multivalent polypeptide composition operablly linked a cytotoxic or immunogenic agent.

Another aspect of the invention provides a method for treating a human to reduce the severity of disorder involving unwanted proliferation/activation of cells expressing the human β-chain of HLA-DR, comprising administering to the patient a a multivalent polypeptidepolypeptide of the present invention. In certain embodiments, the disorder involves unwanted proliferation/activation of lymphoid cells, e.g., selected from B cell non-Hodgkin lymphoma, B cell lymphoma, B cell acute lymphoid leukemia, Burkitt lymphoma, Hodgkin lymphoma, hairy cell leukemia, acute myeloid leukemia, T cell lymphoma, T cell non-Hodgkin lymphoma, chronic myeloid leukemia, chronic lymphoid leukemia, multiple myeloid leukemia and B cell precursor leukemia.

Another aspect of the invention provides a use of a multivalent polypeptide composition operably linked a cytotoxic or immunogenic agent for preparing a pharmaceutical preparation for the treatment of animals According to a preferred embodiment, the polypeptide is directed to a lymphoid cell or a non-lymphoid cell that expresses MHC class II molecules. The latter type of cells occur for example at pathological sites of inflammation and/or autoimmune diseases, e.g. synovial cells, endothelial cells, thyroid stromal cells and glial cells, or it may also comprise genetically altered cells capable of expressing MHC class II molecules.

Preferably, the polypeptide is directed to lymphoid tumor cells. More preferred are lymphoid tumor cells that represent a disease selected from B cell non-Hodgkin lymphoma, B cell lymphoma, B cell acute lymphoid leukemia, Burkitt lymphoma, Hodgkin lymphoma, hairy cell leukemia, acute myeloid leukemia and B cell precursor leukemia. Most preferred are lymphoid tumor cells from a cell line taken from the list of GRANTA-519, PRIESS, KARPAS-422, DOHH-2, MHH-CALL-4, MN-60, BJAB, L-428, BONNA-12, EOL-1, MHH-PREB-1 and MHH-CALL-2 cell lines.

In certain embodiments, the polypeptide binds to at least one epitope in the alpha-chain of an HLA-DR molecule. In such embodiments, the polypeptide preferably binds to at least one epitope in the first domain of the alpha-chain of HLA-DR, the first domain being the N-terminal domain of the chain. For instance, the polypeptide can be selected to bind to at least one epitope within the alpha-helix ranging from Glu55 to Tyr79 of the alpha-chain of HLA-DR.

In other embodiments, the polypeptide binds to at least one epitope in the beta-chain of an HLA-DR molecule. Preferably, the polypeptide binds to at least one epitope in the first domain of the beta-chain of HLA-DR, the first domain being the N-terminal domain of the chain.

In certain embodiments, the mechanism of killing a target cell induced by the polypeptide involves an innate pre-programmed process of said cell. Preferably, the polypeptide induces a killing mechanism, which is not an apoptotic cell death process.

In a preferred embodiment the polypeptide induces a killing mechanism which is dependent on the action of proteases other than caspases, e.g., is a caspase-independent mechanism.

In a further embodiment the multivalent composition comprises at least one full antibody which is selected from classes $IgG_1$, 2a, 2b, 3, 4, IgA, and IgM.

In a further embodiment the multivalent composition comprises at least one of a $F(ab')_2$ antibody fragment or miniantibody fragment.

In a preferred embodiment the multivalent composition comprises at least two monovalent antibody fragments selected from Fv, scFv, dsFv and Fab fragments, and further comprises a cross-linking moiety or moieties.

The present invention also provides a composition including a polypeptide comprising at least one antibody-based antigen-binding domain with a binding specificity for human HLA-DR wherein binding of said polypeptide to said epitope causes or leads to suppression of the immune response and wherein said antigen-binding domain includes a combination of a VH domain and a VL domain, wherein said combination is found in one of the clones taken from the list of MS-GPC-1, MS-GPC-6, MS-GPC-8, MS-GPC-10, MS-GPC-8-1, MS-GPC-8-6, MS-GPC-8-9, MS-GPC-8-10, MS-GPC-8-17, MS-GPC-8-18, MS-GPC-8-27, MS-GPC-8-6-2, MS-GPC-8-6-19, MS-GPC-8-6-27, MS-GPC-8-6-45, MS-GPC-8-6-13, MS-GPC-8-6-47, MS-GPC-8-10-57, MS-GPC-8-27-7, MS-GPC-8-27-10 and MS-GPC-8-27-41.

Another immunosuppressive composition of the present invention includes a polypeptide comprising at least one antibody-based antigen-binding domain with a binding specificity for a human MHC class II antigen with a $K_d$ of 1 µM, 100 nM, 10 nM or even 1 nM or less, wherein treating cells expressing MHC class II antigen with the polypeptide causes or leads to suppression of the immune response, e.g., preferably with an $IC_{50}$ of 1 µM, 100 nM, 10 nM or even 1 nM or less.

Another immunosuppressive composition of the present invention includes a polypeptide comprising at least one antibody-based antigen-binding domain of human composition with a binding specificity for a human MHC class II antigen with a $K_d$ of 1 µM, 100 nM, 10 nM or even 1 nM or less, the antigen-binding domain being isolated by a method which includes isolation of human VL and VH domains from a recombinant antibody display library by ability to bind to human MHC class II antigen, wherein treating cells that express MHC class II with said polypeptide causes or leads to suppression of the immune response.

The subject immunosuppressive compositions can be generated using the antigen-binding domain isolated by the further steps of:

a. generating a library of mutations at least one of the CDR1, CDR2 and CDR3 domains of one or both of the VL and VH domains, and b. isolation of VL and VH domains from the library of variants by ability to bind to human MHC class II antigen with a $K_d$ of 1 μM or less.

In preferred embodiments, the antigen binding domains of the immunosuppressive composition binds to HLA-DR, and preferably to the β-chain of HLA-DR, and even more preferably to the first domain of the β-chain of HLA-DR.

In certain preferred embodiments, the immunosuppressive composition have an $IC_{50}$ for suppressing the immune response of 1 μM, 100 nM, 10 nM or even 1 nM or less.

In certain preferred embodiments, the immunosuppressive composition have an $IC_{50}$ for inhibiting of IL-2 secretion of 1 μM, 100 nM, 10 nM or even 1 nM or less.

In certain preferred embodiments, the immunosuppressive composition have an $IC_{50}$ for inhibiting of T cell proliferation of 1 μM, 100 nM, 10 nM or even 1 nM or less.

In certain preferred embodiments, the immunosuppressive composition have antigen-binding domain that bind to an epitope of one or more HLA-DR types selected from the group consisting of DR1-0101, DR2-15021, DR3-0301, DR4Dw4-0401, DR4Dw10-0402, DR4Dw14-0404, DR6-1302, DR6-1401, DR8-8031, DR9-9012, DRw53-B4*0101 and DRw52-B3*0101, and in preferred embodiments, the antigen-binding domain binds to at least 5 different of said HLA-DR types (e.g., are pan-DR).

In certain embodiments, the immunosuppressive composition have antigen-binding domain includes a combination of a VH domain and a VL domain, wherein said combination is found in one of the clones taken from the list of MS-GPC-1, MS-GPC-6, MS-GPC-8, MS-GPC-10, MS-GPC-8-1, MS-GPC-8-6, MS-GPC-8-9, MS-GPC-8-10, MS-GPC-8-17, MS-GPC-8-18, MS-GPC-8-27, MS-GPC-8-6-2, MS-GPC-8-6-19, MS-GPC-8-6-27, MS-GPC-8-6-45, MS-GPC-8-6-13, MS-GPC-8-6-47, MS-GPC-8-10-57, MS-GPC-8-27-7, MS-GPC-8-27-10 and MS-GPC-8-27-41.

In certain embodiments, the immunosuppressive composition have antigen-binding domain includes a combination of HuCAL VH2 and HuCAL Vλ1, wherein the VH CDR3 sequence is taken from the consensus CDR3 sequence:

XXXXRGXFDX (SEQ ID No. 1)

wherein each X independently represents any amino acid residue; and, wherein the VL CDR3 sequence is taken from the consensus CDR3 sequence:

QSYDXXXX (SEQ ID No. 2)

wherein each n independently represents any amino acid residue.

For instance, the VH CDR3 sequence is SPRYRGAFDY (SEQ ID No. 3) and/or the VL CDR3 sequence is QSYD-LIRH (SEQ ID No. 4) or QSYDMNVH (SEQ ID No. 5).

In certain embodiments, the immunosuppressive composition the antigen-binding domain competes with antigen binding by an antibody having a VH CDR3 sequence represented by the general formula:

XXXXRGXFDX (SEQ ID No. 1)

wherein each X independently represents any amino acid residue; and, a VL CDR3 sequence represented by the general formula:

QSYDXXXX (SEQ ID No. 2)

wherein each X independently represents any amino acid residue.

In certain embodiments, the immunosuppressive composition the antigen-binding domain includes a VL CDR1 sequence represented in the general formula:

SGSXXNIGXNYVX (SEQ ID No. 6)

wherein each n independently represents any amino acid residue. For example, the CDR1 sequence is SGSESNIGNNYVQ (SEQ ID No. 7).

In certain embodiments, the subject immunosuppressive compositions suppress the immune response by one or more of (a) down-regulation of expression of the antigen to which the polypeptide binds; or (b) inhibiting of the interaction between said cell and other cells, wherein said interaction would normally lead to an immune response.

Another aspect of the present invention provides nucleic acids which including a coding sequence for an immunosuppressive polypeptide of the present invention. In certain embodiments, the nucleic acid can be provided as part of a vector, e.g., including the coding sequence and a transcriptional regulatory sequence operably linked thereto. The nucleic acid and vectors of the present invention can be provided as part of a host cell, e.g., which can be used to to produce an immunosuppressive composition.

Another aspect of the present invention provides a method for suppressing activation and/or proliferation of a lymphocyte, comprising contacting the cell with an immunosuppressive polypeptide of the present invention.

The present invention also provides a pharmaceutical preparation comprising the a polypeptide including an antibody-based antigen-binding domain with a binding specificity for a human MHC class II antigen with a $K_d$ of 1 μM or less, e.g., in an amount sufficient to suppress an immune response in an animal, inhibit IL-2 secretion in an animal, and/or inhibit T cell proliferation in an animal.

Another aspect of the present invention relates to the use of a polypeptide including an antibody-based antigen-binding domain with a binding specificity for a human MHC class II antigen with a $K_d$ of 1 μM or less, for the preparation of a pharmaceutical composition for the treatment of animals, such as where said animals are human.

The subject immunosuppressive pharmaceutical preparations can be used for suppressing IL-2 secretion by a cell of the immune system. For example, these preparations can be administered to the patient in an effective amount to reduce the level of immunological responsiveness in the patient.

Still another aspect of the present invention provides a method for suppressing IL-2 secretion by a lymphocyte, comprising contacting the cell with an immunosuppressive polypeptide of the present invention.

The subject method can be used for immunosuppressing a human, e.g., by administering to the patient an effective amount of an immunosuppressive polypeptide of the present invention to reduce the level of immunological responsiveness.

The invention further relates to a diagnostic composition containing at least one polypeptide and/or nucleic acid according to the invention, optionally together with further reagents, such as buffers, for performing the diagnosis.

In a preferred embodiment the diagnostic composition contains the polypeptide according to the invention crosslinked by at least one moiety. Such moieties can be for example antibodies recognizing an epitope present on the polypeptide such as the FLAG peptide epitope (Hopp et al., 1988; Knappik and Plückthun, 1994) or bifunctional chemical compounds reacting with a nucleophilic amino acid side chain as present in cysteine or lysine (King et al., 1994). Methods for cross-linking polypeptides are well known to the practitioner of ordinary skill in the art.

A diagnostic composition containing at least one nucleic acid and/or variant thereof according to the invention is also contemplated.

Furthermore, the present invention relates to a kit comprising at least one polypeptide according to the present invention, and a cross-linking moiety.

Additionally, the present invention relates to a kit comprising (i) a polypeptide according to the present invention, (ii) a detectable moiety or moieties, and (iii) reagents and/or solutions to effect and/or detect binding of (i) to an antigen.

The present invention further relates to a multivalent composition comprising at least one polypeptide and comprising at least two antigen binding domains.

Still another aspect of the present invention provides a method for conducting a pharmaceutical business comprising:
 a. isolating one or more antigen-binding domains that bind to antigens expressed on the surface of human cells;
 b. generating a multivalent composition comprising a plurality of said antigen-binding domains, which multivalent composition kills with an $EC_{50}$ of 50 nM or less transformed or activated cells where neither cytotoxic entities nor immunological mechanisms are needed to cause or lead to said killing.;
 c. conducting therapeutic profiling of the multivalent compositions for efficacy and toxicity in animals;
 d. preparing a package insert describing the multivalent composition for treatment of proliferative disorders; and
 e. marketing the multivalent composition for treatment of proliferative disorders.

The present invention also provides a method for conducting a life science business comprising:
 a. isolating one or more antigen-binding domains that bind to antigens expressed on the surface of human cells;
 b. generating a multivalent composition comprising a plurality of said antigen-binding domains, which multivalent composition kills with an $EC_{50}$ of 50 nM or less transformed or activated cells where neither cytotoxic entities nor immunological mechanisms are needed to cause or lead to said killing.;
 c. licensing, jointly developing or selling, to a third party, the rights for selling the multivalent compositions.

In such embodiments, the the antigen-binding domain can be isolated by a method which includes
 a. isolation of VL and VH domains of human composition from a recombinant antibody display library by ability to bind to epitopes of HLA-DR,
 b. generating a library of variants at least one of the CDR1, CDR2 and CDR3 domains of one or both of the VL and VH domains, and
 c. isolation of VL and VH domains from the library of variants by ability to epitopes of HLA-DR with a Kd of 1 µM or less.

Another business method contemplated by the present invention includes:
 a. isolating one or more antigen-binding domains that bind to MHC class II expressed on the surface of human cells with a $K_d$ of 1 µM or less;
 b. generating a composition comprising said antigen-binding domains, which composition is immunosuppressant with an $IC_{50}$ of 100 nM or less;
 c. conducting therapeutic profiling of the multivalent compositions for efficacy and toxicity in animals;
 d. preparing a package insert describing the use of the composition for immunosuppression therapy; and
e. marketing the multivalent composition for use as an immunosuppressant.

The present invention also provides a method for conducting a life science business comprising:

a. isolating one or more antigen-binding domains that bind to MHC class II expressed on the surface of human cells with a $K_d$ of 1 μM or less;
b. generating a composition comprising said antigen-binding domains, which composition is immunosuppressant with an $IC_{50}$ of 100 nM or less;
c. licensing, jointly developing or selling, to a third party, the rights for selling the compositions.

As used herein, the term "peptide" relates to molecules consisting of one or more chains of multiple, i.e. two or more, amino acids linked via peptide bonds.

The term "protein" refers to peptides where at least part of the peptide has or is able to acquire a defined three-dimensional arrangement by forming secondary, tertiary, or quaternary structures within and/or between its peptide chain(s). This definition comprises proteins such as naturally occurring or at least partially artificial proteins, as well as fragments or domains of whole proteins, as long as these fragments or domains are able to acquire a defined three-dimensional arrangement as described above.

The term "polypeptide" is used interchangeably to refer to peptides and/or proteins. Moreover, the terms "polypeptide" and "protein", as the context will admit, include multi-chain protein complexes, such as immunoglobulin polypeptides having separate heavy and light chains.

In this context, "polypeptide comprising at least one antibody-based antigen-binding domain" refers to an immunoglobulin (or antibody) or to a fragment thereof. The term "fragment", with respect to antibody domains and the like, refers to a fragment of an immunoglobulin which retains the antigen-binding moiety of an immunoglobulin. Functional immunoglobulin fragments according to the present invention may be Fv (Skerra and Plückthun, 1988), scFv (Bird et al., 1988; Huston et al., 1988), disulfide-linked Fv (Glockshuber et al., 1992; Brinkmann et al., 1993), Fab, F(ab')2 fragments or other fragments well-known to the practitioner skilled in the art, which comprise the variable domains of an immunoglobulin or functional immunoglobulin fragment.

Examples of polypeptides consisting of one chain are single-chain Fv antibody fragments, and examples for polypeptides consisting of multiple chains are Fab antibody fragments.

The term "antibody" as used herein, unless indicated otherwise, is used broadly to refer to both antibody molecules and a variety of antibody derived molecules. Such antibody derived molecules comprise at least one variable region (either a heavy chain of light chain variable region) and include such fragments as described above, as well as individual antibody light chains, individual antibody heavy chains, chimeric fusions between antibody chains and other molecules, and the like.

The "antigen-binding site" of an immunoglobulin molecule refers to that portion of the molecule that is necessary for binding specifically to an antigen. An antigen binding site preferably binds to an antigen with a $K_d$ of 1 μM or less, and more preferably less than 100 nM, 10 nM or even 1 nM in certain instances. Binding specifically to an antigen is intended to include binding to the antigen which significantly higher affinity than binding to any other antigen.

The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

For the purposes of this application, "valent" refers to the number of antigen binding sites the subject polypeptide possess. Thus, a bivalent polypeptide refers to a polypeptide with two binding sites. The term "multivalent polypeptide" encompasses bivalent, trivalent, tetravalent, etc. forms of the polypeptide.

As used herein, a "multivalent composition" means a composition comprising a polypeptide having at least two of said antigen-binding domains, e.g., a multivalent polypeptide. Preferably, said at least two antigen-binding domains are in close proximity so as to mimic the structural arrangement relative to each other of binding sites comprised in a full immunoglobulin molecule. Examples for multivalent compositions are full immunoglobulin molecules (e.g. IgG, IgA or IgM molecules) or multivalent fragments thereof (e.g. F(ab')$_2$). Additionally, multivalent compositions of higher valencies may be formed from two or more multivalent compositions (e.g. two or more full immunoglobulin molecules), e.g. by cross-linking. Multivalent compositions, however, may be formed as well from two or more monovalent immunoglobulin fragments, e.g. by self-association as in mini-antibodies, or by cross-linking.

Accordingly, an "antibody-based antigen-binding domain" refers to polypeptide or polypeptides which form an antigen-binding site retaining at least some of the structural features of an antibody, such as at least one CDR sequence. In certain preferred embodiments, antibody-based antigen-binding domain includes sufficient structure to be considered a variable domain, such as three CDR regions and interspersed framework regions. Antibody-based antigen-binding domain can be formed single polypeptide chains corresponding to VH or VL sequences, or by intermolecular or intramolecular association of VH and VL sequences.

The term "recombinant antibody library" describes a variegated library of antigen binding domains. For instance, the term includes a collection of display packages, e.g., biological particles, which each have (a) genetic information for expressing at least one antigen binding domain on the surface of the particle, and (b) genetic information for providing the particle with the ability to replicate. For instance, the package can display a fusion protein including an antigen binding domain. The antigen binding domain portion of the fusion protein is presented by the display package in a context which permits the antigen binding domain to bind to a target epitope that is contacted with the display package. The display package will generally be derived from a system that allows the sampling of very large variegated antibody libraries. The display package can be, for example, derived from vegetative bacterial cells, bacterial spores, and bacterial viruses.

In an exemplary embodiment of the present invention, the display package is a phage particle which comprises a peptide fusion coat protein that includes the amino acid sequence of a test antigen binding domains. Thus, a library of replicable phage vectors, especially phagemids (as defined herein), encoding a library of peptide fusion coat proteins is generated and used to transform suitable host cells. Phage particles formed from the chimeric protein can be separated by affinity selection based on the ability of the antigen binding site associated with a particular phage particle to specifically bind a target eptipope. In a preferred embodiment, each individual phage particle of the library includes a copy of the corresponding phagemid encoding the peptide fusion coat protein displayed on the surface of that package. Exemplary phage for generating the present variegated peptide libraries include M13, f1, fd, If1, Ike, Xf, Pf1, Pf3, λ, T4, T7, P2, P4, φX-174, MS2 and f2.

The term "generating a library of variants of at least one of the CDR1, CDR2 and CDR3" refers to a process of generating a library of variant antigen binding sites in which the members of the library differ by one or more changes in CDR sequences, e.g., not FR sequences. Such libraries can be generated by random or semi-random mutagenesis of one or more CDR sequences from a selected antigen binding site.

As used herein, an "antibody-based antigen-binding domain of human composition" preferably means a polypeptide comprising at least an antibody VH domain and an antibody VL domain, wherein a homology search in a database of protein sequences comprising immunoglobulin sequences results for both the VH and the VL domain in an immunoglobulin domain of human origin as hit with the highest degree of sequence identity. Such a homology search may be a BLAST search, e.g. by accessing sequence databases available through the National Center for Biological Information and performing a "BasicBLAST" search using the "blastp" routine. See also Altschul et al. (1990) J Mol Biol 215:403-410. Preferably, such a composition does not result in an adverse immune response thereto when administered to a human recipient. In certain preferred embodiments, the subject antigen-binding domains of human composition include the framework regions of native human immunoglobulins, as may be cloned from activated human B cells, though not necessarily all of the CDRs of a native human antibody.

As used herein, the term "mini-antibody fragment" means a multivalent antibody fragment comprising at least two antigen-binding domains multimerized by self-associating domains fused to each of said domains (Pack, 1994), e.g. dimers comprising two scFv fragments, each fused to a self-associating dimerization domain. Dimerization domains, which are particularly preferred, include those derived from a leucine zipper (Pack and Plückthun, 1992) or helix-turn-helix motif (Pack et al., 1993).

As used herein, "activated cells" means cells of a certain population of interest, which are not resting. Activation might be caused by mitogens (e.g., lipopoysaccharide, phytohemagglutinine) or cytokines (e.g., interferon gamma). Preferably, said activation occurs during tumor transformation (e.g., by Epstein-Barr virus, or "spontaneously"). Preferably, activated cells are characterized by the features of MHC class II molecules expressed on the cell surface and one or more additional features including increased cell size, cell division, DNA replication, expression of CD45 or CD11 and production/secretion of immunoglobulin.

As used herein, "non-activated cells" means cells of a population of interest, which are resting and non-dividing. Said non-activated cells may include resting B cells as purified from healthy human blood. Such cells can, preferably, be characterized by lack or reduced level of MHC class II molecules expressed on the cell surface and lack or reduced level of one or more additional features including increased cell size, cell division, DNA replication, expression of CD45 or CD11 and production/secretion of immunoglobulin.

As used herein, the term "$EC_{50}$" means the concentration of multivalent forms of the subject compositions which produces 50% of its maximum response or effect, such as cell killing.

"At least 5-fold lower $EC_{50}$" means that the concentration of a multivalent composition comprising at least one polypeptide of the present invention that is required to kill 50% of activated cells is at least five times less than the concentration of the multivalent composition required to kill non-activated cells. Preferably, the concentration required to kill 50% of non-activated cells cannot be achieved with therapeutically appropriate concentrations of the multivalent composition. Most preferably, the $EC_{50}$ value is determined in the test described below in the appended examples.

The term "immunosuppress" refers to the prevention or diminution of the immune response, as by irradiation or by administration of antimetabolites, antilymphocyte serum, or specific antibody.

The term "immune response" refers to any response of the immune system, or a cell forming part of the immune system (lymphocytes, granulocytes, macrophages, etc), to an antigenic stimulus, including, without limitation, antibody production, cell-mediated immunity, and immunological tolerance.

As used herein, the term "$IC_{50}$" with respect to immunosuppression, refers to the concentration of the subject compositions which produces 50% of its maximum response or effect, such as inhibition of an immune response, such as may be manifest by inhibition of IL2 secretion, down-regulation of IL2 expression, or reduced rate of cell proliferation.

The phrase "cytotoxic entities", with reference to a manner of cell killing, refers to mechanisms which are complement-dependent. Likewise, the phrase "immuological mechanism", with reference to a manner of cell killing, refers to macrophage-dependent and/or neutrophil-dependent killing of cells.

"Lymphoid cells" when used in reference to a cell line or a cell, means that the cell line or cell is derived from the lymphoid lineage. "Lymphoid cells" include cells of the B and the T lymphocyte lineages, and of the macrophage lineage.

Cells, which are "non lymphoid cells and express MHC class II", are cells other than lymphoid cells that express MHC class II molecules, e.g. during a pathological inflammatory response. For example, said cells may include synovial cells, endothelial cells, thyroid stromal cells and glial cells, and it may also comprise genetically altered cells capable of expressing MHC class II molecules.

The terms "apoptosis" and "apoptotic activity" refer to the form of cell death in mammals that is accompanied by one or more characteristic morphological and biochemical features, including nuclear and condensation of cytoplasm, chromatin aggregation, loss of plasma membrane microvilli, partition of cytoplasm and nucleus into membrane bound vesicles (apoptotic bodies) which contain ribosomes, morphologically intact mitochondria and nuclear material, degradation of chromosomal DNA or loss of mitochondrial function. Apoptosis follows a very stringent time course and is executed by caspases, a specific group of proteases. Apoptotic activity can be determined and measured, for instance, by cell viability assays, Annexin V staining or caspase inhibition assays. Apoptosis can be induced using a cross-linking antibody such as anti-CD95 as described in Example H.

As used herein, the term "first domain of the α-chain of HLA-DR" means the N-terminal domain of the alpha-chain of the MHC class II DR molecule.

As used herein, the term "first domain of the β-chain of HLA-DR" means the N-terminal domain of the beta-chain of the MHC class II DR molecule.

The term "innate pre-programmed process" refers to a process that, once it is started, follows an autonomous cascade of mechanisms within a cell, which does not require any further auxiliary support from the environment of said cell in order to complete the process.

As used herein, the term "HuCAL" refers to a fully synthetic human combinatorial antibody library as described in Knappik et al. (2000).

The term "variable region" as used herein in reference to immunoglobulin molecules has the ordinary meaning given to the term by the person of ordinary skill in the act of immunology. Both antibody heavy chains and antibody light chains may be divided into a "variable region" and a "constant region". The point of division between a variable region and a heavy region may readily be determined by the person of ordinary skill in the art by reference to standard texts describing antibody structure, e.g., Kabat et al "Sequences of Proteins of Immunological Interest: 5th Edition" U.S. Department of Health and Human Services, U.S. Government Printing Office (1991).

As used herein, the term "CDR3" refers to the third complementarity-determining region of the VH and VL domains of antibodies or fragments thereof, wherein the VH CDR3 covers positions 95 to 102 (possible insertions after positions 100 listed as 100a to 100z), and VL CDR3 positions 89 to 96 (possible insertions in Vλ after position 95 listed as 95a to 95c) (see Knappik et al., 2000).

As used herein, the term "hybridizes under stringent conditions" is intended to describe conditions for hybridization and washing under which nucleotide sequences at least 60% homologous to each other typically remain hybridized to each other. Preferably, the conditions are such that sequences at least 65%, more preferably at least 70%, and even more preferably at least 75% homologous to each other typically remain hybridized to each other. Such stringent conditions are known to those skilled in the art and can be found in Current Protocols in Molecular Biology, John Wiley & Sons, New York. (1989), 6.3.1-6.3.6. A preferred, non-limiting example of stringent hybridization conditions is hybridization in 6× sodium chloride/sodium citrate (SSC) at about 45° C., followed by one or more washes in 0.2×SSC, 0.1% SDS at 50°-65° C.

The term "immunosuppression" as used herein refers to suppression of immune response resulting from T-cell activation, particularly antigen-mediated T-cell activation. T-cell activation by antigen can be measured by a variety of art-recognized methods. For example, IL-2 secretion by activated T-cells can be used to measure antigen-stimulated T-cell activation. Alternatively, T-cell proliferation as measured by a number of art-recognized methods (such as $^3$H-labeled dNTP incorporation into replicating DNA) can be used to monitor antigen-induced T-cell activation. Immunesuppression of T-cell activation by mAb's or fragments thereof refers to suppression of immune response as measured by any one of the proper methods (such as the ones mentioned above) by at least about 50%, or 60%, more preferably at least about 70% or 80%, most preferably at least about 85% or even 90%, 95%, 99%.

A "protein coding sequence" or a sequence which "encodes" a particular polypeptide or peptide, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eukaryotic mRNA, genomic DNA sequences from procaryotic or eukaryotic DNA, and even synthetic DNA sequences. A transcription termination sequence will usually be located 3' to the coding sequence.

Likewise, "encodes", unless evident from its context, will be meant to include DNA sequences which encode a polypeptide, as the term is typically used, as well as DNA sequences which are transcribed into inhibitory antisense molecules.

As used herein, the term "transfection" means the introduction of a heterologous nucleic acid, e.g., an expression vector, into a recipient cell by nucleic acid-mediated gene transfer. "Transient transfection" refers to cases where exogenous DNA does not integrate into the genome of a transfected cell, e.g., where episomal DNA is transcribed into mRNA and translated into protein. A cell has been "stably transfected" with a nucleic acid construct when the nucleic acid construct is capable of being inherited by daughter cells.

"Expression vector" refers to a replicable DNA construct used to express DNA which encodes the desired protein and which includes a transcriptional unit comprising an assembly of (1) agent(s) having a regulatory role in gene expression, for example, promoters, operators, or enhancers, operatively linked to (2) a DNA sequence encoding a desired protein (such as a polypeptide of the present invention) which is transcribed into mRNA and translated into protein, and (3) appropriate transcription and translation initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

In the expression vectors, regulatory elements controlling transcription or translation can be generally derived from mammalian, microbial, viral or insect genes The ability to replicate in a host, usually conferred by an origin of replication, and a selection gene to facilitate recognition of transformants may additionally be incorporated. Vectors derived from viruses, such as retroviruses, adenoviruses, and the like, may be employed.

"Transcriptional regulatory sequence" is a generic term used throughout the specification to refer to DNA sequences, such as initiation signals, enhancers, and promoters and the like which induce or control transcription of protein coding sequences with which they are operably linked. It will be understood that a recombinant gene can be under the control of transcriptional regulatory sequences which are the same or which are different from those sequences which control transcription of the naturally-occurring form of the gene, if any.

"Operably linked" when describing the relationship between two DNA regions simply means that they are functionally related to each other. For example, a promoter or other transcriptional regulatory sequence is operably linked to a coding sequence if it controls the transcription of the coding sequence.

As used herein, the term "fusion protein" is art recognized and refer to a chimeric protein which is at least initially expressed as single chain protein comprised of amino acid sequences derived from two or more different proteins, e.g., the fusion protein is a gene product of a fusion gene.

As used herein, "proliferating" and "proliferation" refer to cells undergoing mitosis.

The "growth rate" of a cell refers to the rate of proliferation of the cell and the state of differentiation of the cell.

The term "cell-proliferative disorder" denotes malignant as well as nonmalignant populations of transformed cells which morphologically often appear to differ from the surrounding tissue.

As used herein, "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

As used herein, "immortalized cells" refers to cells which have been altered via chemical and/or recombinant means such that the cells have the ability to grow through an indefinite number of divisions in culture.

As used herein the term "animal" refers to mammals, preferably mammals such as humans. Likewise, a "patient" or "subject" to be treated by the method of the invention can mean either a human or non-human animal.

According to the methods of the invention, the peptide may be administered in a pharmaceutically acceptable composition. In general, pharmaceutically-acceptable carriers for monoclonal antibodies, antibody fragments, and peptides are well-known to those of ordinary skill in the art. As used herein, the term "pharmaceutically acceptable carrier" includes any and all solvents, dispersion media, coatings, antibacterial and antifungal agents, isotonic and absorption delaying agents and the like. In preferred embodiments, the subject carrier medium which does not interfere with the effectiveness of the biological activity of the active ingredients and which is not excessively toxic to the hosts of the concentrations of which it is administered. The administration(s) may take place by any suitable technique, including subcutaneous and parenteral administration, preferably parenteral. Examples of parenteral administration include intravenous, intraarterial, intramuscular, and intraperitoneal, with intravenous being preferred.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds, e.g., the subject polypeptides, in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Upon formulation, solutions can be administered in a manner compatible with the dosage formulation and in such amount as is therapeutically effective. The formulations are easily administered in a variety of dosage forms such as injectable solutions, drug release capsules and the like.

As used herein, the term "prophylactic or therapeutic" treatment refers to administration to the host of the medical condition. If it is administered prior to exposure to the condition, the treatment is prophylactic (i.e., it protects the host against tumor formation), whereas if administered after initiation of the disease, the treatment is therapeutic (i.e., it combats the existing tumor).

A multivalent composition of at least one polypeptide according to the invention is capable of causing cell death of activated cells, preferably lymphoid tumor cells without requiring any further additional measures such as chemotherapy and with limited immunogenic side effects on the treated patient. Further, the multivalent composition comprising a polypeptide according to the invention has the capability of binding to at least one epitope on the target antigen, however, several epitope binding sites might be combined in one molecule. Preferably, the multivalent composition comprising a polypeptide according to the invention shows at least 5-fold, or more preferably 10-fold higher killing activity against activated cells compared to non-activated cells. This higher activity on activated cells can be expressed as the at least 5-fold lower $EC_{50}$ value on activated versus non-activated cells or as the higher percentage of killing of activated cells versus non-activated cells when using the same concentration of protein. Under the latter alternative, the multivalent composition comprising a polypeptide according to the invention at a given polypeptide concentration kills at least 50%, preferably at least 80%, of activated cells, whereas the same concentration of a multivalent composition comprising a polypeptide according to the invention under the same incubation conditions kills less than 15%, preferably less than 10% of the non-activated cells. The assay conditions for determining the $EC_{50}$ value and the percentage killing activity are described below.

BRIEF DESCRIPTION OF THE DRAWINGS

FIG. 2 Reactivity of the anti-HLA-DR antibody fragments (MS-GPC-1, 6, 8 and 10, etc.) and IgG forms of MS-GPC-8, MS-GPC-8-10-57, MS-GPC-8-27-41 & MS-GPC-8-6-17 to various cell lines expressing MHC class II molecules. "+" represents strong reactivity as detected using standard immunofluorescence procedure. "+/−" represents weak reactivity and "−" represents no detected reactivity between an anti-HLA-DR antibody fragment or IgG and a particular cell line. Percentage of cells killed by each anti-HLA-DR antibody fragments (scFv) and some of the correponding mAb's in IgG format are also presented. Values greater than 50% are in bold.

Figure 5:
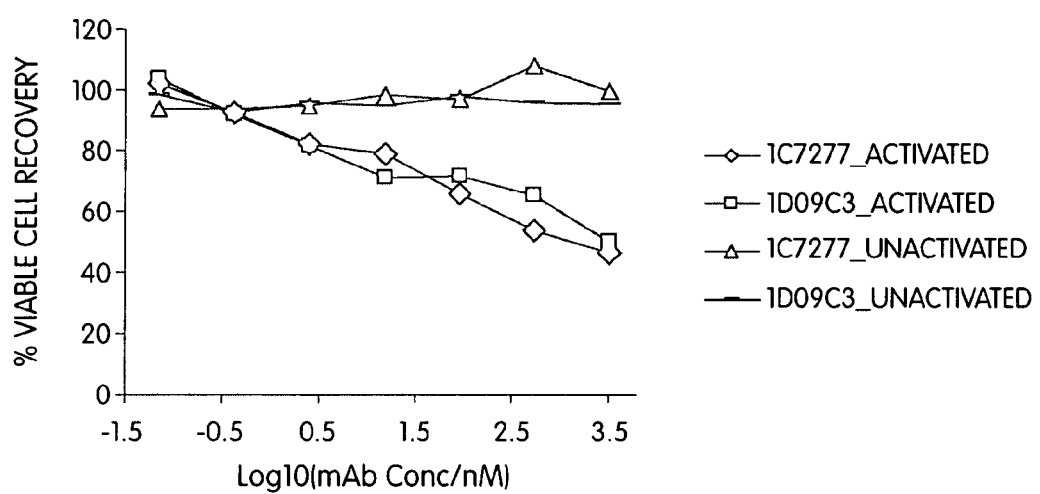

FIG. 5 Killing of activated versus non-activated cells. The lymphoma line MHH-PREB-1 cells are activated with Lipopolysaccharide, Interferon-gamma and phyto-hemagglutin, and subsequently incubated for 4 hr with 0.07 to 3300 nM of the IgG forms of the anti-HLA-DR antibody fragments MS-GPC-8-10-57 and MS-GPC-8-27-41. No loss of viability in the control non-activated MHH-PREB-1 cells is seen. Viable cell recovery is expressed as % of untreated controls.

Figure 6A:
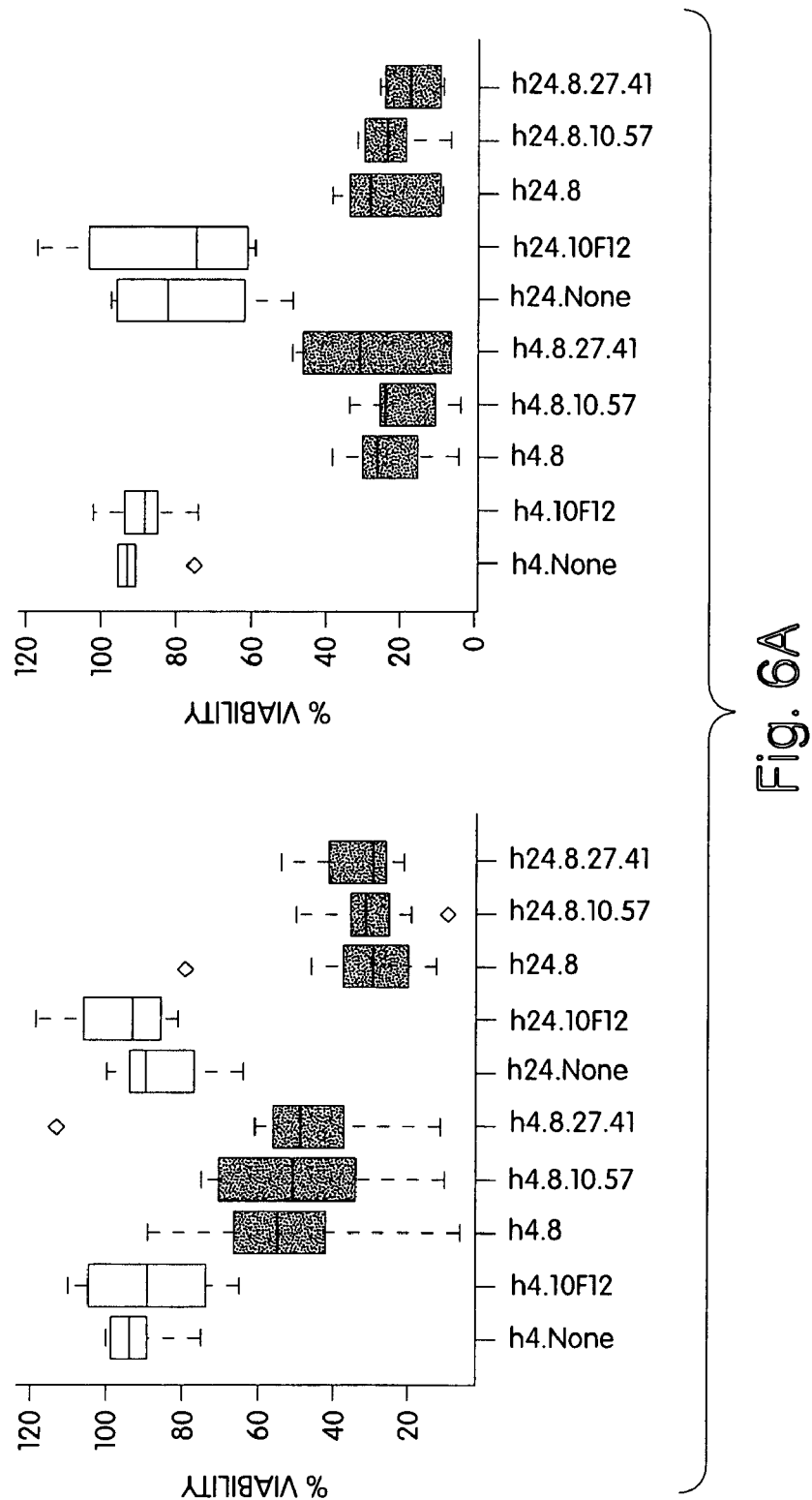
Figure 6B:
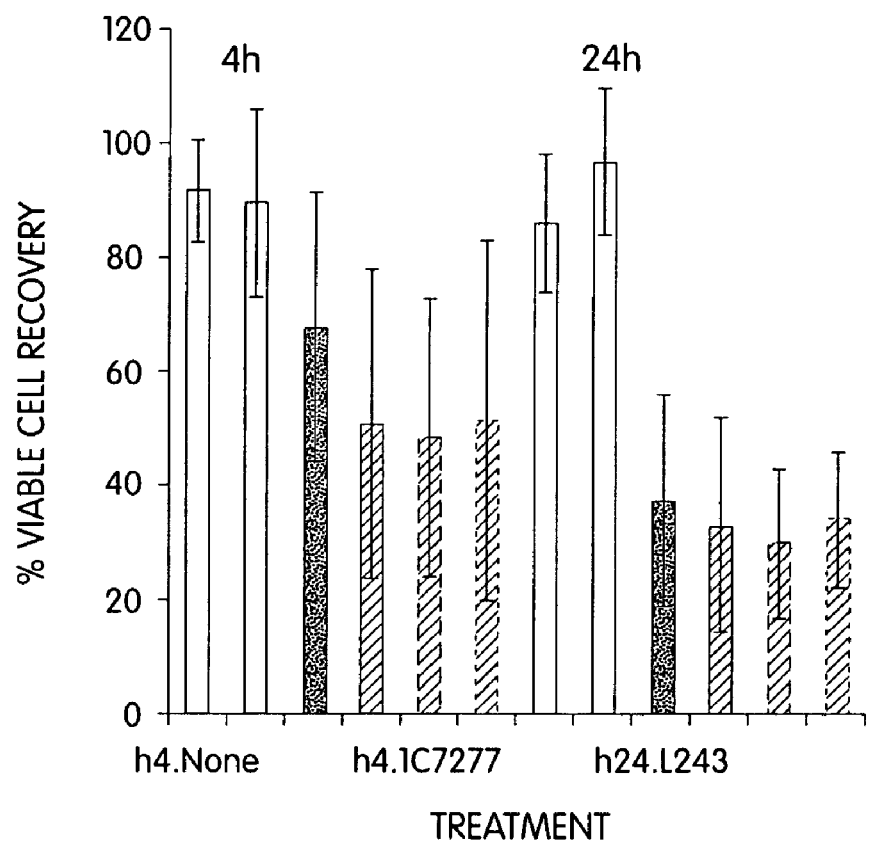

FIG. 6 a) Killing efficiency of control (no antibody, unreactive murine IgG; light grey), and human (MS-GPC-8, MS-GPC-8-10-57 & MS-GPC-8-27-41; dark grey) IgG forms of anti-HLA-DR antibody fragments against CLL cells isolated from patients. Left panel, box-plot display of viability data from 10 patient resting cell cultures against antibodies after incubation for four (h4) and twenty four hours (h24). Right panel box-plot display of viability data from 6 patient activated cell cultures against antibodies after incubation for four (h4) and twenty four hours (h24). b & c) Killing efficiency of human (B8, 1C7277 & 1D09C3) and control murine (L243 & 10F12) anti-DR mAbs against CLL cells isolated from patients. Average % viable cell recovery determined by fluorescence microscopy ±S.D. of CLL cells from 10 patients is shown after 4 h or 24 h incubation with 100 nM of mAbs, compared to unteated cells. All cell samples showed strong DR expression (mean fluorescence intensity 123-865 by FACS analysis using FITC-L243). In 6c, data from activated vs. resting cells are compared.

FIG. 7 Concentration dependent cell viability for certain anti-HLA-DR antibody fragments of the invention. Vertical lines indicate the $EC_{50}$ value estimated by logistic non-linear regression on replica data obtained for each of the antibody fragments. a) Killing curves of cross-linked bivalent anti-HLA-DR antibody F(ab) fragment dimers MS-GPC-10 (circles and solid line), MS-GPC-8 (triangles and dashed line) and MS-GPC-1 (crosses and dotted line). b) Killing curves of cross-linked bivalent anti-HLA-DR antibody (Fab) fragment dimers MS-GPC-8-17 (circles and solid line), and murine IgGs 8D1 (triangles and dashed line) and L243 (crosses and dotted line). c) Killing curves of cross-linked bivalent anti-HLA-DR antibody (Fab) fragment dimers GPC-8-6-2 (crostriangles and dashed line), and murine IgGs 8D1 (circles and solid line) and L243 (crosses and dotted line). d) Killing curves of IgG forms of human anti-HLA-DR antibody fragments MS-GPC-8-10-57 (crosses and dotted line), MS-GPC-8-27-41 (exes and dash-dot line), and murine IgGs 8D1 (circles and solid line) and L243 (triangles and dashed line). All concentrations are given in nM of the bivalent agent (IgG or cross-linked (Fab) dimer).

FIG. 8 Mechanism and selectivity of anti-DR induced cell death. a) Comparison of death induced in PRIESS cells by the Fab fragment of human anti-DR mAb B8 crosslinked with anti-FLAG, and anti-CD95 mAb, respectively. Incubation of PRIESS cells with the anti-HLA-DR antibody fragment MS-GPC-8, cross-linked using the anti-FLAG M2 mAb, shows more rapid killing than a culture of PRIESS cells induced into apoptosis using anti-CD95 mAb. An Annexin V/PI staining technique identifies necrotic cells by Annexin V positive and PI positive staining. b) Comparison of apoptosis induced in PRIESS cells after anti-DR and anti-CD95 mAb treatment. Incubation of PRIESS cells with the anti-HLA-DR antibody fragment MS-GPC-8, cross-linked using the anti-FLAG M2 mAb, shows little evidence of an apoptotic mechanism compared to an apoptotic culture of PRIESS cells induced using anti-CD95 mAb. An Annexin V/PI staining technique identifies apoptotic cells by Annexin V positive and PI negative staining. c) Activated but not resting normal human B cells are killed by anti-DR mAb treatment. B cells isolated from PBL by magnetic sorting (B Cell Isolation Kit, Miltenyi Biotec, Bergisch-Gladbach, Germany) were treated with 50 nM of different mAbs (unactivated), or stimulated with pokeweed mitogen (Gibco BRL) for 3 days (activated) and treated with mAbs subsequently.

FIG. 9 a) Immunosuppressive properties of the IgG forms of the anti-HLA-DR antibody fragments MS-GPC-8-10-57, MS-GPC-8-27-41 & MS-GPC-8-6-13 using an assay to determine inhibition of IL-2 secretion from T-hybridoma cells. b) Immunosuppressive properties of the monovalent Fab forms of the anti-HLA-DR antibody fragments MS-GPC-8-27-41 & MS-GPC-8-6-19 using an assay to determine inhibition of IL-2 secretion from T-hybridoma cells. c) Secretion of IL-2 by T-cell hybridoma Hyb1 is inhibited by human and mouse HLA-DR mAb's. d) T-cell proliferation is inhibited by mouse and human HLA-DR mAb's. e) T-cell proliferation stimulated by specific antigen hen egg lysozyme (HEL) is inhibited by mouse and human HLA-DR mAb's ex vivo. f) T-cell proliferation stimulated by specific antigen ovalbumin (OVA) is inhibited by mouse and human HLA-DR mAb's ex vivo. g) In vivo efficacy of human HLA-DR mAb's using the mouse model of delayed-type-hypersensitivity (DTH) induced by oxazolone (OXA) as measured by ear-thickness. h) Time course of in vivo efficacy of human HLA-DR mAb 1D09C3 in treating the mouse model of delayed-type-hypersensitivity (DTH) induced by dinitroflurobenzene (DNFB) as measured by ear-thickness. i) Dose response of in vivo efficacy of human HLA-DR mAb 1D09C3 in treating the mouse model of delayed-type-hypersensitivity (DTH) induced by dinitrofluorbenzene (DNFB) as measured by ear-thickness.

Figure 10:
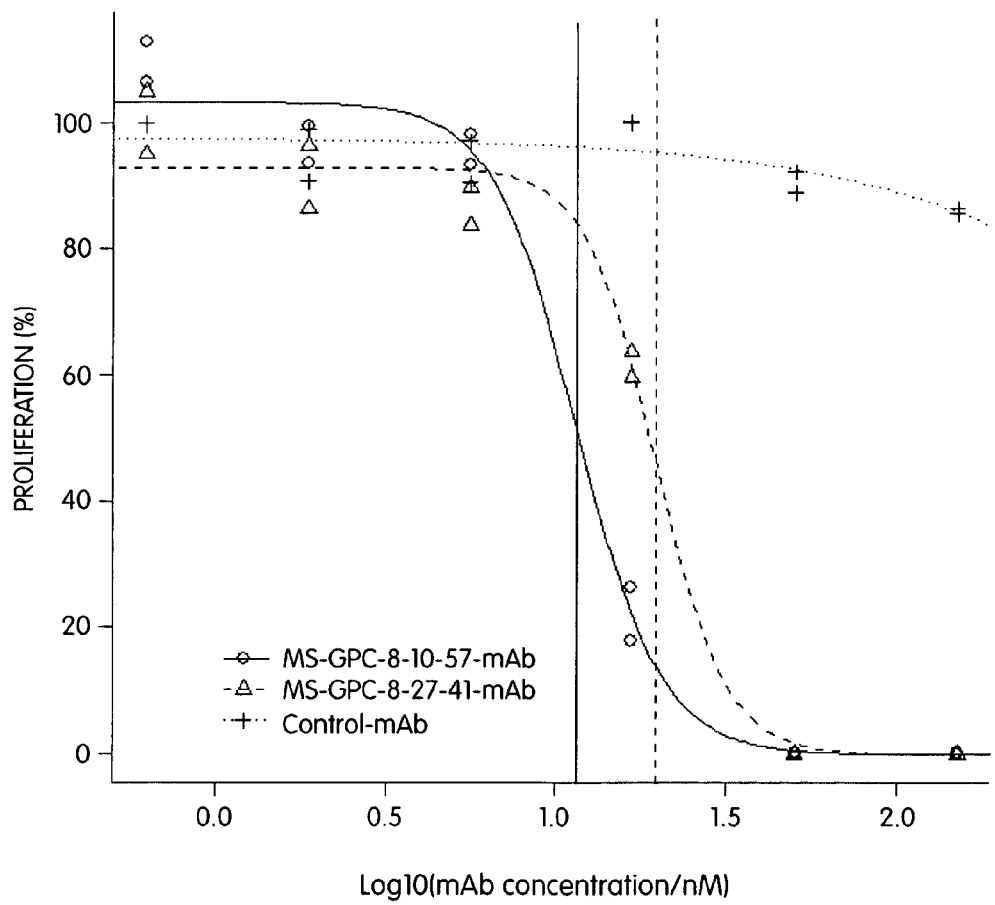

FIG. 10 Immunosuppressive properties of the IgG forms of the anti-HLA-DR antibody fragments MS-GPC-8-10-57 and MS-GPC-8-27-41 in an assay to determine inhibition of T cell proliferation.

Figure 3:
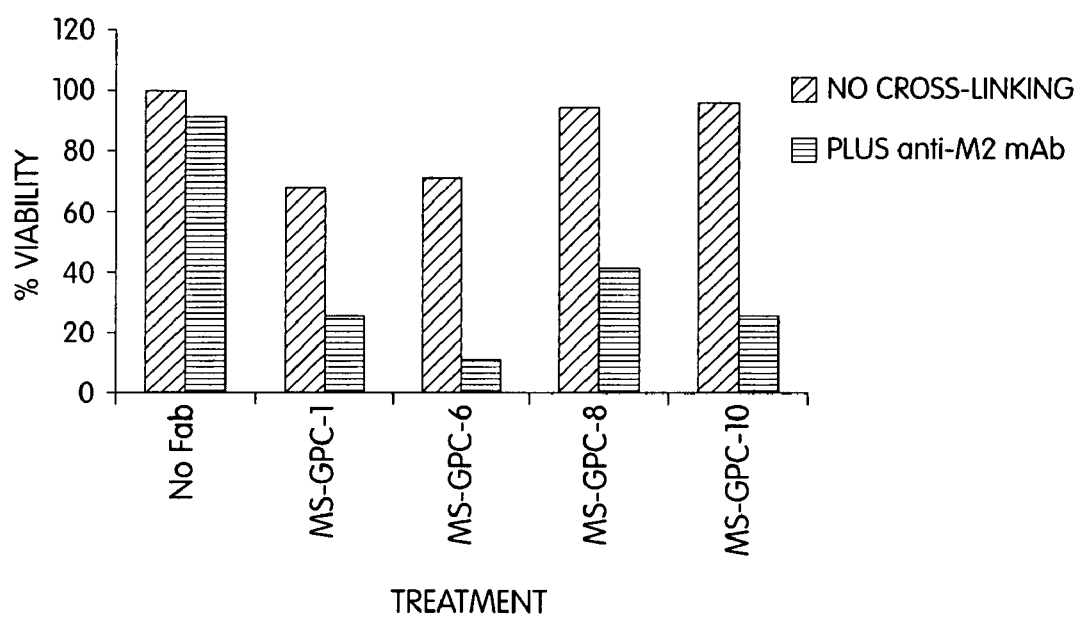
FIG. 3 Viability of tumor cells in the presence of monovalent and cross-linked anti-HLA-DR antibody fragments as assessed by trypan blue staining. Viability of GRANTA-519 cells was assessed after 4 h incubation with anti-HLA-DR antibody fragments (MS-GPC-1, 6, 8 and 10) with and without anti-FLAG M2 mAb as cross-linking agent.
Figure 11:
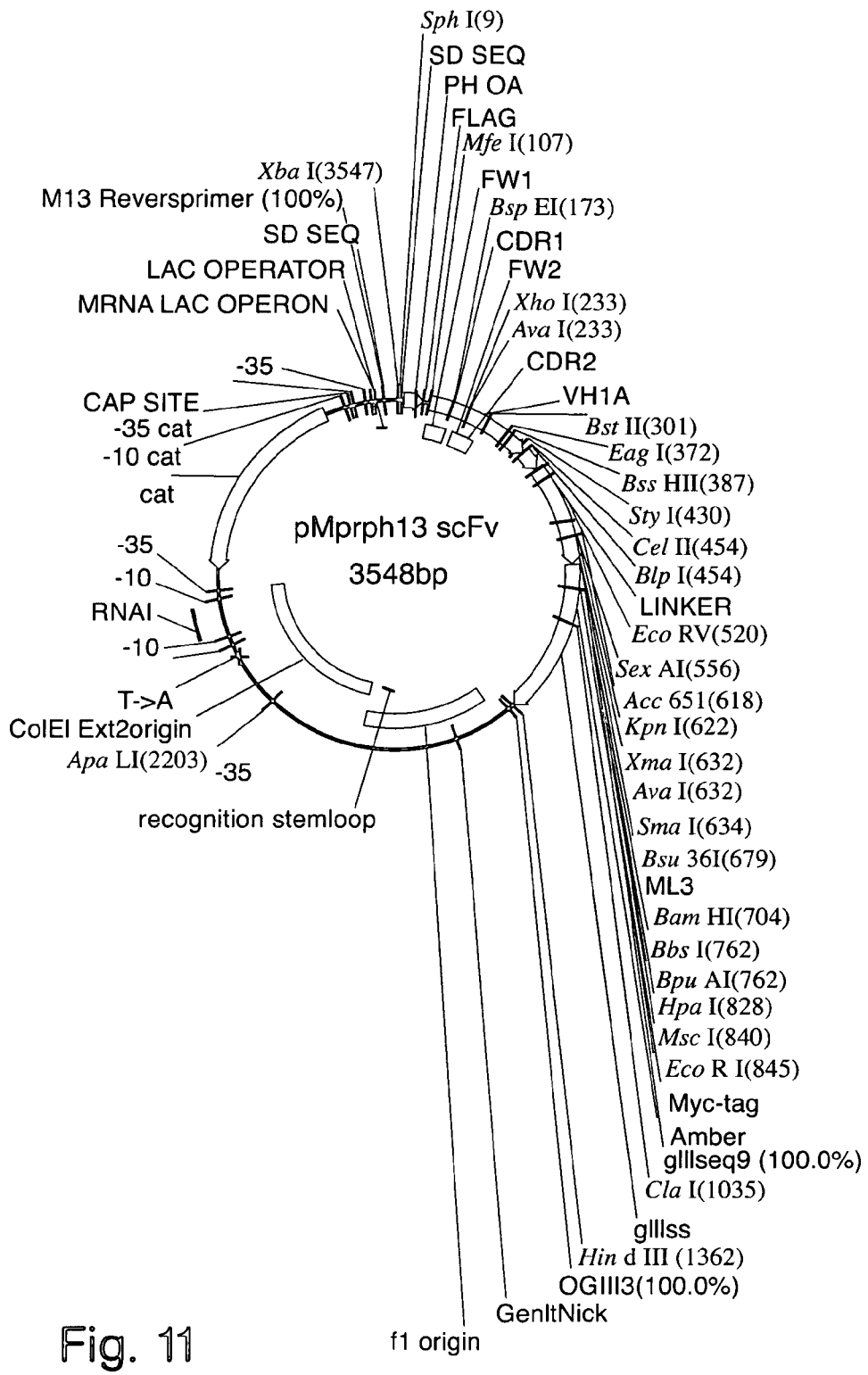

FIG. 11 Vector map and sequence (SEQ ID NO: 33) of scFv phage display vector pMORPH13_scFv. The vector pMORPH13_scFv is a phagemid vector comprising a gene encoding a fusion between the C-terminal domain of the gene III protein of filamentous phage and a HuCAL scFv. In FIG. 11, a vector comprising a model scFv gene (combination of VH1A and Vλ3 (Knappik et al., 2000) is shown. The original HuCAL master genes (Knappik et al. (2000): see FIG. 3 therein) have been constructed with their authentic N-termini: VH1A, VH1B, VH2, VH4 and VH6 with Q (=CAG) as the first amino acid. VH3 and VH5 with E (=GAA) as the first amino acid. Vector pMORPH13_scFv comprises the short FLAG peptide sequence (DYKD SEQ ID NO: 9) fused to the VH chain, and thus all HuCAL VH chains in, and directly derived from, this vector have E (=GAA) at the first position (e.g. in pMx7_FS vector, see FIG. 12).

Figure 12:
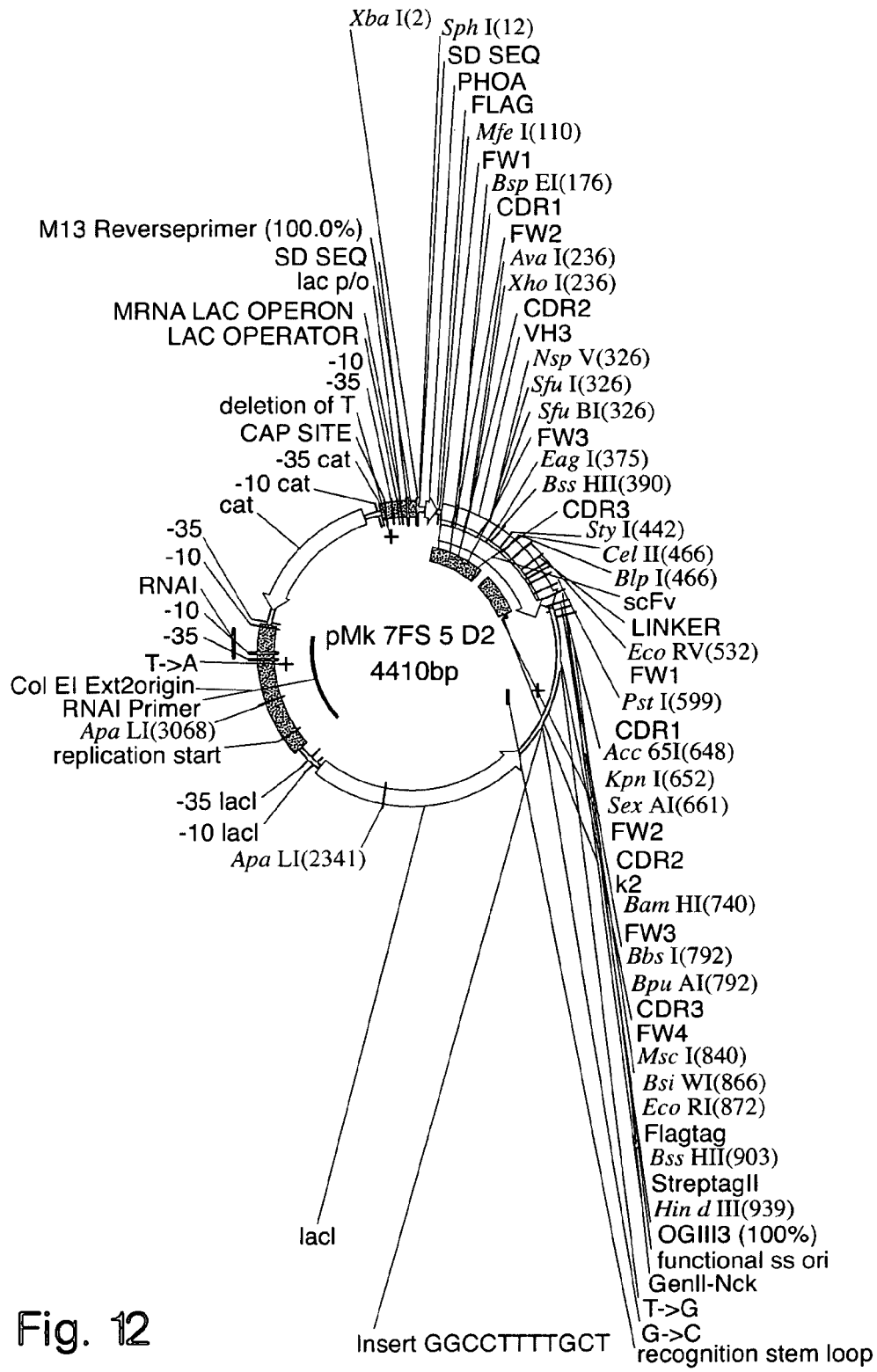

FIG. 12 Vector map and sequence (SEQ ID NO: 34) of scFv expression vector pM×7_FS_5D2. The expression vector pM×7_FS_5D2 leads to the expression of HuCAL scFv fragments (in FIG. 12, the vector comprises a gene encoding a "dummy" antibody fragment called "5D2") when VH-CH1 is fused to a combination of a FLAG tag (Hopp et al., 1988; Knappik and Plückthun, 1994) and a STREP tag II (WSHPQFEK SEQ ID NO: 8) (IBA GmbH, Göttingen, Germany; see: Schmidt and Skerra, 1993; Schmidt and Skerra, 1994; Schmidt et al., 1996; Voss and Skerra, 1997).

Figure 13:
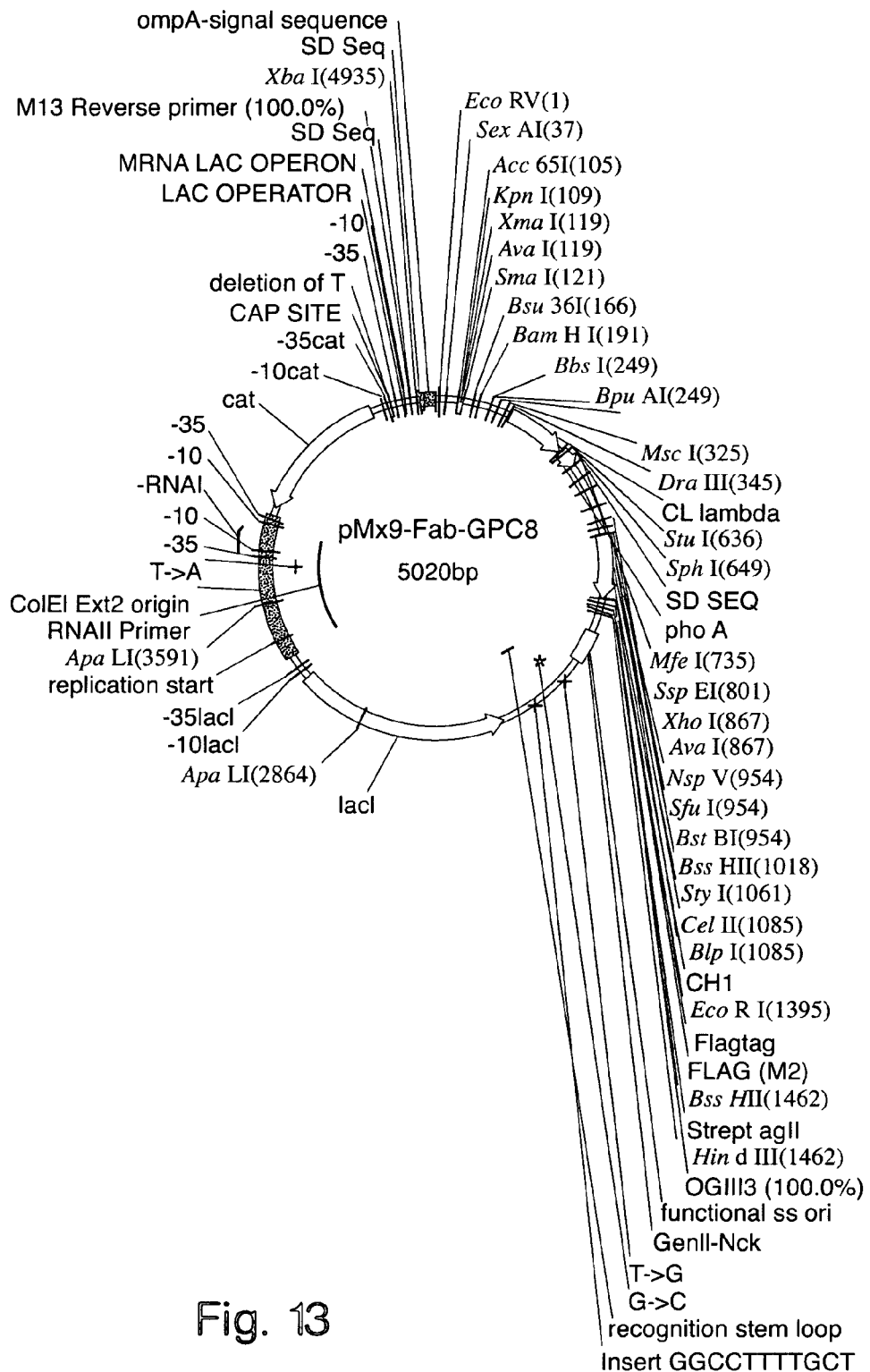
Figure 14:
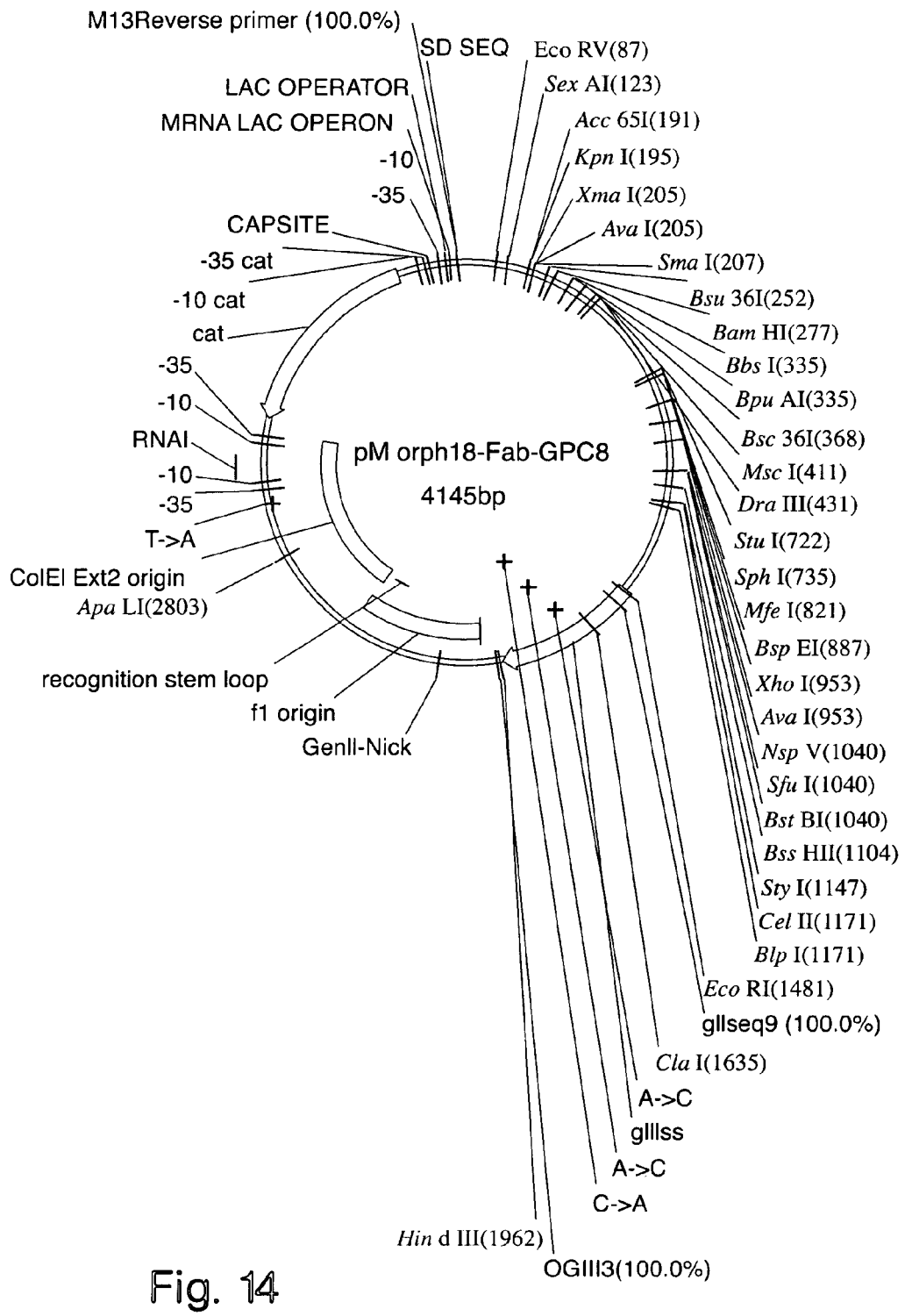

FIG. 13 Vector map and sequence (SEQ ID NO: 35) of Fab expression vector pMx9_Fab_GPC8. The expression vector pMx9_Fab_GPC8 leads to the expression of HuCAL Fab fragments (in FIG. 13, the vector comprises the Fab fragment MS-GPC8) when VH-CH1 is fused to a combination of a FLAG tag (Hopp et at., 1988; Knappik and Plückthun, 1994) and a STREP tag II (WSHPQFEK, SEQ ID No. 8) (IBA GmbH, Göttingen, Germany; see: Schmidt and Skerra, 1993; Schmidt and Skerra, 1994; Schmidt et at., 1996; Voss and Skerra, 1997). In pMx9_Fab vectors, the HuCAL Fab fragments cloned from the scFv fragments (see figure caption of FIG. 11) do not have the short FLAG peptide sequence (DYKD, SEQ ID No. 9) fused to the VH chain, and all HuCAL VH chains in, and directly derived from, that vector have Q (=CAG) at the first position FIG. 14 Vector map and sequence (SEQ ID NO: 36) of Fab phage display vector pMORPH18_Fab_GPC8. The derivatives of vector pMORPH18 are phagemid vectors comprising a gene encoding a fusion between the C-terminal domain of the gene III protein of filamentous phage and the VH-CH1 chain of a HuCAL antibody. Additionally, the vector comprises the separately encoded VL-CL chain. In FIG. 14, a vector comprising the Fab fragment MS-GPC-8 is shown. In pMORPH18_Fab vectors, the HuCAL Fab fragments cloned from the scFv fragments (see figure caption of FIG. 11) do not have the short FLAG peptide sequence (DYKD, SEQ ID No. 9) fused to the VH chain, and all HuCAL VH chains in, and directly derived from, that vector have Q (=CAG) at the first position.

FIG. 15 Amino acid sequences of VH and VL domains of MS-GPC-1 (SEQ ID NOS 37 and 38, respectively), MS-GPC-6 (SEQ ID NOS 39 and 40, respectively), MS-GPC-8 (SEQ ID NOS 41 and 42, respectively), MS-GPC-10 (SEQ ID NOS 43 and 44, respectively), MS-GPC-8-6 (SEQ ID NOS 41 and 46, respectively), MS-GPC-8-10 (SEQ ID NOS 41 and 48, respectively), MS-GPC-8-17 (SEQ ID NOS 41 and 50, respectively), MS-GPC-8-27 (SEQ ID NOS 41 and 52, respectively), MS-GPC-8-6-13 (SEQ ID NOS 41 and 54, respectively), MS-GPC-8-10-57 (SEQ ID NOS 41 and 56, respectively), MS-GPC-8-27-41 (SEQ ID NOS 41 and 58, respectively), MS-GPC-8-1 (SEQ ID NOS 41 and 28, respectively), MS-GPC-8-9 (SEQ ID NOS 41 and 31, respectively), MS-GPC-8-18 (SEQ ID NOS 41 and 32, respectively), MS-GPC-8-6-2 (SEQ ID NOS 41 and 45, respectively), MS-GPC-8-6-19 (SEQ ID NOS 41 and 47, respectively), MS-GPC-8-6-27 (SEQ ID NOS 41 and 49, respectively), MS-GPC-8-6-45 (SEQ ID NOS 41 and 51, respectively), MS-GPC-8-6-47 (SEQ ID NOS 41 and 53, respectively), MS-GPC-8-27-7 (SEQ ID NOS 41 and 55, respectively), and MS-GPC-8-27-10 (SEQ ID NOS 41 and 57, respectively). The sequences in FIG. 15 show amino acid 1 of VH as constructed in the original HuCAL master genes (Knappik et al. (2000): see FIG. 3 therein). In scFv constructs, as described in this application, amino acid 1 of VH is always E (see figure caption of FIG. 11), in Fab constructs as described in this application, amino acid 1 of VH is always Q (see figure caption of FIG. 13).

FIG. 16. FIGS. 16A-E show the in vivo effect of the human anti-DR mAb 1D09C3 in lymphoma xenograft models.

Figure 16A:
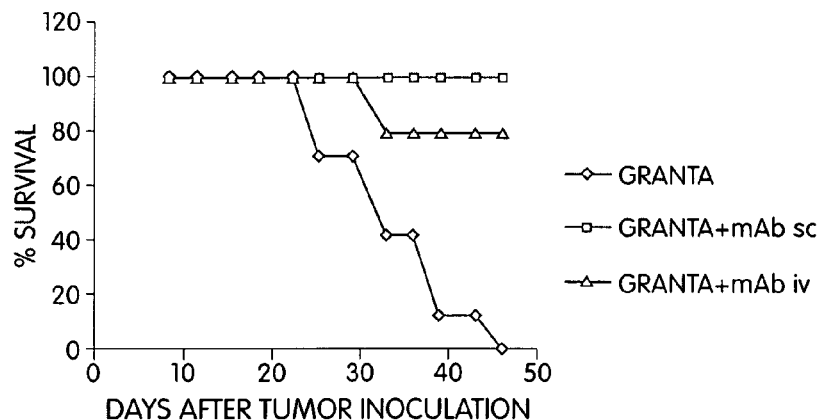

FIG. 16A shows survival of SCID mice injected s.c. with the non-Hodgkin lymphoma line GRANTA-519. MAb dose was 3×1 mg/mouse given on days 5, 7, and 9. Seven mice in the control and five in each mAb treated group.

Figure 16B:
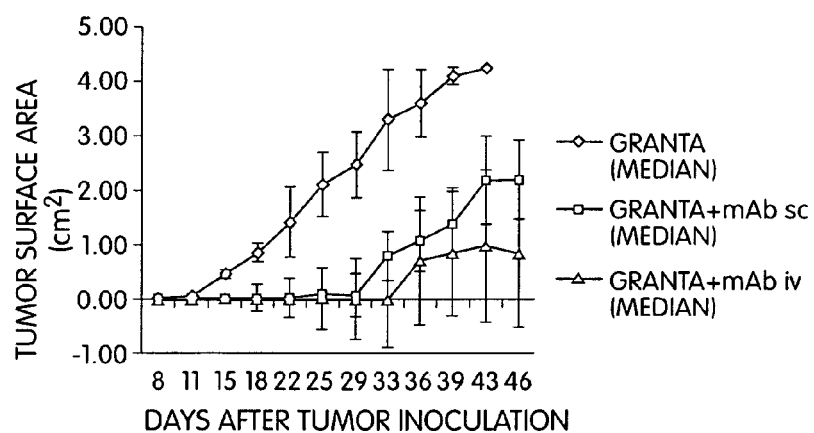

FIG. 16B shows the effect of mAb on subcutaneous tumor growth. Same experiment as in FIG. 16A.

Figure 16C:
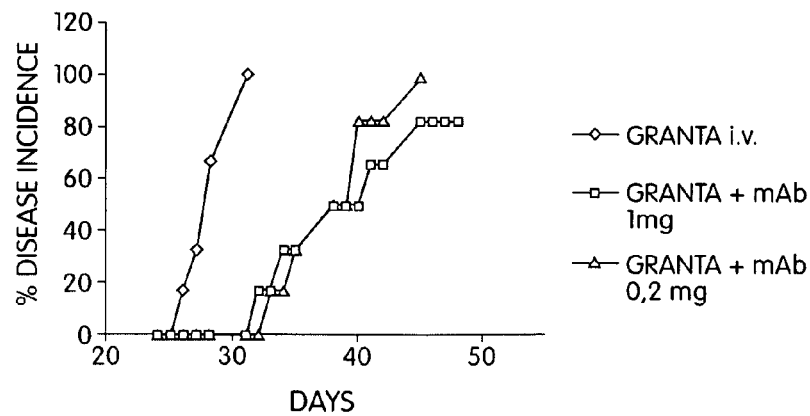

FIG. 16C shows the effect of mAb on disease incidence in SCID mice injected i.v. with GRANTA-519. MAb was administered i.v., 3× as above. Six mice were in each group.

Figure 16D:

FIG. 16D shows representative tumor size in untreated mice.

Figure 16E:

FIG. 16E shows representative tumor size in mice treated with mAb.

DETAILED DESCRIPTION OF THE INVENTION

The following examples illustrate the invention.

EXAMPLES

All buffers, solutions or procedures without explicit reference can be found in standard textbooks, for example Current Protocols of ImLmunology (1997 and 1999) or Sambrook et al., 1989. Where not given otherwise, all materials were purchased from Sigma, Deisenhofen, Del., or Merck, Darmstadt, Del., or sources are given in the literature cited. Hybridoma cell lines LB3.1 and L243 were obtained from LGC Reference Materials, Middlesex, UK; data on antibody 8D1 were generously supplied by Dr. Matyas Sandor, University of Michigan, Madison, Wis., USA.

1. Preparation of a Human Antigen

To demonstrate that we could identify cytotoxic antigen-binding domains of human composition, we first prepared a purified form of a human antigen, the human MHC class II DR protein (DRA*0101/DRB1*0401) from the DR-homozygous B-lymphoblastoid line PRIESS cells (Gorga et al., 1984; Gorga et al., 1986; Gorga et al., 1987; Stern et al., 1992) and the human-mouse chimeric molecule DR-I$^E$ from the transfectant M12.C3.25 (Ito et al., J. Exp. Med. 183:2635-2644, 1996) by using standard methods of affinity purification (Gorga et al., 1984) as follows.

First, PRIESS cells (ECACC, Salisbury UK) were cultured in RPMI and 10% fetal calf serum (FCS) using standard conditions, and 1010 cells were lysed in 200 ml phosphate buffered saline (PBS) (pH 7.5) containing 1% NP-40 (BDH, Poole, UK), 25 mM iodoacetamide, 1 mM phenylmethylsulfonylfluoride (PMSF) and 10 mg/L each of the protease inhibitors chymostatin, antipain, pepstatin A, soybean trypsin inhibitor and leupeptin. The lysate was centrifuged at 10,000×g (30 minutes, 4° C.) and the resulting supernatant was supplemented with 40 ml of an aqueous solution containing 5% sodium deoxycholate, 5 mM iodoacetamide and 10 mg/L each of the above protease inhibitors and centrifuged at 100,000×g for two hours (4° C.). To remove material that bound non-specifically and endogenous antibodies, the resulting supernatant was made 0.2 mM with PMSF and passed overnight (4° C.) through a rabbit serum affigel-10 column (5 ml; for preparation, rabbit serum (Charles River, Wilmington, Mass., USA) was incubated with Affigel 10 (BioRad, Munich, Del.) at a volume ratio of 3:1 and washed following manufacturer's directions) followed by a Protein G Sepharose Fast Flow column (2 ml; Pharmacia) using a flow rate of 0.2 ml/min.

Second, the pre-treated lysate was batch incubated with 5 ml Protein G Sepharose Fast Flow beads coupled to the murine anti-HLA-DR antibody LB3.1 (obtained by Protein G-Sepharose FF (Pharmacia) affinity chromatography of a supernatant of hybridoma cell line LB3.1) (Stern et al., 1993) overnight at 4° C. using gentle mixing, and then transferred into a small column which was then washed extensively with three solutions: (1) 100 ml of a solution consisting of 50 mM Tris/HCl (pH 8.0), 150 mM NaCl, 0.5% NP-40, 0.5% sodium deoxycholate, 10% glycerol and 0.03% sodium azide at a flow rate of 0.6 ml/min). (2) 25 ml of a solution consisting of 50 mM Tris/HCl (pH 9.0), 0.5 M NaCl, 0.5% NP-40, 0.5% sodium deoxycholate, 10% glycerol and 0.03% sodium azide at a flow rate of 0.9 ml/min; (3) 25 ml of a solution consisting of 2 mM Tris/HCl (pH 8.0), 1% octyl-β-D-glucopyranoside, 10% glycerol and 0.03% sodium azide at a flow rate of 0.9 ml/min.

Third, MHC class II DR protein (DRA*0101/DRB1*0401) was eluted using 15 ml of a solution consisting of 50 mM diethylamine/HCl (pH 11.5), 150 mM NaCl, 1 mM EDTA, 1 mM EGTA, 1% octyl-β-D-glucopyranoside (Alexis Corp., Lausen, CH), 10% glycerol, 10 mM iodoacetamide and 0.03% sodium azide at a flow rate of 0.4 ml/min. 800 µl fractions were immediately neutralised with 100 µl 1M Tris/HCl (pH 6.8), 150 mM NaCl and 1% octyl-β-D-glucopyranoside. The incubation of the lysate with LB3.1-Protein G Sepharose Fast Flow beads was repeated until the lysate was exhausted of MHC protein. Pure eluted fractions of the MHC class II DR protein (as analyzed by SDS-PAGE) were pooled and concentrated to 1.0-1.3 g/L using Vivaspin concentrators (Greiner, Solingen, Del.) with a 30 kDa molecular weight cut-off. Approximately 1 mg of the MHC class II DR preparation was re-buffered with PBS containing 1% octyl-β-D-glucopyranoside using the same Vivaspin concentrator to enable direct coupling of the protein to BIAcore CM5 chips.

2. Screening of HuCAL

2.1. Introduction

Since the important biological activities of anti-DR mAbs, e.g., inhibition of CD4 T cell—antigen presenting cell (APC) interaction and tumoricide activity are associated with specificity for the first, N-terminal domains of DR molecules (Vidovic', D. et al., 1995, *Eur. J. Immunol.* 25:3349-3355), we used purified DR molecules as well as human-murine chimeric MHC-II molecules (DR first domains grafted onto a murine class II molecule, see Ito, K. et al., 1996, *J. Exp. Med.* 183:2635-2644) for screeining the Human Combinatorial Antibody Library (HuCAL®) by alternating whole cell panning with protein solid-phase-panning.

We identified certain antigen binding antibody fragments (in this case, scFvs) of human composition (MS-GPC-1/scFv-17, MS-GP-6/scFv-8A, MS-GPC-8/scFv-B8, MS-GPC-10/scFv-E6, etc., see FIGS. 1 and 2) against the human antigen (DRA*0101/DRB1*0401) from a human antibody library based on a novel concept that has been recently developed (Knappik et al., 2000). A consensus framework resulting in a total of 49 different frameworks here represents each of the VH- and VL-subfamilies frequently used in human immune responses. These master genes were designed to take into account and eliminate unfavorable residues promoting protein aggregation as well as to create unique restriction sites leading to modular composition of the genes. In HuCAL-ScFv, both the VH- and VL-CDR3 encoding regions of the 49 master genes were randomized.

2.2. Phagemid Rescue, Phage Amplification and Purification

The HuCAL-scFv (Knappik et al., 2000) library, cloned into a phagemid-based phage display vector pMORPH13_scFv (see FIG. 11), in *E. coli* TG-1 was amplified in 2×TY medium containing 34 µg/ml chlorarnphenicol and 1% glucose (2×TY-CG). After helper phage infection (VCSM13) at 37° C. at an $OD_{600}$ of about 0.5, centrifugation and resuspension in 2×TY/34 µg/ml chloramphenicol/50 µg/ml kanamycin/0.1 mM IPTG, cells were grown overnight at 30° C. Phage were PEG-precipitated from the supernatant (Ausubel et al., 1998), resuspended in PBS/20% glycerol and stored at −80° C. Phage amplification between two panning rounds was conducted as follows: mid-log phase TG1-cells were infected with eluted phage and plated onto LB-agar supplemented with 1% of glucose and 34 µg/ml of chloramphenicol. After overnight incubation at 30° C. colonies were scraped off, adjusted to an $OD_{600}$ of 0.5 and helper phage added as described above.

2.3. Manual Solid Phase Panning

Wells of MaxiSorp™ microtiterplates (Nunc, Roskilde, DK) were coated with MHC-class II DRA*0101/DRB1*0401 (prepared as above) dissolved in PBS (2 µg/well). After blocking with 5% non-fat dried milk in PBS, $1$-$5 \times 10^{12}$ HuCAL-scFv phage purified as above were added for 1 h at 20° C. After several washing steps, bound phages were eluted by pH-elution with 100 mM triethylamine and subsequent neutralization with 1 M Tris-Cl pH 7.0. Three rounds of panning were performed with phage amplification conducted between each round as described above.

2.4. Mixed Solid Phase/whole Cell Panning

Three rounds of panning and phage amplification were performed as described in 2.3. and 2.2. with the exception that in the second round between $1 \times 10^7$ and $5 \times 10^7$ PRIESS cells in 1 ml PBS/10% FCS were used in 10 ml Falcon tubes for whole cell panning. After incubation for 1 h at 20° C. with the phage preparation, the cell suspension was centrifuged (2,000 rpm for 3 min) to remove non-binding phage, the cells were washed three times with 10 ml PBS, each time followed by centrifugation as described. Phage that specifically bound to the cells were eluted off by pH-elution using 100 mM HCl. Alternatively, binding phage could be amplified by directly adding *E. coli* to the suspension after triethlyamine treatment (100 mM) and subsequent neutralization.

2.5 Identification of HLA-DR Binding scFv Fragments

Clones obtained after three rounds of solid phase panning (2.3) or mixed solid phase/whole cell panning (2.4) were screened by FACS analysis on PRIESS cells for binding to HLA-DR on the cell surface. For expression, the scFv fragments were cloned via XbaI/EcoRI into pMx7_FS as expression vector (see FIG. 12). Expression conditions are shown below in example 3.2

Aliquots of $10^6$ PRIESS cells were transferred at 4° C. into wells of a 96-well microtiterplate. ScFv in blocking buffer (PBS/5% FCS) were added for 60 min and detected using an anti-FLAG M2 antibody (Kodak) (1:5000 dilution) followed by a polyclonal goat anti-mouse IgG antibody-R-Phycoerythrin-conjugate (Jackson ImmunoResearch, West Grove, Pa., USA, Cat. No. 115-116-146, F(ab')$_2$ fragment) (1:200 dilution). Cells were fixed in 4% paraformaldehyde for storage at 4° C. $10^4$ events were collected for each assay on the FACS-Calibur (BD Immunocytometry Systems, San Jose, Calif., USA).

Only fifteen out of over 500 putative binders were identified which specifically bound to PRIESS cells. Twelve scFv-s also bound to the chimeric MHC-II molecule, but showed no reactivity to either I-E$^d$ (the murine part of chimeric MHC-II27), or unrelated proteins, such as lysozyme, transferrin, bovine serum albumine and human gamma globuline (FIG. 1), indicating that they were specific for the first domains of DR molecules. Some of these clones were further analysed for their immunomodulatory ability and for their killing activity as described below. Table 1 contains the sequence characteristics of clones MS-GPC-1 (scFv-17), MS-GPC-6 (scFv-8A), MS-GPC-8 (scFv-B8) and MS-GPC-10 (scFv-E6) identified thereby. The VH and VL families and the CDR3s listed refer to the HuCAL consensus-based antibody genes as described (Knappik et al., 2000); the sequences of the VH and VL CDRs are shown in Table 1, and the full sequences of the VH and VL domains are shorn in FIG. 15.

The fine specificity of scFv-s was tested on a panel of DR-homozygous typing cells, and MHC-II transfectants. Ten of 12 scFv-s reacted with all major allelic froms of DR represented in the cell panel (DR1 through 14), and 4 of 12 recognized additional MHC-II molecules (DRw52 and w53, DP and DQ molecules; FIG. 2). Thus, these antibodies potentially could be used widely as therapeutic agents across human populations virtually irrespective of polymorphic differences in MHC-II molecules. Most importantly, four of the 12 hits exhibited strong tumor killing activity, when cross-linked with anti-tag antibody (see FIG. 2, in bold). The monovalent fragments were not tumoricidal, corresponding to previous observations (Vidovic', D. et al., 1995, *Eur. J. Immunol.* 25:3349-3355).

3. Generation of Fab-fragments 3.1. Conversion of scFv to Fab

Since the tumoricidal hits had modest affinities ($K_d$-s ranging from 346 nM to 81 μM in single chain Fv (scFv) format), they were subjected to "in vitro affinity maturation". The parental scFv-s were first converted into Fab format that is less prone to aggregation and hence should give more reliable $K_{off}$ values.

The Fab-fragment antigen binding polypeptides MS-GPC-1-Fab/17-Fab, MS-GP-6-Fab/8A-Fab, MS-GPC-8-Fab/B8-Fab and MS-GPC-10-Fab/E6-Fab were generated from their corresponding scFv fragments as follows. Both heavy and light chain variable domains of scFv fragments were cloned into pMx9_Fab (FIG. 13), the heavy chain variable domains as MfeI/StyI-fragments, the variable domains of the kappa light chains as EcoRV/BsiWI-fragments. The lambda chains were first amplified from the corresponding pMORPH13_scFv vector as template with PCR-primers CRT5 (5' primer) and CRT6 (3' primer), wherein CRT6 introduces a unique DraIII restriction endonuclease site.

CRT5 (SEQ ID No.10):

5'GTGGTGGTTCCGATATC 3'

CRT6 (SEQ ID No.11):

5'AGCGTCACACTCGGTGCGGCTTTCGGCTGGCCAAGAACGGGTTA 3'

The PCR product is cut with EcoRV/DraIII and cloned into pMx9_Fab (see FIG. 13). The Fab light chains could be detected with a polyclonal goat anti-human IgG antibody-R-Phycoerythrin-conjugate (Jackson ImmunoResearch, West Grove, Pa., USA, Cat. No. 109-116-088, F(ab')$_2$ fragment) (1:200 dilution).

3.2. Expression and Purification of HuCAL-antibody Fragments in *E. coli*

Expression in *E. coli* cells (JM83) of scFv and Fab fragments from pMx7_FS or pMx9_Fab, respectively, were carried out in one liter of 2×TY-medium supplemented with 34 μg/ml chloramphenicol. After induction with 0.5 mM IPTG (scFv) or 0.1 mM IPTG (Fab), cells were grown at 22° C. for 12 hours. Cell pellets were lysed in a French Press (Thermo Spectronic, Rochester, N.Y., USA) in 20 mM sodium phosphate, 0.5 M NaCl, and 10 mM imidazole (pH 7.4). Cell debris was removed by centrifugation and the clear supernatant filtered through 0.2 μm pores before subjecting it to STREP tag purification using a Streptactin matrix and purification conditions according to the supplier (IBA GmbH, Göttingen, Germany). Purification by size exclusion chromatography (SEC) was performed as described by Rheinnecker et al. (1996). The apparent molecular weights were determined by SEC with calibration standards and confirmed in some instances by coupled liquid chromatography-mass spectrometry (TopLab GmbH, Martinsried, Germany).

4. Optimization of Antibody Fragments

In order to optimize certain biological characteristics of the HLA-DR binding antibody fragments, one of the Fab fragments, MS-GPC-8-Fab/B8-Fab, was used to construct a library of Fab antibody fragments by replacing the parental VLλ1 chain by the pool of all lambda chains λ 1-3 randomized in CDR3 from the HuCAL library (Knappik et al., 2000).

In the first round of optimization, both H-CDR2- and L-CDR3-sequences of clones MS-GPC-1/scFv-17, MS-GPC-6/scFv-8A, MS-GPC-8/scFv-B8 and MS-GPC-10/scFv-E6 were randomized by substituting the parental sequence with randomized TRIM®-based oligonucleotide-cassettes (Virnekäs et al., 1994) leading to four different libraries with $7.6 \times 10^6$ to $1.0 \times 10^7$ primary transformants.

For generation of H-CDR2 and L-CDR1-libraries: Tri-nucleotide-containing oligonucleotides starting from O-methyl trinucleotide phosphoramidites (Virnekäs 1994) were synthesized as described (Knappik et al., 2000). The VH2-CDR2-design comprised an olionucleotide encoding for 16 amino acids which was randomized with up to 19 different amino acids (all except for cystein) at the following positions (from N- to C-terminus; amino acid-diversity and ratios in % are given in parentheses): position-1 (19), -2 (40% V/20% D, F, N), -3 (40% V/20% D, V, N), -4 (19), -5 (19), -6 (D), -7 (19), -8 (K), -9 (19), -10 (Y), -11 (70% S/30% G), -12 (50% P/50% T), -13 (S), -14 (L), -15 (K), -16 (S). For the L-CDR1 of the lambda-1-framework two different oligonucleotides (termed as a and b) were designed to encode: a) position-1 (S), -2 (G), -3 (S), -4 (19), -5 (S), -6 (80% N/10% D, K), -7 (I), -8 (G), -9 (19), -10 (19), -11 (19), -12 (V), -13 (19); b) position 1 (50% S, T), -2 (G), -3 (S), -4 (80% S/20% N), -5 (S), 6 (N), -7 (1), -8 (G), -9 (19), -10 (19), -11 (19), -12 (19), -13 (V), -14 (19). The oligonucleotide for the CDR1 of lambda-2 framework was designed to encode: position-1 (19), -2 (G), -3 (S), -4 (89% S/20% T), -5 (S), -6 (D), -7 (80% V, 20% 1), -8 (G), ) -9 (19), -10 (Y), -11 (19), -12 (19), -13 (V), -14 (19). For framwork lambda 3 the following CDR1-design was made: position-1 (33% G, Q, S), -2 (G), -3 (50% D, N), -4 (19), -5 (50% L, I), -6 (33% G, P, R), -7 (19), -8 (19), -9 (19), -10 (50% A, V), -11 (19). All cassettes were introduced into a promoter-less derivative of pMorph4 (Pack et al., in preparation). For all subsequent affinity-maturations the respective H-CDR2 or L-CDR1-cassettes were derived from those plasmids using the respective flanking restriction-nuclease sites as described (Knappik et al., 2000). Prior to cloning of different libraries for affinity maturation all parental scFv were converted into the Fab-format following the standard conversion protocol (Krebs et al., 2001) for the modular HuCAL-library. Based on each of the 4 parental Fabs 17, 8A, B8 and E6 (all H2 lambdal) a sub-library was constructed exhibiting a repertoire of different L-CDR3- and H-CDR2-cassettes. First cloning step included the subsitution of the parental XbaI/DraIII-fragment of Fabs 17, B8, and E6 by a mix of corresponding fragments of all 3 V lambda consensus-genes encoding a repertoire of $5.7 \times 10^6$ different L-CDR3 cassettes. Library-sizes for all 3 parental clones were in the range of 5.1 m-$6.0 \times 10^6$ transformants. These libraries were then used to introduce different H-CDR2-library cassettes via substitution of the XhoI/EagI-fragments. Final library sizes resulted in up to $1.2 \times 10^7$ transformants including 78% correct clones based on DNA-sequence analyis. In case of 8A the LCDR3 optimization was performed by exchanging the parental XbaI/BsiWI-fragment for the corresponding HuCAL-scFv kappa3 sublibrary fragments. As before, this library was then used to insert different HCDR2-cassettes via the Xho/BssHII-fragment. Library sizes were in the range of $1.7 \times 10^6$ cfu after L-CDR3- and $1.0 \times 10^7$ cfu after H-CDR2-cassette insertion including at least 65% correct clones according to DNA-sequence analysis. A fifth library has been constructed based on a consensus-sequence within H-CDR3 of binders 17, B8 and E6. For this purpose parental Fab B8 has been chosen to randomize several positions within H-CDR3 by insertion of a synthetic TRIM-oligonucleotide comprising the following H-CDR3-design from N— to C-terminus: position 1 (all =all exept C), -2 (all), -3 (all), -4 (25% of Y/W/F/H), -4 (R), -5 (G), -6 (50% G/A), -7 (50% F/L), -8 (all). Final library size was in the range of $6.8 \times 10^6$ different transformants comprising 63% correct clones after sequence analysis.

L-CDR1-libraries were generated based on a pool of 20 different Fab-clones derived from the combined light-chain- and H-CDR2-based-optimization. Equimolar amounts of vector DNA from each parental clone was mixed after removal of the EcoRV/BpuAI-insert and religated by insertion of the corresponding fragments encoding a repertoire of different L-CDR1-cassettes. Final library-sizes were in the range of $4.2 \times 10^8$ cfu.

Since clones 17, B8 and E6 exhibited a consensus-motif in H-CDR3, a fifth library was constructed based on the parental clone B8, in which several H-CDR3 positions were randomized while keeping the consensus motif constant. The latter library termed B8M gave rise to $6.8 \times 10^6$ initial transformants. All libraries were subjected to either two rounds of standard solid-phase panning on purified DR, or a solid phase and a whole cell panning.

Several panning-parameters including decreasing amounts of antigen (500 ng and 250 ng/well purified protein, see Schier et al., 1996a and 1996b), or increasing concentrations of $NH_4SCN$ (50 mM, 250 mM, 500 mM in PBS) (Hall and Heckel 1988; MacDonald 1988; Goldblatt 1993; Ferreira & Katzin 1995), or increasing the numbers of wash-cycles (Chen 1999; Low 1996) were applied in the second panning-round to enhance panning-stringency and hence the probability of selecting high affinity Fabs. Phage-antibodies derived from the first round of a manual solid-phase-panning on 250 and 500 ng/well purified HLA-protein, respecitvely, were pooled and used for the second panning round on either 12 ng/well purified protein according to a standard protocol (Krebs et al., 2001), or on 250 ng coated antigen in combination with an additional 30 min incubation-step of different amounts of ammonium-isothiocyanate (50 mM, 250 mM, 500 mM and in PBS) inbetween the standard wash-protocol (5×TBST short and 5×TBST for 5 min at room temperature) and the elution step (100 mM glycine-HCl/500 mM NaCl, pH 2.2). Alternatively, the second panning round was performed on different amounts of PRIESS-cells ranging from $10^1$-$10^5$ cells/well according to a standard whole-cell-panning-protocol (Krebs et al., 2001). Fab-clones for $K_{off}$ rankings were selected only from those panning wells which prior to and after treatment show a significant drop in phage-titer and thus indicating a maximum in bound phages at the highest panning-stringency.

For example, the Fab fragment MS-GPC-8-Fab/B8-Fab (see 3.1) was cloned via XbaI/EcoRI from pMx9_Fab_GPC-8 into pMORPH18_Fab, a phagemid-based vector for phage display of Fab fragments, to generate pMORPH18_Fab_GPC-8 (see FIG. 14). A lambda chain pool comprising a unique DraIII restriction endonuclease site (Knappik et al., 2000) was cloned into pMORPH18_Fab GPC-8 cut with NsiI and DraIII (see vector map of pMORPH18_Fab_GPC-8 in FIG. 14).

The resulting Fab optimization library was screened by two rounds of panning against MHC-class II DRA*0101/DRB1*0401 (prepared as above) as described in 2.3 with the exception that in the second round the antigen concentration for coating was decreased to 12 ng/well. FACS identified optimized clones as described above in 2.5.

Finally, 12 Fabs with improved $K_{off}$ values were selected from the B8, B8M and 8A libraries. The best clone identified (MS-GPC-8-17/7BA) had a $K_d$ of about 58 nM, corresponding to a 5-fold affinity improvement compared to the best unoptimized clone MS-GPC-8/B8 (Table 3e). Libraries 17, E6 and 8A did not yield many clones with improved $K_{off}$ values. Binders selected from the B8 library showed different L-CDR3-sequences, but all maintained the parental H-CDR2-sequence (Knappik et al., 2000), suggesting that the latter is critical for antibody-antigen interaction. For further affinity-improvement, we focussed on binders from the B8 and B8M library.

Seven of these clones, MS-GPC-8-1, MS-GPC-8-6, MS-GPC-8-9, MS-GPC-8-10, MS-GPC-8-17/7BA, MS-GPC-8-18 and MS-GPC-8-27, were further characterized and showed cell killing activity as found for the starting fragment MS-GPC-8/B8. Table 1 contains the sequence characteristics of MS-GPC-8-1, MS-GPC-8-6, MS-GPC-8-9, MS-GPC-8-10, MS-GPC-8-17/7BA, MS-GPC-8-18 and MS-GPC-8-27. The VH and VL families and the CDR3s listed refer to the HuCAL consensus-based antibody genes as described (Knappik et al., 2000). The full sequences of the VH and VL domains of MS-GPC-8-6, MS-GPC-8-10, MS-GPC-8-17/7BA and MS-GPC-8-27 are shown in FIG. 15.

The optimized Fab forms of the anti-HLA-DR antibody fragments MS-GPC-8-6 and MS-GPC-8-17 showed improved characteristics over the starting MS-GPC-8/B8. For example, the $EC_{50}$ of the optimized antibodies was 15-20 and 5-20 nM (compared to 20-40 nM for MS-GPC-8/B8, where the concentration is given as the concentration of the bivalent cross-linked Fab dimer), and the maximum capacity to kill MHH-Call 4 cells determined as 76 and 78% for MS-GPC-8-6 and MS-GPC-8-17 (compared to 65% for MS-GPC-8) respectively.

In the second round, L-CDR1-optimization is performed. The L-CDR1 library was generated from a pool of the 20 best Fab clones, of which 16 (including 7BA) derived from the L-CDR3 optimization and 4 from the H-CDR3 optimzation. To force off-rate selection, prolonged wash cycles and competing antigen were applied to the pool-library.

Specifically, the VL CDR1 regions of a set of anti-HLA-DR antibody fragments derived from MS-GPC-8/B8 (including MS-GPC-8-10 and MS-GPC-8-27) were optimized by cassette mutagenesis using trinucleotide-directed mutagenesis (Virnekäs et al., 1994). In brief, a Vλ1 CDR1 library cassette was synthesized containing six randomized positions (total variability: $7.43 \times 10^6$), and was cloned into a Vλ1 framework. The CDR1 library was digested with EcoRV and BbsI, and the fragment comprising the CDR1 library ligated into the lambda light chains of the MS-GPC-8-derived Fab antibody fragments in pMORPH18_Fab (as described above), digested with EcoRV and BbsI. The resulting library was screened as described above.

The pool-library was subjected to two rounds of standard manual solid-phase panning using decreasing amounts of antigen (250 ng and 7.5 ng/well purified protein) or increasing concentrations of $NH_4SCN$ (100 mM, 500 mM and 2500 mM), using either 2-fold serial dilutions of purified HLA-protein between 250 ng and 7.5 ng/well, or alternatively, constant amounts of 250 ng/well of protein in combination with an additional 30 min incubation step of different amounts of ammonium-isothiocyanate (100 mM, 500 mM and 2500 mM) between the standard wash-protocol and the elution step. In order to enforce off-rate-selection an additional manual solid-phase-panning of 3 selection rounds was performed with the pool-library using 250 ng/well of coated HLA-protein in combination with longer washes (starting from 6×30 min in the first up to 24×30 min in the $3^{rd}$ panning-round) and including different amounts of competing antigen (from 20 nM up to 500 nM) in the wash-buffer.

This strategy yielded Fabs with affinities of ~3 nM (Table 3e). Ten clones were identified as above by binding specifically to HLA-DR (MS-GPC-8-6-2, MS-GPC-8-6-19, MS-GPC-8-6-27, MS-GPC-8-6-45, MS-GPC-8-6-13/305D3, MS-GPC-8-6-47, MS-GPC-8-10-57/1C7277, MS-GPC-8-27-7, MS-GPC-8-27-10 & MS-GPC-8-27-41/1D09C3) and showed cell killing activity as found for the starting fragments MS-GPC-8, MS-GPC-8-10 and MS-GPC-8-27. Table 1 contains the sequence characteristics of MS-GPC-8-6-2, MS-GPC-8-6-19, MS-GPC-8-6-27, MS-GPC-8-6-45, MS-GPC-8-6-13, MS-GPC-8-6-47, MS-GPC-8-10-57, MS-GPC-8-27-7, MS-GPC-8-27-10 & MS-GPC-8-27-41. The VH and VL families and the CDR3s listed refer to the HuCAL consensus-based antibody genes as described (Knappik et al., 2000), the full sequences of the VH and VL domains of MS-GPC-8-6-13, MS-GPC-8-10-57 and MS-GPC-8-27-41 are shown in FIG. 15.

From these 10 clones, four Fab fragments were chosen (MS-GPC-8-6-2, MS-GPC-8-6-13/305D3, MS-GPC-8-10-57, C7277 and MS-GPC-8-27-41/1D09C3) as demonstrating significantly improved $EC_{50}$ of cell killing as described in example 10. Table 1 shows the sequences of clones optimised at the CDR1 region.

Optimisation procedures not only increased the biological efficacy of anti-HLA-DR antibody fragments generated by the optimisation process, but a physical characteristic—affinity of the antibody fragment to HLA-DR protein—was also substantially improved. For example, the affinity of Fab forms of MS-GPC-8/B8 and its optimised descendents was measured using a surface plasmon resonance instrument (Biacore, Upsala Sweden) according to example 7. The affinity of the MS-GPC-8/B8 parental Fab was improved over 100 fold from 346 nM to ~60 nM after VL CDR3 optimisation and further improved to single digit nanomolar affinity (range 3-9 nM) after VL CDR3+1 optimisation (Table 2).

5. Generation of IgG 5.1 Construction of HuCAL-immunoglobulin Expression Vectors Three Fabs (305D3, 1D09C3, and 1C7277) obtained above were converted into $IgG_4$ format, expressed and purified for affinity determination (see below). All 3 $IgG_4$ mAbs exhibited sub-nanomolar affinities (0.3-0.6 nM; Table 3e), and retained their specificity (FIG. 2).

Heavy chains were cloned as follows. The multiple cloning site of pcDNA3.1+ (Invitrogen) was removed (NheI/ApaI), and a stuffer compatible with the restriction sites used for HuCAL-design was inserted for the ligation of the leader sequences (NheI/EcoRI), VH-domains (EcoRI/BlpI) and the immunoglobulin constant regions (BlpI/ApaI). The leader sequence (EMBL M83133) was equipped with a Kozak sequence (Kozak, 1987). The constant regions of human $IgG_1$ (PIR J00228), $IgG_4$ (EMBL K01316) and serum $IgA_1$ (EMBL J00220) were dissected into overlapping oligonucleotides with lengths of about 70 bases. Silent mutations were introduced to remove restriction sites non-compatible with the HuCAL-design. The oligonucleotides were spliced by overlap extension-PCR.

Light chains were cloned as follows. The multiple cloning site of pcDNA3.1/Zeo+ (Invitrogen) was replaced by two different stuffers. The κ-stuffer provided restriction sites for insertion of a κ-leader (NheI/EcoRV), HuCAL-scFv Vκ-domains (EcoRV/BsiWI) and the κ-chain constant region (BsiWI/ApaI). The corresponding restriction sites in the λ-stuffer were NheI/EcoRV (λ-leader), EcoRV/HpaI (Vλ-domains) and HpaI/ApaI (λ-chain constant region). The κ-leader (EMBL Z00022) as well as the λ-leader (EMBL L27692) were both equipped with Kozak sequences. The constant regions of the human κ-(EMBL J00241) and λ-chain (EMBL M18645) were assembled by overlap extension-PCR as described above.

5.2 Generation of IgG-Expressing CHO-cells

All cells were maintained at 37° C. in a humidified atmosphere with 5% $CO_2$ in media recommended by the supplier. CHO-K1 (CRL-9618) were from ATCC and were co-transfected with an equimolar mixture of IgG heavy and light chain expression vectors. Double-resistant transfectants were selected with 600 μg/ml $G_{418}$ and 300 μg/ml Zeocin (Invitrogen) followed by limiting dilution The supernatant of single clones was assessed for IgG expression by capture-ELISA. Positive clones were expanded in RPMI-1640 medium supplemented with 10% ultra-low IgG-FCS (Life Technologies). After adjusting the pH of the supernatant to 8.0 and sterile filtration, the solution was subjected to standard protein A column chromatography (Poros 20A, PE Biosystems).

The IgG forms of anti-HLA-DR antigen binding domains show improved characteristics over the antibody fragments. These improved characteristics include affinity (Example 7) and killing efficiency (Examples 9, 10 and 14).

6. HLA-DR Specificity Assay and Epitope Mapping

To demonstrate that antigen-binding domains selected from the HuCAL library bound specifically to a binding site on the N-terminal domain of human MHCII receptor largely conserved between alleles and hitherto unknown in the context of cell killing by receptor cross linking, we undertook an assessment of their binding specificity, and it was attempted to characterise the binding epitope.

The Fab antibody fragments MS-GPC-8-27-7, MS-GPC-8-27-10, MS-GPC-8-6-13, MS-GPC-8-27-41/1D09C3, MS-GPC-8-6-47, MS-GPC-8-10-57 11C7277, MS-GPC-8-6-27, MS-GPC-8/B8 and MS-GPC-8-6 showed specificity of binding to HLA-DR protein but not to non-HLA-DR proteins. Fab fragments selected from the HuCAL library were tested for reactivity with the following antigens: HLA-DR protein (DRA*0101/DRB1*0401; prepared as example 1, and a set of unrelated non-HLA-DR proteins consisting of BSA, testosterone-BSA, lysozyme and human apotransferrin. An empty well (Plastic) was used as negative control. Coating of the antigen MHCII was performed over night at 1 μg/well in PBS (Nunc-MaxiSorp TM) whereas for the other antigens (BSA, Testosterone-BSA, Lysozyme, Apotransferrin) 10 μg/well was used. Next day wells were blocked in 5% non-fat milk for 1 hr followed by incubation of the respective antibodies (anti-MHCII-Fabs and an unrelated Fab (MacI-8A)) at 100 ng/well for 1 hour. After washing in PBS the anti-human IgG F(ab')$_2$-peroxidase-conjugate at a 1:10,000 dilution in TBS (supplemented with 5% w/v non-fat drymilk/0.05% v/v Tween 20) was added to each well for 1 h. Final washes were carried out in PBS followed the addition the substrate POD (Roche). Color-development was read at 370 nM in an ELISA-Reader.

Figure 1B:
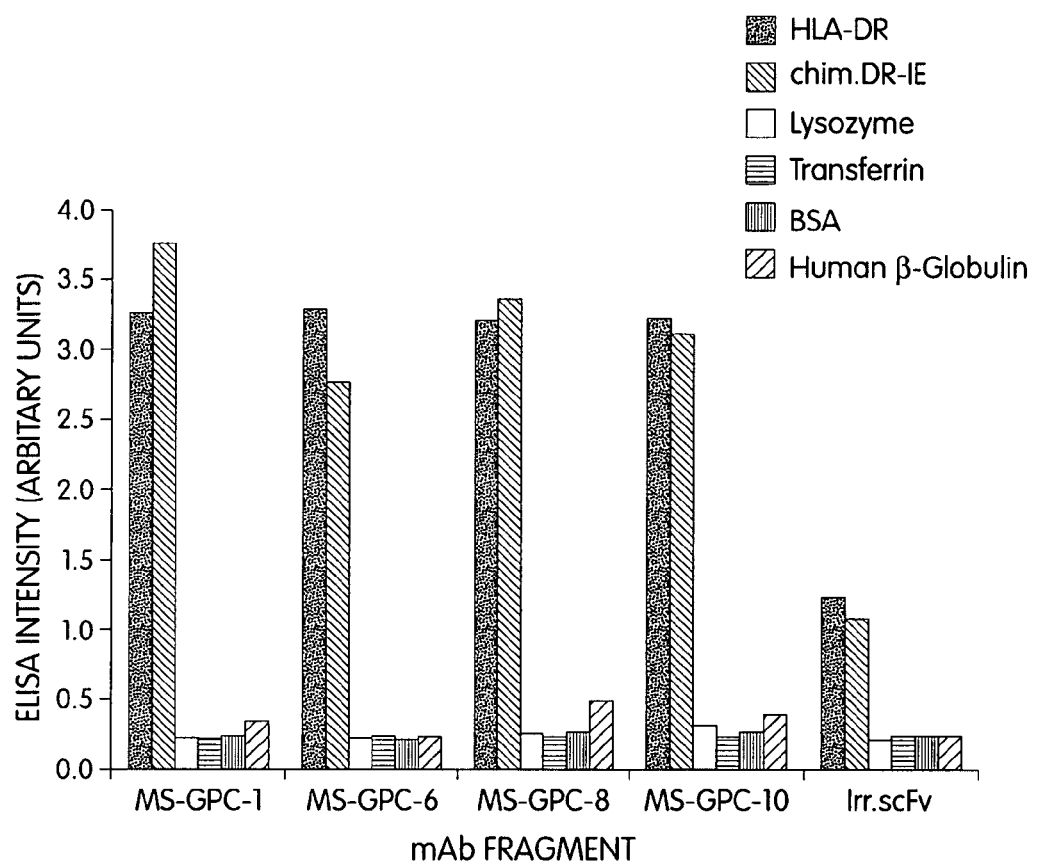
FIG. 1 a) Specificity of the anti-HLA-DR antibody fragments: Binding of MS-GPC-8-27-7, MS-GPC-8-27-10, MS-GPC-8-6-13, MS-GPC-8-27-41, MS-GPC-8-6-47, MS-GPC-8-10-57, MS-GPC-8-6-27, MS-GPC-8 and MS-GPC-8-6 to HLA-DR protein, negative control proteins (BSA, testosterone-BSA, lysozyme and human apotransferrin), and an empty microtiter plate well (plastic). Specificity was assessed using standard ELISA procedures. b) Specificity of the anti-HLA-DR antibody fragments MS-GPC-1, 6, 8 & 10 isolated from the HuCAL library to HLA-DR protein, a mouse-human chimeric HLA protein and negative control proteins (lysozyme, transferrin, BSA and human β-globulin). Specificity was assessed using standard ELISA procedures. A non-related antibody fragment (irr. scFv) was used as control. c) Specificity of anto-HLA-DR antibody fragments (scFv) and some of the corresponding mAb's in IgG format against a panel of human or mousr HLA-DR antigens and unrelated control antigens.

All anti-HLA-DR antibody fragments MS-GPC-8-27-7, MS-GPC-8-27-10, MS-GPC-8-6-13, MS-GPC-8-27-41, MS-GPC-8-6-47, MS-GPC-8-10-57, MS-GPC-8-6-27, MS-GPC-8 and MS-GPC-8-6 demonstrated high specificity for HLA-DR, as evidenced by the much higher mean fluorescence intensity resulting from incubation of these antibody fragments with HLA-DR derived antigens compared to controls (FIG. 1a). In a similar experiment, the Fab fragments MS-GPC-1, MS-GPC-6, MS-GPC-8 and MS-GPC-10 were found to bind to both the DRA*0101/DRB1*0401 (preparaed as above) as well as to a chimeric DR-IE consisting of the N-terminal domains of DRA*0101 and DRB1*0401 with the remaining molecule derived from a murine class II homologue IEd (Ito et al., 1996) (FIG. 1b).

To demonstrate the broad-DR reactivity of anti-HLA-DR antibody fragments and IgGs of the invention, the scFv forms of MS-GPC-1, 6, 8 and 10, and IgG forms of MS-GPC-8, MS-GPC-8-10-57, MS-GPC-8-27-51 & MS-GPC-8-6-13 were tested for reactivity against a panel of Epstein-Barr virus transformed B cell lines obtained from ECACC (Salisbury UK), each homozygous for one of the most frequent DR alleles in human populations (list of cell lines and alleles shown in FIG. 2). The antibody fragments were also tested for reactivity against a series of L cells transfected to express human class II isotypes other than DRB1: L105.1, L257.6, L25.4, L256.12 & L21.3 that express the molecules DRB3*0101, DRB4*0101, DPO103/0402, DP 0202/0201, and DQ0201/0602 respectively (Klohe et al., 1988).

Reactivity of an antigen-binding fragment to the panel of cell-lines expressing various MHC— class II molecules was demonstrated using an immunofluorescence procedure as for example, described by Otten et al (1997). Staining was performed on $2 \times 10^5$ cells using an anti-FLAG M2 antibody as the second reagent against the M2 tag carried by each anti-HLA-DR antibody fragment and a fluorescein labelled goat anti-mouse Ig (BD Pharmingen, Torrey Pine, Calif., USA) as a staining reagent. Cells were incubated at 4° C. for 60 min with a concentration of 200 nM of the anti-HLA-DR antibody fragment, followed by the second and third antibody at concentrations determined by the manufacturers. For the IgG form, the second antibody was omitted and the IgG detected using a FITC-labeled mouse anti-human IgG$_4$ (Serotec, Oxford, UK). Cells were washed between incubation steps. Finally the cells were washed and subjected to analysis using a FACS Calibur (BD Immunocytometry Systems, San Jose, Calif., USA).

FIG. 2 shows that the scFv-fragments MS-GPC-1, 6, 8 and 10, and IgG forms of MS-GPC-8, MS-GPC-8-10-57, MS-GPC-8-27-51 & MS-GPC-8-6-13 react with all DRB1 all o types tested. This observation taken together with the observation that all anti-HLA-DR antibody fragments react with chimeric DR-IE, suggests that all selected anti-HLA-DR antibody fragments recognize the extracellular first domain of the monomorphic DRα chain or a monomorphic epitope on extracellular first domain of the DRβ chain.

We then attempted to localize the binding domains of MS-GPC-8-10-57 and MS-GPC-8-27-41 further by examining competitive binding with murine antibodies for which the binding domains on HLA-DR are known. The murine antibodies L243 and LB3.1 are known to bind to the α1 domain, 1-1C4 and 8D1 to the β1 domain and 10F12 to the β2 domain (Vidovic et al. 1995b). To this end, an assay was developed wherein a DR-expressing cell line (LG-2) was at first incubated with the IgG$_4$ forms of MS-GPC-8-10-57 or MS-GPC-8-27-41, the Fab form of MS-GPC-8-10-57 or the Fab form of GPC 8, and an unrelated control antibody. Subsequently murine antibodies were added and the murine antibodies were detected. If the binding site of MS-GPC-8-10-57 or MS-GPC-8-27-41 overlaps with the binding of a murine antibody, then a reduced detection of the murine antibody is expected.

Binding of the IgG$_4$ forms of GPC-8-27-41 and MS-GPC-8-10-57 and the Fab form of MS-GPC-8-10-57 substantially inhibited (mean fluorescence intensity reduced by >90%) the binding of 1-1C4 and 8D1, whereas L243, LB3.1 and 10F12 and a control were only marginally affected. The Fab form of MS-GPC-8 reduced binding of 1-1C4 by ~50% (mean fluorescence dropped from 244 to 118), abolished 8D1 binding and only marginally affected binding of L243, LB3.1 and 10F12 or the control. An unrelated control antibody had no effect on either binding. Thus, MS-GPC-8-10-57 and MS-GPC-8-27-41 seem to recognise a β1 domain epitope that is highly conserved among allelic HLA-DR molecules.

The whole staining procedure was performed on ice. $1 \times 10^7$ cells of the human B-lymphoblastoid cell line LG-2 was preblocked for 20 min. in PBS containing 2% FCS and 35 μg/ml Guinea Pig IgG ("FACS-Buffer"). These cells were divided into 3 equal parts A, B, and C of approximately $3.3 \times 10^6$ cells each, and it was added to A) 35 μg MS-GPC-8-10-57 or MS-GPC-8-27-41 IgG$_4$, to B) 35 μg MS-GPC-8-10-57 Fab or MS-GPC-8 Fab, and to C) 35 μg of an unrelated IgG$_4$ antibody as negative control, respectively, and incubated for 90 min. Subsequently A, B, C were divided in 6 equal parts each containing $5.5 \times 10^5$ cells, and 2 μg of the following murine antibodies were added each to one vial and incubated for 30 min: 1) purified mIgG; 2) L243; 3) LB3.1; 4) 1-1 C4; 5) 8D1; 6) 10F12. Subsequently, 4 ml of PBS were added to each vial, the vials were centrifuged at 300×g for 8 min, and the cell pellet resuspended in 50 μl FACS buffer containing a 1 to 25 dilution of a goat-anti-murine Ig-FITC conjugate at 20 μg/ml final concentration (BD Pharmingen, Torrey Pines, Calif., USA). Cells were incubated light-protected for 30 min. Afterwards, cells were washed with 4 ml PBS, centrifuged as above and resuspended in 500 μl PBS for analysis in the flow cytometer (FACS Calibur, BD Immunocytometry Systems, San Jose, Calif., USA).

The PepSpot technique (U.S. Pat. No. 6,040,423; Heiskanen et al., 1999) is used to further identify the binding epitope for MS-GPC 8-10-57. Briefly, an array of 73 overlapping 15-mer peptides is synthesised on a cellulose membrane by a solid phase peptide synthesis spotting method (WO 00/12575). These peptide sequences are derived from the sequence of the α1 and β1 domains of HLA-DR4Dw14, HLA-DRA1*0101 (residues 1-81) and HLA-DRB1*0401 (residues 2-92), respectively, and overlap by two amino acids. Second, such an array is soaked in 0.1% Tween-20/PBS (PBS-T), blocked with 5% BSA in PBS-T for 3 hours at room temperature and subsequently washed three times with PBS-T. Third, the prepared array is incubated for 90 minutes at room temperature with 50 ml of a 5 mg/l solution of the IgG form of GPC-8-10-57 in 1% BSA/PBS-T. Fourth, after binding, the membrane is washed three times with PBS-T and subsequently incubated for 1 hour at room temperature with a goat anti-human light chain antibody conjugated to horseradish peroxidase diluted 1/5,000 in 1% BSA/PBS-T. Finally, the membrane is washed three times with PBS-T and any binding determined using chemiluminescence detection on X-ray film. As a control for unspecific binding of the goat anti-human light chain antibody, the peptide array is stripped by the following separate washings each at room temperature for 30 min: PBS-T (2 times), water, DMF, water, an aequeous solution containing 8 M urea, 1% SDS, 0.5% DTT, a solution of 50% ethanol, 10% acetic acid in water (3 times each) and, finally, methanol (2 times). The membrane is again blocked, washed, incubated with goat anti-human 1 light chain antibody conjugated to horseradish peroxidase and developed as described above.

7. Affinity of Anti-HLA-DR Antibody and Antibody Fragments

In order to demonstrate the superior binding properties of anti-HLA antibody fragments of the invention, we measured their binding affinities to the human MHC class II DR protein (DRA*0101/DRB1*0401) using standard equipment employing plasmon resonance principles. Surprisingly, we achieved affinities in the sub-nanomolar range for IgG forms of certain anti-HLA-DR antibody fragments of the invention. For example, the affinity of the IgG forms of MS-GPC-8-27-41, MS-GPC-8-6-13 & MS-GPC-8-10-57 was measured as 0.3, 0.5 and 0.6 nM respectively (Table 3a). Also, we observed high affinities in the range of 2-8 nM for Fab fragments affinity matured at the CDR1 and CDR3 light chain regions (Table 3b). Fab fragments affinity matured at only the CDR3 light chain region showed affinities in the range of 40 to 100 nM (Table 3c), and even Fab fragments of non-optimised HuCAL antigen binding domains showed affinities in the sub µM range (Table 3d). Only a moderate increase in $K_{on}$ (2-fold) was observed following CDR3 optimisation ($K_{on}$ remained approximately constant throughout the antibody optimization process in the order of $1\times10^5$ $M^{-1}$ $s^{-1}$), whilst a significant decrease in $K_{off}$ was a surprising feature of the optimisation process—sub $100$ $s^{-1}$, sub $10$ $s^{-1}$, sub $1$ $s^{-1}$ and sub $0.1$ $s^{-1}$ for the unoptimised Fabs, CDR3 optimised Fabs, CDR3/CDR1 optimised Fabs and IgG forms of anti-HLA-DR antibody fragments of the invention.

The affinities for anti-HLA antibody fragments of the invention were measured as follows. All measurements were conducted in HBS buffer (20 mM HEPES, 150 mM NaCl, pH 7.4) at a flow rate of 20 µl/min at 25° C. on a BIAcore3000 instrument (Biacore AB, Sweden). MHC class II DR protein (prepared as example 1) was diluted in 100 mM sodium acetate pH 4.5 to a concentration of 50-100 mg/ml, and coupled to a CM5 chip (Biacore AB) using standard EDC-NHS coupling chemistry with subsequent ethanolamine treatment as manufacturers directions. The coating density of MHCII was adjusted to between 500 and 4000 RU. Affinities were measured by injection of 5 different concentrations of the different antibodies and using the standard software of the Biacore instrument. Regeneration of the coupled surface was achieved using 10 mM glycine pH 2.3 and 7.5 mM NaOH.

8. Multivalent Killing Activity of Anti HLA-DR Antibodies and Antibody Fragments To demonstrate the effect of valency on cell killing, a cell killing assay was performed using monovalent, bivalent and multivalent compositions of anti-HLA-DR antibody fragments of the invention against GRANTA-519 cells. Anti-HLA-DR antibody fragments from the HuCAL library showed much higher cytotoxic activity when cross-linked to form a bivalent composition (60-90% killing at antibody fragment concentration of 200 nM) by co-incubation with anti-FLAG M2 mAb (FIG. 3) compared to the monovalent form (5-30% killing at antibody fragment concentration of 200 nM).

Incubation of cell lines alone or only in the presence of anti-FLAG M2 mAb without co-incubation of anti-HLA-DR antibody fragments did not lead to cytotoxicity as measured by cell viability. Treatment of cells as above but using 50 nM of the $IgG_4$ forms (naturally bivalent) of the antibody fragments MS-GPC-8, MS-GPC-8-6-13, MS-GPC-8-10-57 and MS-GPC-8-27-41 without addition of anti-FLAG M2 mAb showed a killing efficiency after 4 hour incubation of 76%, 78%, 78% and 73% respectively.

Furthermore, we observed that higher order valences of the anti-HLA-DR antibody fragments further decrease cell viability significantly. On addition of Protein G to the incubation mix containing the IgG form of the anti-HLA-DR antibody fragments, the multivalent complexes thus formed further decrease cell viability compared to the bivalent composition formed from incubation of the anti-HLA-DR antibody fragments with only the bivalent IgG form.

The killing efficiency of anti-HLA-DR antibody fragments selected from the HuCAL library was tested on the HLA-DR positive tumor cell line GRANTA-519 (DSMZ, Germany). $2\times10^5$ cells were incubated for 4 h at 37° C. under 6% $CO_2$ with 200 nM anti-HLA-DR antibody fragments in RPMI 1640 (PAA, Germany) supplemented with 2.5% heat inactivated FBS (Biowhittaker Europe, BE), 2 mM L-glutamine, 1% non-essential amino acids, 1 mM sodium pyruvate and 0.1 mg/ml kanamycin. Each anti-HLA-DR antibody fragment was tested for its ability to kill activated tumor cells as a monovalent anti-HLA-DR antibody fragment or as a bivalent composition by the addition of 100 nM of a bivalent cross-linking anti-FLAG M2 mAb. After 4 h incubation at 37° C. under 6% $CO_2$, cell viability was determined by trypan blue staining and subsequent counting of remaining viable cells (Current Protocols in Immunology, 1997).

The above experiment was repeated using KARPAS-422cells against a multivalent form of IgG forms of MS-GPC-8-10-57 and MS-GPC-8-27-41 prepared by a pre-incubation with a dilution series of the bacterial protein Protein G. Protein G has a high affinity and two binding sites for IgG antibodies, effectively cross-linking them to yield a total binding valency of 4. In a control using IgG alone without preincubation with Protein G, approximately 55% of cells were killed, while cell killing using IgG pre-incubated with Protein G gave a maximum of approximately 75% at a molar ratio of IgG antibody/Protein G of ~6 (based on a molecular weight of Protein G of 28.5 kD). Higher or lower molar ratios of IgG antibody/Protein G approached the cell killing efficiency of the pure IgG antibodies.

9. Killing Efficiency of anti-HLA-DR Antibody Fragments

Experiments to determine the killing efficiency of the anti-HLA-DR cross-linked antibody fragments against other tumor cell lines that express HLA-DR molecules were conducted analogous to example 8. Tumor cell lines that show greater than 50% cell killing with the cross linked Fab form of MS-GPC-8 after 4 h incubation include MHH-CALL4, MN 60, BJAB, BONNA-12 which represent the diseases B cell acute lymphoid leukemia, B cell acute lymphoid leukemia, Burkitt lymphoma and hairy cell leukemia respectively. Use of the cross-linked Fab form of the anti-HLA-DR antibody fragments MS-GPC-1, 6 and 10 also shows similar cytotoxic activity to the above tumor cell lines when formed as a bivalent agent using the cross-linking anti-FLAG M2 mAb.

The method described in example 8 was used to determine the maximum killing capacity for each of the cross-linked bivalent anti-HLA-DR antibody fragments against PRIESS cells. The maximum killing capacity observed for MS-GPC-1, MS-GPC-6, MS-GPC-8 & MS-GPC-10 was measured as 83%, 88%, 84% and 88% respectively. Antibody fragments generated according to example 4, when cross linked using anti-FLAG M2 mAb as above, also showed improved killing ability against GRANTA and PRIESS cells (Table 4).

10. Killing Efficiency of Anti-HLA-DR IgG Antibodies of Human Composition

The optimized IgG$_4$ mAbs were tested for induction of tumor cell death on a panel of 24 DR$^+$ and 4 DR$^-$ cell lines, representing a variety of lymphoma/leukemia types (Table 5). Compared to corresponding murine antibodies (Vidovic et al, 1995b; Nagy & Vidovic, 1996; Vidovic & Toral; 1998), we were surprised to observe significantly improved killing efficiency of IgG forms of certain anti-HLA-DR antibody fragments of the invention (Table 5). The killing is dependent on HLA-DR expression, but is HLS-DR subtype independent.

For the cell killing assay, cells at $2\times10^6$/ml concentration were incubated in RPMI 1640 supplemented with 2.5% fetal calf serum (Biowhittaker Europe, Belgium) and different concentrations (50 nM in most experiments) of human anti-DR mAb at 37° C. for 4 hrs (and 24 h in some experiments). Control cultures were without mAb or with a murine anti-DR mAb 10F12 that fails to induce cell death. Cell cultures were set up in duplicate in flat bottom 96 well plates. Since dead cells disintegrate very fast (within 30 min),% killing was determined based on viable cell recovery as follows: (viable untreated−viable treated/viable untreated)×100. Viable and dead cells were distinguished by trypan blue staining for light microscopy, fluorescein diacetate (FDA; 100 µg/ml final concentration; live cells) and propidium iodide (PI, 40 µg/ml final concentration; dead cells) for fluorescent microscopy, and PI for FACS analysis. To obtain absolute cell counts by FACS analysis, each culture was supplemented with equal amounts of FACS "Truecount" calibrating beads. Cell counts were determined by the formula: viable cells× total beads/counted beads. The three different methods of cell counting (light and fluorescent microscopy and FACS) yielded comparable results.

Following the method described in examples 8 and 9 and above but at 50 nM, repeated measurements (3 to 5 replica experiments where cell number was counted in duplicate for each experiment) were made of the killing efficiency of the IgG forms of certain antibody fragments of the invention.

The mAbs induced death in a wide range (23 of the 25) DR$^+$ lymphoid tumor lines. When applied at a final concentration of only 50 nM, IgGs of the antibody fragments MS-GPC-8/B8, MS-GPC-8-6-13/305D3, MS-GPC-8-10-57/1C7277 & MS-GPC-8-27-41/1D09C3 killed more than 50% of cells from 17, 20, 19 and 22 respectively of a panel of 25 human tumor cell lines that express HLA-DR antigen at a level greater than 10 fluorescent units as determined by example 11. For comparison, two murine anti-DR mAbs, L243 (Vidovic et al, 1995b) and 8D1 (Vidovic & Toral; 1998) known to induce cell death[7,10] were tested on the same panel at 4 fold higher concentration (200 nM) than the human mAbs. The murine mAbs usually killed less cells than human mAbs, or failed to induce death in some DR$^+$ lines. Over all, they reduced cell viability to a level below 50% viable cells in only 13 and 12 of the 25 HLA-DR expressing cells lines, respectively.

In direct comparisons, the human mAbs achieved 50% killing efficiency at 20 to 30 fold lower concentrations than the murine mAbs (see below). Statistical analysis of the data in Table 5 revealed a non-linear correlation between killing efficiency and the level of DR expression, with a significantly greater killing efficiency and better correlation for the human mAbs because of the failure of the murine mAbs to kill a number of DR$^+$ lines.

Figure 4:
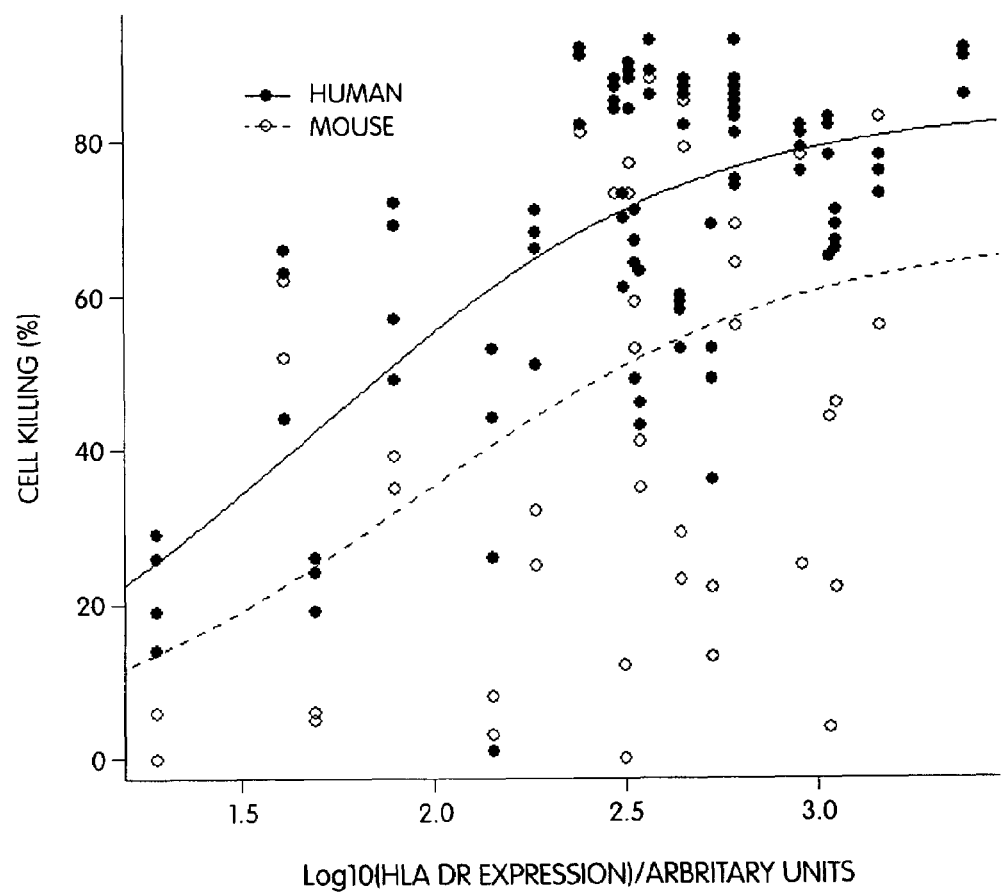
FIG. 4 Scatter plots and fitted logistic curves of data from Table 5 showing improved killing efficiency of 50 nM solutions of the IgG form of the human antibody fragments of the invention treated compared to treatment with 200 nM solutions of murine antibodies. Open circles represent data for cell lines treated with the murine antibodies L243 and 8D1 and closed circles for human antibodies MS-GPC-8, MS-GPC-8-27-41, MS-GPC-8-10-57 and MS-GPC-8-6-13. Fitted logistic curves for human (solid) and mouse (dashed) mAb cell killing data show the overall superiority of the treatment with human mAbs at 50 nM compared to the mouse mAbs despite treatment at a final concentration of 200 nM.

Indeed, even at the significantly increased concentration, the two murine antibodies treated at 200 nM showed significantly less efficient killing compared to the IgG forms of anti-HLA-DR antibody fragments of the invention. Not only do IgG forms of the human anti-HLA-DR antibody fragments of the invention show an overall increase in cell killing at lower concentrations compared to the murine antibodies, but they show less variance in killing efficiency across different cell lines. The coefficient of variance in killing for the human antibodies in this example is 32% (mean % killing=68+/−22% (SD)), compared to over 62% (mean % killing=49+/−31% (SD)) for the mouse antibodies. Statistically controlling for the effect on killing efficiency due to HLA expression by fitting logistic regression models to mean percentage killing against log(mean HLA-DR expression) supports this observation (FIG. 4). Not only is the fitted curve for the murine antibodies consitently lower than that for the human, but a larger variance in residuals from the murine antibody data (SD=28%) is seen compared to the variance in residuals from the human antibody data (16%). The superior performance of human mAbs could be explained, at least in part, by their higher affinity ($K_d$-s 0.3-0.6 nM, see Table 3e, compared to L243 10 nM, and 8D1>30 nM (Z. A. Nagy, unpublished)).

The cell line MHH-PREB-1 was singled out and not accounted as part of the panel of 25 cell lines despite its expression of HLA-DR antigen at a level greater than 10 fluorescent units due to the inability of any of the above antibodies to induce any significant reduction of cell viability. This is further explained in example 12.

The viability of DR$^-$cell lines was not significantly affected.

11. Killing Selectivity of Antigen-binding Domains Against a Human Antigen for Activated Versus Non-activated Cells Since MHC-II molecules are constitutively expressed on B lymphocytes, the most obvious potential side effect of anti-DR mAb treatment would be the killing of normal B cells. Human peripheral B cells were therefore used to demonstrate that human anti-HLA-DR mAb-mediated cell killing is dependent on cell-activation. 50 ml of heparinised venous blood was taken from an HLA-DR typed healthy donor and fresh peripheral blood mononuclear cells (PBMC) were isolated by Ficoll-Hypaque Gradient Centrifugation (Histopaque-1077; Sigma) as described in Current Protocols in Immunology (John Wiley & Sons, Inc.; 1999). Purified B cells (~5% of peripheral blood leukocytes) were obtained from around $5\times10^7$ PBMC using the B-cell isolation kit and MACS LS$^+$/VS$^+$ columns (Miltenyi Biotec, Germany) according to manufacturers guidelines. Successful depletion of non-B cells was verified by FACS analysis of an aliquot of isolated B cells (HLA-DR positive and CD19 positive). Double staining and analysis is done with commercially available antibodies (BD Immunocytometry Systems, San Jose, Calif., USA) using standard procedures as for example described in Current Protocols in Immunology (John Wiley & Sons, Inc.; 1999). An aliquot of the isolated B cells was tested for the ability of the cells to be activated by stimulation with Pokeweed mitogen (PWM) (Gibco BRL, Cat. No. 15360-019) diluted 1:25 in RPMI 1640 (PAA, Germany) supplemented with 10% FCS (Biowhittaker Europe, BE), 2 mM L-glutamine, 1% non-essential amino acids, 1 mM sodium pyruvate and 0.1 mg/ml kanamycin by incubation at 37° C. under 6% CO$_2$ for three days. Successful activation was verified by FACS analysis of HLA-DR expression on the cell surface (Current Protocols in Immunology, John Wiley & Sons, Inc.; 1999).

The selectivity for killing of activated cells versus non-activated cells was demonstrated by incubating $1\times10^6$/ml B cells activated as above compared to non-activated cells, respectively with 50 nM of the IgG forms of MS-GPC-8-10-57, MS-GPC-8-27-41 or the murine IgG 10F12 (Vidovic et al, 1995b) in the medium described above but supplemented with 2.5% heat inactivated FCS instead of 10%, or with medium alone. After incubation at 37° C. under 6% $CO_2$ for 1 or 4 h, cell viability was determined by fluorescein diacetate staining (FDA) of viable and propidium iodide staining (PI) of dead cells and subsequent counting of the green (FDA) and red (PI) fluorescent cells using a fluorescence microscope (Leica, Germany) using standard procedures (Current Protocols in immunology, 1997).

B cell activation was shown to be necessary for cell killing. In non-activated cells after 1 hr of incubation with the anti-HLA-DR antibodies, the number of viable cells in the media corresponded to 81%, 117% 126% and 96% of the pre-incubation cell density for MS-GPC-8-10-57 (IgG), MS-GPC-8-27-41 (IgG), 10F12 and medium alone, respectively. In contrast, the number of viable activated B cells after 1 h incubation corresponded to 23%, 42% 83% and 66% of the pre-incubation cell density for MS-GPC-8-10-57 (IgG), MS-GPC-8-27-41 (IgG), 10F12 and medium alone, respectively. After 4 hr of incubation, 78%, 83% 95% and 97% of the pre-incubation cell density for MS-GPC-8-10-57 (IgG), MS-GPC-8-27-41 (IgG), 10F12 and medium alone were found viable in non-activated cells, whereas the cell density had dropped to 23%, 24% 53% and 67% of the pre-incubation cell density for MS-GPC-8-10-57 (IgG), MS-GPC-8-27-41 (IgG), 10F12 and medium alone, respectively, in activated cells.

Figure 8A:
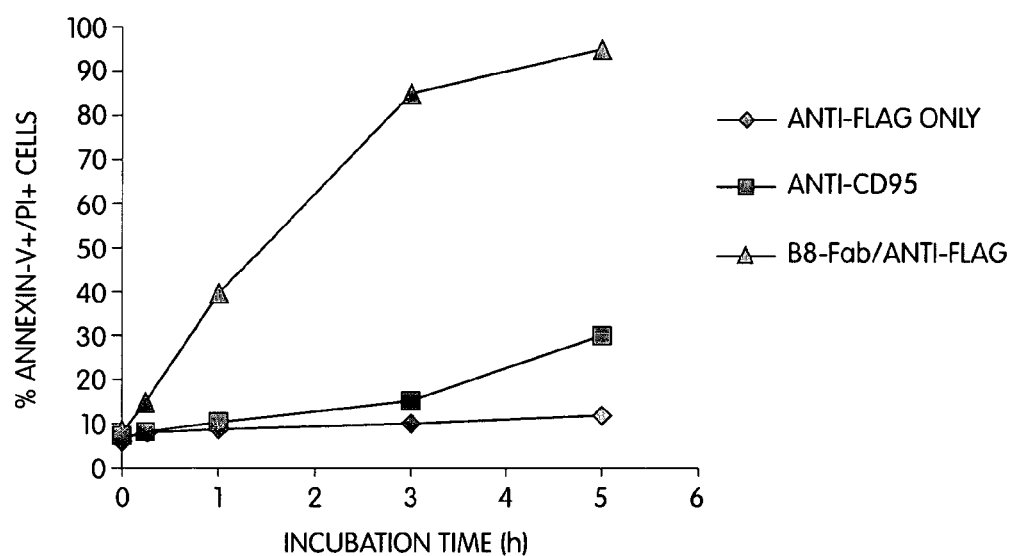
Figure 8B:
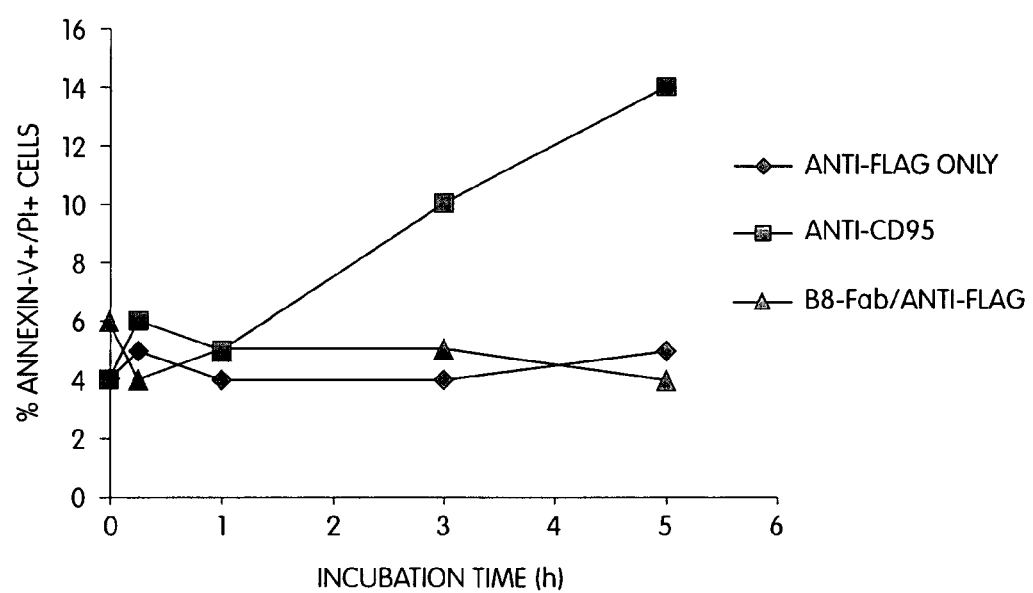
Figure 8C:
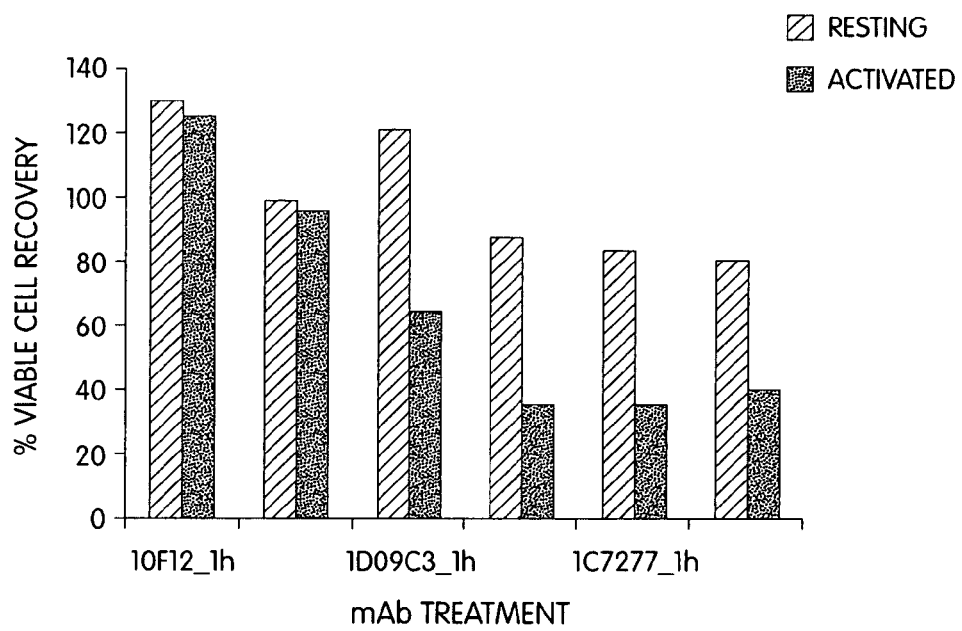

In conclusion, as shown in FIG. 8c, the viability of purified resting B cells was not significantly altered by human anti-DR mAbs. In contrast, pokeweed mitogen-activated B cells from the same donor were killed by these mAbs. No death of either unactivated or activated B cells was induced by the control antibody 10F12. Similar results were obtained with resting and lipopolysaccharide-stimulated spleenic B cells from DR-transgenic mice (Ito, K. et al. *J. Exp. Med.* 183:2635-2644, 1996) (data not shown). Thus, it appears that the mAbs can kill activated but not resting MHC-II positive normal cells in addition to tumor cells, suggesting a dual requirement of both MHC-II expression and cell activation for mAb-induced death. Since the majority (up to 99%) of peripheral B cells is resting, the potential side effect due to killing of normally activated B cells in a leukaemia patient is negligible.

12. Killing activity of Anti-HLA Antibody Fragments Against the Cell Line MHH PreB 1

As evidenced in Table 5, we observed that our cross-linked anti-HLA-DR antibody fragments or IgGs did not readily kill a particular tumor cell line expressing HLA-DR at significant levels (MHH-PREB-1). We hypothesized that although established as a stable cell line, cells in this culture were not sufficiently activated. We therefore stimulated these cells with interferon-gamma, and lipopoysaccharide. Activation was evidenced by an increase in the cell surface expression of CD40 and HLA-DR.

Non-adherently growing MHH preB1 cells were cultivated in RPMI medium containing the following additives (all from Gibco BRL and Bio Whittaker): 10% FCS, 2 mM L-glutamine, 1% non-essential amino acids, 1 mM sodium pyruvate and 1× Kanamycin. Aliquots were activated to increase expression of HLA-DR molecule by incubation for one day with Lipopolysaccharide (LPS, 10 µg/ml), Interferon-gamma (IFN-γ, Roche, 40 ng/ml) and phyto-hemagglutinin (PHA, 5 µg/ml). The cell surface expression of HLA-DR molecules was monitored by flow cytometry with the FITC-conjugated mAb L243 (BD Immunocytometry Systems, San Jose, Calif., USA). Incubation of MHH preB1 for one day in the presence of LPS, IFN-γ and PHA resulted in a 2-fold increase in HLA-DR surface density (mean fluorescence shift from 190 to 390). Cell killing was performed for 4 hrs in the above medium but containing a reduced FCS concentration (2.5%). A concentration series of the IgG forms of MS-GPC-8-27-41/1D09C3 & MS-GPC-8-10-57/1C7277 was employed, consisting of final antibody concentrations of 3300, 550, 92, 15, 2.5, 0.42 and 0.07 nM, on each of an aliquot of non-activated and activated cells. Viable cells were identified microscopically by exclusion of Trypan blue. Whereas un-activated cell viability remains unaffected by the antibody up to the highest antibody concentration used, cell viability is dramatically reduced with increasing antibody concentration in activated MHH PreB1 cells (FIG. 5).

In addition, we found that cell proliferation was apparently not needed, since tumor cells in mitosis-arrest remained susceptible to mAb-mediated killing (data not shown).

In contracts to the mAbs we describe here, two additional anti-HLA-DR mAbs with therapeutic potential, Lym-1 (Epstein et al., *Cancer Res.* 47:830-840, 1987; DeNardo et al., *Int. J. Cancer* 96 (suppl.3):96, 1988) and 1D10 (Gingrich et al., *Blood* 75:2375-2387, 1990), achieve selectivity in a different way. These two mAbs recognize what appear to be posttranslational modifications on DR molecules that occur preferentially in B-cell derived tumors, although some expression was noted also on normal B cells and monocytes (Epstein et al., 1987; DeNardo et al., 1988). Neither of these mAbs has inherent tumoricidal activity, and thus, Lym-1 is developed in a $^{131}$I-labelled form (Oncolym®), whereas the efficacy of 1D10 relies on intact immunological effector mechanisms of the patient, similarly to other mAbs (Vose et al., *J. Clin. Oncol.* 19:389-397, 2001; Dyer et al., *Blood* 73:1431-1439, 1989) already available for the clinic. Furthermore, Lym-1 is a murine mAb with substantial immunogenicity for humans, and 1D10 is a humanized murine mAb. Our fully human mAbs with strong inherent tumoricidal activity and selectivity for activated/tumor transformed cells demonstrate a substantially different profile and mechanism of action from these two mAbs, and thus promise a novel therapeutic approach to lymphoma/leukemia.

13. Killing Efficiency of Anti-HLA-DR IgG Antibodies of Human Composition Against ex-vivo Chronic Lymphoid Leukemia Cells We investigated whether the human anti-DR mAbs would also be active on freshly isolated leukemic cells, in addition to established cell lines. Using purified malignant B cells obtained from the peripheral blood of 10 un-typed chronic lymphoid leukemia (CLL) patients (Buhmann et al., *Blood* 93:1992-2002, 1999), we demonstrated that IgG forms of anti-HLA-DR antibody fragments of the invention showed efficacy in killing of clinically relevant cells using an ex-vivo assay (FIG. 6). Although the killing kinetics are slightly slower than those of in vitro experiments using established cell lines, significant killing is achieved over 24 hours of Ab incubation, despite the low rate of CLL cell proliferation.

B-cells were isolated and purified from 10 unrelated patients suffering from CLL (samples kindly provided by Prof Hallek, Ludwig Maximillian University, Munich) according to standard procedures (Buhmann et al., (1999)). $2 \times 10^5$ cells were treated with 100 nM of IgG forms of the anti-HLA-DR antibody fragments MS-GPC-8, MS-GPC-8-10-57 or MS-GPC-8-27-41 and incubated for 4 or 24 hours analogous to examples 8 and 9. A replica set of cell cultures was established and activated by incubation with HeLa-cells expressing CD40 ligand on their surface for three days before treatment with antibody (Buhmann et al., 1999). As controls, the murine IgG 10F12 (Vidovic et al., 1995b) or no antibody was used. Cell viability for each experiment was determined as described in example 12.

Figure 6C:
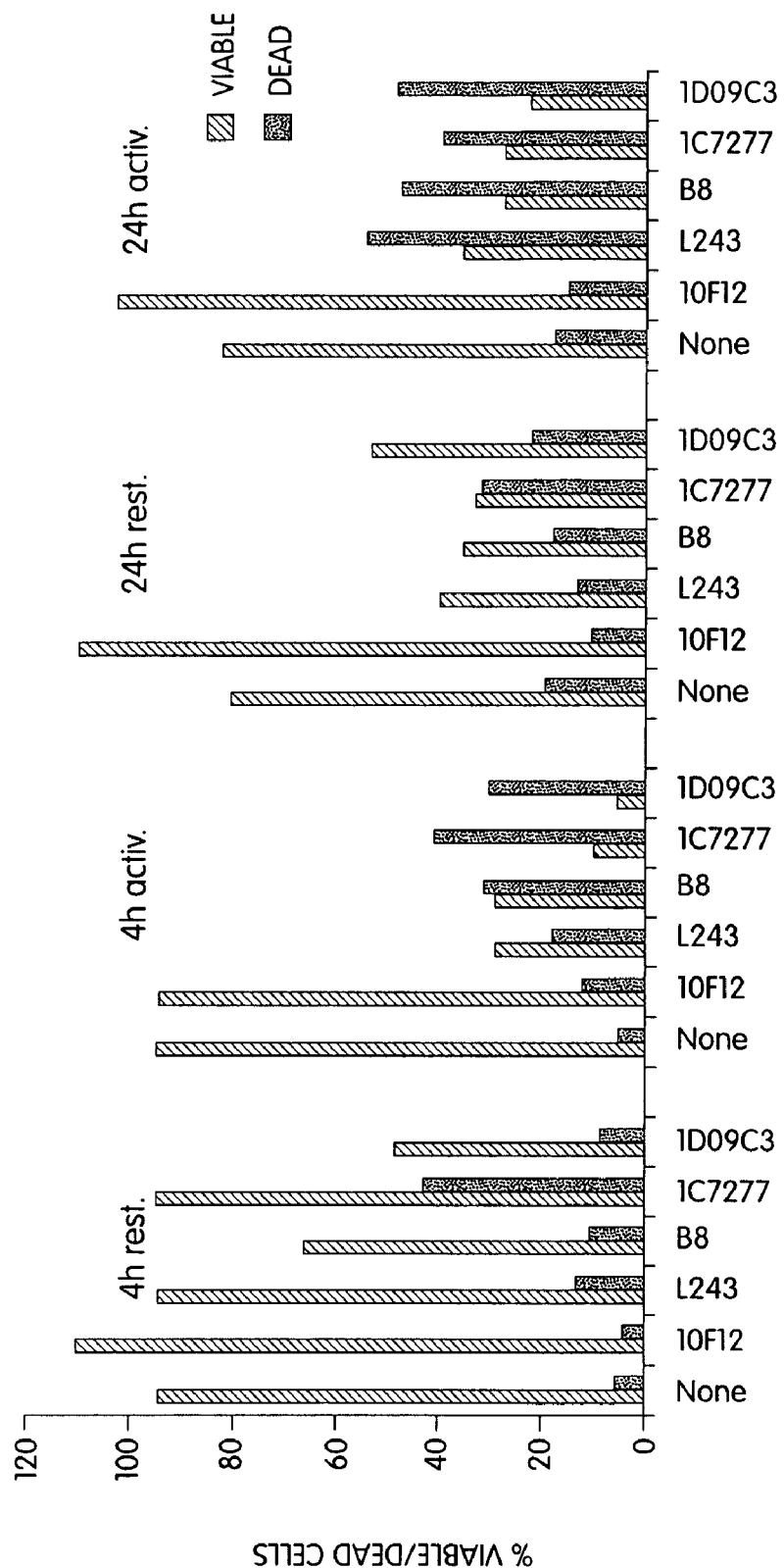

Surprisingly, IgG forms of the anti-HLA-DR antibody fragments of the invention showed highly efficient and uniform killing—even across this diverse set of patient material. After only 4 hours of treatment, all three human IgGs gave a significant reduction in cell viability compared to the controls, and after 24 hours only 33% of cells remained viability (FIG. 6). We found that on stimulating the ex-vivo cells further according to Buhmann et al. (1999), the rate of killing was increased such that after only 4 hours culture with the human antibodies, only 24% of cells remained viable on average for all patient samples and antibody fragments of the invention. The control murine anti-DR mAb 10F12, which has no inherent tumoricidal activity (Vidovic', D. et al., Eur. J. Immunol. 25:3349-3355, 1995), had no effect on CLL cells (FIG. 6c).

14. Determination of $EC_{50}$ for anti-HLA-DR Antibody Fragments

We demonstrated superior Effective Concentration at 50% effect ($EC_{50}$) values in a cell-killing assay for certain forms of anti-HLA-DR antibody fragments selected from the HuCAL library compared to cytotoxic murine anti-HLA-DR antibodies (Table 6).

The $EC_{50}$ for anti-HLA-DR antibody fragments selected from the HuCAL library were estimated using the HLA-DR positive cell line PRIESS or LG2 (ECACC, Salisbury UK). $2\times10^5$ cells were incubated for 4 h at 37° C. under 6% $CO_2$ in RPMI 1640 (PAA, Germany) supplemented with 2.5% heat inactivated FBS (Biowhittaker Europe, BE), 2 mM L-glutamine, 1% non-essential amino acids, 1 mM sodium pyruvate and 0.1 mg/ml kanamycin, together with dilution series of bivalent anti-HLA-DR antibody fragments. For the dilution series of Fab antibody fragments, an appropriate concentration of Fab fragment and anti-FLAG M2 antibody were premixed to generate bivalent compositions of the anti-HLA-DR antibody fragments. The concentrations stated refer to the concentration of bivalent composition such that the IgG and Fab $EC_{50}$ values can be compared.

After 4 h incubation with bivalent antibody fragments at 37° C. under 6% $CO_2$, cell viability was determined by fluorescein diacetate staining and subsequent counting of remaining viable cells (Current Protocols in Immunology, 1997). Using standard statistical software, non-linear logistic regression curves were fitted to replica data points and the $EC_{50}$ estimated for each antibody fragment.

Figure 7A:
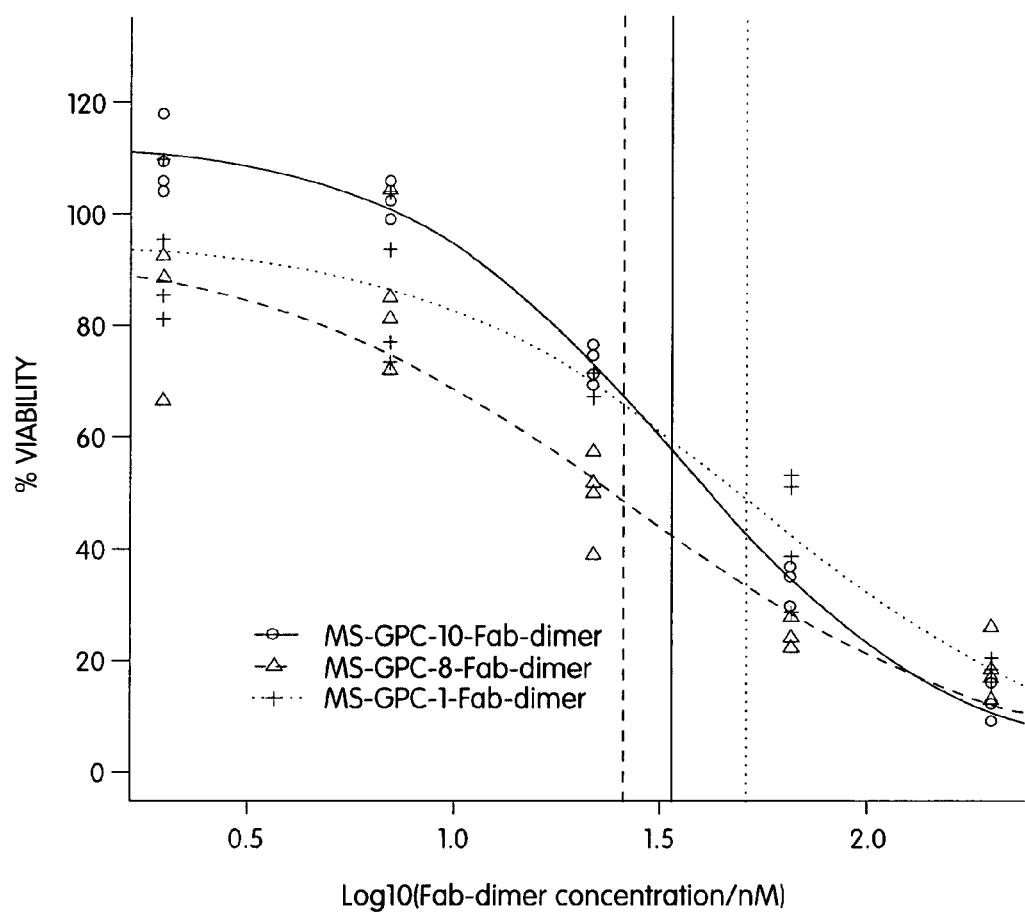
Figure 7B:
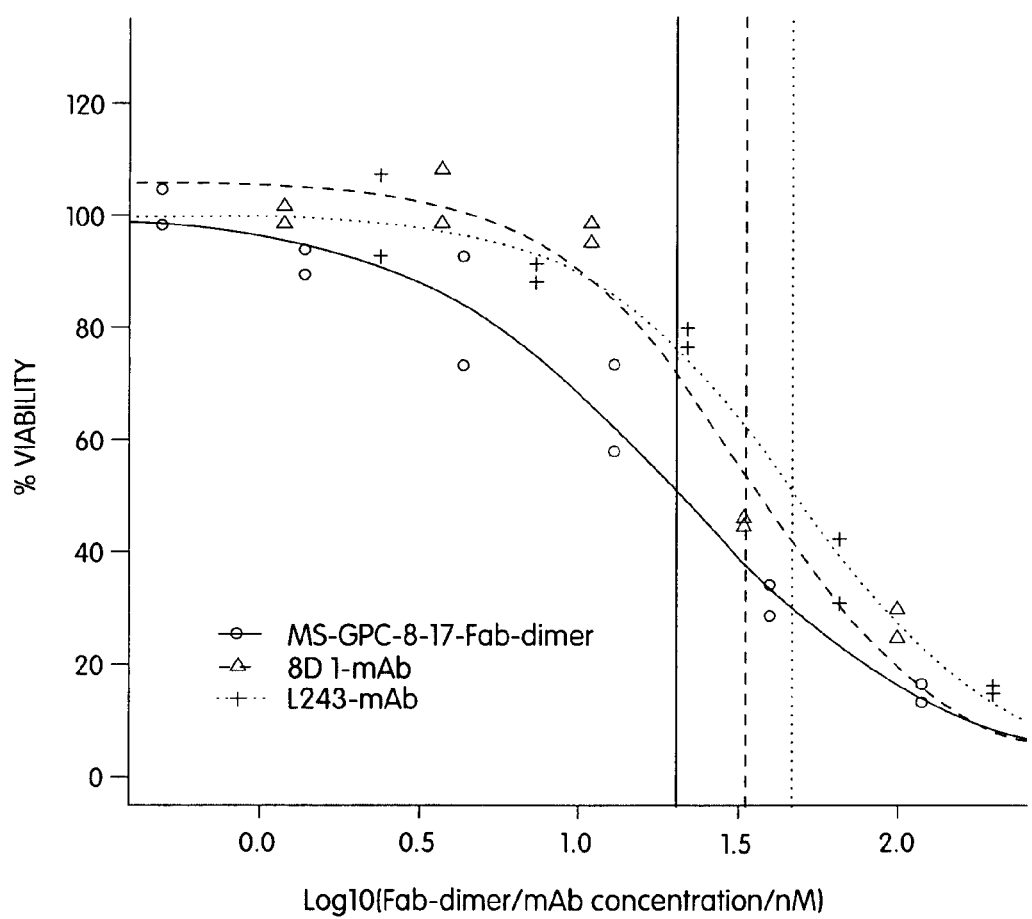
Figure 7C:
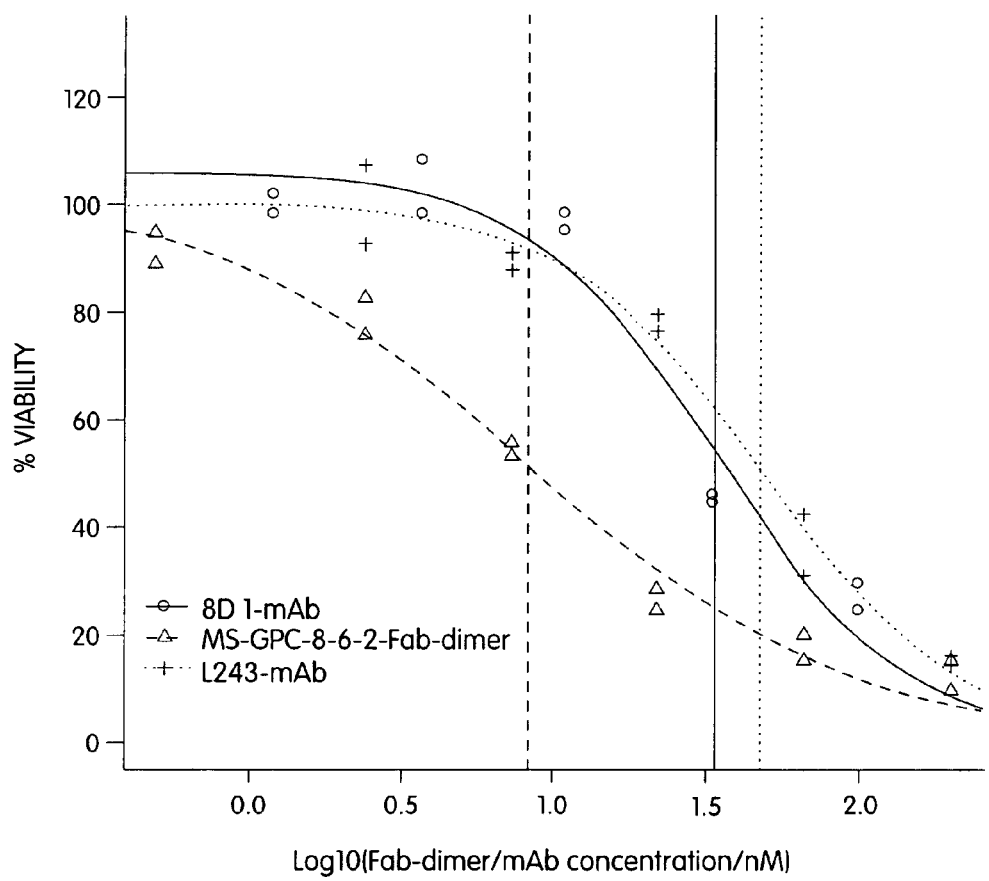

When cross-linked using the anti-FLAG M2 antibody, the Fab fragments MS-GPC-1, MS-GPC-8 & MS-GPC-10 selected from the HuCAL library (Example 4) showed an $EC_{50}$ of less than 120 nM as expressed in terms of the concentration of the monovalent fragments, which corresponds to a 60 nM $EC_{50}$ for the bivalent cross-linked (Fab)dimer-anti-Flag M2 conjugate. (FIG. 7a). When cross-linked using the anti-FLAG M2 antibody, anti-HLA-DR antibody fragments optimised for affinity within the CDR3 region (Example 4) showed a further improved $EC_{50}$ of less than 50 nM, or 25 nM in terms of the bivalent cross-linked fragment (FIG. 7b), and those additionally optimised for affinity within the CDR1 region showed an $EC_{50}$ of less than 30 nM (15 nM for bivalent fragment). In comparison, the $EC_{50}$ of the cytotoxic murine anti-HLA-DR antibodies 8D1 (Vidovic & Toral; 1998) and L243 (Vidovic et al; 1995b) showed an $EC_{50}$ of over 30 and 40 nM, respectively, within the same assay (FIG. 7c).

Figure 7D:
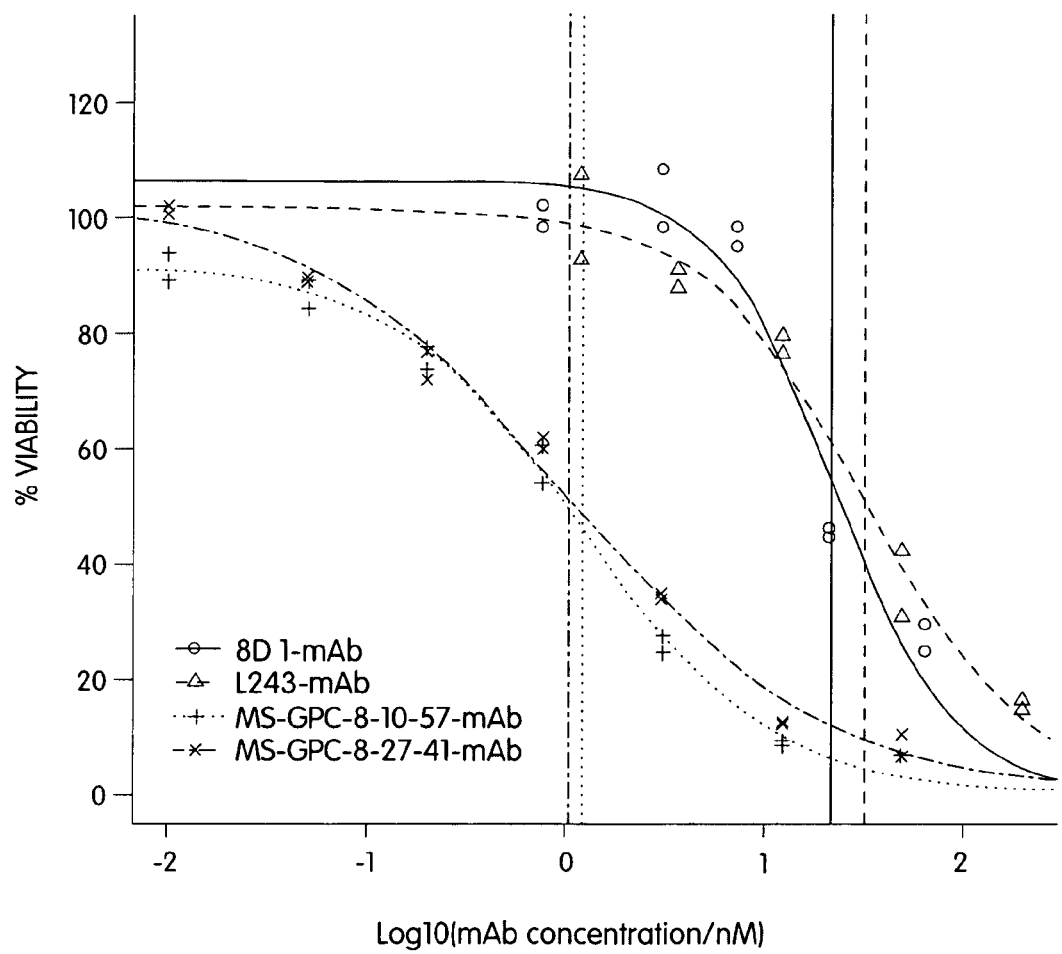

Surprisingly, the IgG form of certain antibody fragments of the invention showed approximately 1.5 orders of magnitude improvement in $EC_{50}$ compared to the murine antibodies (FIG. 7d). For example, the IgG forms of MS-GPC-8-10-57 & MS-GPC-8-27-41 showed an $EC_{50}$ of 1.2 and 1.2 nM respectively. Furthermore, despite being un-optimised for affinity, the IgG form of MS-GPC-8 showed an $EC_{50}$ of less than 10 nM.

As has been shown in examples 11 and 12, the efficiency of killing of un-activated cells (normal peripheral B and MHH PreB cells respectively) is very low. After treatment with 50 nM of the IgG forms of MS-GPC-8-10-57 & MS-GPC-8-27-41, 78% and 83% of normal peripheral B cells, respectively, remain viable after 4 hours. Furthermore, at only 50 nM concentration or either IgG, virtually 100% viability is seen for MHH PreB1 cells. Indeed, a decrease in the level of viability to below 50% cannot be achieved with these unactivated cells using reasonable concentration ranges (0.1 to 300 nM) of IgG or bivalent cross-linked Fab forms of the anti-HLA-DR antibody fragments of the invention. Therefore, the $EC_{50}$ for these un-activated cell types can be estimated to be at least 5 times higher than that shown for the non-optimised Fab forms ($EC_{50}$~60 nM with respect to cross-linked bivalent fragment), and at least 10 times and 100 times higher than $EC_{50}$s shown for the VHCDR3 optimised Fabs (~25 nM with respect to cross-linked bivalent fragment) and IgG forms of MS-GPC-8-10-57 (~1.2 nM) & MS-GPC-8-27-41 (~1.2 nM) respectively.

15. Mechanism of Cell-killing

The examples described above show that cell death occurs—needing only certain multivalent anti-HLA-DR antibody fragments to cause killing of activated cells. No further cytotoxic entities or immunological mechanisms were needed to cause cell death, therefore demonstrating that cell death is mediated through an innate pre-programmed mechanism of the activated cell. The mechanism of apoptosis is a widely understood process of pre-programmed cell death. We were surprised by certain characteristics of the cell killing we observed that suggested the mechanism of killing for activated cells when exposed to our human anti-HLA-DR antibody fragments was not what is commonly understood in the art as "apoptosis". For example, the observed rate of cell killing appeared to be significantly greater than the rate reported for apoptosis of immune cells (about 10-15 hrs; Truman et al., 1994). Two experiments were conducted to demonstrate that the mechanism of cell killing proceeded by a non-apoptotic mechanism.

First, we used Annexin-V-FITC and propidium iodide (PI) staining techniques to distinguish between apoptotic and non-apoptotic cell death—cells undergoing apoptosis, "apoptotic cells", (Annexin-V positive/PI negative) can be distinguished from necrotic ("Dead") (Annexin-V positive/PI positive) and fully functional cells (Annexin-V negative/PI negative). Using the procedures recommended by the manufacturers of the AnnexinV and PI assays, $1\times10^6$/ml PRIESS cells were incubated at 37° C. under 6% $CO_2$ with or without 200 nM anti-HLA-DR antibody fragment MS-GPC-8 together with 100 nM of the cross-linking anti-FLAG M2 mAb in RPMI 1640 (PAA, DE) supplemented with 2.5% heat inactivated FCS (Biowhittaker Europe, BE), 2 mM L-glutamine, 1% non-essential amino acids, 1 mM sodium pyruvate and 0.1 mg/ml kanamycin. To provide an apoptotic cell culture as control, $1\times10^6$/ml PRIESS cells were induced to enter apoptosis by incubation in the above medium at 37° C. under 6% $CO_2$ with 50 µg/ml of the apoptosis-inducing anti-CD95 mAb DX2 (BD Pharniingen, Torrey Pine, Calif., USA) crosslinked with 10 μg/ml Protein-G. At various incubation times (1, 15 and 60 min., 3 and 5 hrs) 200 μl samples were taken, washed twice and stained with Annexin-V-FITC (BD Pharmingen, Torrey Pine, Calif., USA) and PI using Annexin-V binding buffer following the manufacturer's protocol. The amount of staining with Annexin-V-FITC and PI for each group of cells is analysed with a FACS Calibur (BD Immunocytometry Systems, San Jose, Calif., USA).

Cell death induced through the cross-linked anti-HLA-DR antibody fragments shows a significantly different pattern of cell death than that of the anti-CD95 apoptosis inducing antibody or the cell culture incubated with anti-FLAG M2 mAb alone. The percentage of dead cells (as measured by Annexin-V positive/PI positive staining) for the anti-HLA-DR antibody fragment/anti-FLAG M2 mAb treated cells increases far more rapidly than that of the anti-CD95 or the control cells (FIG. 8a). In contrast, the percentage of apoptotic cells (as measured by Annexin-V positive/PI negative staining) increases more rapidly for the anti-CD95 treated cells compared to the cross-linked anti-HLA-DR antibody fragments or the control cells (FIG. 8b).

Second, we inhibited caspase activity using zDEVD-fmk, an irreversible Caspase-3 inhibitor, and zVAD-fmk, a broad spectrum Caspase inhibitor (both obtained from BioRad, Munich, DE). The mechanism of apoptosis is characterized by activity of caspases, and we hypothesized that if caspases were not necessary for anti HLA-DR mediated cell death, we would observe no change in the viability of cells undergoing cell death in the presence of these caspase inhibitors compared to those without. $2 \times 10^5$ PRIESS cells were preincubated for 3 h at 37° C. under 6% $CO_2$ with serial dilutions of the two caspase inhibitors ranging from 180 μM to 10 mM in RPMI 1640 (PAA, DE) supplemented with 2.5% heat inactivated FCS (Biowhittaker Europe, BE), 2 mM L-glutamine, 1% non-essential amino acids, 1 mM sodium pyruvate and 0.1 mg/ml kanamycin. HLA-DR mediated cell death was induced by adding 200 nM of the human anti-HLA-DR antibody fragment MS-GPC-8 and 100 nM of the cross-linking anti-M2 mAb. An anti-CD95 induced apoptotic cell culture served as a control for the activity of inhibitors (Drenou et al., 1999). After further incubation at 37° C. and 6% $CO_2$, cell viability after 4 and 24 h was determined by trypan blue staining and subsequent counting of non-stained cells. As we expected, cell viability of the anti-HLA-DR treated cell culture was not significantly modified by the presence of the Caspase inhibitors, while cell death induced through anti-CD95 treatment was significantly decreased for the cell culture pre-incubated with the Caspase inhibitors. We therefore concluded that the cell death induced by the human anti-DR mAbs does not occur via the classical apoptotic pathway that can be inhibited by zDEVD-fin or zVAD-fmk.

16. In vivo Therapy for Cancer using an HLA-DR Specific Antibody

To test the in vivo efficacy, we inoculated immunocompromised (such as scid, nude or Rag-1 knockout) SCID (severe combined immunodeficient) mice subcutaneously (s.c.) or intraveneously (i.v.) with the non-Hodgkin B cell lymphoma line GRANTA-519 (see in Table 5), and monitored tumor development in mice treated with mAb, in comparison to solvent-treated animals.

In general, mice are treated i.v. or s.c with the IgG form of the anti-HLA-DR antibody fragments MS-GPC-8, MS-GPC-8-10-57, MS-GPC-8-27-41 or others of the invention prepared as described above, using doses of 1 to 25 mg/kg over 5 days. Survival of anti-HLA-DR treated and control untreated mice is monitored for up to 8 weeks after cessation of treatment. Tumor progression in the mice inoculated s.c. is additionally quantified by measuring tumor surface area.

For example, eight weeks old female C.B.-17 scid mice were injected with anti-asialoGM1 antibody (Wako Chemicals, Neuss, Germany; 25 μl diluted 4 fold in PBS, i v.) to suppress natural killer (NK) cell activity, on days 0, 1, and 2. On day 1, $5 \times 10^6$ GRANTA-519 cells were injected s.c. into the right flank, or i.v. The endpoint in the s.c. model is a tumor surface area of >5 $cm^2$, skin ulceration above the tumor, or death, and in the i.v. model hind leg paralysis or death. Mice were treated with 1 mg or 0.2 mg 1D09C3 mAb s.c. or i.v. on days 5, 7 and 9. Control mice received PBS. Mice were monitored, and tumor length and width were measured by a slide-gauge twice a week.

Significant prolongation of survival of up to 80% of anti-HLA-DR treated mice is observed during the experiment, and up to 50% mice survive at the end of the experiment. In the s.c. tumor experiment, at day 48, 100% of s.c. mAb treated mice were alive and 80% of i.v. mAb treated mice were alive (death is not related to mAb treatment or tumor), while all control mice died within the observation period (FIG. 16a). In s.c. inoculated and untreated mice, the tumor reaches a surface area of 2-3 $cm^2$, while in anti-HLA-DR treated animals the tumor surface area is significantly less. FIG. 16d shows representative tumor size in mice treated or untreated by mAb of the instant invention. Tumor growth was also significantly retarded in the treated animals (FIG. 16b). In the i.v. tumor experiment, a significant delay (about 30 days) in disease onset was observed in the mAb treated groups (FIG. 16c). The 30 day survival rate for i.v. mAb treated mice is 100%, while the survival rate for control mice is 0%. Even at day 40, the survival rate for i.v. mAb treated mice is 50%/20% (for high/low doses, respectively). Tumor-induced paralysis is also significantly reduced in the i.v. mAb treated mice as compared to the control group mice which are all paralysized by day 40.

These experiments demonstrate that antigen-binding domains of human composition can successfully be used as a therapeutic for the treatment of cancer. The in vitro, ex vivo and in vivo efficacy data presented here are strong evidence that such mAbs offer the potential to become useful and potent therapeutic agents for the treatment of different $DR^+$ lymphoma and leukemia.

17. Immunosuppression using anti-HLA-DR Antibody Fragments Measured by Reduction in IL-2 Secretion Various diseases are caused by or associated with activated T-cells. For example, delayed-type hyper sensitivity (DTH) is caused by T-cells activated by antigen-presenting cells (APCs) via MHC receptors. Thus, inhibition of interaction between the MHC class II molecule and the T-cell receptor (TCR) can inhibit certain undesirable immune responses.

Figure 9A:
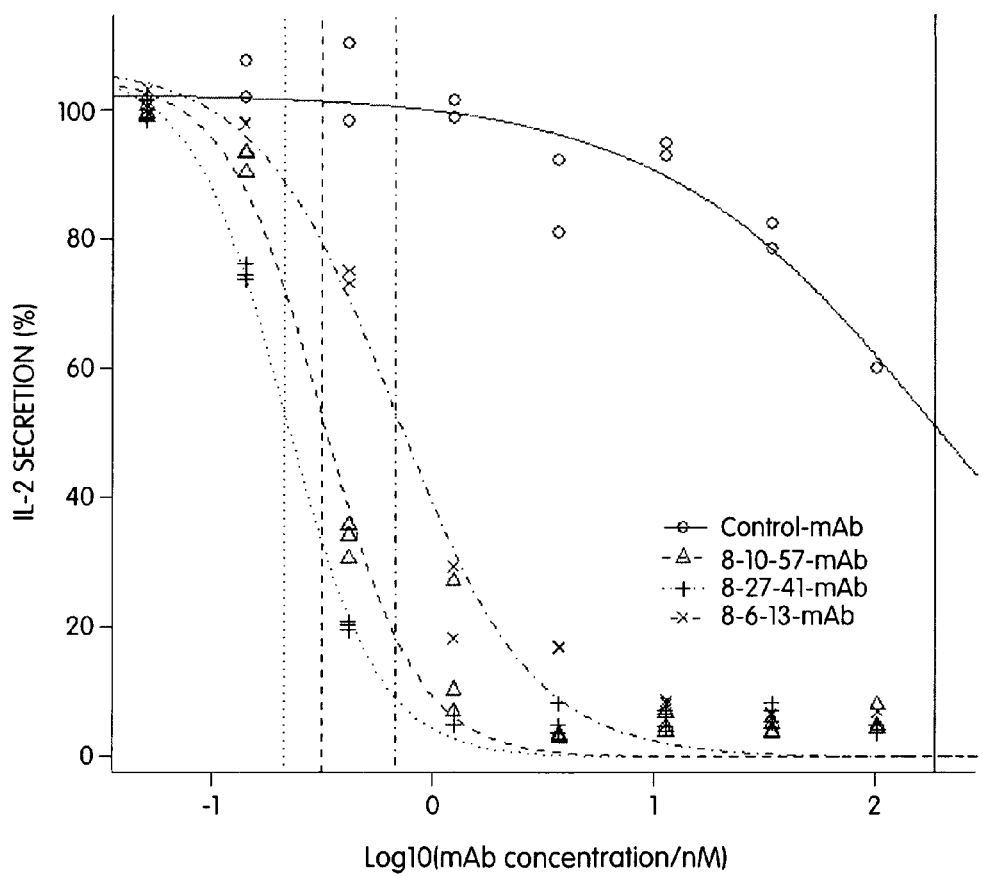
Figure 9B:
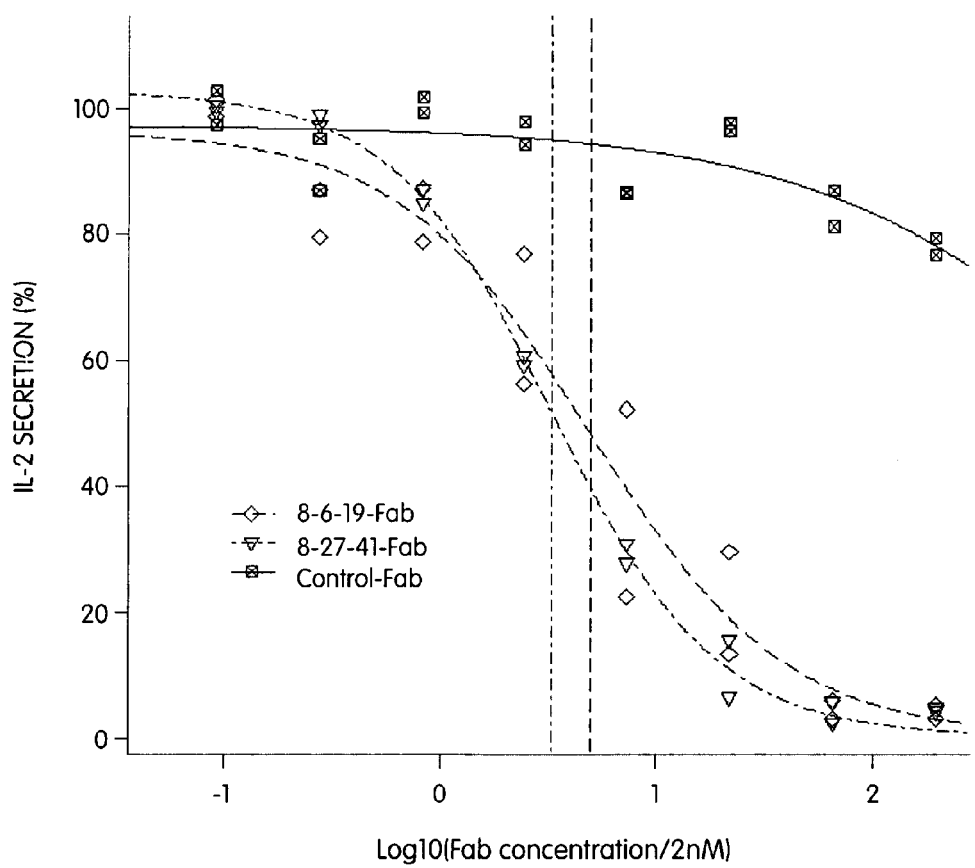
Figure 9C:
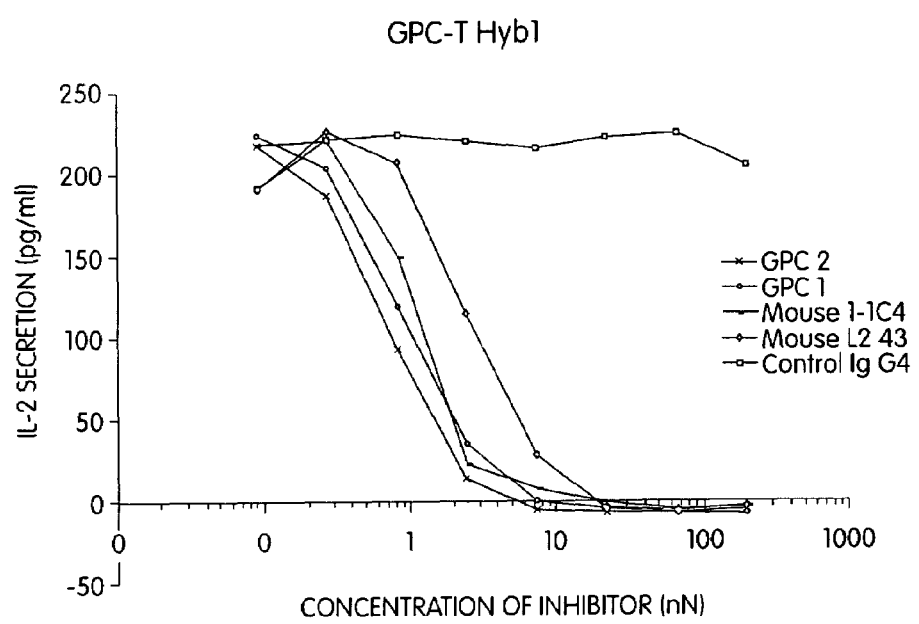

We were surprised to observe that certain anti-HLA-DR antibody fragments of the invention also displayed substantial immunomodulatory properties within an assay measuring IL-2 secretion from immortalized T-cells (T-cell hybridoma). IgG forms of the antibody fragments MS-GPC-8-6-13/305D3, MS-GPC-8-10-57/1C7277 & MS-GPC-8-27-41/1D09C3 showed very strong immunosuppressive properties in this assay with sub-nanomolar $IC_{50}$ values and virtually 100% maximal inhibition (FIG. 9a). Particularly surprising was our observation that certain monvalent compositions of the antibody fragments of the invention were able to strongly inhibit IL-2 secretion in the same assay. For example, Fab forms of the VH CDR3-selected and VL CDR3/VL CDR1 optimised antibody fragments showed low single-digit nM $IC_{50}$'s and also almost 100% maximal inhibition (FIG. 9b). Other monvalent anti-HLA-DR antibody fragments of the invention showed significant immunosuppressive properties in the assay compared to control IgG and Fab fragments (Table 7). FIG. 9c also shows immunomodulatory properties of the mouse 1-2 C4 and L243 mAb as well as the GPC 1 and 2 Ab's.

The immunomodulatory properties of anti-HLA-DR antibody fragments was investigated by measuring IL-2 secretion from the hybridoma cell line T-Hyb1 stimulated using DR-transgenic antigen presenting cells (APC) under conditions of half-maximal antigen stimulation. IL-2 secretion was detected and measured using a standard ELISA method provided by the OptiEIA mouse IL-2 kit of Pharmingen (Torrey Pine, Calif., USA). APCs were isolated from the spleen of unimmunized chimeric 0401-IE transgenic mice (Ito et al. 1996) according to standard procedures. $1.5 \times 10^5$ APCs were added to 0.2 ml wells of 96-well in RPMI medium containing the following additives (all from Gibco BRL and PAA): 10% FCS, 2 mM L-glutamine, 1% non-essential amino acids, 1 mM sodium pyruvate and 0.1 g/l kanamycin. Hen egg ovalbumin was added to a final concentration of 200 µg/ml in a final volume of 100 ul of the above medium, the cells incubated with this antigen for 30 min at 37° C. under 6% $CO_2$. Anti-HLA-DR antibody fragments were added to each well at various concentrations (typically in a range from 0.1 to 200 nM), the plate incubated for 1 h at 37° C./6% $CO_2$ and $2 \times 10^5$ T-Hyb1 cells added to give a final volume of 200 µl in the above medium. After incubation for 24 h, 100 µl of supernatant was transferred to an ELISA plate (Nunc-Immuno Plate MaxiSorp surface, Nunc, Roskilde, DK) previously coated with IL-2 Capture Antibody (BD Pharmingen, Torrey Pine, Calif., USA), the amount of IL-2 was quantified according to the manufacturer's directions using the OptiEIA Mouse IL-2 kit and the plate read using a Victor V reader (Wallac, Finland). Secreted IL-2 in pg/ml was calibrated using the IL-2 standards provided in the kit.

The T-cell hybridoma line T-Hyb1 was established by fusion of a T-cell receptor negative variant of the thymoma line BW 5147 (ATCC) and lymph node cells from chimeric 0401-IE transgenic mice previously immunized with hen egg ovalbumin (Ito et al. 1996). The clone T-Hyb1 was selected for the assay since it responded to antigen specific stimulation with high IL-2 secretion.

18. Immunosuppression using an HLA-DR Specific Antibody Measured by T Cell Proliferation Immunomodulatory properties of the anti-HLA-DR antibody fragments were also seen within an assay that measures T cell proliferation. The $IC_{50}$ value for inhibition of T cell proliferation of the IgG form of MS-GPC-8-10-57/1C7277 and MS-GPC-8-27-41/1D09C3 were 11 and 20 nM respectively (FIG. 10). The anti-HLA-DR antibody fragments were tested as follows to inhibit the proliferative T cell response of antigen-primed lymph node cells from mice carrying a chimeric mouse-human class II transgene with an RA-associated peptide binding site, and lack murine class II molecules (Muller et al., 1990; Woods et al., 1994; Current Protocols in Immunology, Vol. 2, 7.21; Ito et al., 1996). Here, the immunization takes place in vivo, but the inhibition and readout are ex vivo. Transgenic mice expressing MHC class II molecules with binding sites of the RA associated molecule, DRB*0401 were commercially obtained. These mice lack murine MHC class II, and thus, all Th responses are channelled through a single human RA-associated MHC class II molecule (Ito et al., 1996). These transgenic mice represent a model for testing human class II antagonists.

Figure 9D:
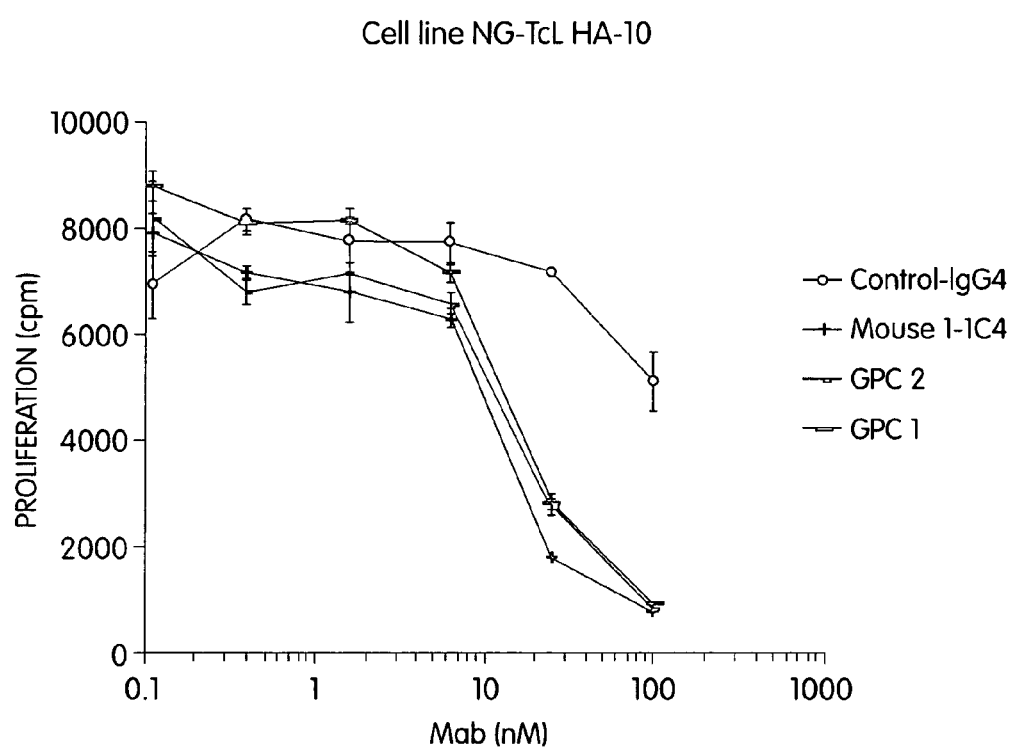

The inhibitory effect of the anti-HLA-DR antibody fragments and their IgG forms were tested on T-cell proliferation measured using chimeric T-cells and antigen presenting cells isolated from the lymph nodes of chimeric 0401-$I^E$ transgenic mice (Taconic, USA) previously immunized with hen egg ovalbumin (Ito et al., 1996) according to standard procedures. $1.5 \times 10^5$ cells are incubated in 0.2 ml wells of 96-well tissue culture plates in the presence of ovalbumin (30 µg per well—half-maximal stimulatory concentration) and a dilution series of the anti-HLA-DR antibody fragment or IgG form under test (0.1 nM-200 nM) in serum free HL-1 medium containing 2 mM L-glutamine and 0.1 g/L Kanamycin for three days. Antigen specific proliferation is measured by $^3$H-methyl-thymidin(1 µCi/well) incorporation during the last 16 hrs of culture (Falcioni et al., 1999). Cells are harvested, and $^3$H incorporation measured using a scintillation counter (TopCount, Wallac Finland). Inhibition of T-cell proliferation on treatment with the anti-HLA-DR antibody fragment and its IgG form was observed by comparison to control wells containing antigen. FIG. 9d showed that the proliferation of the T-cell line NG-TcL HA-10 was significantly inhibited by the two GPC antibodies (MS-GPC-8-10-57/1C7277 and MS-GPC-8-27-41/1D09C3), at least to the same extent of the mouse 1-1 C4 positive control Ab.

Figure 9E:
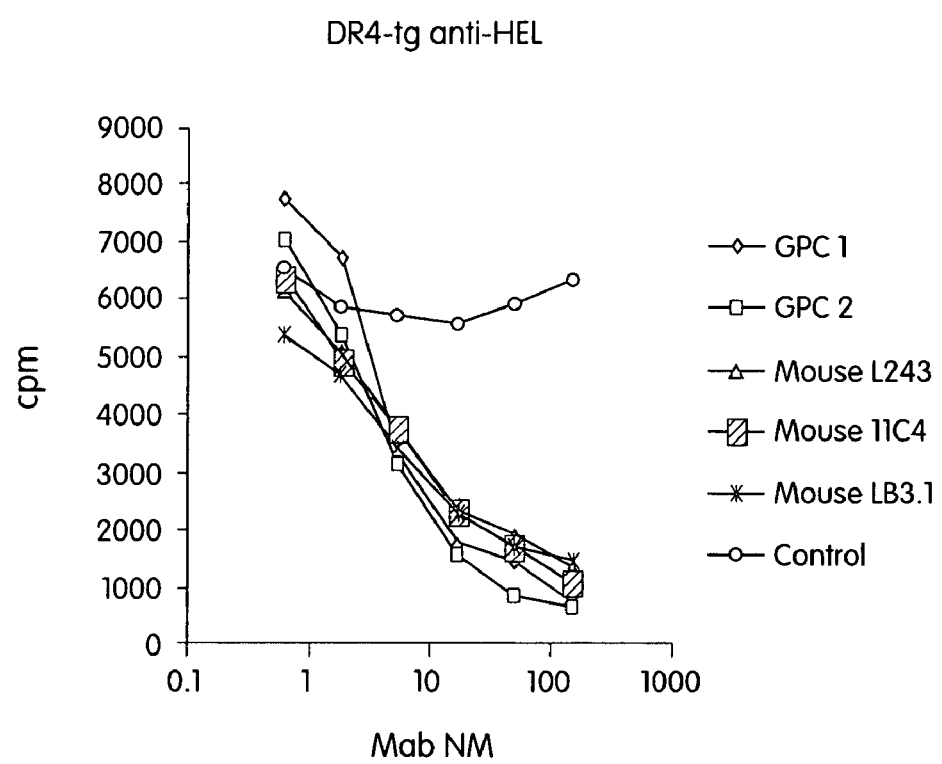
Figure 9F:
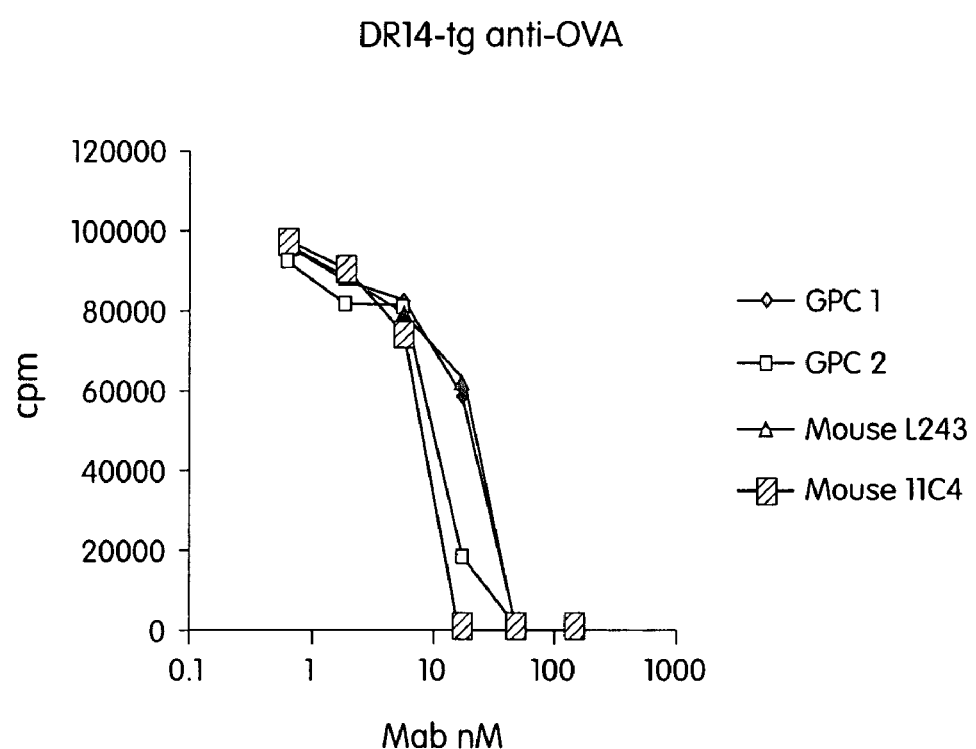

FIGS. 9e and 9f showed that transgenic T-cell proliferation as measured by $^3$H incorporation in two experiments were significantly inhibited by mAb treatments, including MS-GPC-8-10-57/1C7277 and MS-GPC-8-27-41/1D09C3 human mAb's and mouse L243, 11C4 and LB3.1 Ab's. In these experiments, T-cells are sensitized in vivo by specific antigens (ovalbumin (OVA) in one case, hen egg lysozyme (HEL) in another case), followed by re-stimulation ex vivo by these two antigens respectively for measuring immune stimulation in the form of antigen specific induction of T-cell proliferation. FIGS. 9e and 9f showed that more than 90% inhibition of antigen specific induction of T-cell proliferation is achieved using the human mAb's of the instant invention.

19. Selection of Useful Polypeptide for the Treatment of Cancers

In order to select the most appropriate protein/peptide to enter further experiments and to assess its suitability for use in a therapeutic composition for the treatment of cancers, additional data are collected. Such data for each IgG form of the anti-HLA antigen antibody fragments can include the binding affinity, in vitro killing efficiency as measured by $EC_{50}$ and cytotoxicity across a panel of tumor cell lines, the maximal percentage cell killing as estimated in vitro, and tumor reduction data and mouse survival data from in vivo animal models.

The IgG form of the anti-HLA antigen antibody fragments that shows the highest affinity, the lowest $EC_{50}$ for killing, the highest maximal percentage cell killing and broadest across various tumor cell lines, the best tumor reduction data and/or the best mouse-survival data may be chosen to enter further experiments. Such experiments may include, for example, therapeutic profiling and toxicology in animals and phase I clinical trials in humans.

20. In vivo Efficacy of Immunosuppression using an HLA-DR Specific Antibody in Treating Delayed-Type-Hypersensitivity (DTH)

In order to determine the in vivo efficacy of the immunosuppression activity of the mAb's of the instant invention, we conducted experiments using a mouse model for delayed-type-hypersensitivity (DTH). In this system, mouse ear-swelling in response to treatments by haptens such as oxazalone (OXA) or dinitroflurobenzene (DNFB) were measured to determine the in vivo efficacy of the mAb's of the instant invention.

Specifically, 0.05 ml of 2% OXA or DNFB were applied to the bellies of treatment group mice on day 1 and 2. On day 5, different doses of test mAb's 1D09C3 or control treatments were administered i.v. After waiting for 4 or 8 hours, mice were challenged with 0.02 ml of 0.5% OXA or DNFB. Ear thickness was measured on day 6, 8, 9 and 12, and the results were presented in FIG. 9g, 9h and 9i.

Figure 9G:
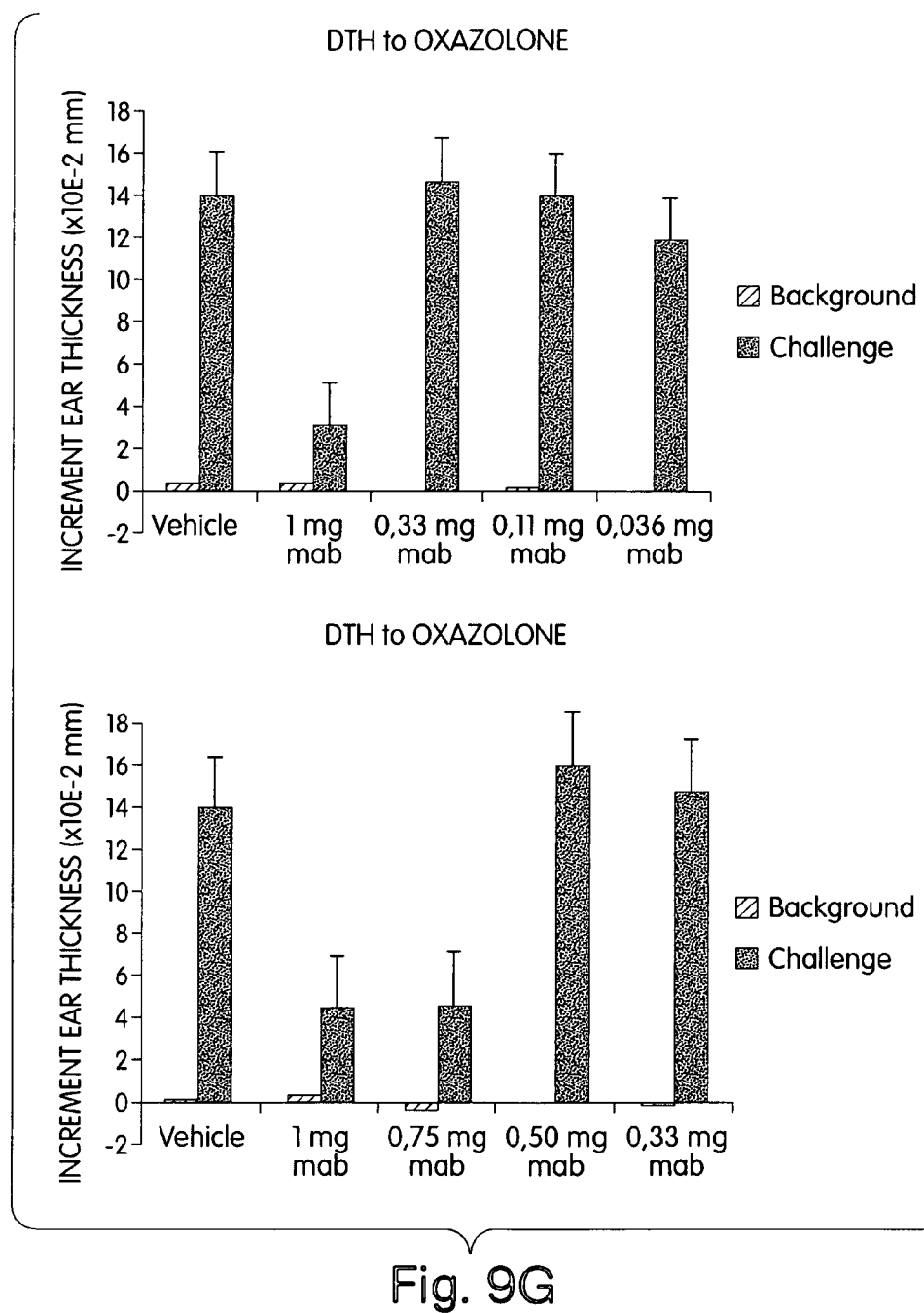

In FIG. 9g, DTH to OXA as measured by ear-thickness was blocked by roughly 75% if 1 mg or 0.75 mg of mAb was administered i.v., while 0.5 mg of mAb or less has no significant effect.

Figure 9H:
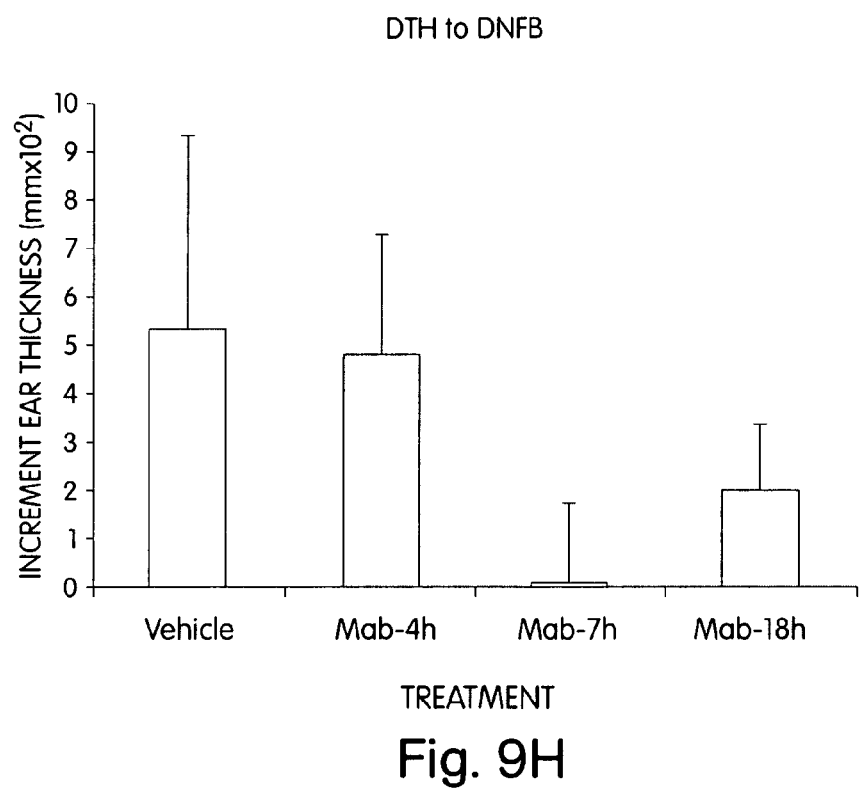
Figure 9I:
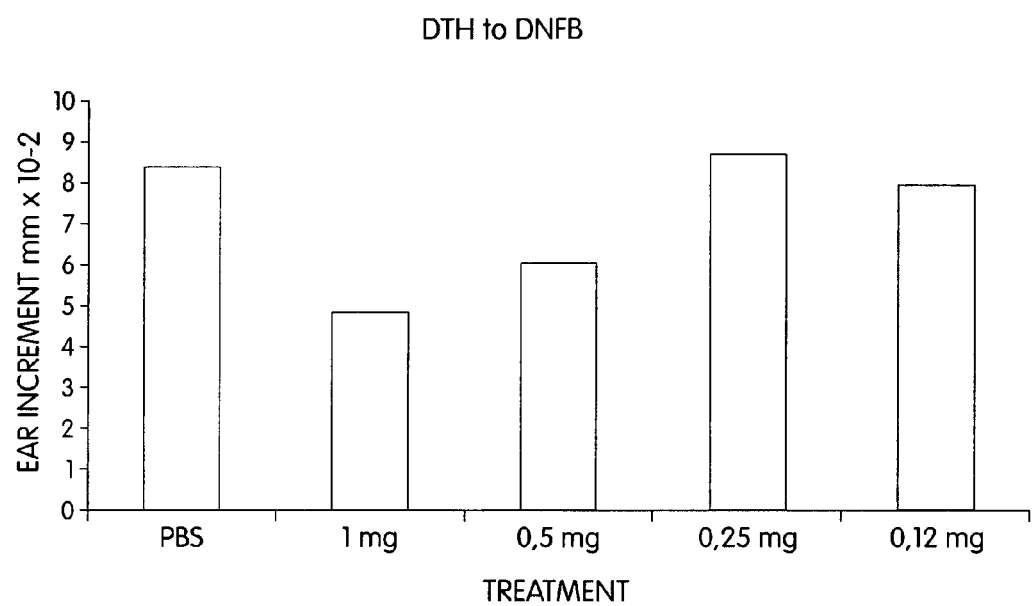

In FIG. 9h, the time course of inhibition, by human anti-DR mAb, of DTH to DNFB in DR-tg mice as measured by ear-thickness was presented. DTH was almost completely blocked ($P<0.005$) at $7^{th}$ hour after treatment with the mAb 1D09C3, followed by a 60% block ($P<0.01$) at 18th hr and no effect at 4 hr. FIG. 9i showed a positive correlation between the dose of mAb (1D09C3) used at the $7^{th}$ hour and the effectiveness of the inhibition of DTH in DR-tg mice. Both 1 mg and 0.5 mg of 1D09C3 significantly ($P<0.005$) inhibited DTH while lower doses have no effect.

These experiments demonstrates that mAb's of the instant invention is capable of specifically inhibiting the very part of the immune system responsible for the unwanted immune reaction. It is an inhibition of immune reaction rather than suppression of existing immune reactios. Since the mAb's of the instant invention are fully human antibodies, rather than murine mAb or humanized murine antibodies, they are expected to have very low immunogenicity in the host and a much longer half life. In addition, most mAb's of the instant invention also have very high affinity in the pico molar range. These mAb's shall prove to be useful for a variety of immune diseases such as DTH and Graft v. Host Disease (GVHD).

21. Selection of useful Polypeptide for the Treatment of Diseases of the Immune System In order to select the most appropriate protein/peptide to enter further experiments and to assess its suitability for use in a therapeutic composition for the treatment of diseases of the immune system, additional data are collected. Such data for each monovalent antibody fragment or IgG form of the anti-HLA antigen antibody fragments can include the affinity, reactivity, specificity, $IC_{50}$-values, for inhibition of IL-2 secretion and of T-cell proliferation, or in vitro killing efficiency as measured by $EC_{50}$ and the maximal percentage cell killing as estimated in vitro, and DR-transgenic models of transplant rejection and graft vs. host disease.

The antibody fragment or IgG form of the anti-HLA antigen antibody fragments that shows the lowest $EC_{50}$, highest affinity, highest killing, best specificity and/or greatest inhibition of T-cell proliferation or IL-2 secretion, and high efficacy in inhibiting transplant rejection and/or graft vs. host disease in appropriate models, might be chosen to enter further experiments. Such experiments may include, for example, therapeutic profiling and toxicology in animals and phase I clinical trials in humans.

TABLE 1

VH and VL families, VL CDR1 and VH/VL CDR 3 sequences of HLA-DR-specific polypeptides

| Clone | VH | CDR3 Length | VH-CDR3-Seq. | VL | VL-CDR1-Seq. | CDR3 Length | VL-CDR3-Seq. | Families |
|---|---|---|---|---|---|---|---|---|
| MS-GPC-1 | H2 | 10 | QYGHRGGFDH (SEQ ID NO: 19) | λ1 | SGSSSNIGSNYVS (SEQ ID NO: 12) | 8 | QSYDFNES (SEQ ID NO: 59) | H2λ1 |
| MS-GPC-6 | H3 | 9 | GYGRYSPDL (SEQ ID NO: 20) | K3 | RASQSVSSSYLA (SEQ ID NO: 62) | 8 | QQYSNLPF (SEQ ID NO: 21) | H3K3 |
| MS-GPC-8 | H2 | 10 | SPRYRGAFDY (SEQ ID NO: 3) | λ1 | SGSSSNIGSNYVS (SEQ ID NO: 12) | 8 | QSYDMPQA (SEQ ID NO: 22) | H2λ1 |
| MS-GPC-10 | H2 | 10 | QLHYRGGFDL (SEQ ID NO: 61) | λ1 | SGSSSNIGSNYVS (SEQ ID NO: 12) | 8 | QSYDLTMG (SEQ ID NO: 23) | H2λ1 |
| MS-GPC-8-1 | H2 | 10 | SPRYRGAFDY (SEQ ID NO: 3) | λ1 | SGSSSNIGSNYVS (SEQ ID NO: 12) | 8 | QSYDFSHY (SEQ ID NO: 24) | H2λ1 |
| MS-GPC-8-6 | H2 | 10 | SPRYRGAFDY (SEQ ID NO: 3) | λ1 | SGSSSNIGSNYVS (SEQ ID NO: 12) | 8 | QSYDYDHY (SEQ ID NO: 60) | H2λ1 |
| MS-GPC-8-9 | H2 | 10 | SPRYRGAFDY (SEQ ID NO: 3) | λ1 | SGSSSNIGSNYVS (SEQ ID NO: 12) | 8 | QSYDIQLH (SEQ ID NO: 25) | H2λ1 |
| MS-GPC-8-10 | H2 | 10 | SPRYRGAFDY (SEQ ID NO: 3) | λ1 | SGSSSNIGSNYVS (SEQ ID NO: 12) | 8 | QSYDLIRH (SEQ ID NO: 4) | H2λ1 |
| MS-GPC-8-17 | H2 | 10 | SPRYRGAFDY (SEQ ID NO: 3) | λ1 | SGSSSNIGSNYVS (SEQ ID NO: 12) | 8 | QSYDFSVY (SEQ ID NO: 26) | H2λ1 |
| MS-GPC-8-18 | H2 | 10 | SPRYRGAFDY (SEQ ID NO: 3) | λ1 | SGSSSNIGSNYVS (SEQ ID NO: 12) | 8 | QSYDFSIY (SEQ ID NO: 27) | H2λ1 |
| MS-GPC-8-27 | H2 | 10 | SPRYRGAFDY (SEQ ID NO: 3) | λ1 | SGSSSNIGSNYVS (SEQ ID NO: 12) | 8 | QSYDMNVH (SEQ ID NO: 5) | H2λ1 |
| MS-GPC-8-6-2 | H2 | 10 | SPRYRGAFDY (SEQ ID NO: 3) | λ1 | SGSESNIGSNYVH (SEQ ID NO: 13) | 8 | QSYDYDHY (SEQ ID NO: 60) | H2λ1 |

TABLE 1-continued

VH and VL families, VL CDR1 and VH/VL CDR 3 sequences of HLA-DR-specific polypeptides

| Clone | VH | CDR3 Length | VH-CDR3-Seq. | VL | VL-CDR1-Seq. | CDR3 Length | VL-CDR3-Seq. | Families |
|---|---|---|---|---|---|---|---|---|
| MS-GPC-8-6-19 | H2 | 10 | SPRYRGAFDY (SEQ ID NO: 3) | λ1 | SGSESNIGSNYVA (SEQ ID NO: 14) | 8 | QSYDYDHY (SEQ ID NO: 60) | H2λ1 |
| MS-GPC-8-6-27 | H2 | 10 | SPRYRGAFDY (SEQ ID NO: 3) | λ1 | SGSDSNIGANYVT (SEQ ID NO: 15) | 8 | QSYDYDHY (SEQ ID NO: 60) | H2λ1 |
| MS-GPC-8-6-45 | H2 | 10 | SPRYRGAFDY (SEQ ID NO: 3) | λ1 | SGSEPNIGSNYVF (SEQ ID NO: 16) | 8 | QSYDYDHY (SEQ ID NO: 60) | H2λ1 |
| MS-GPC-8-6-13 | H2 | 10 | SPRYRGAFDY (SEQ ID NO: 3) | λ1 | SGSESNIGANYVT (SEQ ID NO: 29) | 8 | QSYDYDHY (SEQ ID NO: 60) | H2λ1 |
| MS-GPC-8-6-47 | H2 | 10 | SPRYRGAFDY (SEQ ID NO: 3) | λ1 | SGSESNIGSNYVS (SEQ ID NO: 30) | 8 | QSYDYDHY (SEQ ID NO: 60) | H2λ1 |
| MS-GPC-8-10-57 | H2 | 10 | SPRYRGAFDY (SEQ ID NO: 3) | λ1 | SGSESNIGNNYVQ (SEQ ID NO: 7) | 8 | QSYDLIRH (SEQ ID NO: 4) | H2λ1 |
| MS-GPC-8-27-7 | H2 | 10 | SPRYRGAFDY (SEQ ID NO: 3) | λ1 | SGSESNIGNNYVG (SEQ ID NO: 17) | 8 | QSYDMNVH (SEQ ID NO: 5) | H2λ1 |
| MS-GPC-8-27-10 | H2 | 10 | SPRYRGAFDY (SEQ ID NO: 3) | λ1 | SGSESNIGANYVN (SEQ ID NO: 18) | 8 | QSYDMNVH (SEQ ID NO: 5) | H2λ1 |
| MS-GPC-8-27-41 | H2 | 10 | SPRYRGAFDY (SEQ ID NO: 3) | λ1 | SGSESNIGNNYVQ (SEQ ID NO: 7) | 8 | QSYDMNVH (SEQ ID NO: 5) | H2λ1 |

TABLE 2

| Steps in Antibody optimisation | Fab | $k_{on}$ [s$^{-1}$M$^{-1}$] × 10$^5$ ± SD | $k_{off}$ [s$^{-1}$] × 10$^{-3}$ ± SD | $K_D$ [nM] ± SD | L-CDR3 | L-CDR1 |
|---|---|---|---|---|---|---|
| Parental Fab | MS-GPC-8 | 0.99 ± 0.40 | 29.0 ± 8.40 | 346.1 ± 140.5[a)] | QSYDMPQA (SEQ ID NO: 22) | SGSSSNIGSNYVS (SEQ ID NO: 12) |
| L-CDR3–optim. | -8-1 | 1.93 | 20.9 | 108[e)] | | |
| L-CDR3–optim. | -8-6 | 0.96 ± 0.14 | 5.48 ± 0.73 | 58.6 ± 11.7[b)] | | |
| L-CDR3–optim. | -8-9 | 1.85 | 16.6 | 90.1[e)] | | |
| L-CDR3–optim. | -8-10 | nd | 7.0[e)] | nd | | |
| L-CDR3–optim. | -8-17 | 1.0 | 5.48 | 54.7[e)] | | |
| L-CDR3–optim. | -8-18 | 1.06 | 8.3 | 78.3[e)] | | |
| L-CDR3–optim. | -8-27 | nd | 6.6[e)] | nd | | |
| L-CDR3–optim. | -8-6 | 0.96 ± 0.14 | 5.48 ± 0.73 | 58.6 ± 11.7[b)] | QSYDYDHY (SEQ ID NO: 60) | SGSSSNIGSNYVS (SEQ ID NO: 12) |
| L-CDR3+1-opt. | -8-6-2 | 1.23 ± 0.11 | 0.94 ± 0.07 | 7.61 ± 0.25[c)] | QSYDYDHY (SEQ ID NO: 60) | SGSESNIGSNYVH (SEQ ID NO: 13) |
| L-CDR3+1-opt. | -8-6-19 | 1.10 ± 0.08 | 0.96 ± 0.15 | 8.74 ± 1.33[c)] | QSYDYDHY (SEQ ID NO: 60) | SGSESNIGSNYVA (SEQ ID NO: 14) |
| L-CDR3+1-opt. | -8-6-27 | 1.80 ± 0.24 | 1.10 ± 0.15 | 6.30 ± 0.63[d)] | QSYDYDHY (SEQ ID NO: 60) | SGSDSNIGANYVT (SEQ ID NO: 15) |
| L-CDR3+1-opt. | -8-6-45 | 1.20 ± 0.07 | 1.03 ± 0.04 | 8.63 ± 0.61[c)] | QSYDYDHY (SEQ ID NO: 60) | SGSEPNIGSNYVF (SEQ ID NO: 16) |
| L-CDR3+1-opt. | -8-6-13 | 1.90 ± 0.26 | 0.55 ± 0.05 | 2.96 ± 0.46[c)] | QSYDYDHY (SEQ ID NO: 60) | SGSESNIGANYVT (SEQ ID NO: 29) |
| L-CDR3+1-opt. | -8-6-47 | 1.97 ± 0.29 | 0.62 ± 0.04 | 3.18 ± 0.33[c)] | QSYDYDHY (SEQ ID NO: 60) | SGSESNIGSNYVS (SEQ ID NO: 30) |
| L-CDR3+1-opt. | -8-10-57 | 1.65 ± 0.21 | 0.44 ± 0.06 | 2.67 ± 0.25[c)] | QSYDLIRH (SEQ ID NO: 4) | SGSESNIGNNYVQ (SEQ ID NO: 7) |
| L-CDR3+1-opt. | -8-27-7 | 1.74 ± 0.21 | 0.57 ± 0.07 | 3.30 ± 0.34[d)] | QSYDMNVH (SEQ ID NO: 5) | SGSESNIGNNYVG (SEQ ID NO: 17) |

TABLE 2-continued

| Steps in Antibody optimisation | Fab | $k_{on}$ [s$^{-1}$M$^{-1}$] × 10$^5$ ± SD | $k_{off}$ [s$^{-1}$] × 10$^{-3}$ ± SD | $K_D$ [nM] ± SD | L-CDR3 | L-CDR1 |
|---|---|---|---|---|---|---|
| L-CDR3+1-opt. | -8-27-10 | 1.76 ± 0.21 | 0.53 ± 0.05 | 3.01 ± 0.21[c] | QSYDMNVH (SEQ ID NO: 5) | SGSESNIGANYVN (SEQ ID NO: 18) |
| L-CDR3+1-opt. | -8-27-41 | 1.67 ± 0.16 | 0.49 ± 0.03 | 2.93 ± 0.27[d] | QSYDMNVH (SEQ ID NO: 5) | SGSESNIGNNYVQ (SEQ ID NO: 7) |

[a] Affinity data of MS-GPC-8 are based on 8 different Fab-preparations which were measured on 4 different chips (2 × 500, 1000, 4000 RU)
[b] For MS-GPC-8-6 mean and standard deviation of 3 different preparations on 3 different chips (500, 4000, 3000 RU) is shown.
[c] 3000 RU MHCII were immobilized on a CM5-chip. For each measurement 7 different concentrations from 1 µM to 16 nM were injected on the surface. Dissociation time: 150 sec, regeneration was reached by 6 µl 10 mM Glycine pH 2.3 followed by 8 µl 7.5 mM NaOH. For MS-GPC-8-6-19 mean and standard deviation of 4 different preparations are shown whereas for all other binders mean and standard deviation of 3 different preparations are shown.
[d] One protein preparation is measured on 3 different chips (3000, 2800 and 6500 RU).
[e] Affinity determination of maturated MHCII binder on a 4000 RU density chips; single measurement.
Molecular weights were determined after size exclusion chromatography and found 100% monomeric with the right molecular weight between 45 and 48 kDa.

TABLE 3a

Affinities of selected IgG$_4$ monoclonal antibodies constructed from F$_{ab}$'s. Errors represent standard deviations

| Binder (IgG$_4$) | $k_{on}$ [M$^{-1}$s$^{-1}$] × 10$^5$ | $k_{off}$ [s$^{-1}$] × 10$^{-5}$ | $K_D$ [nM] |
|---|---|---|---|
| MS-GPC-8-27-41 | 1.1 ± 0.2 | 3.1 ± 0.4 | 0.31 ± 0.06 |
| MS-GPC-8-6-13 | 0.7 ± 0.1 | 3.0 ± 1.0 | 0.50 ± 0.20 |
| MS-GPC-8-10-57 | 0.7 ± 0.2 | 4.0 ± 1.0 | 0.60 ± 0.20 |

TABLE 3b

Affinities of binders obtained out of affinity maturation of CDR1 light chain optimisation following CDR3 heavy chain optimisation. Errors represent standard deviations

| Binder (F$_{ab}$) | $k_{on}$ [M$^{-1}$s$^{-1}$] × 10$^5$ | $k_{off}$ [s$^{-1}$] × 10$^{-3}$ | $K_D$ [nM] |
|---|---|---|---|
| MS-GPC-8-6-2 | 1.20 ± 0.10 | 0.94 ± 0.07 | 7.6 ± 0.3 |
| MS-GPC-8-6-19 | 1.10 ± 0.10 | 1.00 ± 0.20 | 9.0 ± 1.0 |
| MS-GPC-8-6-27 | 1.80 ± 0.20 | 1.10 ± 0.20 | 6.3 ± 0.6 |
| MS-GPC-8-6-45 | 1.20 ± 0.07 | 1.03 ± 0.04 | 8.6 ± 0.6 |
| MS-GPC-8-6-13 | 1.90 ± 0.30 | 0.55 ± 0.05 | 3.0 ± 0.5 |
| MS-GPC-8-6-47 | 2.00 ± 0.30 | 0.62 ± 0.04 | 3.2 ± 0.3 |
| MS-GPC-8-10-57 | 1.70 ± 0.20 | 0.44 ± 0.06 | 2.7 ± 0.3 |
| MS-GPC-8-27-7 | 1.70 ± 0.20 | 0.57 ± 0.07 | 3.3 ± 0.3 |

TABLE 3b-continued

Affinities of binders obtained out of affinity maturation of CDR1 light chain optimisation following CDR3 heavy chain optimisation. Errors represent standard deviations

| Binder (F$_{ab}$) | $k_{on}$ [M$^{-1}$s$^{-1}$] × 10$^5$ | $k_{off}$ [s$^{-1}$] × 10$^{-3}$ | $K_D$ [nM] |
|---|---|---|---|
| MS-GPC-8-27-10 | 1.80 ± 0.20 | 0.53 ± 0.05 | 3.0 ± 0.2 |
| MS-GPC-8-27-41 | 1.70 ± 0.20 | 0.49 ± 0.03 | 2.9 ± 0.3 |

TABLE 3c

Binders obtained out of affinity maturation of GPC8 by CDR3 light chain optimisation

| Binder (F$_{ab}$) | $k_{on}$ [M$^{-1}$s$^{-1}$] × 10$^5$ | $k_{off}$ [s$^{-1}$] × 10$^{-3}$ | $K_D$ [nM] |
|---|---|---|---|
| MS-GPC 8-18 | 1.06 | 8.30 | 78.3 |
| MS-GPC 8-9 | 1.85 | 16.60 | 90.1 |
| MS-GPC 8-1 | 1.93 | 20.90 | 108.0 |
| MS-GPC 8-17 | 1.00 | 5.48 | 54.7 |
| MS-GPC-8-6[a] | 1.20 ± 0.10 | 5.50 ± 0.70 | 8.0 ± 12.0 |

Chip density 4000 RU MHCII
[a] For MS-GPC-8-6 mean and standard deviation of 3 different preparations on 3 different chips (500, 4000, 3000 RU) is shown.

TABLE 3d

Binders obtained out of HuCAL in scFv form and their converted Fabs

| | scF$_v$ | | | F$_{ab}$ | | |
|---|---|---|---|---|---|---|
| Binder | $k_{on}$ [M$^{-1}$s$^{-1}$] × 10$^5$ | $k_{off}$ [s$^{-1}$] × 10$^{-3}$ | $K_D$ [nM] | $k_{on}$ [M$^{-1}$s$^{-1}$] × 10$^5$ | $k_{off}$ [s$^{-1}$] × 10$^{-3}$ | $K_D$ [nM] |
| MS-GPC 1 | 0.413 | 61 | 1500 | 0.639 | 53 | 820 |
| MS-GPC 6 | 0.435 | 200 | 4600 | 0.135 | 114 | 8470 (1 curve) |
| MS-GPC 8 | 0.114 | 76 | 560 | 0.99 +/−0.40[b] | 29.0 +/−8.4 | 346[a] +/−141 |
| MS-GPC 10 | 0.187 | 180 | 9625 | 0.22 | 63 | 2860 |

Chip density 500 RU MHCII
[a] Affinity data of MS-GPC-8 are based on 8 different Fab-preparations which were measured on 4 different chips (2 × 500, 1000, 4000 RU) and are shown with standard deviation.
[b] Mean ± S.D. of three independent measurements.

TABLE 3e

Affinity improvements achieved by antibody optimization

| mAb | Format | Optimization | $k_{on}$ [s$^{-1}$M$^{-1}$] × 10$^5$ | $k_{off}$ [s$^{-1}$] × 10$^{-3}$ | $K_D$ [nM][a] |
|---|---|---|---|---|---|
| B8 | Fab | parental | 0.99 ± 0.4[b] | 29.0 ± 8.4 | 346.1 ± 140.5 |
| 7BA | Fab | L-CDR3 | 0.96 ± 0.14 | 5.48 ± 0.73 | 58.6 ± 11.7 |
| 305D3 | Fab | L-CDR3+1 | 1.90 ± 0.26 | 0.55 ± 0.05 | 2.96 ± 0.46 |
| 1C7277 | Fab | L-CDR3+1 | 1.65 ± 0.21 | 0.44 ± 0.06 | 2.67 ± 0.25 |
| 1D09C3 | Fab | L-CDR3+1 | 1.67 ± 0.16 | 0.49 ± 0.03 | 2.93 ± 0.27 |
| 305D3 | IgG$_4$ | L-CDR3+1 | 0.71 ± 1.6 | 0.33 ± 1.0 | 0.5 ± 0.20 |
| 1C7277 | IgG$_4$ | L-CDR3+1 | 0.11 ± 2.0 | 0.31 ± 0.4 | 0.3 ± 0.06 |
| 1D09C3 | IgG$_4$ | L-CDR3+1 | 0.71 ± 1.2 | 0.41 ± 1.1 | 0.6 ± 0.20 |

[a] Affinities were determined by BiaCore.
[b] Mean ± S.D. of three independent measurements.

TABLE 4

Killing efficiency after 4 hour incubation of cells with cross-linked anti-HLA-DR antibody fragments, and maximum killing after 24 hour incubation

| Cross-linked Fab fragment | Killing efficiency against GRANTA | Maximum killing against PRIESS |
|---|---|---|
| MS-GPC-1 | + | + |
| MS-GPC-6 | + | + |
| MS-GPC-8 | + | + |
| MS-GPC-10 | + | + |
| MS-GPC-8-6 | ++ | ++ |
| MS-GPC-8-17 | ++ | ++ |
| MS-GPC-8-6-13 | +++ | +++ |
| MS-GPC-8-10-57 | +++ | +++ |
| MS-GPC-8-27-41 | +++ | +++ |

TABLE 5

Killing efficiency of anti-HLA-DR IgG antibodies of human composition compared to murine anti-HLA-DR antibodies against a panel of lymphoid tumor cell lines.

| Cell Lines | | | HLA-DR expression[a] MFL | % Killing by mAb[b] | | | | | |
|---|---|---|---|---|---|---|---|---|---|
| | | | | Murine mAbs | | | Human mAbs | | |
| Name | DR type | Tumor Type | L243 | L243 | 8D1 | B8 | 1D09C3 | 1C7277 | 305D3 |
| LG-2 | 1, 1 | B-lymphoblastoid | 458 | 79 | 85 | 86 | 87 | 88 | 82 |
| PRIESS | 4, 4 | B-lymphoblastoid | 621 | 87 | 83 | 85 | 88 | 93 | 74 |
| ARH-77 | 12 | B-lymphoblastoid | 301 | 88 | 73 | 84 | 85 | 88 | 87 |
| GRANTA-519 | 2, 11 | B cell non-Hodgkin | 1465 | 83 | 56 | 76 | 78 | 78 | 73 |
| KARPAS-422 | 2, 4 | B cell non-Hodgkin | 211 | 25 | 32 | 51 | 66 | 68 | 71 |
| KARPAS-299 | 1, 2 | T cell non-Hodgkin | 798 | 78 | 25 | 81 | 82 | 79 | 76 |
| DOHH-2 | 1, 2 | B cell lymphoma | 444 | 29 | 23 | 58 | 59 | 60 | 53 |
| SR-786 | 1, 2 | T cell lymphoma | 142 | 3 | 8 | 1 | 53 | 44 | 26 |
| MHH-CALL-4 | 1, 2 | B-ALL | 348 | 35 | 41 | 43 | 63 | 46 | 43 |
| MN-60 | 10, 13 | B-ALL | 1120 | 46 | 22 | 71 | 69 | 66 | 67 |
| BJAB | 12, 13 | Burkitt lymph. | 338 | 53 | 59 | 49 | 71 | 67 | 64 |
| RAJI | 10, 17 | Burkitt lymph. | 617 | 69 | 64 | 81 | 84 | 86 | 83 |
| L-428 | 12 | Hodgkin's lymph. | 244 | 82 | 81 | 82 | 91 | 91 | 92 |
| HDLM-2 | | Hodgkin's lymph. | 326 | 77 | 73 | 89 | 88 | 84 | 90 |
| HD-MY-Z | | Hodgkin's lymph. | 79 | 35 | 39 | 49 | 69 | 57 | 72 |
| KM-H2 | | Hodgkin's lymph. | 619 | 81 | 56 | 75 | 86 | 88 | 87 |
| L1236 | | Hodgkin's lymph. | 41 | 52 | 62 | 44 | 63 | 66 | 66 |
| BONNA-12 | | hairy cell leuk. | 2431 | 92 | 91 | 91 | 92 | 91 | 86 |
| HC-1 | | hairy cell leuk. | 372 | 88 | 89 | 89 | 93 | 86 | 93 |
| NALM-1 | 1, 4 | CML | 1078 | 44 | 4 | 83 | 82 | 78 | 65 |
| L-363 | | plasma cell leu. | 49 | 6 | 5 | 26 | 26 | 24 | 19 |
| EOL-1 | | AML (eosinophil) | 536 | 22 | 13 | 36 | 69 | 49 | 53 |
| LP-1 | | multiple myeloma | 315 | 12 | 0 | 61 | 73 | 70 | 73 |
| RPMI-8226 | | multiple myeloma | 19 | 6 | 0 | 14 | 29 | 26 | 19 |
| MHH-PREB-1 | | B cell non-Hodgkin | 175 | 3 | 3 | 2 | 4 | 8 | 11 |
| MHH-CALL-2 | | B cell precursor leu. | + | 5 | 5 | | | | |
| OPM-2 | | multiple myeloma | 3 | 13 | 0 | 8 | 1 | 4 | 5 |
| KASUMI-1 | | AML | 5 | 0 | 0 | 8 | 10 | 10 | 6 |

TABLE 5-continued

Killing efficiency of anti-HLA-DR IgG antibodies of human composition compared to murine anti-HLA-DR antibodies against a panel of lymphoid tumor cell lines.

| Cell Lines | | | HLA-DR expression[a] MFL | % Killing by mAb[b] | | | | | |
|---|---|---|---|---|---|---|---|---|---|
| | | | | Murine mAbs | | Human mAbs | | | |
| Name | DR type | Tumor Type | L243 | L243 | 8D1 | B8 | 1D09C3 | 1C7277 | 305D3 |
| HL-60 | | AML | 3 | 18 | 0 | 3 | 15 | 9 | 22 |
| LAMA-84 | | CML | 7 | 7 | 9 | 5 | 11 | 5 | 7 |

[a]Expressed as mean fluorescence intensity after staning with FITC-labelled L243. Single determination or the average of 2 to 3 experiments per cell line.
[b]Based on viable cell recovery after treatment with 200 nM murine or 50 nM human mAb at 37 C. for 4 h. Determined by light or fluorescence microscopic cell counting or FACS analysis, as described in Experimental protocol. Each number represents an average from 2 to 6 independent experiments.

TABLE 6

$EC_{50}$ values for certain anti-HLA-DR antibody fragments of the invention in a cell-killing assay against lymphoid tumor cells. All $EC_{50}$ refer to nanomolar concentrations of the bivalent agent (IgG or cross-linked Fab) such that values for cross-linked Fab and IgG forms can be compared.

| Antibody fragment | Form | Cell line tested | $EC_{50}$ of cell killing (nM) +/− SE for bivalent agent |
|---|---|---|---|
| MS-GPC-1 | Fab | PRIESS | 54 ± 14 |
| MS-GPC-8 | Fab | PRIESS | 31 ± 9 |
| MS-GPC-10 | Fab | PRIESS | 33 ± 5 |
| MS-GPC-8-17 | Fab | PRIESS | 16 ± 4 |
| MS-GPC-8-6-2 | Fab | PRIESS | 8 ± 2 |
| MS-GPC-8-10-57 | Fab | LG2 | 7.2 |
| MS-GPC-8-27-41 | Fab | LG2 | 7.2 |
| MS-GPC-8-27-41 | Fab | PRIESS | 7.7 |
| MS-GPC-8 | $IgG_4$ | PRIESS | 8.3 |
| MS-GPC-8-27-41 | $IgG_4$ | PRIESS | 1.1 ± 0.1 |
| MS-GPC-8-10-57 | $IgG_4$ | PRIESS | 1.1 ± 0.2 |
| MS-GPC-8-27-41 | $IgG_4$ | LG2 | 1.23 ± 0.2 |
| MS-GPC-8-10-57 | $IgG_4$ | LG2 | 1.0 ± 0.1 |
| 8D1 | mIgG | PRIESS | 33 |
| L243 | mIgG | PRIESS | 47 |

TABLE 7

$IC_{50}$ values for certain anti-HLA-DR antibody fragments of the invention in an assay to determine IL-2 secretion after antigen-specific stimulation of T-Hyb 1 cells. $IC_{50}$ for the IgG forms (bivalent) are represented as molar concentrations, while in order to provide easy comparison, $IC_{50}$s for the Fab forms (monovalent) are expressed in terms of half the concentration of the Fab to enable direct comparison to IgG forms.

| Anti-HLA-DR antibody fragment | Form | $IC_{50}$ (IgG/nM) ((Fab)/2/nM) Mean | SE | Maximum inhibition(%) |
|---|---|---|---|---|
| MS-GPC-8-10-57 | IgG | 0.31 | 0.01 | 100 |
| MS-GPC-8-27-41 | IgG | 0.28 | 0.07 | 100 |
| MS-GPC-8-6-13 | IgG | 0.42 | 0.06 | 100 |
| MS-GPC-8-6-2 | IgG | 3.6 | 1.1 | 100 |
| MS-GPC-8-6 | IgG | 6.7 | 2.0 | 100 |
| MS-GPC-8 | IgG | 11.0 | 0.8 | 100 |
| MS-GPC-8-6-2 | Fab | 4.7 | 1.9 | 100 |
| MS-GPC-8-6-13 | Fab | 2.1 | 0.8 | 100 |
| MS-GPC-8-6-19 | Fab | 5.3 | 0.2 | 100 |
| MS-GPC-8-10-57 | Fab | 2.9 | 1.0 | 100 |
| MS-GPC-8-6-27 | Fab | 3.0 | 1.2 | 100 |
| MS-GPC-8-6-47 | Fab | 2.6 | 0.6 | 100 |
| MS-GPC-8-27-7 | Fab | 5.9 | 2.2 | 100 |
| MS-GPC-8-27-10 | Fab | 7.3 | 1.9 | 100 |
| MS-GPC-8-27-41 | Fab | 3.6 | 0.7 | 100 |
| MS-GPC-8-6 | Fab | 20 | | 100 |
| MS-GPC-8 | Fab | 110 | | 100 |

TABLE 8

Antibody Name Conversion Table

| | |
|---|---|
| MS-GPC-8 | B8 |
| MS-GPC-8-17 | 7BA |
| MS-GPC-8-6-13 | 305D3 |
| MS-GPC-8-10-57 | 1C7277 |
| MS-GPC-8-27-41 | 1D09C3 |
| MS-GPC-1 | 17 |
| MS-GPC-6 | 8A |
| MS-GPC-10 | E6 |

The following is a partial list of references cited in the instant application. The contects of these references are hereby incorporated herein by reference.

REFERENCES

Adorini L, Mueller S, Cardinaux F, Lehmann P V, Falcioni F, Nagy Z A, (1988), Nature 334: 623.

Ausubel, F. M., Brent, R., Kingston, R. E., Moore, D. D., Seidman, J. G., Smith, J. A. and Struhl, K. (1998) Current protocols in molecular biology. John Wiley & Sons, Inc., New York, U.S.A.

Babbitt B, Allen P M, Matsueda G, Habe E, Unanue E R, (1985), Nature 317:359.

Baxevanis, C. N., Wernet, D., Nagy, Z. A., Maurer, P. H., and Klein, J. (1980). Immunogenetics, 11, 617.

Billing, R., and Chatterjee, S. (1983). Transplant. Proc. 15, 649.

Bird, R. E. et al. Single-chain antigen-binding proteins [published erratum appears in Science 1989 Apr 28;244(4903): 409]. Science 242, 423-6 (1988).

Bonagura, V. R., Ma, a., McDowell, J., Lewison, A., King, D. W. and Suciu-Foca, N. (1987). Cell. Immunolo., 108(2), 356.

Brinkmann, U., Reiter, Y., Jung, S., Lee, B. & Pastan, I. (1993). A recombinant immunotoxin containing a disulfide-stabilized Fv fragment. Proc. Natl. Acad. Sci. U.S.A. 90, 7538-7542.

Brown J H, Jardetsky T S, Gorga J C, Stern L J, Urban R G, Strominger J L, Wiley D C., (1993), Nature 364: 33.

Buhmann R, Nolte A, Westhaus D, Emmerich B, Hallek M., (1999) Blood 93: 1992

Cambier J C, Morrison D C, Chien M M, Lehmann K R: J., (1991), Immunol. 146: 2075.

Current Protocols in Immunology, Vol. 2, 7.21 (1997).

Current Protocols in Immunology (John Wiley & Sons, Inc.; 1999).

Drenou B, Blancheteau V, Burgess D H, Fauchet R, Charron D J, Mooney N A., (1999), J. Immunol. 163: 4115.

Falcioni et al. (1999). Nat Biotechnol. 17: 562-567.

Glockshuber, R., Malia, M., Pfitzinger, I. & Plückthun, A. (1990). A comparison of strategies to stabilize immunoglobulin Fv-fragrnents. Biochemistry 29, 1362-1367.

Gorga, J. C., Foran, J., Burakoff, S. J., Strominger, J. L., (1984) Meth Emzym., 108, 607-613.

Gorga, J. C., Horejsi, V., Johnson, D. R., Raghupathy, R., Strominger, J. L., J. Biol. Chem. 262 (1987)16087-94.

Gorga, J. C., Knudsen, P. J., Foran, J. A., Strominger, J. L., Burakoff, S. J., (1986), Cell. Immunol. 103 160-73.

Heiskanen T, Lundkvist A, Soliymani R, Koivunen E, Vaheri A, Lankinen H (1999) Virology, 262(2), 321.

Hopp, T. P., Prickett, K. S., Price, V. L., Libby, R. T., March, C. J., Cerretti, D. P., Urdal, D. L. & Conlon, P. J. (1988), Bio/Technology 6, 1204-1210.

Huston, J. S. et al. Protein engineering of antibody binding sites: recovery of specific activity in an anti-digoxin single-chain Fv analogue produced in *Escherichia coli*. Proc Natl Acad Sci U S A 85, 5879-83 (1988).

Ito K, Bian H. -J, Molina M, Han J, Magram J, Saar E, Belunis C, Bolin D R, Arceo R, Campbell R, Falcioni F, Vidovic' D, Nagy Z A., (1996), J. Exp. Med. 183: 2635-2644.

Jones et al., (1986), Nature 321: 522-525.

Jonker, M., Schellekens, P. T., Harpprecht, J., and Slingerland, W. (1991), Transplant. Proc., 23, 264.

Jonker, M., van Lambalgen, R., Mitchell, D. J., Durham, S. K., and Steinman, L. (1988), Autoimmunity, 1, 399.

Kabelitz D, Janssen O., (1989), Cell. Immunol. 120: 21.

Kashmiri S. V., Iwahashi, M., Tamura., Padlan, E. A., Milenic, D. E. & Sclom, J (2001) Crit Rev Oncol Hematol. 38: 3-16.

King, D. J., Turner, A., Farnsworth, A. P. H., Adair, J. R., Owens, R. J., Pedley, R. B., Baldock, D., Proudfoot, K. A., Lawson, A. D. G., Beeley, N. R. A., Millar, K., Millican, T. A., Boyce, B. A., Antoniw, P., Mountain, A., Begent, R. H. J., Shochat, D. and Yarranton, G. T., (1994), Cancer Res. 54, 6176.

Klohe E P, Watts R, Bahl M, Alber C, Yu W -Y, Anderson R, Silver J, Gregersen P K, Karr R K., (1988), J. Immunol. 141: 2158-2164.

Knappik, A. & Plückthun, A., (1994), Biotechniques 17, 754-761.

Knappik, A., Ge, L., Honegger, A., Pack, P., Fischer, M., Wellnhofer, G., Hoess A., Wölle, J., Plückthun, A. and Virnekäs, B., (2000), J. Mol. Biol. 296, 55.

Kahoury E. L. and Marshall L. A., (1990) Cell. Tissue Res., 262(2):217-24

Kozak, M. (1987) J. Mol. Biol. 196, 947.

Kuby, J. Immunology:1994, $2^{nd}$ edition.

Mourad W, Geha R S, Chatila T J., (1990), J. Exp. Med. 172: 1513.

Muller et al., (1990), J. Immunol., 145: 4006.

Nabavi N, Freeman G J, Gault A, Godfrey D, Nadler L M, Glimcher L H., (1992) Nature 360: 266.

Nagy, Z & Vidovic, D. (1996) Monoclonal antibody fragments having immunosuppressant activity. WO9617874.

Naquet, P., Marchetto, S., and Pierres, M., (1983), Immunogenetics, 18, 559.

Newell M K, VanderWall J, Beard K S, Freed J H., (1993), Proc. Natl. Acad. Sci. USA 90: 10459.

Otten et al (1997) pp 5.4.1-5.4.19 in Current Protocols in Immunology, Eds. Coligan et al. Green & Wiley, New York.

Pack, P. and Plückthun, A., (1992), Biochemistry 31, 1579-1584.

Pack, P., (1994), Ph.D. thesis, Ludwig-Maximilians-Universität München.

Pack, P., Kujau, M., Schroeckh, V., Knüpfer, U., Wenderoth, R., Riesenberg D. and Plückthun, A. (1993), Bio/Technology 11, 1271-1277.

Palacios R, Martinez-Maza 0, Guy K., (1983), Proc. Natl. Acad. Sci. USA 80: 3456.

Palacios R., (1985), Proc. Natl. Acad. Sci. USA 82: 6652.

Presta, (1992), Curr. Op. Struct. Biol. 2: 593-596.

Pichla, S. L., Murali, R. & Burnett, R. M (1997) J Struct Biol. 119: 6-16.

Riechmann et al., (1988), Nature 332: 323-329.

Rheinnecker, M., Hardt, C., Ilag, L. L., Kufer, P., Gruber, R., Hoess, A., Lupas, A., Rottenberger, C., Pluckthun, A. and Pack, P., (1996), J. Immunol. 157, 2989.

Rosenbaum J T, Adelman N E, McDevitt H O., (1981), J. Exp. Med. 154:1694.

Sambrook et al., 1989, Molecular Cloning: a Laboratory Manual, 2nd ed.

Schmidt, T. G. M. & Skerra, A. (1993). Prot. Engineering 6, 109-122.

Schmidt, T. G. M. & Skerra, A. (1994). J. Chromatogr. A 676, 337-345.

Schmidt, T. G. M. et al. (1996). J. Mol. Biol. 255, 753-766.

Skerra, A. and Plückthun, A. (1988). Science 240, 1038.

Slavin-Chiorini, D. C., Kashmiri, S. V., Milenic, D. E., Poole, D. J., Bernono, E., Schlom, J. & Hand, P. H (1997) Cancer Biother Radiopharm 12: 305-316.

Smith, R. M., Morgan, A., and Wraith, D. C. (1994). Immunology, 83, 1.

Stausbøl-Grøn, B., Wind, T., Kjar, S., Kahns, L., Hansen, N. J. V., Kristensen, P. and Clark, B. F. C. (1996) FEBS Lett. 391, 71.

Stern J. L. and Wiley, D. C., (1992), Cell 68 465-477.

Stern, A. S: and Podlaski, F. J, (1993) Techniques in Protein Chemistry IV, Academic Press Inc., San Diego, Calif.

Stevens, H. P., Roche, N., Hovius, S. E., and Jonker, M., (1990), Transplant. Proc., 22, 1783.

Truman J -P, Choqueux C, Tschopp J, Vedrenne J, Le Deist F, Charron D, Mooney N., (1997), Blood 89:1996.

Truman J -P, Ericson M L, Choqueux-Seebold J M, Charron D J, Mooney N A., (1994), Internatl. Immunol. 6: 887.

Vaickus L, Jones V E, Morton C L, Whitford K, Bacon R N., (1989), Cell. Immunol. 119: 445.

Vidovic D, Falcioni F, Bolin D R, Nagy Z A., (1995a), Eur. J. Immunol., 25: 1326.

Vidovic D, Falcioni F, Siklodi B, Belunis C J, Bolin D R, Ito K, Nagy Z A., (1995b), Eur J. Immunol., 25:3349.

Vidovic, D. & Laus, R. (2000) Selective apoptosis of neoplastic cells by the HLA-DR-specific monoclonal antibody. WO00/12560.

Vidovic D, & Toral, J. (1998). Selective apoptosis of neoplastic cells by the HLA-DR-specific monoclonal antibody. Cancer Letters 128: 127-135.

Virnekäs, B, Ge, L., Plukthun, A., Schneider, K. C., Wellenhofer, G. & Moroney, S. E. (1994) Nucleic Acids Res 22: 5600-5607.

Vode, J. M., Colcher, D., Gobar, L., Bierman, P. J., Augustine, S., Tempero, M., Leichner, P., Lynch, J. C., Goldenberg, D. & Armitage, J. O. (2000) Leuk Lymphoma 38: 91-101.

Voss, S. & Skerra, A. (1997). Protein Eng. 10, 975-982.

Waldor, M. K., Sriram, S., McDevitt, H. O., and Steinman, L. (1983). Proc. Natl. Acad. Sci. USA, 80, 2713.

Winter, G., Griffiths, A. D., Hawkins, R. E. and Hoogenboom, H. R. (1994) Making antibodies by phage display technology. Annu. Rev. Immunol. 12, 433.

Woods et al., (1994), J Exp Med. 180: 173-81.

---

We claim:

1. A composition including a polypeptide comprising an antibody-based antigen-binding domain of human composition with binding specificity for a HLA-DR antigen expressed on the surface of a human cell, wherein treating cells expressing said antigen with a multivalent polypeptide having two or more of said antigen-binding domains causes or leads to killing of said cells, wherein said antigen-binding domain includes a combination of a VH domain and a VL domain, wherein said combination is found in one of the clones selected from the group consisting of MS-GPC-1 (SEQ ID NOs. 37 and 38, respectively), MS-GPC-6 (SEQ ID NOs. 39 and 40, respectively), MS-GPC-8 (SEQ ID NOs. 41 and 42, respectively), MS-GPC-10 (SEQ ID NOs. 43 and 44, respectively), MS-GPC-8-1 (SEQ ID NOs. 41 and 28, respectively), MS-GPC-8-6 (SEQ ID NOs. 41 and 46, respectively), MS-GPC-8-9 (SEQ ID NOs. 41 and 31, respectively), MS-GPC-8-10 (SEQ ID NOs. 41 and 48, respectively), MS-GPC-8-17 (SEQ ID NOs. 41 and 50, respectively), MS-GPC-8-18 (SEQ ID NOs. 41 and 32, respectively), MS-GPC-8-27 (SEQ ID NOs. 41 and 52, respectively), MS-GPC-8-6-2 (SEQ ID NOs. 41 and 45, respectively), MS-GPC-8-6-19 (SEQ ID NOs. 41 and 47, respectively), MS-GPC-8-6-27 (SEQ ID NOs. 41 and 49, respectively), MS-GPC-8-6-45 (SEQ ID NOs. 41 and 51, respectively), MS-GPC-8-6-13 (SEQ ID NOs. 41 and 54, respectively), MS-GPC-8-6-47 (SEQ ID NOs. 41 and 53, respectively), MS-GPC-8-10-57 (SEQ ID NOs. 41 and 56, respectively), MS-GPC-8-27-7 (SEQ ID NOs. 41 and 55, respectively), MS-GPC-8-27-10 (SEQ ID NOs. 41 and 57, respectively) and MS-GPC-8-27-41 (SEQ ID NOs. 41 and 58, respectively).

2. A composition including a polypeptide comprising an antibody-based antigen-binding domain of human composition with binding specificity for a HLA-DR antigen expressed on the surface of a human cell, wherein treating cells expressing said antigen with a multivalent polypeptide having two or more of said antigen-binding domains causes or leads to killing of said cells, wherein said antigen-binding domain includes a combination of HuCAL VH2 and HuCAL Vλ1, wherein the VH CDR3, VL CDR1 and VL CDR3 is found in one of the clones selected from the group consisting of MS-GPC-1 (SEQ ID NOs. 37 and 38, respectively), MS-GPC-6 (SEQ ID NOs. 39 and 40, respectively), MS-GPC-8 (SEQ ID NOs. 41 and 42, respectively), MS-GPC-10 (SEQ ID NOs. 43 and 44, respectively), MS-GPC-8-1 (SEQ ID NOs. 41 and 28, respectively), MS-GPC-8-6 (SEQ ID NOs. 41 and 46, respectively), MS-GPC-8-9 (SEQ ID NOs. 41 and 31, respectively), MS-GPC-8-10 (SEQ ID NOs. 41 and 48, respectively), MS-GPC-8-17 (SEQ ID NOs. 41 and 50, respectively), MS-GPC-8-18 (SEQ ID NOs. 41 and 32, respectively), MS-GPC-8-27 (SEQ ID NOs. 41 and 52, respectively), MS-GPC-8-6-2 (SEQ ID NOs. 41 and 45, respectively), MS-GPC-8-6-19 (SEQ ID NOs. 41 and 47, respectively), MS-GPC-8-6-27 (SEQ ID NOs. 41 and 49, respectively), MS-GPC-8-6-45 (SEQ ID NOs. 41 and 51, respectively), MS-GPC-8-6-13 (SEQ ID NOs. 41 and 54, respectively), MS-GPC-8-6-47 (SEQ ID NOs. 41 and 53, respectively), MS-GPC-8-10-57 (SEQ ID NOs. 41 and 56, respectively), MS-GPC-8-27-7 (SEQ ID NOs. 41 and 55, respectively), MS-GPC-8-27-10 (SEQ ID NOs. 41 and 57, respectively) and MS-GPC-8-27-41 (SEQ ID NOs. 41 and 58, respectively).

3. A composition including a polypeptide comprising an antibody-based antigen-binding domain of human composition with binding specificity for a HLA-DR antigen expressed on the surface of a human cell, wherein treating cells expressing said antigen with a multivalent polypeptide having two or more of said antigen-binding domains causes or leads to killing of said cells, wherein said antigen-binding domain includes a combination of HuCAL VH2 and HuCAL Vλ1, wherein the VH CDR3 sequence is taken from the consensus CDR3 sequence

XXXXRGXFDX (SEQ ID NO: 1)

wherein each X independently represents any amino acid residue; and/or wherein the VL CDR3 sequence is taken from the consensus CDR3 sequence

QSYDXXXX (SEQ ID NO: 2)

wherein each X independently represents any amino acid residue.

4. The composition of claim 3, wherein the VH CDR3 sequence of said antigen-binding domain is SPRYRGAFDY (SEQ ID NO: 3) and/or the VL CDR3 sequence of said antigen-binding domain is QSYDLIRH (SEQ ID NO: 4) or QSYDMNVH (SEQ ID NO: 5).

5. A composition including a polypeptide comprising an antibody-based antigen-binding domain of human composition with binding specificity for a HLA-DR antigen expressed on the surface of a human cell, wherein treating cells expressing said antigen with a multivalent polypeptide having two or more of said antigen-binding domains causes or leads to killing of said cells, wherein said antigen-binding domain includes a combination of HuCAL VH2 and HuCAL Vλ1, wherein the Vλ1 CDR1 sequence is represented in the general formula

SGSXXNIGXNYVX (SEQ ID NO: 6)

wherein each X independently represents any amino acid residue.

6. The composition of claim 5, wherein the CDR1 sequence is SGSESNIGNNYVQ (SEQ ID NO: 7).

7. The composition of any one of claims 1-4, 5, and 6, wherein the multivalent polypeptide has an $EC_{50}$ for killing transformed cells at least 5-fold lower than the $EC_{50}$ for killing normal cells.

8. The composition of any one of claims and 1-4, 5, and 6, wherein the multivalent polypeptide has an $EC_{50}$ for killing activated cells at least 5-fold lower than the $EC_{50}$ for killing unactivated cells.

9. The composition of any of claims and 1-4, 5, and 6, wherein the multivalent polypeptide has an $EC_{50}$ of 50 nM or less for killing transformed cells.

10. The composition of any of claims and 1-4, 5, and 6, wherein the multivalent polypeptide has an EC50 for killing lymphoid tumor cells of 10 nM or less.

11. The composition of any of claims 1-4, 5, and 6, wherein the multivalent polypeptide kills activated lymphoid cells.

12. The composition of claim 11, wherein said activated lymphoid cells are lymphoid tumor cells representing a disease selected from the group consisting of B cell non-Hodgkin lymphoma, B cell lymphoma, B cell acute lymphoid leukemia, Burkitt lymphoma, Hodgkin lymphoma, hairy cell leukemia, acute myeloid leukemia, T cell lymphoma, T cell non-Hodgkin lymphoma, chronic myeloid leukemia, chronic lymphoid leukemia, and multiple myeloma.

13. The composition of claim 11, wherein said activated lymphoid cells are from a cell line selected from the group consisting of PRIESS (ECACC Accession No: 86052111), GRANTA-519 (DSMZ Accession No: ACC 342), and KARPAS-422 (DSMZ Accession No: ACC 32) cell lines.

14. The composition of any of claims 1-4, 5, and 6, wherein the multivalent polypeptide has an $EC_{50}$ of 100 nM or less for killing KARPAS-422 (DSMZ Accession No: ACC 32) cells.

15. The composition of any of claims and 1-4, 5, and 6, wherein the multivalent polypeptide has an $EC_{50}$ of 50 nM or less for killing KARPAS-422 (ACC 32 from DSMZ) cells.

16. The composition of any of claims and 1-4, 5, and 6, wherein the multivalent polypeptide has an $EC_{50}$ of 10 nM or less for killing PRIESS (ECACC Accession No: 86052111) cells.

17. The composition of any of claims and 1-4, 5, and 6, wherein said cells are non-lymphoid cells that express HLA-DR molecules.

18. The composition of any of claims and 1-4, 5, and 6, wherein said antigen-binding domain binds to the β-chain of HLA-DR.

19. The composition of claim 18, wherein said antigen-binding domain binds to the first domain of the β-chain of HLA-DR.

20. The composition of any of claims 1-4, 5, and 6, wherein said antigen-binding domain binds to one or more HLA-DR types selected from the group consisting of DR1-0101, DR2-15021, DR3-0301, DR4Dw4-0401, DR4Dw10-0402, DR4Dw14-0404, DR6-1302, DR6-1401, DR8-8031, DR9-9012, DRw53-B4*0101 and DRw52-B3*0101.

21. The composition of claim 20, wherein said antigen-binding domain binds to at least 5 different of said HLA-DR types.

22. The composition of any one of claims 1-4, 5, and 6, wherein said antibody-based antigen-binding domain is part of a multivalent polypeptide including at least a $F(ab')_2$ antibody fragment or a mini-antibody fragment.

23. The composition of any one of claims 1-4, 5, and 6, wherein said antibody-based antigen-binding domain is part of a multivalent polypeptide comprising at least two monovalent antibody fragments selected from Fv, scFv, dsFv and Fab fragments, and further comprises a cross-linking moiety or moieties.

24. The composition of any one of claims 1-4, 5, and 6, wherein said antibody-based antigen-binding domain is part of a multivalent polypeptide comprising at least one full antibody selected from the antibodies of classes $IgG_1$, 2a, 2b, 3, 4, IgA, and IgM.

25. The composition of any one of claims 1-4, 5, and 6, wherein said antibody-based antigen-binding domain is part of a multivalent polypeptide that is formed prior to binding to a cell.

26. The composition of any of claims and 1-4, 5, and 6, wherein said antibody-based antigen-binding domain is part of a multivalent polypeptide that is formed after binding to a cell.

27. The composition of any one of claims 1-4, 5, and 6, formulated in a pharmaceutically acceptable carrier and/or diluent.

28. A diagnostic composition including the composition of any of claims 1-4, 5, and 6.

29. The diagnostic composition of claim 28, further comprising a cross-linking moiety or moieties.

30. A kit to identify patients that can be treated with a composition of any of claims 1-4, 5, and 6, formulated in a pharmaceutically acceptable carrier and/or diluent comprising:
    a. a composition of any of claims and 1-4, 5, and 6; and
    b. means to measure the degree of killing or immunosuppression of said cells.

31. A kit comprising:
    a. a composition according to any one of claims 1-4, 5, and 6, and
    b. a cross-linking moiety.

32. A kit comprising:
    a. a composition according to any one of claims 1-4, 5, and 6, and
    b. a detectable moiety or moieties, and
    c. reagents and/or solutions to effect and/or detect binding of (a) to an antigen.

33. The composition of any one of claims 1-4, 5, and 6 operably linked to a cytotoxic agent.

34. The composition of any one of claims 1-4, 5, and 6 operably linked to an immunogenic agent.

35. The composition of claim 3, wherein said antigen-binding domain further comprises a VL CDR1 sequence represented in the general formula
    SGSXXNIGXNYVX (SEQ ID NO: 6)
    wherein each X independently represents any amino acid residue.

36. The composition of claim 35, wherein the VL CDR1 sequence is SGSESNIGNNYVQ (SEQ ID NO: 7).

37. The composition of any of claims 1-4, 5, and 6, wherein said antigen-binding domain binds to human HLA-DR with a $K_d$ of 1 μM or less.

38. The composition of any of claims 1-4, 5, and 6, wherein said antigen-binding domain binds to the α-chain of HLA-DR.

39. The composition of any of claims 1-4, 5, and 6, wherein said multivalent polypeptide has an $EC_{50}$ of 100 nM or less for killing activated lymphoid cells.

40. A composition including a polypeptide comprising at least one antibody-based antigen-binding domain with a binding specificity for human HLA-DR antigen, wherein treating cells expressing HLA-DR with said polypeptide causes or leads to suppression of an immune response, and wherein said antigen-binding domain includes a combination of a VH domain and a VL domain, wherein said combination is found in one of the clones taken from the group consisting of MS-GPC-1 (SEQ ID NOs. 37 and 38, respectively), MS-GPC-6 (SEQ ID NOs. 39 and 40, respectively), MS-GPC-8 (SEQ ID NOs. 41 and 42, respectively), MS-GPC-10 (SEQ ID NOs. 43 and 44, respectively), MS-GPC-8-1 (SEQ ID NOs. 41 and 28, respectively), MS-GPC-8-6 (SEQ ID NOs. 41 and 46, respectively), MS-GPC-8-9 (SEQ ID NOs. 41 and 31, respectively), MS-GPC-8-10 (SEQ ID NOs. 41 and 48, respectively), MS-GPC-8-17 (SEQ ID NOs. 41 and 50, respectively), MS-GPC-8-18 (SEQ ID NOs. 41 and 32, respectively), MS-GPC-8-27 (SEQ ID NOs. 41 and 52, respectively), MS-GPC-8-6-2 (SEQ ID NOs. 41 and 45, respectively), MS-GPC-8-6-19 (SEQ ID NOs. 41 and 47, respectively), MS-GPC-8-6-27 (SEQ ID NOs. 41 and 49, respectively), MS-GPC-8-6-45 (SEQ ID NOs. 41 and 51, respectively), MS-GPC-8-6-13 (SEQ ID NOs. 41 and 54, respectively), MS-GPC-8-6-47 (SEQ ID NOs. 41 and 53, respectively), MS-GPC-8-10-57 (SEQ ID NOs. 41 and 56, respectively), MS-GPC-8-27-7 (SEQ ID NOs. 41 and 55, respectively), MS-GPC-8-27-10 (SEQ ID NOs. 41 and 57, respectively) and MS-GPC-8-27-41 (SEQ ID NOs. 41 and 58, respectively).

41. A composition including a polypeptide comprising at least one antibody-based antigen-binding domain with a binding specificity for a human HLA-DR antigen with a $K_d$ of 1 µM or less, wherein treating cells expressing said antigen with said polypeptide causes or leads to suppression of an immune response, wherein said antigen-binding domain includes of a combination of HuCAL VH2 and HuCAL Vλ1, wherein the VH CDR3, VL CDR1 and VL CDR3 is found in one of the clones selected from the group consisting of MS-GPC-1 (SEQ ID NOs. 37 and 38, respectively), MS-GPC-6 (SEQ ID NOs. 39 and 40, respectively), MS-GPC-8 (SEQ ID NOs. 41 and 42, respectively), MS-GPC-10 (SEQ ID NOs. 43 and 44, respectively), MS-GPC-8-1 (SEQ ID NOs. 41 and 28, respectively), MS-GPC-8-6 (SEQ ID NOs. 41 and 46, respectively), MS-GPC-8-9 (SEQ ID NOs. 41 and 31, respectively), MS-GPC-8-10 (SEQ ID NOs. 41 and 48, respectively), MS-GPC-8-17 (SEQ ID NOs. 41 and 50, respectively), MS-GPC-8-18 (SEQ ID NOs. 41 and 32, respectively), MS-GPC-8-27 (SEQ ID NOs. 41 and 52, respectively), MS-GPC-8-6-2 (SEQ ID NOs. 41 and 45, respectively), MS-GPC-8-6-19 (SEQ ID NOs. 41 and 47, respectively), MS-GPC-8-6-27 (SEQ ID NOs. 41 and 49, respectively), MS-GPC-8-6-45 (SEQ ID NOs. 41 and 51, respectively), MS-GPC-8-6-13 (SEQ ID NOs. 41 and 54, respectively), MS-GPC-8-6-47 (SEQ ID NOs. 41 and 53, respectively), MS-GPC-8-lO-57 (SEQ ID NOs. 41 and 56, respectively), MS-GPC-8-27-7 (SEQ ID NOs. 41 and 55, respectively), MS-GPC-8-27-10 (SEQ ID NOs. 41 and 57, respectively) and MS-GPC-8-27-41 (SEQ ID NOs. 41 and 58, respectively).

42. A composition including a polypeptide comprising at least one antibody-based antigen-binding domain with a binding specificity for a human HLA-DR antigen with a $K_d$ of 1 µM or less, wherein treating cells expressing said antigen with said polypeptide causes or leads to suppression of an immune response, wherein said antigen-binding domain includes a combination of HuCAL VH2 and HuCAL Vλ1, wherein the VH CDR3 sequence is taken from the consensus CDR3 sequence

XXXXRGXFDX (SEQ ID NO: 1)

wherein each X independently represents any amino acid residue; and/or wherein the VL CDR3 sequence is taken from the consensus CDR3 sequence

QSYDXXXX (SEQ ID NO: 2)

wherein each X independently represents any amino acid residue.

43. The composition of claim 42, wherein the VH CDR3 sequence of said antigen-binding domain is SPRYRGAFDY (SEQ ID NO: 3) and/or the VL CDR3 sequence of said antigen-binding domain is QSYDLIRH (SEQ ID NO: 4) or QSYDMNVH (SEQ ID NO: 5).

44. A composition including a polypeptide comprising at least one antibody-based antigen-binding domain with a binding specificity for a human HLA-DR antigen with a $K_d$ of 1 µM or less, wherein treating cells expressing said antigen with said polypeptide causes or leads to suppression of an immune response, wherein said antigen-binding domain includes a combination of HuCAL VH2 and HuCAL Vλ1, wherein the Vλ1 CDR1 sequence is represented in the general formula

SGSXXNIGXNYVX (SEQ ID NO: 6)

wherein each X independently represents any amino acid residue.

45. The composition of claim 44, wherein the CDR1 sequence is SGSESNIGNNYVQ (SEQ ID NO: 7).

46. The composition of any of claims 40 or 41-43, 44 and 45, wherein said antigen-binding domain binds to the β-chain of HLA-DR.

47. The composition of claim 46, wherein said antigen-binding domain binds to an epitope of the first domain of the β-chain of HLA-DR.

48. The composition of any of claims 40 or 41-43, 44 and 45, wherein said cells are lymphoids cells.

49. The composition of any of claims 40 or 41-43, 44 and 45, wherein said cells are non-lymphoid cells and express HLA-DR antigens.

50. The composition of any of claims 40 or 41-43, 44 and 45, having an $IC_{50}$ for suppressing an immune response of 1 µM or less.

51. The composition of any of claims 40 or 41-43, 44 and 45, having an $IC_{50}$ for inhibition of IL-2 secretion of 1 µM or less.

52. The composition of any of claims 40 or 41-43, 44 and 45, having an $IC_{50}$ for inhibiting T cell proliferation of 1 µM or less.

53. The composition of any of claims 40 or 41-43, 44 and 45, wherein said antigen-binding domain binds to one or more HLA-DR types selected from the group consisting of DR1-0101, DR2-15021, DR3-0301, DR4Dw4-0401, DR4Dw10-0402, DR4Dw14-0404, DR6-1302, DR6-1401, DR8-8031, DR9-9012, DRw53-B4*0101 and DRw52-B3*0101.

54. The composition of claim 53, wherein said antigen-binding domain binds to at least 5 different of said HLA-DR types.

55. The composition of any of claims 40 or 41-43, 44 and 45, formulated in a pharmaceutically acceptable carrier and/or diluent.

56. A pharmaceutical preparation comprising the composition of claim 50 in an amount sufficient to suppress an immune response in an animal.

57. A pharmaceutical preparation comprising the composition of claim 51 in an amount sufficient to inhibit IL-2 secretion in an animal.

58. A pharmaceutical preparation comprising the composition of claim 52 in an amount sufficient to inhibit T cell proliferation in an animal.

59. The composition of any of claims 40 and 41-43, 44 and 45, wherein said antigen-binding domain binds to the α-chain of HLA-DR.

60. The composition of claim 42, wherein said antigen-binding domain further comprises a VL CDR1 sequence represented in the general formula

SGSXXNIGXNYVX (SEQ ID NO: 6)

wherein each X independently represents any amino acid residue.

61. The composition of claim 60, wherein the VL CDR1 sequence is SGSESNIGNNYVQ (SEQ ID NO: 7).

62. A human IgG antibody generated by cloning into an immunoglobulin expression system an antigen-binding domain of human composition with binding specificity for human HLA-DR antigen, wherein:

(a) treating cells expressing said antigen with said IgG causes or leads to killing of said cells; and (b) said antigen-binding domain includes a combination of a VH and a VL domain, wherein said combination is found in one of the clones selected from the group consisting of: MS-GPC-8-6-13 (SEQ ID NOs. 41 and 54, respectively), MS-GPC-8-10-57 (SEQ ID NOs. 41 and 56, respectively) and MS-GPC-8-27-41 (SEQ ID NOs. 41 and 58, respectively).

63. The human IgG antibody of claim 62, wherein the IgG antibody is an IgG$_4$ antibody.

64. A human IgG antibody generated by cloning into an immunoglobulin expression system an antigen-binding domain of human composition with a binding specificity for human HLA-DR antigen, wherein:

(a) treating cells expressing HLA-DR with said IgG causes or leads to suppression of an immune response; and,
(b) said antigen-binding domain includes a combination of a VH and a VL domain, wherein said combination is found in one of the clones selected from the group consisting of: MS-GPC-8-6-13 (SEQ ID NOs. 41 and 54, respectively), MS-GPC-8-10-57 (SEQ ID NOs. 41 and 56, respectively) and MS-GPC-8-27-41(SEQ ID NOs. 41 and 58, respectively).

65. The human IgG antibody of claim 64, wherein the IgG antibody is an IgG$_4$ antibody.

\* \* \* \* \*

SEQUENCE LISTING

```
<160> NUMBER OF SEQ ID NOS: 62

<210> SEQ ID NO 1
<211> LENGTH: 10
<212> TYPE: PRT
<213> ORGANISM: Artificial Sequence
<220> FEATURE:
<221> NAME/KEY: VARIANT
<222> LOCATION: (1)..(4)
<223> OTHER INFORMATION: Xaa represents any amino acid residue
<220> FEATURE:
<221> NAME/KEY: VARIANT
<222> LOCATION: (7)..(7)
<223> OTHER INFORMATION: Xaa represents any amino acid residue
<220> FEATURE:
<221> NAME/KEY: VARIANT
<222> LOCATION: (10)..(10)
<223> OTHER INFORMATION: Xaa represents any amino acid residue
<220> FEATURE:
<223> OTHER INFORMATION: sequence for VHconCDR3

<400> SEQUENCE: 1

Xaa Xaa Xaa Xaa Arg Gly Xaa Phe Asp Xaa
1               5                   10

<210> SEQ ID NO 2
<211> LENGTH: 8
<212> TYPE: PRT
<213> ORGANISM: Artificial Sequence
<220> FEATURE:
<221> NAME/KEY: VARIANT
<222> LOCATION: (5)..(8)
<223> OTHER INFORMATION: Xaa represents any amino acid residue
<220> FEATURE:
<223> OTHER INFORMATION: sequence for VLconCDR3

<400> SEQUENCE: 2

Gln Ser Tyr Asp Xaa Xaa Xaa Xaa
1               5

<210> SEQ ID NO 3
<211> LENGTH: 10
<212> TYPE: PRT
<213> ORGANISM: artificial sequence
<220> FEATURE:
<223> OTHER INFORMATION: sequence for MS-GPC8-VH-CDR3,MS-GPC8-1-VH-CDR3,
      MS-GPC8-6-VH-CDR3,MS-GPC8-9-VH-CDR3,MS-GPC8-10-VH-CDR3,
      MS-GPC8-17-VH-CDR3,MS-GPC8-18-VH-CDR3,
<220> FEATURE:
<223> OTHER INFORMATION: MS-GPC8-27-VH-CDR3,MS-GPC8-6-2-VH-CDR3,
      MS-GPC8-6-13-VH-CDR3,MS-GPC8-6-19-VH-CDR3 sequence for
      MS-GPC8-6-27-VH-CDR3,MS-GPC8-6-45-VH-CDR3,MS-GPC8-10-57-VH-CDR3,
      MS-GPC8-27-7-VH-CDR3,
<220> FEATURE:
<223> OTHER INFORMATION: MS-GPC8-27-10-VH-CDR3, MS-GPC8-27-41-VH-CDR3,
```

```
      MS-GPC8-6-47-VH-CDR3

<400> SEQUENCE: 3

Ser Pro Arg Tyr Arg Gly Ala Phe Asp Tyr
1               5                   10

<210> SEQ ID NO 4
<211> LENGTH: 8
<212> TYPE: PRT
<213> ORGANISM: artificial sequence
<220> FEATURE:
<223> OTHER INFORMATION: sequence for MS-GPC8-10-VL-CDR3,
      MS-GPC8-10-57-VL-CDR3

<400> SEQUENCE: 4

Gln Ser Tyr Asp Leu Ile Arg His
1               5

<210> SEQ ID NO 5
<211> LENGTH: 8
<212> TYPE: PRT
<213> ORGANISM: artificial sequence
<220> FEATURE:
<223> OTHER INFORMATION: sequence for MS-GPC8-27-VL-CDR3,
      MS-GPC8-27-7-VL-CDR3,MS-GPC8-27-10-VL-CDR3,MS-GPC8-27-41-VL-CDR3

<400> SEQUENCE: 5

Gln Ser Tyr Asp Met Asn Val His
1               5

<210> SEQ ID NO 6
<211> LENGTH: 13
<212> TYPE: PRT
<213> ORGANISM: artificial sequence
<220> FEATURE:
<221> NAME/KEY: VARIANT
<222> LOCATION: (4)..(5)
<223> OTHER INFORMATION: Xaa represents any amino acid residue
<220> FEATURE:
<221> NAME/KEY: VARIANT
<222> LOCATION: (9)..(9)
<223> OTHER INFORMATION: Xaa represents any amino acid residue
<220> FEATURE:
<221> NAME/KEY: VARIANT
<222> LOCATION: (13)..(13)
<223> OTHER INFORMATION: Xaa represents any amino acid residue
<220> FEATURE:
<223> OTHER INFORMATION: sequence for VLconCDR1

<400> SEQUENCE: 6

Ser Gly Ser Xaa Xaa Asn Ile Gly Xaa Asn Tyr Val Xaa
1               5                   10

<210> SEQ ID NO 7
<211> LENGTH: 13
<212> TYPE: PRT
<213> ORGANISM: artificial sequence
<220> FEATURE:
<223> OTHER INFORMATION: sequence for MS-GPC-8-10-57-VL-CDR1,
      MS-GPC-8-27-41-VL-CDR1

<400> SEQUENCE: 7

Ser Gly Ser Glu Ser Asn Ile Gly Asn Asn Tyr Val Gln
1               5                   10

<210> SEQ ID NO 8
<211> LENGTH: 8
<212> TYPE: PRT
<213> ORGANISM: artificial sequence
```

```
<220> FEATURE:
<223> OTHER INFORMATION: sequence for Streptaq

<400> SEQUENCE: 8

Trp Ser His Pro Gln Phe Glu Lys
1               5

<210> SEQ ID NO 9
<211> LENGTH: 4
<212> TYPE: PRT
<213> ORGANISM: artificial sequence
<220> FEATURE:
<223> OTHER INFORMATION: FLAG peptide

<400> SEQUENCE: 9

Asp Tyr Lys Asp
1

<210> SEQ ID NO 10
<211> LENGTH: 17
<212> TYPE: DNA
<213> ORGANISM: artificial sequence
<220> FEATURE:
<223> OTHER INFORMATION: sequence for PrimerCRT5

<400> SEQUENCE: 10
gtggtggttc cgatatc                                                   17

<210> SEQ ID NO 11
<211> LENGTH: 44
<212> TYPE: DNA
<213> ORGANISM: artificial sequence
<220> FEATURE:
<223> OTHER INFORMATION: sequence for PrimerCRT6

<400> SEQUENCE: 11
agcgtcacac tcggtgcggc tttcggctgg ccaagaacgg gtta                     44

<210> SEQ ID NO 12
<211> LENGTH: 13
<212> TYPE: PRT
<213> ORGANISM: artificial sequence
<220> FEATURE:
<223> OTHER INFORMATION: sequence for MS-GPC1-VL-CDR1,MS-GPC8-VL-CDR1,
      MS-GPC10-VL-CDR1,MS-GPC8-1-VL-CDR1,MS-GPC8-6-VL-CDR1,
      MS-GPC8-9-VL-CDR1,MS-GPC8-10-VL-CDR1,MS-GPC8-17-VL-CDR1,
      MS-GPC8-18-VL-CDR1,MS-GPC8-27-VL-CDR1,

<400> SEQUENCE: 12

Ser Gly Ser Ser Ser Asn Ile Gly Ser Asn Tyr Val Ser
1               5                   10

<210> SEQ ID NO 13
<211> LENGTH: 13
<212> TYPE: PRT
<213> ORGANISM: artificial sequence
<220> FEATURE:
<223> OTHER INFORMATION: sequence for MS-GPC8-6-2-VL-CDR1

<400> SEQUENCE: 13

Ser Gly Ser Glu Ser Asn Ile Gly Ser Asn Tyr Val His
1               5                   10

<210> SEQ ID NO 14
<211> LENGTH: 13
<212> TYPE: PRT
<213> ORGANISM: artificial sequence
```

```
<220> FEATURE:
<223> OTHER INFORMATION: sequence for MS-GPC8-6-19-VL-CDR1

<400> SEQUENCE: 14

Ser Gly Ser Glu Ser Asn Ile Gly Ser Asn Tyr Val Ala
1               5                   10

<210> SEQ ID NO 15
<211> LENGTH: 13
<212> TYPE: PRT
<213> ORGANISM: artificial sequence
<220> FEATURE:
<223> OTHER INFORMATION: sequence for MS-GPC8-6-27-VL-CDR1

<400> SEQUENCE: 15

Ser Gly Ser Asp Ser Asn Ile Gly Ala Asn Tyr Val Thr
1               5                   10

<210> SEQ ID NO 16
<211> LENGTH: 13
<212> TYPE: PRT
<213> ORGANISM: artificial sequence
<220> FEATURE:
<223> OTHER INFORMATION: sequence for MS-GPC8-6-45-VL-CDR1

<400> SEQUENCE: 16

Ser Gly Ser Glu Pro Asn Ile Gly Ser Asn Tyr Val Phe
1               5                   10

<210> SEQ ID NO 17
<211> LENGTH: 13
<212> TYPE: PRT
<213> ORGANISM: artificial sequence
<220> FEATURE:
<223> OTHER INFORMATION: sequence for MS-GPC8-27-7-VL-CDR1

<400> SEQUENCE: 17

Ser Gly Ser Glu Ser Asn Ile Gly Asn Asn Tyr Val Gly
1               5                   10

<210> SEQ ID NO 18
<211> LENGTH: 13
<212> TYPE: PRT
<213> ORGANISM: artificial sequence
<220> FEATURE:
<223> OTHER INFORMATION: sequence for MS-GPC8-27-10-VL-CDR1

<400> SEQUENCE: 18

Ser Gly Ser Glu Ser Asn Ile Gly Ala Asn Tyr Val Asn
1               5                   10

<210> SEQ ID NO 19
<211> LENGTH: 10
<212> TYPE: PRT
<213> ORGANISM: artificial sequence
<220> FEATURE:
<223> OTHER INFORMATION: sequence for MS-GPC1-VH-CDR3

<400> SEQUENCE: 19

Gln Tyr Gly His Arg Gly Gly Phe Asp His
1               5                   10

<210> SEQ ID NO 20
<211> LENGTH: 9
<212> TYPE: PRT
<213> ORGANISM: artificial sequence
<220> FEATURE:
```

-continued

<223> OTHER INFORMATION: sequence for MS-GPC6-VH-CDR3

<400> SEQUENCE: 20

Gly Tyr Gly Arg Tyr Ser Pro Asp Leu
1               5

<210> SEQ ID NO 21
<211> LENGTH: 8
<212> TYPE: PRT
<213> ORGANISM: artificial sequence
<220> FEATURE:
<223> OTHER INFORMATION: sequence for MS-GPC6-VL-CDR3

<400> SEQUENCE: 21

Gln Gln Tyr Ser Asn Leu Pro Phe
1               5

<210> SEQ ID NO 22
<211> LENGTH: 8
<212> TYPE: PRT
<213> ORGANISM: artificial sequence
<220> FEATURE:
<223> OTHER INFORMATION: sequence for MS-GPC8-VL-CDR3

<400> SEQUENCE: 22

Gln Ser Tyr Asp Met Pro Gln Ala
1               5

<210> SEQ ID NO 23
<211> LENGTH: 8
<212> TYPE: PRT
<213> ORGANISM: artificial sequence
<220> FEATURE:
<223> OTHER INFORMATION: sequence for MS-GPC10-VL-CDR3

<400> SEQUENCE: 23

Gln Ser Tyr Asp Leu Thr Met Gly
1               5

<210> SEQ ID NO 24
<211> LENGTH: 8
<212> TYPE: PRT
<213> ORGANISM: artificial sequence
<220> FEATURE:
<223> OTHER INFORMATION: sequence for MS-GPC8-1-VL-CDR3

<400> SEQUENCE: 24

Gln Ser Tyr Asp Phe Ser His Tyr
1               5

<210> SEQ ID NO 25
<211> LENGTH: 8
<212> TYPE: PRT
<213> ORGANISM: artificial sequence
<220> FEATURE:
<223> OTHER INFORMATION: sequence for MS-GPC8-9-VL-CDR3

<400> SEQUENCE: 25

Gln Ser Tyr Asp Ile Gln Leu His
1               5

<210> SEQ ID NO 26
<211> LENGTH: 8
<212> TYPE: PRT
<213> ORGANISM: artificial sequence
<220> FEATURE:
<223> OTHER INFORMATION: sequence for MS-GPC8-17-VL-CDR3

<400> SEQUENCE: 26

Gln Ser Tyr Asp Phe Ser Val Tyr
1               5

<210> SEQ ID NO 27
<211> LENGTH: 8
<212> TYPE: PRT
<213> ORGANISM: artificial sequence
<220> FEATURE:
<223> OTHER INFORMATION: sequence for MS-GPC8-18-VL-CDR3

<400> SEQUENCE: 27

Gln Ser Tyr Asp Phe Ser Ile Tyr
1               5

<210> SEQ ID NO 28
<211> LENGTH: 109
<212> TYPE: PRT
<213> ORGANISM: artificial sequence
<220> FEATURE:
<223> OTHER INFORMATION: sequence for MS-GPC8-1-VL

<400> SEQUENCE: 28

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Phe Ser His
                85                  90                  95

Tyr Val Phe Gly Gly Gly Thr Lys Leu Thr Val Leu Gly
            100                 105

<210> SEQ ID NO 29
<211> LENGTH: 13
<212> TYPE: PRT
<213> ORGANISM: artificial sequence
<220> FEATURE:
<223> OTHER INFORMATION: sequence for MS-GPC8-6-13-VL-CDR1

<400> SEQUENCE: 29

Ser Gly Ser Glu Ser Asn Ile Gly Ala Asn Tyr Val Thr
1               5                   10

<210> SEQ ID NO 30
<211> LENGTH: 13
<212> TYPE: PRT
<213> ORGANISM: artificial sequence
<220> FEATURE:
<223> OTHER INFORMATION: sequence for MS-GPC8-6-47-VL-CDR1

<400> SEQUENCE: 30

Ser Gly Ser Glu Ser Asn Ile Gly Ser Asn Tyr Val Ser
1               5                   10

<210> SEQ ID NO 31
<211> LENGTH: 109

<212> TYPE: PRT
<213> ORGANISM: artificial sequence
<220> FEATURE:
<223> OTHER INFORMATION: sequence for MS-GPC8-9-VL

<400> SEQUENCE: 31

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Ile Gln Leu
                85                  90                  95

His Val Phe Gly Gly Gly Thr Lys Leu Thr Val Leu Gly
            100                 105

<210> SEQ ID NO 32
<211> LENGTH: 109
<212> TYPE: PRT
<213> ORGANISM: artificial sequence
<220> FEATURE:
<223> OTHER INFORMATION: sequence for MS-GPC8-18-VL

<400> SEQUENCE: 32

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Phe Ser Ile
                85                  90                  95

Tyr Val Phe Gly Gly Gly Thr Lys Leu Thr Val Leu Gly
            100                 105

<210> SEQ ID NO 33
<211> LENGTH: 3548
<212> TYPE: DNA
<213> ORGANISM: artificial sequence
<220> FEATURE:
<223> OTHER INFORMATION: sequence for pMORPH13_scFv

<400> SEQUENCE: 33
agagcatgcg taggagaaaa taaaatgaaa caaagcacta ttgcactggc actcttaccg      60
ttgctcttca cccctgttac caaagccgac tacaaagatg aagtgcaatt ggttcagtct     120
ggcgcggaag tgaaaaaacc gggcagcagc gtgaaagtga ctgcaaagc ctccggaggc      180 acttttagca gctatgcgat tagctgggtg cgccaagccc ctgggcaggg tctcgagtgg     240
atgggcggca ttattccgat ttttggcacg gcgaactacg cgcagaagtt tcagggccgg    300

-continued

```
gtgaccatta ccgcggatga aagcaccagc accgcgtata tggaactgag cagcctgcgt    360
agcgaagata cggccgtgta ttattgcgcg cgttattatg atcgtatgta taatatggat    420
tattggggcc aaggcaccct ggtgacggtt agctcagcgg gtggcggttc tggcggcgt    480
gggagcggtg gcggtggttc tggcggtggt ggttccgata tcgaactgac ccagccgcct    540
tcagtgagcg ttgcaccagg tcagaccgcg cgtatctcgt gtagcggcga tgcgctgggc    600
gataaatacg cgagctggta ccagcagaaa cccgggcagg cgccagttct ggtgattat    660
gatgattctg accgtccctc aggcatcccg gaacgcttta gcggatccaa cagcggcaac    720
accgcgaccc tgaccattag cggcactcag gcggaagacg aagcggatta ttattgccag    780
agctatgacg ctcatatgcg tcctgtgttt ggcggcggca cgaagttaac cgttcttggc    840
caggaattcg agcagaagct gatctctgag gaggatctga actagggtgg tggctctggt    900
tccggtgatt ttgattatga aaagatggca aacgctaata gggggctat gaccgaaaat    960
gccgatgaaa acgcgctaca gtctgacgct aaaggcaaac ttgattctgt cgctactgat    1020
tacggtgctg ctatcgatgg tttcattggt gacgtttccg gccttgctaa tggtaatggt    1080
gctactggtg attttgctgg ctctaattcc caaatggctc aagtcggtga cggtgataat    1140
tcacctttaa tgaataattt ccgtcaatat ttaccttccc tccctcaatc ggttgaatgt    1200
cgcccttttg tctttggcgc tggtaaacca tatgaatttt ctattgattg tgacaaaata    1260
aacttattcc gtggtgtctt tgcgtttctt ttatatgttg ccacctttat gtatgtattt    1320
tctacgtttg ctaacatact gcgtaataag gagtcttgat aagcttgacc tgtgaagtga    1380
aaaatggcgc agattgtgcg acattttttt tgtctgccgt ttaatgaaat tgtaaacgtt    1440
aatattttgt taaaattcgc gttaaatttt tgttaaatca gctcattttt taaccaatag    1500
gccgaaatcg gcaaaatccc ttataaatca aagaataga ccgagatagg gttgagtgtt    1560
gttccagttt ggaacaagag tccactatta agaacgtgg actccaacgt caaagggcga    1620
aaaaccgtct atcagggcga tggcccacta cgagaaccat caccctaatc aagttttttg    1680
gggtcgaggt gccgtaaagc actaaatcgg aaccctaaag ggagccccg atttagagct    1740
tgacggggaa agccggcgaa cgtggcgaga aggaaggga agaaagcgaa aggagcgggc    1800
gctagggcgc tggcaagtgt agcggtcacg ctgcgcgtaa ccaccacacc cgccgcgctt    1860
aatgcgccgc tacagggcgc gtgctagcca tgtgagcaaa aggccagcaa aaggccagga    1920
accgtaaaaa ggccgcgttg ctggcgtttt tccataggct ccgcccccct gacgagcatc    1980
acaaaaatcg acgctcaagt cagaggtggc gaaacccgac aggactataa agataccagg    2040
cgtttccccc tggaagctcc ctcgtgcgct ctcctgttcc gaccctgccg cttaccggat    2100
acctgtccgc ctttctccct cgggaagcg tggcgctttc tcatagctca cgctgtaggt    2160
atctcagttc ggtgtaggtc gttcgctcca agctgggctg tgtgcacgaa ccccccgttc    2220
agtccgaccg ctgcgcctta ccggtaact atcgtcttga gtccaacccg gtaagacacg    2280
acttatcgcc actggcagca gccactggta acaggattag cagagcgagg tatgtaggcg    2340
gtgctacaga gttcttgaag tggtggccta actacggcta cactagaaga acagtatttg    2400
gtatctgcgc tctgctgtag ccagttacct tcggaaaaag agttggtagc tcttgatccg    2460
gcaaacaaac caccgctggt agcggtggtt ttttgtttg caagcagcag attacgcgca    2520
gaaaaaaagg atctcaagaa gatcctttga tcttttctac ggggtctgac gctcagtgga    2580
acgaaaactc acgttaaggg attttggtca gatctagcac caggcgttta agggcaccaa    2640
taactgcctt aaaaaaatta cgccccgccc tgccactcat cgcagtactg ttgtaattca    2700
```

| | |
|---|---|
| ttaagcattc tgccgacatg gaagccatca caaacggcat gatgaacctg aatcgccagc | 2760 |
| ggcatcagca ccttgtcgcc ttgcgtataa tatttgccca tagtgaaaac gggggcgaag | 2820 |
| aagttgtcca tattggctac gtttaaatca aaactggtga aactcaccca gggattggct | 2880 |
| gagacgaaaa acatattctc aataaaccct ttagggaaat aggccaggtt ttcaccgtaa | 2940 |
| cacgccacat cttgcgaata tatgtgtaga aactgccgga aatcgtcgtg gtattcactc | 3000 |
| cagagcgatg aaaacgtttc agtttgctca tggaaaacgg tgtaacaagg gtgaacacta | 3060 |
| tcccatatca ccagctcacc gtctttcatt gccatacgga actccgggtg agcattcatc | 3120 |
| aggcgggcaa gaatgtgaat aaaggccgga taaaacttgt gcttattttt ctttacggtc | 3180 |
| tttaaaaagg ccgtaatatc cagctgaacg gtctggttat aggtacattg agcaactgac | 3240 |
| tgaaatgcct caaaatgttc tttacgatgc cattgggata tatcaacggt ggtatatcca | 3300 |
| gtgatttttt tctccatttt agcttcctta gctcctgaaa atctcgataa ctcaaaaaat | 3360 |
| acgcccggta gtgatcttat ttcattatgg tgaaagttgg aacctcaccc gacgtctaat | 3420 |
| gtgagttagc tcactcatta ggcaccccag gctttacact ttatgcttcc ggctcgtatg | 3480 |
| ttgtgtggaa ttgtgagcgg ataacaattt cacacaggaa acagctatga ccatgattac | 3540 |
| gaatttct | 3548 |

<210> SEQ ID NO 34
<211> LENGTH: 4410
<212> TYPE: DNA
<213> ORGANISM: artificial sequence
<220> FEATURE:
<223> OTHER INFORMATION: sequence for pMx7_FS_5D2

<400> SEQUENCE: 34

| | |
|---|---|
| tctagagcat gcgtaggaga aaataaaatg aaacaaagca ctattgcact ggcactctta | 60 |
| ccgttgctct tcaccctgt taccaaagcc gactacaaag atgaagtgca attggtggaa | 120 |
| agcggcggcg gcctggtgca accgggcggc agcctgcgtc tgagctgcgc ggcctccgga | 180 |
| tttacccttta gcagctatgc gatgagctgg gtgcgccaag cccctgggaa gggtctcgag | 240 |
| tgggtgagcg cgattagcgg tagcggcggc agcacctatt atgcggatag cgtgaaaggc | 300 |
| cgttttacca tttcacgtga taattcgaaa acaccctgt atctgcaaat gaacagcctg | 360 |
| cgtgcggaag atacggccgt gtattattgc gcgcgtgtta agaagcattt ttctcgtaag | 420 |
| aattggtttg attattgggg ccaaggcacc ctggtgacgg ttagctcagc gggtggcggt | 480 |
| tctggcggcg gtgggagcgg tggcggtggt tctggcggtg gtggttccga tatcgtgatg | 540 |
| acccagagcc cactgagcct gccagtgact ccgggcgagc ctgcgagcat agctgcaga | 600 |
| agcagccaaa gcctgctgca tagcaacggc tataactatc tggattggta ccttcaaaaa | 660 |
| ccaggtcaaa gcccgcagct attaatttat ctgggcagca accgtgccag tggggtcccg | 720 |
| gatcgtttta gcggctctgg atccggcacc gattttaccc tgaaaattag ccgtgtggaa | 780 |
| gctgaagacg tgggcgtgta ttattgccag cagcattata ccacccgcc gacctttggc | 840 |
| cagggtacga aagttgaaat taaacgtacg gaattcgact ataaagatga cgatgacaaa | 900 |
| ggcgcgccgt ggagccaccc gcagtttgaa aaatgataag cttgacctgt gaagtgaaaa | 960 |
| atggcgcaga ttgtgcgaca ttttttttgt ctgccgttta attaagggg ggggggggcc | 1020 |
| ggcctggggg ggggtgtaca tgaaattgta acgttaata ttttgttaaa attcgcgtta | 1080 |
| aattttttgtt aaatcagctc attttttaac caataggccg aaatcggcaa aatcccttat | 1140 |

```
aaatcaaaag aatagaccga gatagggttg agtgttgttc cagtttggaa caagagtcca    1200
ctattaaaga acgtggactc caacgtcaaa gggcgaaaaa ccgtctatca gggcgatggc    1260
ccactacgag aaccatcacc ctaatcaagt tttttggggt cgaggtgccg taaagcacta    1320
aatcggaacc ctaaagggag cccccgattt agagcttgac ggggaaagcc ggcgaacgtg    1380
gcgagaaagg aagggaagaa agcgaaagga gcgggcgcta gggcgctggc aagtgtagcg    1440
gtcacgctgc gcgtaaccac cacacccgcc gcgcttaatg cgccgctaca gggcgcgtgc    1500
tagactagtg tttaaaccgg accgggggg ggcttaagtg ggctgcaaaa caaaacggcc    1560
tcctgtcagg aagccgcttt tatcgggtag cctcactgcc cgctttccag tcgggaaacc    1620
tgtcgtgcca gctgcatcag tgaatcggcc aacgcgcggg gagaggcggt ttgcgtattg    1680
ggagccaggg tggttttct tttcaccagt gagacgggca acagctgatt gcccttcacc    1740
gcctggccct gagagagttg cagcaagcgg tccacgctgg tttgcccag caggcgaaaa    1800 tcctgtttga tggtggtcag cggcgggata taacatgagc tgtcctcggt atcgtcgtat    1860
cccactaccg agatgtccgc accaacgcgc agcccggact cggtaatggc acgcattgcg    1920
cccagcgcca tctgatcgtt ggcaaccagc atcgcagtgg gaacgatgcc ctcattcagc    1980
atttgcatgg tttgttgaaa accggacatg gcactccagt cgccttcccg ttccgctatc    2040
ggctgaattt gattgcgagt gagatattta tgccagccag ccagacgcag acgcgccgag    2100
acagaactta atgggccagc taacagcgcg atttgctggt ggcccaatgc gaccagatgc    2160
tccacgccca gtcgcgtacc gtcctcatgg gagaaaataa tactgttgat gggtgtctgg    2220
tcagagacat caagaaataa cgccggaaca ttagtgcagg cagcttccac agcaatagca    2280
tcctggtcat ccagcggata gttaataatc agcccactga cacgttgcgc gagaagattg    2340
tgcaccgccg ctttacaggc ttcgacgccg cttcgttcta ccatcgacac gaccacgctg    2400
gcacccagtt gatcggcgcg agatttaatc gccgcgacaa tttgcgacgg cgcgtgcagg    2460
gccagactgg aggtggcaac gccaatcagc aacgactgtt tgcccgccag ttgttgtgcc    2520
acgcggttag gaatgtaatt cagctccgcc atcgccgctt ccactttttc ccgcgttttc    2580
gcagaaacgt ggctggcctg gttcaccacg cgggaaacgg tctgataaga gacaccggca    2640
tactctgcga catcgtataa cgttactggt ttcacattca ccaccctgaa ttgactctct    2700
tccgggcgct atcatgccat accgcgaaag gttttgcgcc attcgatgct agccatgtga    2760
gcaaaaggcc agcaaaaggc caggaaccgt aaaaaggccg cgttgctggc gtttttccat    2820
aggctccgcc cccctgacga gcatcacaaa aatcgacgct caagtcagag gtggcgaaac    2880
ccgacaggac tataaagata ccaggcgttt ccccctggaa gctccctcgt gcgctctcct    2940
gttccgaccc tgccgcttac cggatacctg tccgcctttc tcccttcggg aagcgtggcg    3000
ctttctcata gctcacgctg taggtatctc agttcggtgt aggtcgttcg ctccaagctg    3060
ggctgtgtgc acgaacccc cgttcagccc gaccgctgcg ccttatccgg taactatcgt    3120
cttgagtcca acccggtaag acacgactta tcgccactgg cagcagccac tggtaacagg    3180
attagcagag cgaggtatgt aggcggtgct acagagttct tgaagtggtg cctaactac    3240 ggctacacta gaagaacagt atttggtatc tgcgctctgc tgtagccagt taccttcgga    3300
aaaagagttg gtagctcttg atccggcaaa caaaccaccg ctggtagcgg tggtttttt    3360 gtttgcaagc agcagattac gcgcagaaaa aaggatctc aagaagatcc tttgatcttt    3420
tctacggggt ctgacgctca gtggaacgaa aactcacgtt aagggatttt ggtcagatct    3480
agcaccaggc gtttaagggc accaataact gccttaaaaa aattacgccc cgccctgcca    3540
```

```
ctcatcgcag tactgttgta attcattaag cattctgccg acatggaagc catcacaaac      3600
ggcatgatga acctgaatcg ccagcggcat cagcaccttg tcgccttgcg tataatattt      3660
gcccatagtg aaaacggggg cgaagaagtt gtccatattg gctacgttta aatcaaaact      3720
ggtgaaactc acccagggat tggctgagac gaaaaacata ttctcaataa acccttaggg      3780
gaaataggcc aggttttcac cgtaacacgc acatcttgc gaatatatgt gtagaaactg       3840
ccggaaatcg tcgtggtatt cactccagag cgatgaaaac gtttcagttt gctcatggaa      3900
aacggtgtaa caagggtgaa cactatccca tatcaccagc tcaccgtctt tcattgccat      3960
acggaactcc gggtgagcat tcatcaggcg ggcaagaatg tgaataaagg ccggataaaa      4020
cttgtgctta ttttctttta cggtctttaa aaaggccgta atatccagct gaacggtctg      4080
gttataggta cattgagcaa ctgactgaaa tgcctcaaaa tgttctttac gatgccattg      4140
ggatatatca acggtggtat atccagtgat ttttttctcc attttagctt ccttagctcc      4200
tgaaaatctc gataactcaa aaaatacgcc cggtagtgat cttatttcat tatggtgaaa      4260
gttggaacct cacccgacgt ctaatgtgag ttagctcact cattaggcac cccaggcttt      4320
acactttatg cttccggctc gtatgttgtg tggaattgtg agcggataac aatttcacac      4380
aggaaacagc tatgaccatg attacgaatt                                       4410
```

<210> SEQ ID NO 35
<211> LENGTH: 5020
<212> TYPE: DNA
<213> ORGANISM: artificial sequence
<220> FEATURE:
<223> OTHER INFORMATION: sequence for pMx9_Fab_GPC8

<400> SEQUENCE: 35

```
atcgtgctga cccagccgcc ttcagtgagt ggcgcaccag gtcagcgtgt gaccatctcg      60
tgtagcggca gcagcagcaa cattggcagc aactatgtga gctggtacca gcagttgccc      120
gggacggcgc cgaaactgct gatttatgat aacaaccagc gtccctcagg cgtgccggat      180
cgttttagcg gatccaaaag cggcaccagc gcgagccttg cgattacggg cctgcaaagc      240
gaagacgaag cggattatta ttgccagagc tatgacatgc ctcaggctgt gtttggcggc      300
ggcacgaagt taaccgttc ttggccagcc gaaagccgca ccgagtgtga cgctgttttcc       360 gccgagcagc gaagaattgc aggcgaacaa agcgaccctg gtgtgcctga ttagcgactt      420
ttatccggga gccgtgacag tggcctggaa ggcagatagc agccccgtca aggcgggagt      480
ggagaccacc acaccctcca aacaaagcaa caacaagtac gcggccagca gctatctgag      540
cctgacgcct gagcagtgga gtcccacag aagctacagc tgccaggtca cgcatgaggg      600
gagcaccgtg aaaaaaccg ttgcgccgac tgaggcctga taagcatgcg taggagaaaa      660
taaaatgaaa caaagcacta ttgcactggc actcttaccg ttgctcttca ccctgttac      720 caaagcccag gtgcaattga agaaagcgg cccggccctg gtgaaaccga cccaaaccct      780 gacccctgacc tgtaccttt ccggatttag cctgtccacg tctggcgttg gcgtgggctg      840
gattcgccag ccgcctggga aagccctcga gtggctggct ctgattgatt gggatgatga      900
taagtattat agcaccagcc tgaaaacgcg tctgaccatt agcaaagata cttcgaaaaa      960
tcaggtggtg ctgactatga ccaacatgga cccggtggat acggcacct attattgcgc      1020 gcgttctcct cgttatcgtg gtgctttga ttattgggc caaggcaccc tggtgacggt      1080
tagctcagcg tcgaccaaag gtccaagcgt gtttccgctg ctccagca gcaaaagcac      1140
```

```
cagcggcggc acggctgccc tgggctgcct ggttaaagat tatttcccgg aaccagtcac   1200
cgtgagctgg aacagcgggg cgctgaccag cggcgtgcat acctttccgg cggtgctgca   1260
aagcagcggc ctgtatagcc tgagcagcgt tgtgaccgtg ccgagcagca gcttaggcac   1320
tcagacctat atttgcaacg tgaaccataa accgagcaac accaaagtgg ataaaaaagt   1380
ggaaccgaaa agcgaattcg actataaaga tgacgatgac aaaggcgcgc cgtggagcca   1440
cccgcagttt gaaaaatgat aagcttgacc tgtgaagtga aaatggcgc agattgtgcg   1500 acatttttt tgtctgccgt ttaattaaag ggggggggg ccggcctgg ggggggtgt   1560 acatgaaatt gtaaacgtta atattttgtt aaaattcgcg ttaaattttt gttaaatcag   1620
ctcatttttt aaccaatagg ccgaaatcgg caaatccct tataaatcaa aagaatagac   1680
cgagataggg ttgagtgttg ttccagtttg gaacaagagt ccactattaa agaacgtgga   1740
ctccaacgtc aaagggcgaa aaccgtctat cagggcgat ggcccactac gagaaccatc   1800
accctaatca gtttttggg ggtcgaggtg ccgtaaagca ctaaatcgga accctaaagg   1860
gagcccccga tttagagctt gacggggaaa gccggcgaac gtggcgagaa aggaagggaa   1920
gaaagcgaaa ggagcgggcg ctagggcgct ggcaagtgta gcggtcacgc tgcgcgtaac   1980
caccacaccc gccgcgctta atgcgccgct acagggcgcg tgctagacta gtgtttaaac   2040
cggaccgggg gggggcttaa gtgggctgca aaacaaaacg gcctcctgtc aggaagccgc   2100
ttttatcggg tagcctcact gcccgctttc cagtcgggaa acctgtcgtg ccagctgcat   2160
cagtgaatcg gccaacgcgc ggggagaggc ggtttgcgta ttgggagcca gggtggtttt   2220
tcttttcacc agtgagacgg gcaacagctg attgcccttc accgcctggc cctgagagag   2280
ttgcagcaag cggtccacgc tggttttgccc cagcaggcga aaatcctgtt tgatggtggt   2340
cagcggcggg atataacatg agctgtcctc ggtatcgtcg tatcccacta ccgagatgtc   2400
cgcaccaacg cgcagcccgg actcggtaat ggcacgcatt cgcccagcg ccatctgatc   2460 gttggcaacc agcatcgcag tgggaacgat gccctcattc agcatttgca tggtttgttg   2520
aaaaccggac atggcactcc agtcgccttc ccgttccgct atcggctgaa tttgattgcg   2580
agtgagatat ttatgccagc cagccagacg cagacgcgcc gagacagaac ttaatgggcc   2640
agctaacagc gcgatttgct ggtggcccaa tgcgaccaga tgctccacgc ccagtcgcgt   2700
accgtcctca tgggagaaaa taatactgtt gatgggtgtc tggtcagaga catcaagaaa   2760
taacgccgga acattagtgc aggcagcttc cacagcaata gcatcctggt catccagcgg   2820
atagttaata atcagcccac tgacacgttg cgcgagaaga ttgtgcaccg ccgctttaca   2880
ggcttcgacg ccgcttcgtt ctaccatcga cacgaccacg ctggcaccca gttgatcggc   2940
gcgagattta atcgccgcga caatttgcga cggcgcgtgc agggccagac tggaggtggc   3000
aacgccaatc agcaacgact gtttgcccgc cagttgttgt gccacgcggt taggaatgta   3060
attcagctcc gccatcgccg cttccacttt tccccgcgtt ttcgcagaaa cgtggctggc   3120
ctggttcacc acgcgggaaa cggtctgata agagacaccg gcatactctg cgacatcgta   3180
taacgttact ggtttcacat tcaccaccct gaattgactc tcttccgggc gctatcatgc   3240
cataccgcga aaggttttgc gccattcgat gctagccatg tgagcaaaag gccagcaaaa   3300
ggccaggaac cgtaaaaagg ccgcgttgct ggcgttttc cataggctcc gcccccctga   3360
cgagcatcac aaaaatcgac gctcaagtca gaggtggcga aacccgacag gactataaag   3420
ataccaggcg tttccccctg gaagctccct cgtgcgctct cctgttccga ccctgccgct   3480
taccggatac ctgtccgcct ttctcccttc gggaagcgtg gcgctttctc atagctcacg   3540
```

```
ctgtaggtat ctcagttcgg tgtaggtcgt tcgctccaag ctgggctgtg tgcacgaacc    3600
ccccgttcag cccgaccgct gcgccttatc cggtaactat cgtcttgagt ccaacccggt    3660
aagacacgac ttatcgccac tggcagcagc cactggtaac aggattagca gagcgaggta    3720
tgtaggcggt gctacagagt tcttgaagtg gtggcctaac tacggctaca ctagaagaac    3780
agtatttggt atctgcgctc tgctgtagcc agttaccttc ggaaaaagag ttggtagctc    3840
ttgatccggc aaacaaacca ccgctggtag cggtggtttt tttgtttgca agcagcagat    3900
tacgcgcaga aaaaaggat ctcaagaaga tcctttgatc ttttctacgg ggtctgacgc     3960
tcagtggaac gaaaactcac gttaagggat tttggtcaga tctagcacca ggcgtttaag    4020
ggcaccaata actgccttaa aaaaattacg ccccgccctg ccactcatcg cagtactgtt    4080
gtaattcatt aagcattctg ccgacatgga agccatcaca acggcatga tgaacctgaa     4140
tcgccagcgg catcagcacc ttgtcgcctt gcgtataata tttgcccata gtgaaaacgg    4200
gggcgaagaa gttgtccata ttggctacgt ttaaatcaaa actggtgaaa ctcacccagg    4260
gattggctga cgaaaaac atattctcaa taaacccttt agggaaatag gccaggtttt      4320
caccgtaaca cgccacatct tgcgaatata tgtgtagaaa ctgccggaaa tcgtcgtggt    4380
attcactcca gagcgatgaa aacgtttcag tttgctcatg gaaaacggtg taacaagggt    4440
gaacactatc ccatatcacc agctcaccgt ctttcattgc catacggaac tccgggtgag    4500
cattcatcag gcgggcaaga atgtgaataa aggccggata aaacttgtgc ttattttct     4560
ttacggtctt taaaaaggcc gtaatatcca gctgaacggt ctggttatag gtacattgag    4620
caactgactg aaatgcctca aaatgttctt tacgatgcca ttgggatata tcaacggtgg    4680
tatatccagt gattttttc tccatttag cttccttagc tcctgaaaat ctcgataact       4740
caaaaaatac gcccggtagt gatcttattt cattatggtg aaagttggaa cctcacccga    4800
cgtctaatgt gagttagctc actcattagg caccccaggc tttacacttt atgcttccgg    4860
ctcgtatgtt gtgtggaatt gtgagcggat aacaatttca cacaggaaac agctatgacc    4920
atgattacga atttctagat aacgagggca aaaaatgaaa aagacagcta tcgcgattgc    4980
agtggcactg gctggtttcg ctaccgtagc gcaggccgat                          5020

<210> SEQ ID NO 36
<211> LENGTH: 4145
<212> TYPE: DNA
<213> ORGANISM: artificial sequence
<220> FEATURE:
<223> OTHER INFORMATION: sequence for pMORPH18_Fab_GPC8

<400> SEQUENCE: 36
tcagataacg agggcaaaaa atgaaaaaga cagctatcgc gattgcagtg gcactggctg      60
gtttcgctac cgtagcgcag gccgatatcg tgctgaccca gccgccttca gtgagtggcg     120
caccaggtca gcgtgtgacc atctcgtgta gcggcagcag cagcaacatt ggcagcaact     180
atgtgagctg gtaccagcag ttgcccggga cggcgccgaa actgctgatt tatgataaca    240
accagcgtcc ctcaggcgtg ccggatcgtt ttagcggatc caaaagcggc accagcgcga    300
gccttgcgat tacgggcctg caaagcgaag acgaagcgga ttattattgc cagagctatg    360
acatgcctca ggctgtgttt ggcggcggca cgaagtttaa ccgttcttgg ccagccgaaa    420
gccgcaccga gtgtgacgct gtttccgccg agcagcgaag aattgcaggc gaacaaagcg    480
accctggtgt gcctgattag cgactttat ccgggagccg tgacagtggc ctggaaggca      540
```

```
gatagcagcc ccgtcaaggc gggagtggag accaccacac cctccaaaca aagcaacaac    600
aagtacgcgg ccagcagcta tctgagcctg acgcctgagc agtggaagtc ccacagaagc    660
tacagctgcc aggtcacgca tgaggggagc accgtggaaa aaaccgttgc gccgactgag    720
gcctgataag catgcgtagg agaaaataaa atgaaacaaa gcactattgc actggcactc    780
ttaccgttgc tcttcacccc tgttaccaaa gcccaggtgc aattgaaaga aagcggcccg    840
gccctggtga aaccgaccca aaccctgacc ctgacctgta ccttttccgg atttagcctg    900
tccacgtctg gcgttggcgt gggctggatt cgccagccgc tgggaaaagc cctcgagtgg    960
ctggctctga ttgattggga tgatgataag tattatagca ccagcctgaa aacgcgtctg   1020
accattagca aagatacttc gaaaaatcag gtggtgctga ctatgaccaa catggacccg   1080
gtggatacgg ccacctatta ttgcgcgcgt tctcctcgtt atcgtggtgc ttttgattat   1140
tggggccaag gcaccctggt gacggttagc tcagcgtcga ccaaaggtcc aagcgtgttt   1200
ccgctggctc cgagcagcaa aagcaccagc ggcggcacgg ctgccctggg ctgcctggtt   1260
aaagattatt tcccggaacc agtcaccgtg agctggaaca gcggggcgct gaccagcggc   1320
gtgcataccc ttccggcggt gctgcaaagc agcggcctgt atagcctgag cagcgttgtg   1380
accgtgccga gcagcagctt aggcactcag acctatattt gcaacgtgaa ccataaaccg   1440
agcaacacca aagtggataa aaaagtggaa ccgaaaagcg aattcggggg agggagcggg   1500
agcggtgatt ttgattatga aaagatggca aacgctaata aggggctat gaccgaaaat   1560 gccgatgaaa acgcgctaca gtctgacgct aaaggcaaac ttgattctgt cgctactgat   1620
tacggtgctg ctatcgatgg tttcattggt gacgtttccg gccttgctaa tggtaatggt   1680
gctactggtg attttgctgg ctctaattcc caaatggctc aagtcggtga cggtgataat   1740
tcacctttaa tgaataattt ccgtcaatat ttaccttccc tcccctcaatc ggttgaatgt   1800 cgcccttttg tctttggcgc tggtaaacca tatgaatttt ctattgattg tgacaaaata   1860
aacttattcc gtggtgtctt tgcgtttctt ttatatgttg ccacctttat gtatgtattt   1920
tctacgtttg ctaacatact gcgtaataag gagtcttgat aagcttgacc tgtgaagtga   1980
aaaatggcgc agattgtgcg acatttttt tgtctgccgt ttaatgaaat tgtaaacgtt   2040
aatattttgt taaaattcgc gttaaatttt tgttaaatca gctcatttt taaccaatag   2100 gccgaaatcg gcaaaatccc ttataaatca aagaataga ccgagatagg gttgagtgtt   2160
gttccagttt ggaacaagag tccactatta agaacgtgg actccaacgt caaagggcga   2220
aaaaccgtct atcagggcga tggcccacta cgagaaccat caccctaatc aagttttttg   2280
gggtcgaggt gccgtaaagc actaaatcgg aaccctaaag ggagccccg atttagagct   2340 tgacggggaa agccggcgaa cgtggcgaga aggaaggga agaaagcgaa aggagcgggc   2400
gctagggcgc tggcaagtgt agcggtcacg ctgcgcgtaa ccaccacacc cgccgcgctt   2460
aatgcgccgc tacagggcgc gtgctagcca tgtgagcaaa aggccagcaa aaggccagga   2520
accgtaaaaa ggccgcgttg ctggcgtttt tccataggct ccgcccccct gacgagcatc   2580
acaaaaatcg acgctcaagt cagaggtggc gaaacccgac aggactataa agataccagg   2640
cgtttccccc tggaagctcc ctcgtgcgct ctcctgttcc gaccctgccg cttaccggat   2700
acctgtccgc ctttctccct tcgggaagcg tggcgctttc tcatagctca cgctgtaggt   2760
atctcagttc ggtgtaggtc gttcgctcca agctgggctg tgtgcacgaa ccccccgttc   2820
agtccgaccg ctgcgcctta tccggtaact atcgtcttga gtccaacccg gtaagacacg   2880
acttatcgcc actggcagca gccactggta acaggattag cagagcgagg tatgtaggcg   2940
```

```
gtgctacaga gttcttgaag tggtggccta actacggcta cactagaaga acagtatttg    3000
gtatctgcgc tctgctgtag ccagttacct tcggaaaaag agttggtagc tcttgatccg    3060
gcaaacaaac caccgctggt agcggtggtt tttttgtttg caagcagcag attacgcgca    3120
gaaaaaaagg atctcaagaa gatcctttga tcttttctac ggggtctgac gctcagtgga    3180
acgaaaactc acgttaaggg attttggtca gatctagcac caggcgttta agggcaccaa    3240
taactgcctt aaaaaaatta cgccccgccc tgccactcat cgcagtactg ttgtaattca    3300
ttaagcattc tgccgacatg gaagccatca caaacggcat gatgaacctg aatcgccagc    3360
ggcatcagca ccttgtcgcc ttgcgtataa tatttgccca tagtgaaaac ggggggcgaag    3420
aagttgtcca tattggctac gtttaaatca aaactggtga aactcaccca gggattggct    3480
gagacgaaaa acatattctc aataaaccct ttagggaaat aggccaggtt ttcaccgtaa    3540
cacgccacat cttgcgaata tatgtgtaga aactgccgga aatcgtcgtg gtattcactc    3600
cagagcgatg aaaacgtttc agtttgctca tggaaaacgg tgtaacaagg gtgaacacta    3660
tcccatatca ccagctcacc gtctttcatt gccatacgga actccgggtg agcattcatc    3720
aggcgggcaa gaatgtgaat aaaggccgga taaaacttgt gcttattttt ctttacggtc    3780
tttaaaaagg ccgtaatatc cagctgaacg gtctggttat aggtacattg agcaactgac    3840
tgaaatgcct caaaatgttc tttacgatgc cattgggata tatcaacggt ggtatatcca    3900
gtgatttttt tctccatttt agcttcctta gctcctgaaa atctcgataa ctcaaaaaat    3960
acgcccggta gtgatcttat ttcattatgg tgaaagttgg aacctcaccc gacgtctaat    4020
gtgagttagc tcactcatta ggcaccccag gctttacact ttatgcttcc ggctcgtatg    4080
ttgtgtggaa ttgtgagcgg ataacaattt cacacaggaa acagctatga ccatgattac    4140
gaatt                                                                 4145

<210> SEQ ID NO 37
<211> LENGTH: 120
<212> TYPE: PRT
<213> ORGANISM: artificial sequence
<220> FEATURE:
<223> OTHER INFORMATION: sequence for MS-GPC1-VH

<400> SEQUENCE: 37

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Asp Trp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Gln Tyr Gly His Arg Gly Gly Phe Asp His Trp Gly Gln
            100                 105                 110

Gly Thr Leu Val Thr Val Ser Ser
        115                 120

<210> SEQ ID NO 38
```

```
<211> LENGTH: 109
<212> TYPE: PRT
<213> ORGANISM: artificial sequence
<220> FEATURE:
<223> OTHER INFORMATION: sequence for MS-GPC1-VL

<400> SEQUENCE: 38

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Phe Asn Glu
                85                  90                  95

Ser Val Phe Gly Gly Gly Thr Lys Leu Thr Val Leu Gly
            100                 105

<210> SEQ ID NO 39
<211> LENGTH: 118
<212> TYPE: PRT
<213> ORGANISM: artificial sequence
<220> FEATURE:
<223> OTHER INFORMATION: sequence for MS-GPC6-VH

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Gly Arg Tyr Ser Pro Asp Leu Trp Gly Gln Gly Thr
            100                 105                 110

Leu Val Thr Val Ser Ser
        115

<210> SEQ ID NO 40
<211> LENGTH: 110
<212> TYPE: PRT
<213> ORGANISM: artificial sequence
<220> FEATURE:
<223> OTHER INFORMATION: sequence for MS-GPC6-VL

<400> SEQUENCE: 40

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

-continued

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser Asn Leu Pro
                85                  90                  95

Phe Thr Phe Gly Gln Gly Thr Lys Val Glu Ile Lys Arg Thr
            100                 105                 110

<210> SEQ ID NO 41
<211> LENGTH: 120
<212> TYPE: PRT
<213> ORGANISM: artificial sequence
<220> FEATURE:
<223> OTHER INFORMATION: sequence for MS-GPC8-VH, MS-GPC8-1-VH,
      MS-GPC8-6-VH,MS-GPC8-9-VH,MS-GPC8-10-VH,MS-GPC8-17-VH,
      MS-GPC8-18-VH,MS-GPC8-27-VH,MS-GPC8-6-2-VH,MS-GPC8-6-13-VH,
      MS-GPC8-6-27-VH,MS-GPC8-6-45-VH,MS-GPC8-6-47-VH,
<220> FEATURE:
<223> OTHER INFORMATION: MS-GPC8-10-57-VH,MS-GPC8-27-7-VH,
      MS-GPC8-27-10-VH,MS-GPC8-27-41-VH

<400> SEQUENCE: 41

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Pro Arg Tyr Arg Gly Ala Phe Asp Tyr Trp Gly Gln
            100                 105                 110

Gly Thr Leu Val Thr Val Ser Ser
        115                 120

<210> SEQ ID NO 42
<211> LENGTH: 109
<212> TYPE: PRT
<213> ORGANISM: artificial sequence
<220> FEATURE:
<223> OTHER INFORMATION: sequence for MS-GPC8-VL

<400> SEQUENCE: 42

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Met Pro Gln
            85                  90                  95

Ala Val Phe Gly Gly Gly Thr Lys Leu Thr Val Leu Gly
            100                 105

<210> SEQ ID NO 43
<211> LENGTH: 120
<212> TYPE: PRT
<213> ORGANISM: artificial sequence
<220> FEATURE:
<223> OTHER INFORMATION: sequence for MS-GPC10-VH

<400> SEQUENCE: 43

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Gln Leu His Tyr Arg Gly Gly Phe Asp Leu Trp Gly Gln
            100                 105                 110

Gly Thr Leu Val Thr Val Ser Ser
        115                 120

<210> SEQ ID NO 44
<211> LENGTH: 109
<212> TYPE: PRT
<213> ORGANISM: artificial sequence
<220> FEATURE:
<223> OTHER INFORMATION: sequence for MS-GPC10-VL

<400> SEQUENCE: 44

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Leu Thr Met
            85                  90                  95

Gly Val Phe Gly Gly Gly Thr Lys Leu Thr Val Leu Gly
            100                 105

<210> SEQ ID NO 45
<211> LENGTH: 109
<212> TYPE: PRT
<213> ORGANISM: artificial sequence
<220> FEATURE:
<223> OTHER INFORMATION: sequence for MS-GPC8-6-2-VL

<400> SEQUENCE: 45

```
Asp Ile Val Leu Thr Gln Pro Pro Ser Val Ser Gly Ala Pro Gly Gln
1               5                   10                  15

Arg Val Thr Ile Ser Cys Ser Gly Ser Glu Ser Asn Ile Gly Ser Asn
            20                  25                  30

Tyr Val His Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Tyr Asp His
                85                  90                  95

Tyr Val Phe Gly Gly Gly Thr Lys Leu Thr Val Leu Gly
            100                 105
```

<210> SEQ ID NO 46
<211> LENGTH: 109
<212> TYPE: PRT
<213> ORGANISM: artificial sequence
<220> FEATURE:
<223> OTHER INFORMATION: sequence for MS-GPC8-6-VL

<400> SEQUENCE: 46

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Tyr Asp His
                85                  90                  95

Tyr Val Phe Gly Gly Gly Thr Lys Leu Thr Val Leu Gly
            100                 105
```

<210> SEQ ID NO 47
<211> LENGTH: 109
<212> TYPE: PRT
<213> ORGANISM: artificial sequence
<220> FEATURE:
<223> OTHER INFORMATION: sequence for MS-GPC8-6-19-VL

<400> SEQUENCE: 47

```
Asp Ile Val Leu Thr Gln Pro Pro Ser Val Ser Gly Ala Pro Gly Gln
1               5                   10                  15

Arg Val Thr Ile Ser Cys Ser Gly Ser Glu Ser Asn Ile Gly Ser Asn
            20                  25                  30

Tyr Val Ala Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80
```

Ser Glu Asp Glu Ala Asp Tyr Tyr Cys Gln Ser Tyr Asp Tyr Asp His
                85                  90                  95

Tyr Val Phe Gly Gly Gly Thr Lys Leu Thr Val Leu Gly
            100                 105

<210> SEQ ID NO 48
<211> LENGTH: 109
<212> TYPE: PRT
<213> ORGANISM: artificial sequence
<220> FEATURE:
<223> OTHER INFORMATION: sequence for MS-GPC8-10-VL

<400> SEQUENCE: 48

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Leu Ile Arg
                85                  90                  95

His Val Phe Gly Gly Gly Thr Lys Leu Thr Val Leu Gly
            100                 105

<210> SEQ ID NO 49
<211> LENGTH: 109
<212> TYPE: PRT
<213> ORGANISM: artificial sequence
<220> FEATURE:
<223> OTHER INFORMATION: sequence for MS-GPC8-6-27-VL

<400> SEQUENCE: 49

Asp Ile Val Leu Thr Gln Pro Pro Ser Val Ser Gly Ala Pro Gly Gln
1               5                   10                  15

Arg Val Thr Ile Ser Cys Ser Gly Ser Asp Ser Asn Ile Gly Ala Asn
            20                  25                  30

Tyr Val Thr Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Tyr Asp His
                85                  90                  95

Tyr Val Phe Gly Gly Gly Thr Lys Leu Thr Val Leu Gly
            100                 105

<210> SEQ ID NO 50
<211> LENGTH: 109
<212> TYPE: PRT
<213> ORGANISM: artificial sequence
<220> FEATURE:
<223> OTHER INFORMATION: sequence for MS-GPC8-17-VL

<400> SEQUENCE: 50

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Phe Ser Val
                85                  90                  95

Tyr Val Phe Gly Gly Gly Thr Lys Leu Thr Val Leu Gly
            100                 105

<210> SEQ ID NO 51
<211> LENGTH: 109
<212> TYPE: PRT
<213> ORGANISM: artificial sequence
<220> FEATURE:
<223> OTHER INFORMATION: sequence for MS-GPC8-6-45-VL

<400> SEQUENCE: 51

Asp Ile Val Leu Thr Gln Pro Pro Ser Val Ser Gly Ala Pro Gly Gln
1               5                   10                  15

Arg Val Thr Ile Ser Cys Ser Gly Ser Glu Pro Asn Ile Gly Ser Asn
            20                  25                  30

Tyr Val Phe Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Tyr Asp His
                85                  90                  95

Tyr Val Phe Gly Gly Gly Thr Lys Leu Thr Val Leu Gly
            100                 105

<210> SEQ ID NO 52
<211> LENGTH: 109
<212> TYPE: PRT
<213> ORGANISM: artificial sequence
<220> FEATURE:
<223> OTHER INFORMATION: sequence for MS-GPC8-27-VL

<400> SEQUENCE: 52

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75

Gln Ser Glu Asp Glu Ala Asp Tyr Tyr Cys Gln Ser Tyr Asp Met Asn
80                  85                  90                  95
```

Val His Val Phe Gly Gly Gly Thr Lys Leu Thr Val Leu Gly
            100             105             109

<210> SEQ ID NO 53
<211> LENGTH: 109
<212> TYPE: PRT
<213> ORGANISM: artificial sequence
<220> FEATURE:
<223> OTHER INFORMATION: sequence for MS-GPC8-6-47-VL

<400> SEQUENCE: 53

Asp Ile Val Leu Thr Gln Pro Pro Ser Val Ser Gly Ala Pro Gly Gln
1               5                   10                  15

Arg Val Thr Ile Ser Cys Ser Gly Ser Glu Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Tyr Asp His
                85                  90                  95

Tyr Val Phe Gly Gly Gly Thr Lys Leu Thr Val Leu Gly
            100                 105

<210> SEQ ID NO 54
<211> LENGTH: 109
<212> TYPE: PRT
<213> ORGANISM: artificial sequence
<220> FEATURE:
<223> OTHER INFORMATION: sequence for MS-GPC8-6-13-VL

<400> SEQUENCE: 54

Asp Ile Val Leu Thr Gln Pro Pro Ser Val Ser Gly Ala Pro Gly Gln
1               5                   10                  15

Arg Val Thr Ile Ser Cys Ser Gly Ser Glu Ser Asn Ile Gly Ala Asn
            20                  25                  30

Tyr Val Thr Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Tyr Asp His
                85                  90                  95

Tyr Val Phe Gly Gly Gly Thr Lys Leu Thr Val Leu Gly
            100                 105

<210> SEQ ID NO 55
<211> LENGTH: 109
<212> TYPE: PRT
<213> ORGANISM: artificial sequence
<220> FEATURE:
<223> OTHER INFORMATION: sequence for MS-GPC8-27-7-VL

<400> SEQUENCE: 55

Asp Ile Val Leu Thr Gln Pro Pro Ser Val Ser Gly Ala Pro Gly Gln
1               5                   10                  15

```
Arg Val Thr Ile Ser Cys Ser Gly Ser Glu Ser Asn Ile Gly Asn Asn
            20                  25                  30

Tyr Val Gly Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Met Asn Val
                85                  90                  95

His Val Phe Gly Gly Gly Thr Lys Leu Thr Val Leu Gly
            100                 105

<210> SEQ ID NO 56
<211> LENGTH: 109
<212> TYPE: PRT
<213> ORGANISM: artificial sequence
<220> FEATURE:
<223> OTHER INFORMATION: sequence for MS-GPC8-10-57-VL

<400> SEQUENCE: 56

Asp Ile Val Leu Thr Gln Pro Pro Ser Val Ser Gly Ala Pro Gly Gln
1               5                   10                  15

Arg Val Thr Ile Ser Cys Ser Gly Ser Glu Ser Asn Ile Gly Asn Asn
            20                  25                  30

Tyr Val Gln Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Leu Ile Arg
                85                  90                  95

His Val Phe Gly Gly Gly Thr Lys Leu Thr Val Leu Gly
            100                 105

<210> SEQ ID NO 57
<211> LENGTH: 109
<212> TYPE: PRT
<213> ORGANISM: artificial sequence
<220> FEATURE:
<223> OTHER INFORMATION: sequence for MS-GPC8-27-10-VL

<400> SEQUENCE: 57

Asp Ile Val Leu Thr Gln Pro Pro Ser Val Ser Gly Ala Pro Gly Gln
1               5                   10                  15

Arg Val Thr Ile Ser Cys Ser Gly Ser Glu Ser Asn Ile Gly Ala Asn
            20                  25                  30

Tyr Val Asn Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Met Asn Val
                85                  90                  95

His Val Phe Gly Gly Gly Thr Lys Leu Thr Val Leu Gly
            100                 105
```

```
<210> SEQ ID NO 58
<211> LENGTH: 109
<212> TYPE: PRT
<213> ORGANISM: artificial sequence
<220> FEATURE:
<223> OTHER INFORMATION: sequence for MS-GPC8-27-41-VL

<400> SEQUENCE: 58

Asp Ile Val Leu Thr Gln Pro Pro Ser Val Ser Gly Ala Pro Gly Gln
1               5                   10                  15

Arg Val Thr Ile Ser Cys Ser Gly Ser Glu Ser Asn Ile Gly Asn Asn
            20                  25                  30

Tyr Val Gln Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Met Asn Val
                85                  90                  95

His Val Phe Gly Gly Gly Thr Lys Leu Thr Val Leu Gly
            100                 105

<210> SEQ ID NO 59
<211> LENGTH: 8
<212> TYPE: PRT
<213> ORGANISM: artificial sequence
<220> FEATURE:
<223> OTHER INFORMATION: sequence for MS-GPC1-VL-CDR3

<400> SEQUENCE: 59

Gln Ser Tyr Asp Phe Asn Glu Ser
1               5

<210> SEQ ID NO 60
<211> LENGTH: 8
<212> TYPE: PRT
<213> ORGANISM: artificial sequence
<220> FEATURE:
<223> OTHER INFORMATION: sequence for MS-GPC8-6-VL-CDR3,
      MS-GPC8-6-2-VL-CDR3,MS-GPC8-6-13-VL-CDR3,MS-GPC8-6-19-VL-CDR3,
      MS-GPC8-6-27-VL-CDR3,MS-GPC8-6-45-VL-CDR3,MS-GPC8-6-47-VL-CDR3

<400> SEQUENCE: 60

Gln Ser Tyr Asp Tyr Asp His Tyr
1               5

<210> SEQ ID NO 61
<211> LENGTH: 10
<212> TYPE: PRT
<213> ORGANISM: artificial sequence
<220> FEATURE:
<223> OTHER INFORMATION: sequence for MS-GPC10-VH-CDR3

<400> SEQUENCE: 61

Gln Leu His Tyr Arg Gly Gly Phe Asp Leu
1               5                   10

<210> SEQ ID NO 62
<211> LENGTH: 12
<212> TYPE: PRT
<213> ORGANISM: artificial sequence
<220> FEATURE:
```

-continued

```
<223> OTHER INFORMATION: sequence for MS-GPC6-VL-CDR1

<400> SEQUENCE: 62

Arg Ala Ser Gln Ser Val Ser Ser Ser Tyr Leu Ala
1               5                   10
```